United States Patent
Behenna et al.

(10) Patent No.: US 11,014,911 B2
(45) Date of Patent: May 25, 2021

(54) CDK2 INHIBITORS

(71) Applicant: Pfizer Inc., New York, NY (US)

(72) Inventors: Douglas Carl Behenna, San Juan Capistrano, CA (US); Kevin Daniel Freeman-Cook, San Diego, CA (US); Robert Louis Hoffman, San Marcos, CA (US); Asako Nagata, San Diego, CA (US); Sacha Ninkovic, San Diego, CA (US); Scott Channing Sutton, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/774,786

(22) Filed: Jan. 28, 2020

(65) Prior Publication Data

US 2020/0247784 A1 Aug. 6, 2020

Related U.S. Application Data

(60) Provisional application No. 62/959,042, filed on Jan. 9, 2020, provisional application No. 62/799,455, filed on Jan. 31, 2019.

(51) Int. Cl.
*C07D 403/12* (2006.01)
*A61P 35/00* (2006.01)
*C07D 413/12* (2006.01)

(52) U.S. Cl.
CPC ............ *C07D 403/12* (2013.01); *A61P 35/00* (2018.01); *C07D 413/12* (2013.01); *C07B 2200/07* (2013.01)

(58) Field of Classification Search
CPC .............................. C07D 403/12; A61P 35/00
See application file for complete search history.

(56) References Cited

U.S. PATENT DOCUMENTS

| 7,074,809 | B2 | 7/2006 | Arora et al. |
| 7,671,072 | B2 | 3/2010 | Benbow et al. |
| 8,686,007 | B2 | 4/2014 | Ashcraft et al. |
| 9,156,775 | B2 | 10/2015 | Thiele et al. |
| 9,464,065 | B2 | 10/2016 | Schultz et al. |
| 2002/0103185 | A1 | 8/2002 | Sanner et al. |
| 2004/0132726 | A1 | 7/2004 | Arora et al. |
| 2008/0076771 | A1 | 3/2008 | Reiter et al. |

FOREIGN PATENT DOCUMENTS

| WO | 2005/051919 | 6/2005 |
| WO | 2005077345 | 8/2005 |
| WO | 2005077368 | 8/2005 |
| WO | 2005077373 | 8/2005 |
| WO | 2009140621 | 11/2009 |

OTHER PUBLICATIONS

Alexander, et al., "Cyclin E overexpression as a biomarker for combination treatment strategies in inflammatory breast cancer", Oncotarget (2017) 8: 14897-14911.
Asghar, et al.,"The history and future of targeting cyclin-dependent kinases in cancer therapy", Nat. Rev. Drug. Discov. (2015)14(2): 130-146.
Au-Yeung, et al., "Selective Targeting of Cyclin E1-Amplified High-Grade Serous Ovarian Cancer by Cyclin-Dependent Kinase 2 and AKT Inhibition", Clin. Cancer Res. (2017) 23:1862-1874.
Ayhan, et al., "CCNE1 copy-number gain and overexpression identify ovarian clear cell carcinoma with a poor prognosis", Modern Pathology (2017) 30:297-303.
Caldon, et al., "Cyclin E2 overexpression is associated with endocrine resistance but not insensitivity to CDK2 inhibition in human breast cancer cells", Mol. Cancer Ther. (2012) 11:1488-99.
Cicenas, et al., "Highlights of the Latest Advances in Research on CDK Inhibitors", Cancers (2014) 6:2224-2242.
Elsawaf & Sinn, "Triple Negative Breast Cancer: Clinical and Histological Correlations", Breast Care (2011) 6:273-278.
Etemadmoghadam, et al., "Resistance to CDK2 Inhibitors Is Associated with Selection of Polyploid Cells in CCNE1-Amplified Ovarian Cancer", Clin Cancer Res (2013) 19: 5960-71.
Herrera-Abreu, et al., "Early Adaptation and Acquired Resistance to CDK4/6 Inhibition in Estrogen Receptor-Positive Breast Cancer", Cancer Res. (2016) 76: 2301-2313.
Keyomarsi, et al., "Cyclin E and survival in patients with breast cancer", N Engl J Med. (2002) 347:1566-75.
Nakayama, et al., "Gene amplification CCNE1 is related to poor survival and potential therapeutic target in ovarian cancer", Cancer (2010) 116: 2621-34.
Noske, et al., "Detection of CCNE1/URI (19q12) amplification by in situ hybridisation is common in high grade and type II endometrial cancer", Oncotarget (2017) 8:14794-14805.
Oduor, et al., "Trypanosoma brucei glycogen synthase kinase-3, a target for anti-trypanosomal drug development: a public-private partnership to identify novel leads", PLoS Neglected Tropical Diseases (2011), 5(4), e1017.

(Continued)

*Primary Examiner* — Golam M Shameem
(74) *Attorney, Agent, or Firm* — Leslie A. Robinson

(57) ABSTRACT

This invention relates to compounds of Formula (I)

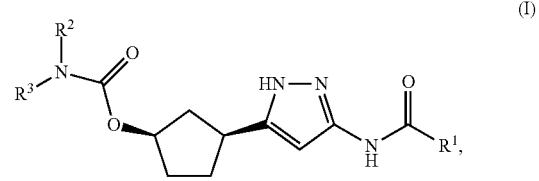

and enantiomers thereof, and to pharmaceutically acceptable salts of Formula (I) and said enantiomers, wherein $R^1$, $R^2$ and $R^3$ are as defined herein. The invention further relates to pharmaceutical compositions comprising such compounds and salts, and to methods and uses of such compounds, salts and compositions for the treatment of abnormal cell growth, including cancer, in a subject in need thereof.

4 Claims, 2 Drawing Sheets

Specification includes a Sequence Listing.

(56) References Cited

OTHER PUBLICATIONS

Ooi, et al., "Gene amplification of CCNE1, CCND1, and CDK6 in gastric cancers detected by multiplex ligation-dependent probe amplification and fluorescence in situ hybridization", Hum Pathol. (2017) 61: 58-67.
Scaltriti, et al., "Cyclin E amplification/overexpression is a mechanism of trastuzumab resistance in HER2+ breast cancer patients", Proc Natl Acad Sci. (2011) 108: 3761-6.
Mascarenhas & Ghoshal, "An efficient tool for identifying inhibitors based on 3D-QSAR and docking using feature-shape pharmacophore of biologically active conformation—A case study with CDK2/CyclinA", Eur. J. Med. Chem., (2008)43:2807-2818.
International Search Report for PCT/IB2020/050653, dated Jul. 24, 2020.
Written Opinion of the International Searching Authority for PCT/IB2020/050653, dated Jul. 24, 2020.

CDK2 INHIBITORS

CROSS-REFERENCE TO RELATED APPLICATIONS

This application claims the benefit of priority to U.S. Provisional Application No. 62/799,455, filed on Jan. 31, 2019, and to U.S. Provisional Application No. 62/959,042, filed on Jan. 9, 2020, each of which is incorporated by reference herein in its entirety.

REFERENCE TO SEQUENCE LISTING

This application is being filed electronically via EFS-Web and includes an electronically submitted sequence listing in .txt format. The .txt file contains a sequence listing entitled "PC72484AUSSEQ_LISTINGupdated_ST25.txt" created on Mar. 10, 2020 and having a size of 2 KB. The sequence listing contained in this .txt file is part of the specification and is herein incorporated by reference in its entirety.

BACKGROUND OF THE INVENTION

Field of the Invention

The present invention relates to compounds of Formula (I) and pharmaceutically acceptable salts thereof, to pharmaceutical compositions comprising such compounds and salts, and to the uses thereof. The compounds, salts and compositions of the present invention may be useful for the treatment of abnormal cell growth, such as cancer, in a subject.

Description of the Related Art

Cyclin-dependent kinases (CDKs) and related serine/threonine protein kinases are important cellular enzymes that perform essential functions in regulating cell division and proliferation. CDKs 1-4, 6, 10, 11 have been reported to play a direct role in cell cycle progression, while CDKs 3, 5 and 7-9 may play an indirect role (e.g., through activation of other CDKs, regulation of transcription or neuronal functions). The CDK catalytic units are activated by binding to regulatory subunits, known as cyclins, followed by phosphorylation. Cyclins can be divided into four general classes ($G_1$, $G_1/S$, S and M cyclins) whose expression levels vary at different points in the cell cycle. Cyclin B/CDK1, cyclin A/CDK2, cyclin E/CDK2, cyclin D/CDK4, cyclin D/CDK6, and likely other heterodynes are important regulators of cell cycle progression.

Overexpression of CDK2 is associated with abnormal regulation of the cell-cycle. The cyclin E/CDK2 complex plays and important role in regulation of the G1/S transition, histone biosynthesis and centrosome duplication. Progressive phosphorylation of retinoblastoma (Rb) by cyclin D/Cdk4/6 and cyclin E/Cdk2 releases the G1 transcription factor, E2F, and promotes S-phase entry. Activation of cyclin A/CDK2 during early S-phase promotes phosphorylation of endogenous substrates that permit DNA replication and inactivation of E2F, for S-phase completion. (Asghar et al. *The history and future of targeting cyclin-dependent kinases in cancer therapy*, Nat. Rev. Drug. Discov. 2015; 14(2): 130-146).

Cyclin E, the regulatory cyclin for CDK2, is frequently overexpressed in cancer. Cyclin E amplification or overexpression has long been associated with poor outcomes in breast cancer. (Keyomarsi et al., Cyclin E and survival in patients with breast cancer. *N Engl J Med*. (2002) 347:1566-75). Cyclin E2 (CCNE2) overexpression is associated with endocrine resistance in breast cancer cells and CDK2 inhibition has been reported to restore sensitivity to tamoxifen or CDK4 inhibitors in tamoxifen-resistant and CCNE2 overexpressing cells. (Caldon et al., Cyclin E2 overexpression is associated with endocrine resistance but not insensitivity to CDK2 inhibition in human breast cancer cells. *Mol. Cancer Ther*. (2012) 11:1488-99; Herrera-Abreu et al., Early Adaptation and Acquired Resistance to CDK4/6 Inhibition in Estrogen Receptor-Positive Breast Cancer, *Cancer Res*. (2016) 76: 2301-2313). Cyclin E amplification also reportedly contributes to trastuzumab resistance in HER2+ breast cancer. (Scaltriti et al. Cyclin E amplification/overexpression is a mechanism of trastuzumab resistance in HER2+ breast cancer patients, *Proc Natl Acad Sci*. (2011) 108: 3761-6). Cyclin E overexpression has also been reported to play a role in basal-like and triple negative breast cancer (TNBC), as well as inflammatory breast cancer. (Elsawaf & Sinn, Triple Negative Breast Cancer: Clinical and Histological Correlations, *Breast Care* (2011) 6:273-278; Alexander et al., Cyclin E overexpression as a biomarker for combination treatment strategies in inflammatory breast cancer, *Oncotarget* (2017) 8: 14897-14911.)

Amplification or overexpression of cyclin E1 (CCNE1) is also associated with poor outcomes in ovarian, gastric, endometrial and other cancers. (Nakayama et al., Gene amplification CCNE1 is related to poor survival and potential therapeutic target in ovarian cancer, Cancer (2010) 116: 2621-34; Etemadmoghadam et al., Resistance to CDK2 Inhibitors Is Associated with Selection of Polyploid Cells in CCNE1-Amplified Ovarian Cancer, *Clin Cancer Res* (2013) 19: 5960-71; Au-Yeung et al., Selective Targeting of Cyclin E1-Amplified High-Grade Serous Ovarian Cancer by Cyclin-Dependent Kinase 2 and AKT Inhibition, *Clin. Cancer Res*. (2017) 23:1862-1874; Ayhan et al., CCNE1 copy-number gain and overexpression identify ovarian clear cell carcinoma with a poor prognosis, *Modern Pathology* (2017) 30: 297-303; Ooi et al., Gene amplification of CCNE1, CCND1, and CDK6 in gastric cancers detected by multiplex ligation-dependent probe amplification and fluorescence in situ hybridization, *Hum Pathol*. (2017) 61: 58-67; Noske et al., Detection of CCNE1/URI (19q12) amplification by in situ hybridisation is common in high grade and type II endometrial cancer, *Oncotarget* (2017) 8: 14794-14805).

The small molecule inhibitor, dinaciclib (MK-7965) inhibits CDK1, CDK2, CDK5 and CDK9 and is currently in clinical development for breast and hematological cancers. Seliciclib (roscovitine or CYC202), which inhibits CDK2, CDK7 and CDK9, was studied in nasopharyngeal cancer and NSCLC, and is currently being investigated in combination with sapacitabine in patients with BRCA mutations. CYC065, which inhibits CDK2 and CDK9, is in early clinical development. Despite significant efforts, there are no approved agents selectively targeting CDK2 to date. Cicenas et al. Highlights of the Latest Advances in Research on CDK Inhibitors. *Cancers*, (2014) 6:2224-2242.

There remains a need to discover CDK inhibitors having novel activity profiles, such as selective CDK2 inhibitors, which may be useful for the treatment of cancer or other proliferative diseases or conditions. In particular, CDK2 inhibitors may be useful in treating CCNE1 or CCNE2 amplified tumors.

BRIEF SUMMARY OF THE INVENTION

The present invention provides, in part, compounds of Formula (I) and pharmaceutically acceptable salts thereof.

Such compounds can inhibit the activity of CDKs, including CDK2, thereby effecting biological functions. In some embodiments, the invention provides compounds that are selective for CDK2. Also provided are pharmaceutical compositions and medicaments, comprising the compounds or salts of the invention, alone or in combination with additional anticancer therapeutic agents.

The present invention also provides, in part, methods for preparing the compounds, pharmaceutically acceptable salts and compositions of the invention, and methods of using the foregoing.

In one aspect, the invention provides a compound of Formula (I):

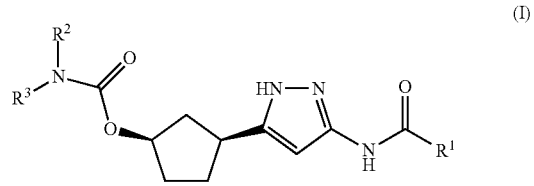

(I)

or a pharmaceutically acceptable salt thereof, wherein:

$R^1$ is -$L^1$-(5-10 membered heteroaryl) or -$L^1$-($C_6$-$C_{12}$ aryl), where said 5-10 membered heteroaryl or $C_6$-$C_{12}$ aryl is optionally substituted by one or more $R^4$;

$R^2$ and $R^3$ are independently H, $C_1$-$C_6$ alkyl, $C_1$-$C_6$ fluoroalkyl, -$L^2$-($C_3$-$C_7$ cycloalkyl) or -$L^2$-(4-7 membered heterocyclyl), where each said $C_1$-$C_6$ alkyl and $C_1$-$C_6$ fluoroalkyl is optionally substituted by one or more $R^5$ and each said $C_3$-$C_7$ cycloalkyl and 4-7 membered heterocyclyl is optionally substituted by one or more $R^6$; or $R^2$ and $R^3$ are taken together with the N-atom to which they are attached to form a 4-6 membered heterocyclyl optionally containing an additional heteroatom selected from O, N($R^7$) and S(O)$_q$ as a ring member, where said 4-6 membered heterocyclyl is optionally substituted by one or more $R^8$;

each $L^1$ and $L^2$ is independently a bond or a $C_1$-$C_2$ alkylene optionally substituted by one or more $R^9$;

each $R^4$ is independently F, Cl, OH, CN, $NR^{10}R^{11}$, $C_1$-$C_4$ alkyl, $C_1$-$C_4$ fluoroalkyl, $C_1$-$C_4$ alkoxy, $C_1$-$C_4$ fluoroalkoxy, $C_3$-$C_8$ cycloalkyl, $C(O)NR^{10}R^{11}$, $SO_2R^{12}$, $SO(=NH)R^{12}$ or $SO_2NR^{10}R^{11}$, where each $C_1$-$C_4$ alkyl and $C_1$-$C_4$ fluoroalkyl is optionally substituted by one or more $R^{13}$;

each $R^5$ is independently OH, $C_1$-$C_4$ alkoxy or $NR^{10}R^{11}$;

each $R^6$ is independently F, OH, $C_1$-$C_4$ alkyl, $C_1$-$C_4$ fluoroalkyl, $C_1$-$C_4$ alkoxy, $C_1$-$C_4$ fluoroalkoxy or $NR^{10}R^{11}$ where each $C_1$-$C_4$ alkyl and $C_1$-$C_4$ fluoroalkyl is optionally substituted by one or more $R^{13}$;

$R^7$ is H, $C_1$-$C_4$ alkyl or C(O)—$C_1$-$C_4$ alkyl;

each $R^8$ is independently F, OH, $C_1$-$C_4$ alkyl, $C_1$-$C_4$ alkoxy or CN;

each $R^9$ is independently F, OH or $C_1$-$C_2$ alkyl;

each $R^{10}$ and $R^{11}$ is independently H or $C_1$-$C_4$ alkyl;

each $R^{12}$ is $C_1$-$C_4$ alkyl or $C_3$-$C_6$ cycloalkyl;

each $R^{13}$ is independently OH, $C_1$-$C_4$ alkoxy or $NR^{14}R^{15}$;

each $R^{14}$ and $R^{15}$ is independently H or $C_1$-$C_4$ alkyl; and q is 0, 1 or 2.

In another aspect, the invention provides a compound of Formula (II):

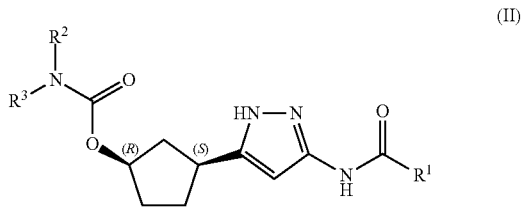

(II)

or a pharmaceutically acceptable salt thereof, wherein:
$R^1$, $R^2$ and $R^3$ are as defined for Formula (I).

In another aspect, the invention provides a compound of Formula (III):

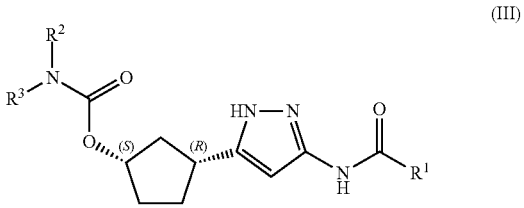

(III)

or a pharmaceutically acceptable salt thereof, wherein:
$R^1$, $R^2$ and $R^3$ are as defined for Formula (I).

In another aspect, the invention provides a pharmaceutical composition comprising a compound of the invention, according to any of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

The invention also provides therapeutic methods and uses comprising administering a compound of the invention, or a pharmaceutically acceptable salt thereof, to a subject.

In one aspect, the invention provides a method for the treatment of abnormal cell growth, in particular cancer, in a subject in need thereof, comprising administering to the subject a therapeutically effective amount of a compound of the invention, or a pharmaceutically acceptable salt thereof. Compounds of the invention may be administered as single agents or may be administered in combination with other anti-cancer therapeutic agents, in particular with standard of care agents appropriate for the particular cancer.

In a further aspect, the invention provides a method for the treatment of abnormal cell growth, in particular cancer, in a subject in need thereof, comprising administering to the subject an amount of a compound of the invention, or a pharmaceutically acceptable salt thereof, in combination with an amount of an additional anti-cancer therapeutic agent, which amounts are together effective in treating said abnormal cell growth.

In another aspect, the invention provides a compound of the invention, or a pharmaceutically acceptable salt thereof, for use in the treatment of a subject in need of such treatment. In some embodiments, the invention provides a compound of the invention, or a pharmaceutically acceptable salt thereof, for use in the treatment of abnormal cell growth, in particular cancer, in a subject.

In a further aspect, the invention provides the use of a compound of the invention, or a pharmaceutically acceptable salt thereof, for the treatment of abnormal cell growth, in particular cancer, in a subject.

In another aspect, the invention provides a pharmaceutical composition for use in the treatment of abnormal cell growth, in particular cancer, in a subject in need thereof, which pharmaceutical composition comprises a compound of the invention, or a pharmaceutically acceptable salt thereof, and a pharmaceutically acceptable carrier or excipient.

In another aspect, the invention provides a compound of the invention, or a pharmaceutically acceptable salt thereof, for use as a medicament, in particular a medicament for the treatment of abnormal cell growth, such as cancer.

In yet another aspect, the invention provides the use of a compound of the invention, or a pharmaceutically acceptable salt thereof, for the manufacture of a medicament for the treatment of abnormal cell growth, such as cancer, in a subject.

In another aspect, the invention provides a method for the treatment of a disorder mediated by CDK2 in a subject, comprising administering to the subject a compound of the invention, or a pharmaceutically acceptable salt thereof, in an amount that is effective for treating said disorder, in particular cancer.

Each of the embodiments of the compounds of the present invention described below can be combined with one or more other embodiments of the compounds of the present invention described herein not inconsistent with the embodiment(s) with which it is combined.

In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein unless explicitly indicated to the contrary.

DETAILED DESCRIPTION OF THE INVENTION

Figure 1:
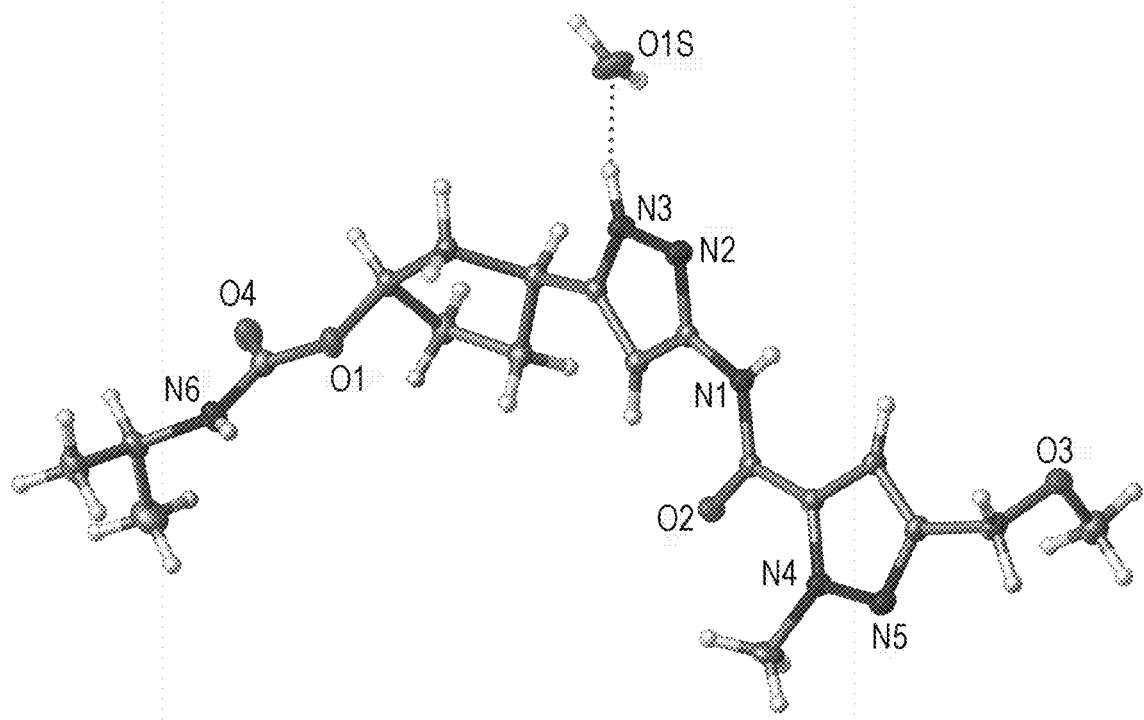
FIG. 1 shows the single crystal X-ray structure of (1R,3S)-3-[3-({[3-(methoxymethyl)-1-methyl-1H-pyrazol-5-yl]carbonyl}amino)-1H-pyrazol-5-yl]cyclopentyl propan-2-yl-carbamate monohydrate (Form 1).

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

"Alkyl" refers to a saturated, monovalent aliphatic hydrocarbon radical including straight chain and branched chain groups having the specified number of carbon atoms. Alkyl substituents typically contain 1 to 12 carbon atoms ("$C_1$-$C_{12}$ alkyl"), frequently 1 to 8 carbon atoms ("$C_1$-$C_8$ alkyl"), or more frequently 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl") or 1 to 2 carbon atoms ("$C_1$-$C_2$ alkyl"). Examples of alkyl groups include methyl, ethyl, n-propyl, isopropyl, n-butyl, sec-butyl, iso-butyl, tert-butyl, n-pentyl, isopentyl, neopentyl, n-hexyl, n-heptyl, n-octyl and the like. Preferred $C_1$-$C_4$ alkyl groups include methyl, ethyl, n-propyl, isopropyl, n-butyl, sec-butyl, iso-butyl, tert-butyl. Preferred $C_1$-$C_6$ alkyl groups include methyl, ethyl, n-propyl, isopropyl, n-butyl, sec-butyl, iso-butyl, tert-butyl, n-pentyl, isopentyl, neopentyl, and n-hexyl.

Alkyl groups described herein as optionally substituted may be substituted by one or more substituent groups, as further defined by the claims herein. Such optional substituent groups are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, 1 to 4 optional substituents, or preferably 1 to 3 optional substituents.

Exemplary substituent groups on alkyl groups include halo, —OH, $C_1$-$C_4$ alkoxy or $NR^xR^y$, where each $R^x$ and $R^y$ is independently H or $C_1$-$C_4$ alkyl. It will be understood that $NR^xR^y$ is used generically herein to refer to amino substituents (e.g., $NR^{10}R^{11}$ as part of optional substituent $R^5$ or $NR^{14}R^{15}$ as part of optional substituent $R^{13}$) as defined by the claims. In some instances, substituted alkyl groups are specifically named by reference to the substituent group. For example, "haloalkyl" refers to an alkyl group having the specified number of carbon atoms that is substituted by one or more halo substituents, and typically contains 1-6 carbon atoms, 1-5 carbon atoms, 1-4 carbon atoms or 1-2 carbon atoms and 1, 2 or 3 halo atoms (i.e., "$C_1$-$C_5$ haloalkyl", $C_1$-$C_4$ haloalkyl" or "$C_1$-$C_2$ haloalkyl").

More specifically, fluorinated alkyl groups may be specifically referred to as "fluoroalkyl" groups, (e.g., $C_1$-$C_6$, $C_1$-$C_5$, $C_1$-$C_4$ or $C_1$-$C_2$ fluoroalkyl groups), which are typically substituted by 1, 2 or 3 fluoro atoms. For example, a $C_1$-$C_4$ fluoroalkyl includes trifluoromethyl (—$CF_3$), difluoromethyl (—$CF_2H$), fluoromethyl (—$CFH_2$), difluoroethyl (—$CH_2CF_2H$), and the like. Such groups may be further substituted by optional substituent groups as further described herein. Similarly, alkyl groups substituted by —OH, $C_1$-$C_4$ alkoxy or $NR^xR^y$ could be referred to as "hydroxyalkyl", "alkoxyalkyl" or "aminoalkyl", in each case having the indicated number of carbon atoms.

In some embodiments of the present invention, alkyl and fluoroalkyl groups are optionally substituted by one or more optional substituents, and preferably by 1 to 4, 1 to 3, or 1 to 2 optional substituents.

"Alkylene" as used herein refers to a divalent hydrocarbyl group having the specified number of carbon atoms which can link two other groups together. Such groups may be referred to as, e.g., a $C_1$-$C_6$ alkylene, $C_1$-$C_4$ alkylene, $C_1$-$C_2$ alkylene, etc. Where specified, an alkylene can also be substituted by other groups and may include one or more degrees of unsaturation (i.e., an alkenylene or alkynylene moiety) or rings. The open valences of an alkylene need not be at opposite ends of the chain. Branched alkylene groups may include —CH(Me)-, —$CH_2$CH(Me)- and —$C(Me)_2$- are also included within the scope of the term alkylenes. Where an alkylene group is described as optionally substituted, the substituents include those as described herein. For example, a $C_1$-$C_2$ alkylene may be methylene or ethylene.

"Alkoxy" refers to a monovalent —O-alkyl group, wherein the alkyl portion has the specified number of carbon atoms. Alkoxy groups typically contain 1 to 8 carbon atoms ("$C_1$-$C_5$ alkoxy"), or 1 to 6 carbon atoms ("$OC_1$-$C_6$ alkoxy"), or 1 to 4 carbon atoms ("$OC_1$-$C_4$ alkoxy"). For example, $C_1$-$C_4$ alkoxy includes methoxy, ethoxy, isopropoxy, tert-butyloxy (i.e., —OCH$_3$, —OCH$_2$CH$_3$, —OCH(CH$_3$)$_2$, —OC(CH$_3$)$_3$), and the like. Alkoxy groups may be optionally substituted by one or more halo atoms, and in particular one or more fluoro atoms, up to the total number of hydrogen atoms present on the alkyl portion. Such groups may be referred to as "haloalkoxy" (or, where fluorinated, more specifically as "fluoroalkoxy") groups having the specified number of carbon atoms and substituted by one or more halo substituents. Typically, such groups contain from 1-6 carbon atoms, preferably 1-4 carbon atoms, and sometimes 1-2 carbon atoms, and 1, 2 or 3 halo atoms (i.e., "$OC_1$-$C_6$ haloalkoxy", "$OC_1$-$C_4$ haloalkoxy" or "$OC_1$-$C_2$ haloalkoxy"). More specifically, fluorinated alkyl groups may be specifically referred to as "fluoroalkoxy" groups, e.g., $C_1$-$C_6$, $C_1$-$C_4$ or $C_1$-$C_2$ fluoroalkoxy groups, which are typically substituted by 1, 2 or 3 fluoro atoms. Thus, a $C_1$-$C_4$ fluoroalkoxy includes, but is not limited to, trifluoromethyloxy (—OCF$_3$), difluoromethyloxy (—OCF$_2$H), fluoromethyloxy (—OCFH$_2$), difluoroethyloxy (—OCH$_2$CF$_2$H), and the like.

"Cycloalkyl" refers to a non-aromatic, saturated carbocyclic ring system containing the specified number of carbon atoms, which may be a monocyclic, spirocyclic, bridged or fused bicyclic or polycyclic ring system that is connected to the base molecule through a carbon atom of the cycloalkyl ring. Typically, the cycloalkyl groups of the invention contain 3 to 8 carbon atoms ("$C_3$-$C_8$ cycloalkyl"), preferably 3 to 7 carbon atoms ("$OC_3$-$C_7$ cycloalkyl") or 3 to 6 carbon atoms ("$OC_3$-$C_6$ cycloalkyl"). Representative examples of cycloalkyl rings include, e.g., cyclopropane, cyclobutane, cyclopentane, cyclohexane, cycloheptane, and the like. Cycloalkyl groups may be optionally substituted, unsubstituted or substituted by the groups described herein.

The terms "heterocyclyl" or "heterocyclic" may be used interchangeably to refer to a non-aromatic, saturated ring system containing the specified number of ring atoms, containing at least one heteroatom selected from N, O and S as a ring member, where ring S atoms are optionally substituted by one or two oxo groups (i.e., $S(O)_q$, where q is 0, 1 or 2) and where the heterocyclic ring is connected to the base molecule via a ring atom, which may be C or N. Where specifically indicated, such heterocyclic rings may be partially unsaturated. Heterocyclic rings include rings which are spirocyclic, bridged, or fused to one or more other heterocyclic or carbocyclic rings, where such spirocyclic, bridged, or fused rings may themselves be saturated, partially unsaturated or aromatic to the extent unsaturation or aromaticity makes chemical sense, provided the point of attachment to the base molecule is an atom of the heterocyclic portion of the ring system. Preferably, heterocyclic rings contain 1 to 4 heteroatoms selected from N, O, and $S(O)_q$ as ring members, and more preferably 1 to 2 ring heteroatoms, provided that such heterocyclic rings do not contain two contiguous oxygen atoms.

Heterocyclyl groups are unsubstituted or substituted by suitable substituent groups as described herein. Such substituents may be present on the heterocylic ring attached to the base molecule, or on a spirocyclic, bridged or fused ring attached thereto. In addition, ring N atoms are optionally substituted by groups suitable for an amine, e.g., alkyl, acyl, carbamoyl, sulfonyl, and the like.

Heterocycles typically include 3-8 membered heterocyclyl groups, and more preferably 4-7 or 4-6 membered heterocyclyl groups, in accordance with the definition herein.

Illustrative examples of saturated heterocycles include, but are not limited to:

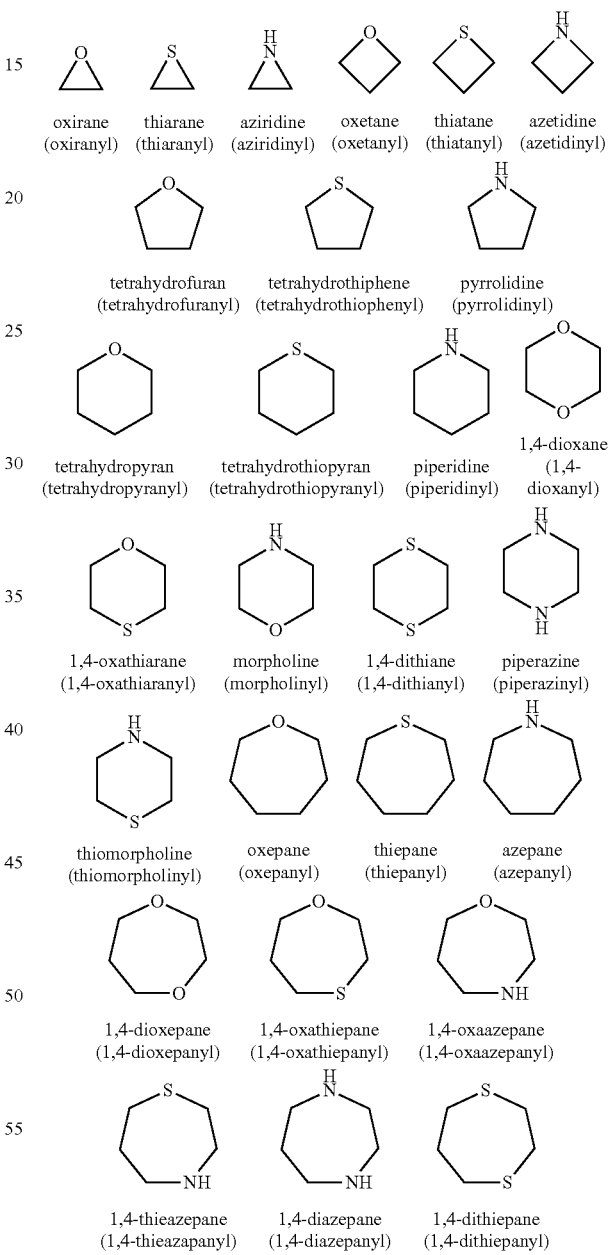

In some embodiments, heterocyclic groups contain 3-8 ring members, including both carbon and non-carbon heteroatoms, and frequently 4-7 or 4-6 ring members. In certain embodiments, substituent groups comprising 4-7 membered heterocycles are selected from azetidinyl, pyrrolidinyl, piperidinyl, piperazinyl, azepanyl, diazepanyl, oxetanyl, tetrahydrofuranyl, tetrahydropyranyl, tetrahydrothiopyranyl, morpholinyl and thiomorpholinyl rings, each of which are optionally substituted as described herein, to the extent such substitution makes chemical sense.

In some embodiments of the present invention, cycloalkyl and heterocyclyl groups are optionally substituted by one or more optional substituents as described herein.

It is understood that no more than two N, O or S atoms are ordinarily connected sequentially, except where an oxo group is attached to S to form a sulfonyl group, or in the case of certain heteroaromatic rings, such as triazole, tetrazole, oxadiazole, thiadiazole, triazine and the like.

"Aryl" or "aromatic" refer to an optionally substituted monocyclic or fused bicyclic or polycyclic ring system having the well-known characteristics of aromaticity, wherein at least one ring contains a completely conjugated pi-electron system. Typically, aryl groups contain 6 to 20 carbon atoms ("$C_6$-$C_{20}$ aryl") as ring members, preferably 6 to 14 carbon atoms ("$C_6$-$C_{14}$ aryl") or more preferably, 6 to 12 carbon atoms ("$C_6$-$C_{12}$ aryl"). Fused aryl groups may include an aryl ring (e.g., a phenyl ring) fused to another aryl or heteroaryl ring or fused to a saturated or partially unsaturated carbocyclic or heterocyclic ring, provided the point of attachment to the base molecule on such fused ring systems is an atom of the aromatic portion of the ring system. Examples, without limitation, of aryl groups include phenyl, biphenyl, naphthyl, anthracenyl, phenanthrenyl, indanyl, indenyl, and tetrahydronaphthyl. The aryl group is unsubstituted or substituted as further described herein.

Similarly, "heteroaryl" or "heteroaromatic" refer to monocyclic or fused bicyclic or polycyclic ring systems having the well-known characteristics of aromaticity that contain the specified number of ring atoms as defined above under "aryl" which include at least one heteroatom selected from N, O and S as a ring member in an aromatic ring. The inclusion of a heteroatom permits aromaticity in 5-membered rings as well as 6-membered rings. Typically, heteroaryl groups contain 5 to 12 ring atoms ("5-12 membered heteroaryl"), and more preferably 5 to 10 ring atoms ("5-10 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Heteroaryl groups may also be fused to another aryl or heteroaryl ring or fused to a saturated or partially unsaturated carbocyclic or heterocyclic ring, provided the point of attachment to the base molecule on such fused ring systems is an atom of the heteroaromatic portion of the ring system. Examples of unsubstituted heteroaryl groups include, but are not limited to, pyrazole, triazole, isoxazole, oxazole, thiazole, thiadiazole, imidazole, pyridine, pyrazine, indazole and benzimidazole. Additional heteroaryl grounds include pyrrole, furan, thiophene, oxadiazole, tetrazole, pyridazine, pyrimidine, benzofuran, benzothiophene, indole, quinoline, isoquinoline, purine, triazine, naphthryidine and carbazole. In frequent embodiments, 5- or 6-membered heteroaryl groups are pyrazole, triazole, isoxazole, oxazole, thiazole, thiadiazole, imidazole, pyridine or pyrazine rings. The heteroaryl group is unsubstituted or substituted as further described herein.

Aryl and heteroaryl moieties described herein as optionally substituted may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings. Optionally substituted aryl or heteroaryl groups typically contain from 1 to 5 optional substituents, sometimes 1 to 4 optional substituents, preferably 1 to 3 optional substituents, or more preferably from 1 to 2 optional substituents as described herein.

Examples of monocyclic heteroaryl groups include, but are not limited to:

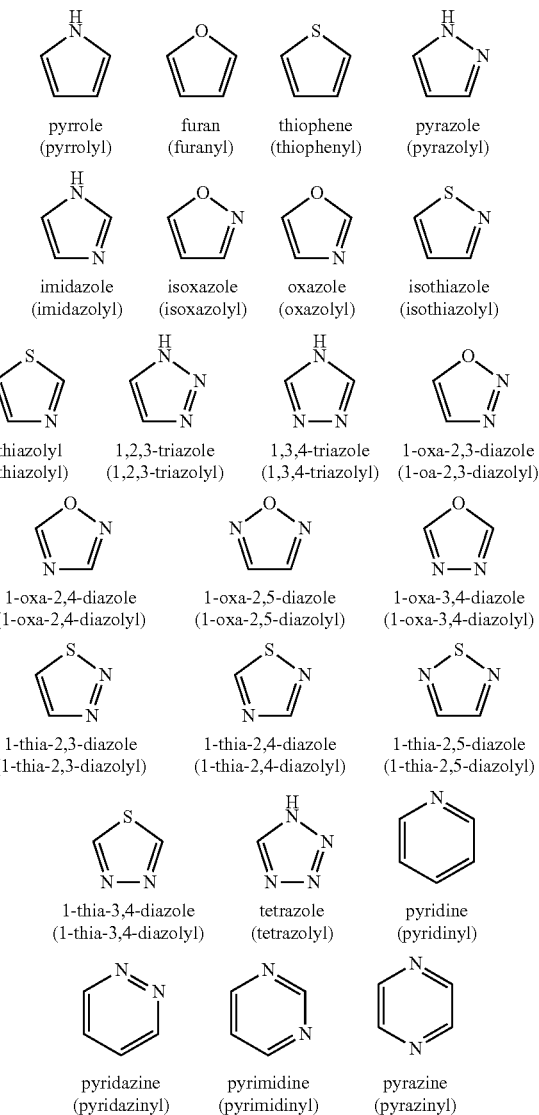

Illustrative examples of fused heteroaryl groups include, but are not limited to:

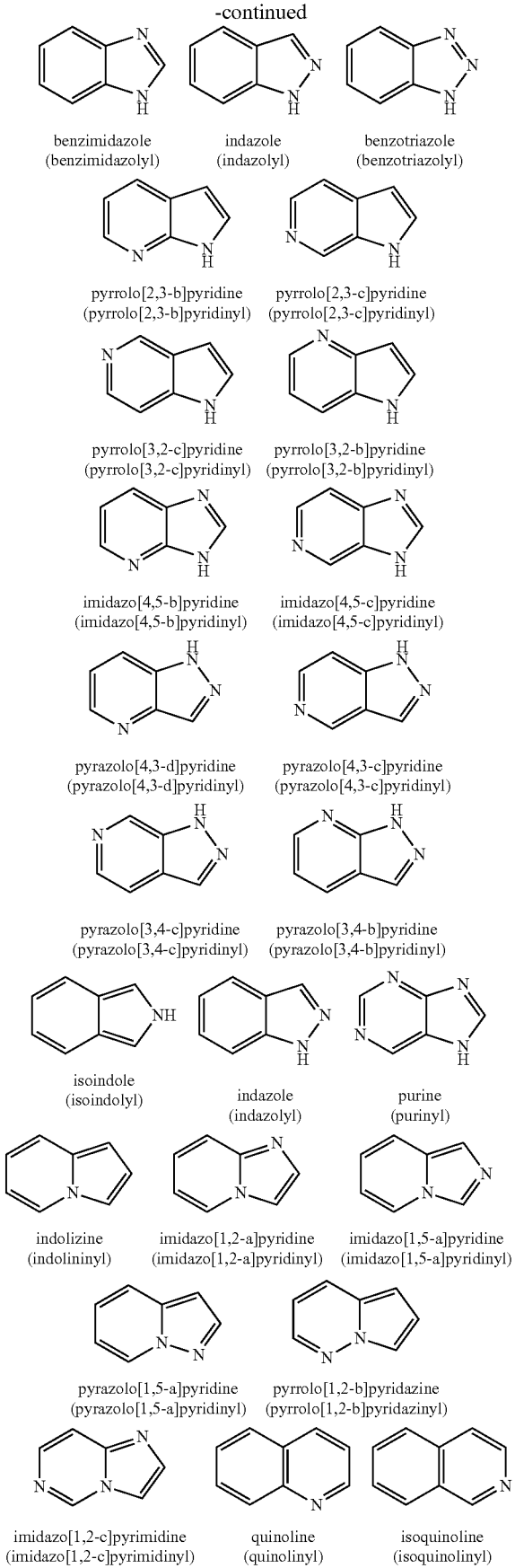
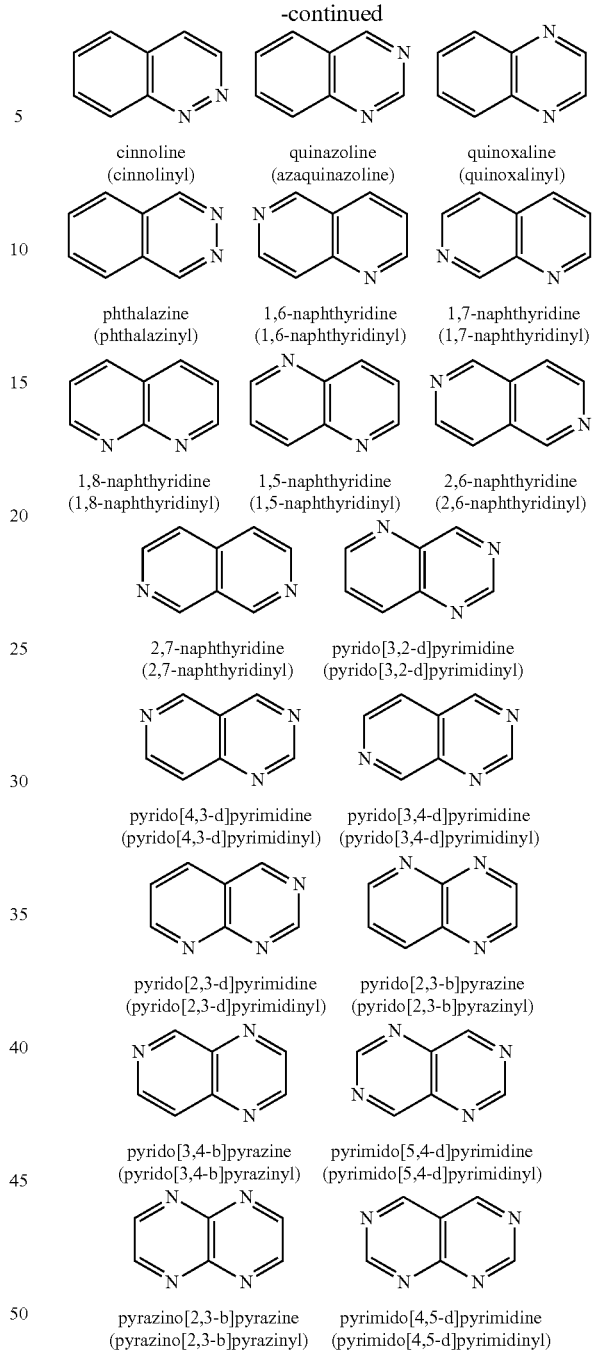

"Hydroxy" refers to an OH group.

"Cyano" refers to a —C≡N group.

"Unsubstituted amino" refers to a group —NH$_2$. Where the amino is described as substituted or optionally substituted, the term includes groups of the form —NR$^x$R$^y$, where each or R$^x$ and R$^y$ is defined as further described herein. For example, "alkylamino" refers to a group —NR$^x$R$^y$, wherein one of R$^x$ and R$^y$ is an alkyl moiety and the other is H, and "dialkylamino" refers to —NR$^x$R$^y$ wherein both of R$^x$ and R$^y$ are alkyl moieties, where the alkyl moieties having the specified number of carbon atoms (e.g., —NH—C$_1$-C$_4$ alkyl or —N(C$_1$-C$_4$ alkyl)$_2$). It will be understood that NR$^x$R$^y$ is used generically to refer to amino substituents (e.g., NR$^{10}$R$^{11}$ as part of an optional substituent group R$^5$ or NR$^{14}$R$^{15}$ as part of an optional substituent group R$^{13}$) as defined by the claims.

"Halogen" or "halo" refers to fluoro, chloro, bromo and iodo (F, Cl, Br, I). Preferably, halo refers to fluoro or chloro (F or Cl).

"Optional" or "optionally" means that the subsequently described event or circumstance may but need not occur, and the description includes instances where the event or circumstance occurs and instances in which it does not.

The terms "optionally substituted" and "substituted or unsubstituted" are used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two. In the case where optional substituents are selected independently from a list of alternatives, the selected groups are the same or different. Throughout the disclosure, it will be understood that the number and nature of optional substituent groups will be limited to the extent that such substitutions make chemical sense.

Frequently, a group described herein as optionally substituted by "one or more" substituent groups is optionally substituted by 1 to 4, preferably optionally substituted by 1 to 3, and more preferably optionally substituted by 1 to 2 such substituents. The recitation herein that a group is "optionally substituted by one or more" of a list of optional substituents may be replaced by "optionally substituted by 1 to 4," "optionally substituted by 1 to 3", "optionally substituted by 1 to 2", "optionally substituted by one, two, three or four", optionally substituted by one, two or three" or "optionally substituted by one or two" of such optional substituent groups.

In one aspect, the invention provides a compound of Formula (I):

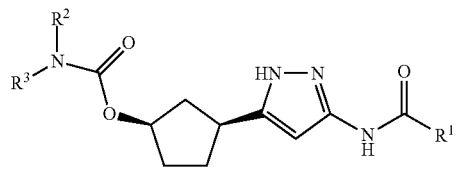

(I)

or a pharmaceutically acceptable salt thereof, wherein:
R$^1$ is -L$^1$-(5-10 membered heteroaryl) or -L$^1$-(C$_6$-C$_{12}$ aryl), where said 5-10 membered heteroaryl or C$_6$-C$_{12}$ aryl is optionally substituted by one or more R$^4$;
R$^2$ and R$^3$ are independently H, C$_1$-C$_6$ alkyl, C$_1$-C$_6$ fluoroalkyl, -L$^2$-(C$_3$-C$_7$ cycloalkyl) or -L$^2$-(4-7 membered heterocyclyl), where each said C$_1$-C$_6$ alkyl and C$_1$-C$_6$ fluoroalkyl is optionally substituted by one or more R$^5$ and each said C$_3$-C$_7$ cycloalkyl and 4-7 membered heterocyclyl is optionally substituted by one or more R$^6$; or
R$^2$ and R$^3$ are taken together with the N-atom to which they are attached to form a 4-6 membered heterocyclyl optionally containing an additional heteroatom selected from O, N(R$^7$) and S(O)$_q$ as a ring member, where said 4-6 membered heterocyclyl is optionally substituted by one or more R$^8$;
each L$^1$ and L$^2$ is independently a bond or a C$_1$-C$_2$ alkylene optionally substituted by one or more R$^9$;
each R$^4$ is independently F, Cl, OH, CN, NR$^{10}$R$^{11}$, C$_1$-C$_4$ alkyl, C$_1$-C$_4$ fluoroalkyl, C$_1$-C$_4$ alkoxy, C$_1$-C$_4$ fluoroalkoxy, C$_3$-C$_8$ cycloalkyl, C(O)NR$^{10}$R$^{11}$, SO$_2$R$^{12}$, SO(=NH)R$^{12}$ or SO$_2$NR$^{10}$R$^{11}$, where each C$_1$-C$_4$ alkyl and C$_1$-C$_4$ fluoroalkyl is optionally substituted by one or more R$^{13}$;
each R$^5$ is independently OH, C$_1$-C$_4$ alkoxy or NR$^{10}$R$^{11}$;
each R$^6$ is independently F, OH, C$_1$-C$_4$ alkyl, C$_1$-C$_4$ fluoroalkyl, C$_1$-C$_4$ alkoxy, C$_1$-C$_4$ fluoroalkoxy or NR$^{10}$R$^{11}$ where each C$_1$-C$_4$ alkyl and C$_1$-C$_4$ fluoroalkyl is optionally substituted by one or more R$^{13}$;
R$^7$ is H, C$_1$-C$_4$ alkyl or C(O)—C$_1$-C$_4$ alkyl;
each R$^8$ is independently F, OH, C$_1$-C$_4$ alkyl, C$_1$-C$_4$ alkoxy or CN;
each R$^9$ is independently F, OH or C$_1$-C$_2$ alkyl;
each R$^{10}$ and R$^{11}$ is independently H or C$_1$-C$_4$ alkyl;
each R$^{12}$ is C$_1$-C$_4$ alkyl or C$_3$-C$_6$ cycloalkyl;
each R$^{13}$ is independently OH, C$_1$-C$_4$ alkoxy or NR$^{14}$R$^{15}$;
each R$^{14}$ and R$^{15}$ is independently H or C$_1$-C$_4$ alkyl; and
q is 0, 1 or 2.

The compounds of Formula (I) are characterized by a syn-relationship between the substituent groups at the 1- and 3-position of the cyclopentyl ring. Compounds of Formula (I) may be present as a single enantiomer having a syn relative configuration at the 1- and 3-positions (i.e., (1R,3S) or (1S,3R)) or as a mixture of syn enantiomeric forms, for example a racemic mixture of (1R,3S) and (1S,3R).

In compounds of Formula (I), R$^1$ is -L$^1$-(5-10 membered heteroaryl) or -L$^1$-(C$_6$-C$_{12}$ aryl), where said 5-10 membered heteroaryl or C$_6$-C$_{12}$ aryl is optionally substituted by one or more R$^4$.

In some embodiments, R$^1$ is -L$^1$-(5-10 membered heteroaryl), where said 5-10 membered heteroaryl is optionally substituted by one or more R$^4$. In some such embodiments, said 5-10 membered heteroaryl is pyrazolyl, triazolyl, isoxazolyl, oxazolyl, thiazolyl, thiadiazolyl, imidazolyl, pyridinyl, pyrazinyl, indazolyl or benzimidazolyl, where said 5-10 membered heteroaryl is optionally substituted by one or more R$^4$. In certain embodiments, said 5-10 membered heteroaryl is pyrazolyl or triazolyl, optionally substituted by one or more R$^4$. In specific embodiments, said 5-10 membered heteroaryl is pyrazolyl optionally substituted by one or more R$^4$. In other embodiments, said 5-10 membered heteroaryl is triazolyl optionally substituted by one or more R$^4$. In other embodiments, said 5-10 membered heteroaryl is isoxazolyl, oxazolyl, thiazolyl, thiadiazolyl, imidazolyl, pyridinyl, pyrazinyl, indazolyl or benzimidazolyl, where said 5-10 membered heteroaryl is optionally substituted by one or more R$^4$. In certain embodiments, said 5-10 membered heteroaryl is isoxazolyl or oxazolyl, optionally substituted by one or more R$^4$. In specific embodiments, said 5-10 membered heteroaryl is isoxazolyl optionally substituted by one or more R$^4$. In other embodiments, said 5-10 membered heteroaryl is thiazolyl, thiadiazolyl or imidazolyl, where said 5-10 membered heteroaryl is optionally substituted by one or more R$^4$. In still other embodiments, said 5-10 membered heteroaryl is pyridinyl, pyrazinyl, indazolyl or benzimidazolyl, where said 5-10 membered heteroaryl is optionally substituted by one or more R$^4$. In some embodiments of each of the foregoing, said 5-10 membered heteroaryl is optionally substituted by one, two, three or four $R^4$. In some embodiments of each of the foregoing, said 5-10 membered heteroaryl is optionally substituted by one or two $R^4$.

In other embodiments, $R^1$ is -$L^1$-($C_6$-$C_{12}$ aryl), where said $C_6$-$C_{12}$ aryl is optionally substituted by one or more $R^4$. In some such embodiments, said $C_6$-$C_{12}$ aryl is phenyl optionally substituted by one or more $R^4$. In some embodiments of each of the foregoing, said $C_6$-$C_{12}$ aryl is optionally substituted by one, two, three or four $R^4$. In some embodiments of each of the foregoing, said $C_6$-$C_{12}$ aryl is optionally substituted by one or two $R^4$.

In compounds of Formula (I), $L^1$ is a bond or a $C_1$-$C_2$ alkylene optionally substituted by one or more $R^9$. In some such embodiments, said $L^1$ is a bond or a $C_1$-$C_2$ alkylene optionally substituted by one, two, three or four $R^9$. In some such embodiments, $L^1$ is a bond or a $C_1$-$C_2$ alkylene optionally substituted by one or two $R^9$. In some such embodiments, $L^1$ is a bond, methylene or ethylene. In some such embodiments, $L^1$ is a bond or methylene. In some embodiments of each of the foregoing, $L^1$ is a bond. In other embodiments of each of the foregoing, $L^1$ is a $C_1$-$C_2$ alkylene optionally substituted by one or more $R^9$. In some such embodiments, said $L^1$ is a $C_1$-$C_2$ alkylene optionally substituted by one, two, three or four $R^9$. In some such embodiments, said $L^1$ is a $C_1$-$C_2$ alkylene optionally substituted by one or two $R^9$. In some such embodiments, $L^1$ is methylene or ethylene (i.e., —$CH_2$ or —$CH_2CH_2$—). In certain embodiments, $L^1$ is methylene.

In compounds of Formula (I), $R^2$ and $R^3$ are independently H, $C_1$-$C_6$ alkyl, $C_1$-$C_6$ fluoroalkyl, -$L^2$-($C_3$-$C_7$ cycloalkyl) or -$L^2$-(4-7 membered heterocyclyl), where each said $C_1$-$C_6$ alkyl and $C_1$-$C_6$ fluoroalkyl is optionally substituted by one or more $R^5$ and each said $C_3$-$C_7$ cycloalkyl and 4-7 membered heterocyclyl is optionally substituted by one or more $R^6$; or $R^2$ and $R^3$ are taken together with the N-atom to which they are attached to form a 4-6 membered heterocyclyl optionally containing an additional heteroatom selected from O, N($R^7$) and S(O)$_q$ as a ring member, where said 4-6 membered heterocyclyl is optionally substituted by one or more $R^8$.

In some embodiments, $R^2$ and $R^3$ are independently H, $C_1$-$C_6$ alkyl, $C_1$-$C_6$ fluoroalkyl, -$L^2$-($C_3$-$C_7$ cycloalkyl) or -$L^2$-(4-7 membered heterocyclyl), where each said $C_1$-$C_6$ alkyl and $C_1$-$C_6$ fluoroalkyl is optionally substituted by one or more $R^5$ and each said $C_3$-$C_7$ cycloalkyl and 4-7 membered heterocyclyl is optionally substituted by one or more $R^6$. In some such embodiments, said $C_1$-$C_6$ alkyl and $C_1$-$C_6$ fluoroalkyl is optionally substituted by one, two, three or four $R^5$ and each said $C_3$-$C_7$ cycloalkyl and 4-7 membered heterocyclyl is optionally substituted by one, two, three or four $R^6$. In some such embodiments, said $C_1$-$C_6$ alkyl and $C_1$-$C_6$ fluoroalkyl is optionally substituted by one or two $R^5$ and each said $C_3$-$C_7$ cycloalkyl and 4-7 membered heterocyclyl is optionally substituted by one or two $R^6$.

In some embodiments, $R^2$ and $R^3$ are independently H, $C_1$-$C_6$ alkyl or $C_1$-$C_6$ fluoroalkyl, where each said $C_1$-$C_6$ alkyl and $C_1$-$C_6$ fluoroalkyl is optionally substituted by one or more $R^5$. In some such embodiments, each said $C_1$-$C_6$ alkyl and $C_1$-$C_6$ fluoroalkyl is optionally substituted by one, two, three or four $R^5$. In some such embodiments, each said $C_1$-$C_6$ alkyl and $C_1$-$C_6$ fluoroalkyl is optionally substituted by one or two $R^5$. In particular embodiments, $R^2$ and $R^3$ are independently H, $C_1$-$C_6$ alkyl or $C_1$-$C_6$ fluoroalkyl. In specific embodiments, $R^2$ is H and $R^3$ is $C_1$-$C_6$ alkyl or $C_1$-$C_6$ fluoroalkyl. In specific embodiments, $R^2$ is H and $R^3$ is $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$ or $C(CH_3)_3$.

In other embodiments, $R^2$ and $R^3$ are independently H, -$L^2$-($C_3$-$C_7$ cycloalkyl) or -$L^2$-(4-7 membered heterocyclyl), where each said $C_3$-$C_7$ cycloalkyl and 4-7 membered heterocyclyl is optionally substituted by one or more $R^6$. In some such embodiments, $R^2$ is H and $R^3$ is -$L^2$-($C_3$-$C_7$ cycloalkyl) or -$L^2$-(4-7 membered heterocyclyl), where each said $C_3$-$C_7$ cycloalkyl and 4-7 membered heterocyclyl is optionally substituted by one or more $R^6$. In particular embodiments, $R^2$ is H and $R^3$ is -$L^2$-($C_3$-$C_7$ cycloalkyl), where said $C_3$-$C_7$ cycloalkyl is optionally substituted by one or more $R^6$. In some embodiments, of each of the foregoing, each said $C_3$-$C_7$ cycloalkyl and 4-7 membered heterocyclyl is optionally substituted by one, two, three or four $R^6$. In some embodiments, of each of the foregoing, each said $C_3$-$C_7$ cycloalkyl and 4-7 membered heterocyclyl is optionally substituted by one or two $R^6$. In some such embodiments, each $R^6$ is $CH_3$.

In compounds of Formula (I), $L^2$ is a bond or a $C_1$-$C_2$ alkylene optionally substituted by one or more $R^9$. In some such embodiments, said $L^2$ is a bond or a $C_1$-$C_2$ alkylene optionally substituted by one, two, three or four $R^9$. In some such embodiments, $L^2$ is a bond or a $C_1$-$C_2$ alkylene optionally substituted by one or two $R^9$. In some such embodiments, $L^2$ is a bond, methylene or ethylene. In some such embodiments, $L^2$ is a bond or methylene. In some embodiments of each of the foregoing, $L^2$ is a bond. In other embodiments of each of the foregoing, $L^2$ is a $C_1$-$C_2$ alkylene optionally substituted by one or more $R^9$. In some such embodiments $L^2$ is a $C_1$-$C_2$ alkylene optionally substituted by one, two, three or four $R^9$. In some such embodiments $L^2$ is a $C_1$-$C_2$ alkylene optionally substituted by one or two $R^9$. In some such embodiments, $L^2$ is methylene or ethylene (i.e., —$CH_2$ or —$CH_2CH_2$—). In certain embodiments, $L^2$ is methylene.

In some embodiments, $R^2$ and $R^3$ are taken together with the N-atom to which they are attached to form a 4-6 membered heterocyclyl optionally containing an additional heteroatom selected from O, N($R^7$) and S(O)$_q$ as a ring member, where said 4-6 membered heterocyclyl is optionally substituted by one or more $R^8$, and where q is 0, 1 or 2. In some such embodiments, said 4-6 membered heterocyclyl is optionally substituted by one, two, three or four $R^8$. In some such embodiments, said 4-6 membered heterocyclyl is optionally substituted by one or two $R^8$.

In some such embodiments, $R^2$ and $R^3$ are taken together with the N-atom to which they are attached to form an optionally substituted, 4-6 membered heterocyclyl, optionally containing an additional heteroatom selected from O, N($R^7$) and S(O)$_q$ as a ring member, where said 4-6 membered heterocyclyl is azetidinyl, pyrrolidinyl, piperidinyl, piperazinyl, morpholinyl or thiomorpholinyl, each optionally substituted by one or more $R^8$. In some such embodiments, $R^2$ and $R^3$ are taken together with the N-atom to which they are attached to form azetidinyl or pyrrolidinyl, each optionally substituted by one or more $R^8$. In specific embodiments, $R^2$ and $R^3$ are taken together with the N-atom to which they are attached to form azetidinyl optionally substituted by one or more $R^8$. In some embodiments, of each of the foregoing, said 4-6 membered heterocyclyl is optionally substituted by one, two, three or four $R^8$. In some embodiments, of each of the foregoing, said 4-6 membered heterocyclyl is optionally substituted by one or two $R^8$. In some such embodiments, each $R^8$ is $CH_3$.

In compounds of Formula (I), each $R^4$ is independently F, Cl, OH, CN, $NR^{10}R^{11}$, $C_1$-$C_4$ alkyl, $C_1$-$C_4$ fluoroalkyl, $C_1$-$C_4$ alkoxy, $C_1$-$C_4$ fluoroalkoxy, $C_3$-$C_8$ cycloalkyl, C(O)$NR^{10}R^{11}$, $SO_2R^{12}$, SO(=NH)$R^{12}$ or $SO_2NR^{10}R^{11}$, where each $C_1$-$C_4$ alkyl and $C_1$-$C_4$ fluoroalkyl is optionally substituted by one or more $R^{13}$. In some embodiments, each $R^4$ is independently $C_1$-$C_4$ alkyl or $C_1$-$C_4$ alkoxy, where each $C_1$-$C_4$ alkyl is optionally substituted by one or more $R^{13}$. In some such embodiments, each $R^{13}$ is $OCH_3$. In some embodiments of each of the foregoing, each $C_1$-$C_4$ alkyl and $C_1$-$C_4$ fluoroalkyl is optionally substituted by one, two, three or four $R^{13}$. In some embodiments of each of the foregoing, each $C_1$-$C_4$ alkyl and $C_1$-$C_4$ fluoroalkyl is optionally substituted by one or two $R^{13}$. In specific embodiments, each $R^4$ (or $R^4$ substituted by $R^{13}$) is independently $CH_3$, $OCH_3$ or $CH_2OCH_3$.

In compounds of Formula (I), each $R^5$ is independently OH, $C_1$-$C_4$ alkoxy or $NR^{10}R^{11}$. In some such embodiments, each $R^5$ is independently OH, $OCH_3$, $NH_2$, $NHCH_3$ or $N(CH_3)_2$.

In compounds of Formula (I), each $R^6$ is independently F, OH, $C_1$-$C_4$ alkyl, $C_1$-$C_4$ fluoroalkyl, $C_1$-$C_4$ alkoxy, $C_1$-$C_4$ fluoroalkoxy or $NR^{10}R^{11}$ where each $C_1$-$C_4$ alkyl and $C_1$-$C_4$ fluoroalkyl is optionally substituted by one or more $R^{13}$. In some embodiments, each $R^6$ is independently $C_1$-$C_4$ alkyl or $C_1$-$C_4$ alkoxy, where each $C_1$-$C_4$ alkyl is optionally substituted by one or more $R^{13}$. In some embodiments of each of the foregoing, each $C_1$-$C_4$ alkyl is optionally substituted by one, two, three or four $R^{13}$. In some embodiments of each of the foregoing, each $C_1$-$C_4$ alkyl is optionally substituted by one or two $R^{13}$. In some such embodiments, $R^{13}$ is $CH_3$ or $OCH_3$. In particular embodiments, each $R^6$ is independently $CH_3$, $OCH_3$ or $CH_2OCH_3$. In particular embodiments, each $R^6$ is independently $CH_3$.

In compounds of Formula (I), $R^7$ is H, $C_1$-$C_4$ alkyl or $C(O)$—$C_1$-$C_4$ alkyl. In some embodiments, $R^7$ is H, $CH_3$ or $C(O)CH_3$.

In compounds of Formula (I), each $R^8$ is independently F, OH, $C_1$-$C_4$ alkyl, $C_1$-$C_4$ alkoxy or CN. In particular embodiments, each $R^8$ is independently F, OH, $CH_3$, $OCH_3$ or CN. In specific embodiments, each $R^8$ is $CH_3$.

In compounds of Formula (I), each $R^9$ is independently F, OH or $C_1$-$C_2$ alkyl. In some embodiments, $R^9$ is F, OH or $CH_3$. In particular embodiments, $R^9$ is F, OH or $CH_3$. In some embodiments, $L^1$ and $L^2$ are a bond or an unsubstituted $C_1$-$C_2$ alkylene, and $R^9$ is absent.

In compounds of Formula (I), each $R^{10}$ and $R^{11}$ is independently H or $C_1$-$C_4$ alkyl.

In particular embodiments, each $R^{10}$ and $R^{11}$ is independently H or $CH_3$.

In compounds of Formula (I), each $R^{12}$ is $C_1$-$C_4$ alkyl or $C_3$-$C_6$ cycloalkyl. In particular embodiments, each $R^{12}$ is $CH_3$, $CH_2CH_3$, $CH_2CH_2CH_3$, $CH(CH_3)_2$ or cyclopropyl.

In compounds of Formula (I), each $R^{13}$ is independently OH, $C_1$-$C_4$ alkoxy or $NR^{14}R^{15}$. In particular embodiments, each $R^{13}$ is independently OH, $OCH_3$ or $NR^{14}R^{15}$ where $R^{14}$ and $R^{15}$ are independently H or $CH_3$. In specific embodiments, each $R^{13}$ is independently OH, $OCH_3$, $NH_2$, $NHCH_3$ or $N(CH_3)_2$.

In compounds of Formula (I), each $R^{14}$ and $R^{15}$ is independently H or $C_1$-$C_4$ alkyl. In particular embodiments, $R^{14}$ and $R^{15}$ are independently H or $CH_3$.

In some embodiments, the compound of Formula (I) has the absolute stereochemistry as shown in Formula (II):

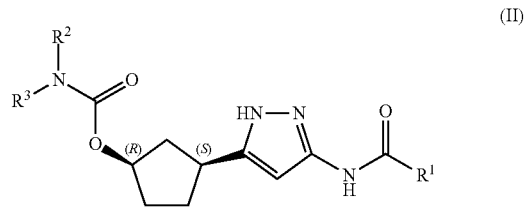

(II)

or a pharmaceutically acceptable salt thereof, wherein: $R^1$, $R^2$ and $R^3$ are as defined for Formula (I).

In some embodiments, the compound of Formula (I) has the absolute stereochemistry as shown in Formula (III):

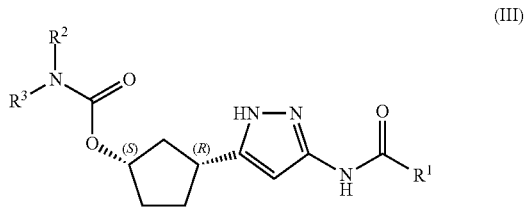

(III)

or a pharmaceutically acceptable salt thereof, wherein: $R^1$, $R^2$ and $R^3$ are as defined for Formula (I).

Compounds of Formula (II) and (III) maintain the syn-relationship between the substituent groups at the 1- and 3-position of the cyclopentyl ring but are present as the enantiomer indicated in substantially enantiomerically pure form.

Each of the aspects and embodiments described herein with respect to Formula (I) is also applicable to compounds of Formulae (II) or (III).

In some embodiments, the invention provides compounds of Formula (I), (II) or (III), or pharmaceutically acceptable salts thereof, wherein:
$R^1$ is -$L^1$-(5-10 membered heteroaryl) optionally substituted by one or two $R^4$;
$R^2$ and $R^3$ are independently H, $C_1$-$C_6$ alkyl, -$L^2$-($C_3$-$C_7$ cycloalkyl), where said $C_3$-$C_7$ cycloalkyl is optionally substituted by one $R^6$;
each $L^1$ and $L^2$ is independently a bond or methylene;
each $R^4$ is independently F, Cl, OH, CN, $NR^{10}R^{11}$, $C_1$-$C_4$ alkyl, $C_1$-$C_4$ fluoroalkyl, $C_1$-$C_4$ alkoxy, $C_1$-$C_4$ fluoroalkoxy, $C_3$-$C_8$ cycloalkyl, $C(O)NR^{10}R^{11}$, $SO_2R^{12}$, $SO(=NH)R^{12}$ or $SO_2NR^{10}R^{11}$, where each $C_1$-$C_4$ alkyl and $C_1$-$C_4$ fluoroalkyl is optionally substituted by one $R^{13}$;
each $R^6$ is independently F, OH, $C_1$-$C_4$ alkyl, $C_1$-$C_4$ fluoroalkyl, $C_1$-$C_4$ alkoxy $C_1$-$C_4$ fluoroalkoxy or $NR^{10}R^{11}$ where each $C_1$-$C_4$ alkyl and $C_1$-$C_4$ fluoroalkyl is optionally substituted by one $R^{13}$;
each $R^{10}$ and $R^{11}$ is independently H or $C_1$-$C_4$ alkyl;
each $R^{12}$ is $C_1$-$C_4$ alkyl or $C_3$-$C_6$ cycloalkyl; and
each $R^{13}$ is independently OH, $C_1$-$C_4$ alkoxy or $NR^{14}R^{15}$.

In other embodiments, the invention provides compounds of Formula (I), (II) or (III), or pharmaceutically acceptable salts thereof, wherein:
$R^1$ is -$L^1$-(5-10 membered heteroaryl) optionally substituted by one or two $R^4$;
$R^2$ and $R^3$ are independently H, $C_1$-$C_6$ alkyl or a $C_3$-$C_7$ cycloalkyl optionally substituted by one $C_1$-$C_4$ alkyl;
$L^1$ is independently a bond or methylene; and
each $R^4$ is independently $C_1$-$C_4$ alkyl optionally substituted by OH or $C_1$-$C_4$ alkoxy.

In further embodiments, the invention provides compounds of Formula (I), (II) or (III), or pharmaceutically acceptable salts thereof, having two or more of the following features:

$R^1$ is -$L^1$-(5-10 membered heteroaryl) where said 5-10 membered heteroaryl is optionally substituted by one or more $R^4$;

$R^2$ and $R^3$ are independently H or $C_1$-$C_6$ alkyl;

$L^1$ is a bond or a $C_1$-$C_2$ alkylene;

each $R^4$ is independently $C_1$-$C_4$ alkyl, where each $C_1$-$C_4$ alkyl is optionally substituted by one or more $R^{13}$;

each $R^{13}$ is independently OH, $C_1$-$C_4$ alkoxy or $NR^{14}R^{15}$; and each $R^{14}$ and $R^{15}$ is independently H or $C_1$-$C_4$ alkyl.

In some such embodiments, the invention provides compounds of Formula (I), (II) or (III), or pharmaceutically acceptable salts thereof, having two or more of the following features:

$R^1$ is -$L^1$-(5-10 membered heteroaryl) optionally substituted by one or more $R^4$ where said 5-10 membered heteroaryl is pyrazolyl;

$R^2$ is H;

$R^3$ is $C_1$-$C_6$ alkyl, preferably $C_1$-$C_4$ alkyl;

$L^1$ is a bond;

each $R^4$ is independently $C_1$-$C_4$ alkyl, where each $C_1$-$C_4$ alkyl is optionally substituted by one or more $R^{13}$;

each $R^{13}$ is independently OH, $OCH_3$ or $NR^{14}R^{15}$; and each $R^{14}$ and $R^{15}$ is independently H or $CH_3$.

In other embodiments, the invention provides compounds of Formula (I), (II) or (III), or pharmaceutically acceptable salts thereof, having two or more of the following features:

$R^1$ is -$L^1$-(5-10 membered heteroaryl) where said 5-10 membered heteroaryl is optionally substituted by one or more $R^4$;

$R^2$ and $R^3$ are independently H or -$L^2$-($C_3$-$C_7$ cycloalkyl), where said $C_3$-$C_7$ cycloalkyl is optionally substituted by one or more $R^6$;

$L^1$ is a bond or a $C_1$-$C_2$ alkylene;

$L^2$ is a bond or a $C_1$-$C_2$ alkylene;

each $R^4$ is independently $C_1$-$C_4$ alkyl, where each $C_1$-$C_4$ alkyl is optionally substituted by one or more $R^{13}$;

each $R^6$ is independently F, OH, or $C_1$-$C_4$ alkyl;

each $R^{13}$ is independently OH, $C_1$-$C_4$ alkoxy or $NR^{14}R^{15}$; and each $R^{14}$ and $R^{15}$ is independently H or $C_1$-$C_4$ alkyl.

In still other embodiments, the invention provides compounds of Formula (I), (II) or (III), or pharmaceutically acceptable salts thereof, having two or more of the following features:

$R^1$ is -$L^1$-(5-10 membered heteroaryl) optionally substituted by one or more $R^4$, where said 5-10 membered heteroaryl is isoxazolyl;

$L^1$ is a $C_1$-$C_2$ alkylene;

$R^2$ is H;

$R^3$ is -$L^2$-($C_3$-$C_7$ cycloalkyl) optionally substituted by one or more $R^6$;

$L^2$ is a bond;

each $R^4$ is independently $C_1$-$C_4$ alkyl, where each $C_1$-$C_4$ alkyl is optionally substituted by one or more $R^{13}$;

each $R^6$ is independently F, OH, or $C_1$-$C_4$ alkyl;

each $R^{13}$ is independently OH, $C_1$-$C_4$ alkoxy or $NR^{14}R^{15}$; and each $R^{14}$ and $R^{15}$ is independently H or $C_1$-$C_4$ alkyl.

In another aspect, the invention provides a compound selected from the group consisting of the compounds exemplified in Examples 1 to 649, inclusive, or a pharmaceutically acceptable salt thereof.

In another aspect, the invention provides a compound selected from the group consisting of:
(1R,3S)-3-(3-{[(2-methoxypyridin-4-yl)acetyl]amino}-1H-pyrazol-5-yl)cyclopentyl propylcarbamate;
(1R,3S)-3-(3-{[(2-methyl-1,3-thiazol-5-yl)acetyl]amino}-1H-pyrazol-5-yl)cyclopentyl propan-2-ylcarbamate;
(1R,3S)-3-(3-{[(1-methyl-1H-indazol-5-yl)acetyl]amino}-1H-pyrazol-5-yl)cyclopentyl ethylcarbamate;
(1R,3S)-3-(3-{[(1-methyl-1H-1,2,3-triazol-5-yl)carbonyl]amino}-1H-pyrazol-5-yl)cyclopentyl (2S)-butan-2-ylcarbamate;
(1R,3S)-3-(3-{[(5-methyl-1,3-oxazol-2-yl)acetyl]amino}-1H-pyrazol-5-yl)cyclopentyl (1-methylcyclopropyl)carbamate;
(1R,3S)-3-(3-{[(5-methoxypyrazin-2-yl)acetyl]amino}-1H-pyrazol-5-yl)cyclopentyl (1-methylcyclopropyl)carbamate;
(1R,3S)-3-(3-{[(5-methyl-1,2-oxazol-3-yl)acetyl]amino}-1H-pyrazol-5-yl)cyclopentyl (1-methylcyclopropyl)carbamate;
(1R,3S)-3-[3-({[3-(methoxymethyl)-1-methyl-1H-pyrazol-5-yl]carbonyl}amino)-1H-pyrazol-5-yl]cyclopentyl (1-methylcyclopropyl)carbamate;
(1R,3S)-3-[3-({[3-(methoxymethyl)-1-methyl-1H-pyrazol-5-yl]carbonyl}amino)-1H-pyrazol-5-yl]cyclopentyl [(2ξ)-4,4,4-trifluorobutan-2-yl]carbamate (Isomer A);
(1R,3S)-3-[3-({[3-(methoxymethyl)-1-methyl-1H-pyrazol-5-yl]carbonyl}amino)-1H-pyrazol-5-yl]cyclopentyl [(2ξ)-4,4,4-trifluorobutan-2-yl]carbamate (Isomer B);
(1R,3S)-3-(3-{[(5-methyl-1,3-oxazol-2-yl)acetyl]amino}-1H-pyrazol-5-yl)cyclopentyl tert-butylcarbamate;
(1R,3S)-3-(3-{[(3-methyl-1,2-oxazol-5-yl)acetyl]amino}-1H-pyrazol-5-yl)cyclopentyl 2,2-dimethylazetidine-1-carboxylate;
(1R,3S)-3-[3-({[3-(methoxymethyl)-1-methyl-1H-pyrazol-5-yl]carbonyl}amino)-1H-pyrazol-5-yl]cyclopentyl propan-2-ylcarbamate;
(1R,3S)-3-[3-({[3-(methoxymethyl)-1-methyl-1H-pyrazol-5-yl]carbonyl}amino)-1H-pyrazol-5-yl]cyclopentyl (2S)-butan-2-ylcarbamate;
(1R,3S)-3-(3-{[(3-methyl-1,2-oxazol-5-yl)acetyl]amino}-1H-pyrazol-5-yl)cyclopentyl (1-methylcyclopropyl)carbamate;
(1R,3S)-3-{3-[(1,2-oxazol-5-ylacetyl)amino]-1H-pyrazol-5-yl}cyclopentyl (2S)-butan-2-ylcarbamate;
(1R,3S)-3-{3-[(1,2-oxazol-3-ylacetyl)amino]-1H-pyrazol-5-yl}cyclopentyl tert-butylcarbamate; and
(1R,3S)-3-(3-{[(5-methyl-1,3,4-thiadiazol-2-yl)acetyl]amino}-1H-pyrazol-5-yl)cyclopentyl (1-methylcyclobutyl)carbamate;
or a pharmaceutically acceptable salt thereof.

In another aspect, the invention provides a compound selected from the group consisting of:
(1R,3S)-3-[3-({[3-(methoxymethyl)-1-methyl-1H-pyrazol-5-yl]carbonyl}amino)-1H-pyrazol-5-yl]cyclopentyl propan-2-ylcarbamate; and
(1R,3S)-3-(3-{[(3-methyl-1,2-oxazol-5-yl)acetyl]amino}-1H-pyrazol-5-yl)cyclopentyl (1-methylcyclopropyl)carbamate;
or a pharmaceutically acceptable salt thereof.

In another aspect, the invention provides (1R,3S)-3-[3-({[3-(methoxymethyl)-1-methyl-1H-pyrazol-5-yl]carbonyl}amino)-1H-pyrazol-5-yl]cyclopentyl propan-2-ylcarbamate, or a pharmaceutically acceptable salt thereof.

In another aspect, the invention provides (1R,3S)-3-[3-({[3-(methoxymethyl)-1-methyl-1H-pyrazol-5-yl]

carbonyl}amino)-1H-pyrazol-5-yl]cyclopentyl propan-2-yl-carbamate in the form of a free base.

In another aspect, the invention provides (1R,3S)-3-[3-({[3-(methoxymethyl)-1-methyl-1H-pyrazol-5-yl]carbonyl}amino)-1H-pyrazol-5-yl]cyclopentyl propan-2-yl-carbamate in the form of a pharmaceutically acceptable salt.

Figure 2:
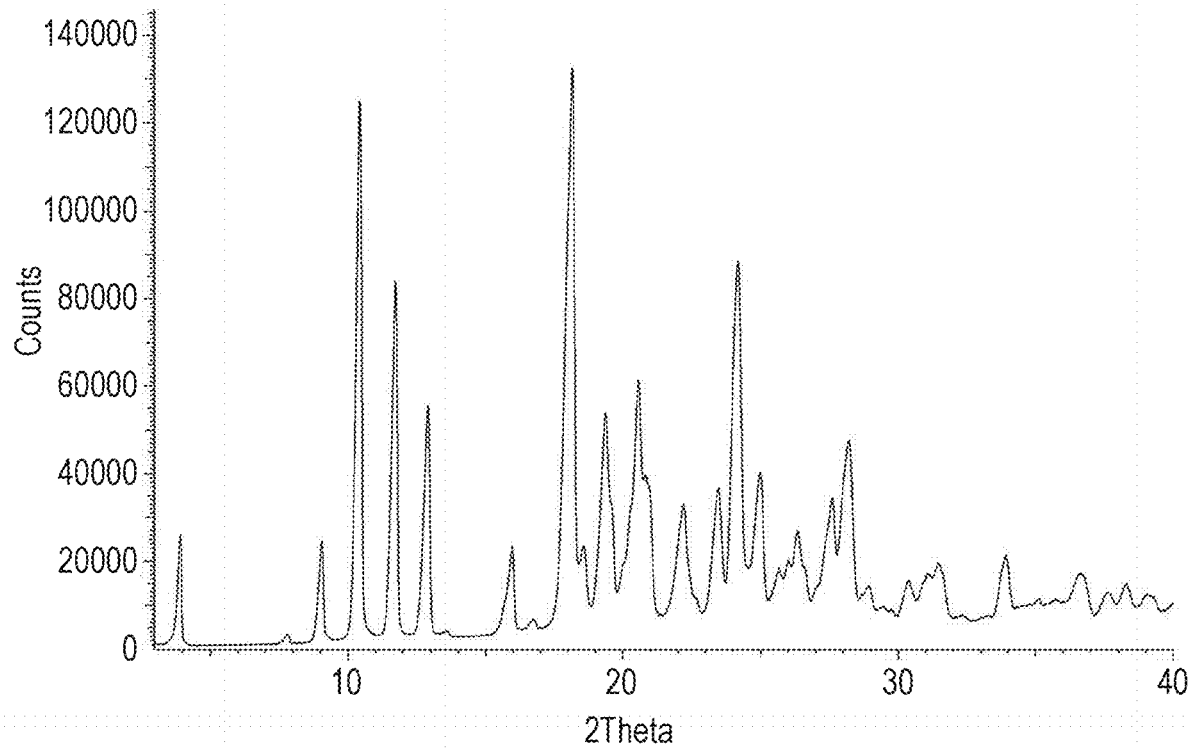
FIG. 2 shows the PXRD spectrum of (1R,3S)-3-[3-({[3-(methoxymethyl)-1-methyl-1H-pyrazol-5-yl]carbonyl}amino)-1H-pyrazol-5-yl]cyclopentyl propan-2-yl-carbamate monohydrate (Form 1).

In some embodiments, the invention provides (1R,3S)-3-[3-({[3-(methoxymethyl)-1-methyl-1H-pyrazol-5-yl]carbonyl}amino)-1H-pyrazol-5-yl]cyclopentyl propan-2-ylcarbamate monohydrate (Form 1). In some such embodiments, the monohydrate (Form 1) is characterized by a powder X-ray diffraction (PXRD) pattern (20) comprising: (a) one, two, three, four, five, or more than five peaks selected from the group consisting of the peaks in Table 1 in °2θ±0.2°2θ; (b) one, two, three, four or five peaks selected from the group consisting of 10.4, 11.7, 12.9, 18.2 and 24.2 in °2θ±0.2°2θ; (c) any two peaks selected from the group consisting of 10.4, 11.7, 12.9, 18.2 and 24.2 in °2θ±0.2°2θ; (d) any three peaks selected from the group consisting of 10.4, 11.7, 12.9, 18.2 and 24.2 in °2θ±0.2°2θ; (e) any four peaks selected from the group consisting of 10.4, 11.7, 12.9, 18.2 and 24.2 in °2θ±0.2°2θ; (f) peaks at 10.4, 11.7, 12.9, 18.2 and 24.2 in °2θ±0.2°2θ; (g) a peak at 10.4, and one, two, three or four peaks selected from the group consisting of 11.7, 12.9, 18.2 and 24.2 in °2θ±0.2°2θ; (h) a peak at 11.7, and one, two, three or four peaks selected from the group consisting of 10.4, 12.9, 18.2 and 24.2 in °2θ±0.2°2θ; (i) a peak at 12.9, and one, two, three or four peaks selected from the group consisting of 10.4, 11.7, 18.2 and 24.2 in °2θ±0.2°2θ; (j) a peak at 18.2, and one, two, three or four peaks selected from the group consisting of 10.4, 11.7, 12.9 and 24.2 in °2θ±0.2°2θ; (k) a peak at 24.2, and one, two, three or four peaks selected from the group consisting of 10.4, 11.7, 12.9, and 18.2 in °2θ±0.2°2θ; or (l) peaks at 26 values essentially the same as shown in FIG. 2.

In another embodiment, the invention provides (1R,3S)-3-(3-{[(3-methyl-1,2-oxazol-5-yl)acetyl]amino}-1H-pyrazol-5-yl)cyclopentyl (1-methylcyclopropyl)carbamate, or a pharmaceutically acceptable salt thereof.

In another embodiment, the invention provides (1R,3S)-3-(3-{[(3-methyl-1,2-oxazol-5-yl)acetyl]amino}-1H-pyrazol-5-yl)cyclopentyl (1-methylcyclopropyl)carbamate in the form of a free base.

In another embodiment, the invention provides (1R,3S)-3-(3-{[(3-methyl-1,2-oxazol-5-yl)acetyl]amino}-1H-pyrazol-5-yl)cyclopentyl (1-methylcyclopropyl)carbamate in the form of a pharmaceutically acceptable salt.

In a specific embodiment, the invention provides a compound having the structure:

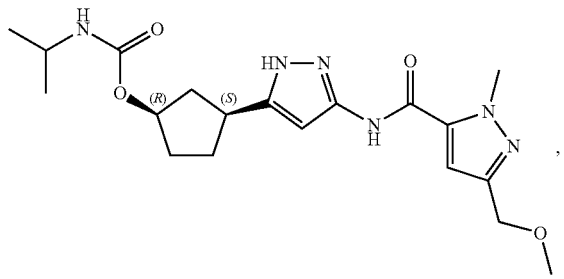

or a pharmaceutically acceptable salt thereof.

In another specific embodiment, the invention provides a compound having the structure:

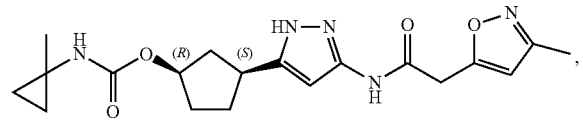

or a pharmaceutically acceptable salt thereof.

In preferred embodiments, the compounds of the invention are selective inhibitors of CDK2, i.e., they have a lower inhibitory constant (e.g., Ki or $IC_{50}$) for CDK2 relative to other enzymatic targets. Emerging data suggest that GSK3β inhibition may be linked to gastrointestinal toxicity, which has been observed with some CDK inhibitors. Compounds that are selective inhibitors of CDK2 versus GSK3β may provide an improved safety profile, improved dosing schedule (e.g., by decreasing the need for dose reduction or dosing holidays), and/or enhanced overall efficacy, due to the potential of higher dosing, use of a continuous dosing regimen, and/or extended time of overall treatment. Similarly, selective inhibitors of CDK2 may have a reduced risk of certain hematologic toxicities that have been reported be linked to inhibition of CDK6.

In some embodiments, the compounds of the invention are selective against CDK2 versus CDK1. In some such embodiments, compounds show at least 10-fold selectivity for CDK2 versus CDK1. In other embodiments, compounds show at least 20-fold selectivity for CDK2 versus CDK1. In specific embodiments, compounds show at least 30-fold selectivity for CDK2 versus CDK1.

In some embodiments, the compounds of the invention are selective against CDK2 versus CDK4 and/or CDK6. In some such embodiments, compounds show at least 10-fold selectivity for CDK2 versus CDK4 and/or CDK6. In other embodiments, compounds show at least 20-fold selectivity for CDK2 versus CDK4 and/or CDK6. In specific embodiments, compounds show at least 30-fold selectivity for CDK2 versus CDK4 and/or CDK6.

In some embodiments, the compounds of the invention are selective against CDK2 versus GSK3β. In some such embodiments, compounds show at least 10-fold selectivity for CDK2 versus GSK3β. In other embodiments, compounds show at least 20-fold selectivity for CDK2 versus GSK3β. In specific embodiments, compounds show at least 30-fold selectivity for CDK2 versus GSK3β.

A "pharmaceutical composition" refers to a mixture of one or more of the compounds of the invention, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients. In other embodiments, the pharmaceutical composition further comprises at least one additional anticancer therapeutic agent.

In one aspect, the invention provides a pharmaceutical composition comprising a compound of the invention, or a pharmaceutically acceptable salt thereof, and a pharmaceutically acceptable carrier or excipient. In some embodiments, the pharmaceutical composition comprises two or more pharmaceutically acceptable carriers and/or excipients.

In some embodiments, the pharmaceutical composition further comprises at least one additional anti-cancer therapeutic agent. In some such embodiments, the combination provides an additive, greater than additive, or synergistic anti-cancer effect.

The term "additive" is used to mean that the result of the combination of two compounds, components or targeted agents is no greater than the sum of each compound, component or targeted agent individually.

The term "synergy" or "synergistic" are used to mean that the result of the combination of two compounds, components or targeted agents is greater than the sum of each compound, component or targeted agent individually. This improvement in the disease, condition or disorder being treated is a "synergistic" effect. A "synergistic amount" is an amount of the combination of the two compounds, components or targeted agents that results in a synergistic effect, as "synergistic" is defined herein.

Determining a synergistic interaction between one or two components, the optimum range for the effect and absolute dose ranges of each component for the effect may be definitively measured by administration of the components over different dose ranges, and/or dose ratios to patients in need of treatment. However, the observation of synergy in in vitro models or in vivo models can be predictive of the effect in humans and other species and in vitro models or in vivo models exist, as described herein, to measure a synergistic effect. The results of such studies can also be used to predict effective dose and plasma concentration ratio ranges and the absolute doses and plasma concentrations required in humans and other species such as by the application of pharmacokinetic and/or pharmacodynamics methods.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and 1,1'-methylene-bis-(2-hydroxy-3-naphthoate)](i.e. pamoate) salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isethionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Alternatively, the compounds useful that are acidic in nature may be capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure.

Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention, and of interconverting salt and free base forms, are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains a carboxylic acid functionality (—COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl, or with a phosphate ether group; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references. Finally, certain inventive compounds may themselves act as prodrugs of other of the inventive compounds.

Also included within the scope of the invention are metabolites of compounds of the formulae described herein, i.e., compounds formed in vivo upon administration of the drug.

In addition to the syn-relationship between the substituent groups at the 1- and 3-position of the cyclopentyl ring in Formulae (I), (II) and (Ill), the compounds of the formulae provided herein may have additional asymmetric carbon atoms as part of substituent groups defined as $R^1$, $R^2$ and $R^3$ or optional substituents attached to these groups. At such additional asymmetric centers, a solid line is used to indicate that all possible stereoisomers at that carbon atom are included, while a solid or dotted wedge indicates that only the isomer shown is meant to be included at such stereocenter unless otherwise indicated. Compounds of the formulae herein can include substituent groups containing cis and trans geometric isomers, rotational isomers, atropisomers, conformational isomers, and tautomers of the compounds of the invention, including compounds exhibiting more than one type of isomerism.

Also included are acid addition salts or base addition salts, wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution.

In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The enantiomeric purity of compounds described herein may be described in terms of enantiomeric excess (ee), which indicates the degree to which a sample contains one enantiomer in greater amounts than the other. A racemic mixture has an ee of 0%, while a single completely pure enantiomer has an ee of 100%. Similarly, diastereomeric purity may be described in terms of diasteriomeric excess (de). As used herein, "enantiomerically pure" or "substantially enantiomerically pure" means a compound that comprises one enantiomer of the compound and is substantially free of the opposite enantiomer of the compound. A typical enantiomerically pure compound comprises greater than about 95% by weight of one enantiomer of the compound and less than about 5% by weight of the opposite enantiomer of the compound, preferably greater than about 97% by weight of one enantiomer of the compound and less than about 3% by weight of the opposite enantiomer of the compound, more preferably greater than about 98% by weight of one enantiomer of the compound and less than about 2% by weight of the opposite enantiomer of the compound, and even more preferably greater than about 99% by weight of one enantiomer of the compound and less than about 1% by weight of the opposite enantiomer of the compound.

The present invention also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, fluorine and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl. Certain isotopically-labeled compounds of the invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Therapeutic Methods and Uses

The invention further provides therapeutic methods and uses comprising administering the compounds of the invention, or pharmaceutically acceptable salts thereof, alone or in combination with other therapeutic agents or palliative agents.

In one aspect, the invention provides a method for the treatment of abnormal cell growth in a subject in need thereof, comprising administering to the subject a therapeutically effective amount of a compound of the invention, or a pharmaceutically acceptable salt thereof.

In another aspect, the invention provides a method for the treatment of abnormal cell growth in a subject in need thereof, comprising administering to the subject an amount of a compound of the invention, or a pharmaceutically acceptable salt thereof, in combination with an amount of an additional therapeutic agent (e.g., an anticancer therapeutic agent), which amounts are together effective in treating said abnormal cell growth.

In another aspect, the invention provides a compound of the invention, or a pharmaceutically acceptable salt thereof, for use in the treatment of abnormal cell growth in a subject.

In a further aspect, the invention provides the use of a compound of the invention, or a pharmaceutically acceptable salt thereof, for the treatment of abnormal cell growth in a subject.

In another aspect, the invention provides a pharmaceutical composition for use in the treatment of abnormal cell growth in a subject in need thereof, which pharmaceutical composition comprises a compound of the invention, or a pharmaceutically acceptable salt thereof, and a pharmaceutically acceptable carrier or excipient.

In another aspect, the invention provides a compound of the invention, or a pharmaceutically acceptable salt thereof, for use as a medicament, in particular a medicament for the treatment of abnormal cell growth.

In yet another aspect, the invention provides the use of a compound of the invention, or a pharmaceutically acceptable salt thereof, for the manufacture of a medicament for the treatment of abnormal cell growth in a subject.

In frequent embodiments of the methods provided herein, the abnormal cell growth is cancer. Compounds of the invention may be administered as single agents or may be administered in combination with other anti-cancer therapeutic agents, in particular standard of care agents appropriate for the particular cancer.

In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by CDK2 in a subject, comprising administering to the subject a compound of the invention, or a pharmaceutically acceptable salt thereof, in an amount that is effective for treating said disorder, in particular cancer.

In certain aspects and embodiments of the compounds, compositions, methods and uses described herein, the compounds of the invention are selective for CDK2 over other CDKs, in particular CDK1. In some embodiments, the compounds of the invention are selective for CDK2 over CDK4 and/or CDK6. In other aspects and embodiments, the compounds of the invention are selective for CDK2 over glycogen synthase kinase 3 beta (GSK3β). Compounds of the invention include compounds of any of the formulae described herein, or pharmaceutically acceptable salts thereof.

In another aspect, the invention provides a method of inhibiting cancer cell proliferation in a subject, comprising administering to the subject a compound of the invention, or a pharmaceutically acceptable salt thereof, in an amount effective to inhibit cell proliferation.

In another aspect, the invention provides a method of inhibiting cancer cell invasiveness in a subject, comprising administering to the subject a compound of the invention, or a pharmaceutically acceptable salt thereof, in an amount effective to inhibit cell invasiveness.

In another aspect, the invention provides a method of inducing apoptosis in cancer cells in a subject, comprising administering to the subject a compound of the invention, or a pharmaceutically acceptable salt thereof, in an amount effective to induce apoptosis.

In another aspect, the invention provides a method of inhibiting cancer cell metastasis in a subject, comprising administering to the subject a compound of the invention, or a pharmaceutically acceptable salt thereof, in an amount effective to inhibit cell metastasis.

In another aspect, the invention provides a method of inhibiting angiogenesis in a subject, comprising administering to the subject a compound of the invention, or a pharmaceutically acceptable salt thereof, in an amount effective to inhibit angiogenesis.

In frequent embodiments of the methods provided herein, the abnormal cell growth is cancer. In some such embodiments, the cancer is selected from breast cancer, ovarian cancer, bladder cancer, uterine cancer, prostate cancer, lung cancer (including NSCLC, SCLC, squamous cell carcinoma or adenocarcinoma), esophageal cancer, head and neck cancer, colorectal cancer, kidney cancer (including RCC), liver cancer (including HCC), pancreatic cancer, stomach (i.e., gastric) cancer or thyroid cancer. In further embodiments of the methods provided herein, the cancer is breast cancer, ovarian cancer, bladder cancer, uterine cancer, prostate cancer, lung cancer, esophageal cancer, liver cancer, pancreatic cancer or stomach cancer.

In other embodiments, the cancer is breast cancer, including, e.g., ER-positive/HR-positive, HER2-negative breast cancer; ER-positive/HR-positive, HER2-positive breast cancer; triple negative breast cancer (TNBC); or inflammatory breast cancer. In some embodiments, the breast cancer is endocrine resistant breast cancer, trastuzumab resistant breast cancer, or breast cancer demonstrating primary or acquired resistance to CDK4/CDK6 inhibition. In some embodiments, the breast cancer is advanced or metastatic breast cancer. In some embodiments of each of the foregoing, the breast cancer is characterized by amplification or overexpression of CCNE1 and/or CCNE2.

In some embodiments of the methods provided herein, the abnormal cell growth is cancer characterized by amplification or overexpression of CCNE1 and/or CCNE2. In some embodiments of the methods provided herein, the subject is identified as having a cancer characterized by amplification or overexpression of CCNE1 and/or CCNE2.

In some embodiments, the cancer is selected from the group consisting of breast cancer and ovarian cancer. In some such embodiments, the cancer is breast cancer or ovarian cancer characterized by amplification or overexpression of CCNE1 and/or CCNE2. In some such embodiments, the cancer is (a) breast cancer or ovarian cancer; (b) characterized by amplification or overexpression of cyclin E1

(CCNE1) or cyclin E2 (CCNE2); or (c) both (a) and (b). In some embodiments, the cancer is ovarian cancer.

In some embodiments, the compound of the invention is administered as first line therapy. In other embodiments, the compound of the invention is administered as second (or later) line therapy. In some embodiments, the compound of the invention is administered as second (or later) line therapy following treatment with an endocrine therapeutic agent and/or a CDK4/CDK6 inhibitor. In some embodiments, the compound of the invention is administered as second (or later) line therapy following treatment with an endocrine therapeutic agent, e.g., an aromatase inhibitor, a SERM or a SERD. In some embodiments, the compound of the invention is administered as second (or later) line therapy following treatment with a CDK4/CDK6 inhibitor. In some embodiments, the compound of the invention is administered as second (or later) line therapy following treatment with one or more chemotherapy regimens, e.g., including taxanes or platinum agents. In some embodiments, the compound of the invention is administered as second (or later) line therapy following treatment with HER2 targeted agents, e.g., trastuzumab.

As used herein, an "effective dosage" or "effective amount" of drug, compound or pharmaceutical composition is an amount sufficient to affect any one or more beneficial or desired, including biochemical, histological and/or behavioral symptoms, of the disease, its complications and intermediate pathological phenotypes presenting during development of the disease. For therapeutic use, a "therapeutically effective amount" refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

An effective dosage can be administered in one or more administrations. For the purposes of this invention, an effective dosage of drug, compound, or pharmaceutical composition is an amount sufficient to accomplish prophylactic or therapeutic treatment either directly or indirectly. As is understood in the clinical context, an effective dosage of drug, compound or pharmaceutical composition may or may not be achieved in conjunction with another drug, compound or pharmaceutical composition.

"Tumor" as it applies to a subject diagnosed with, or suspected of having, a cancer refers to a malignant or potentially malignant neoplasm or tissue mass of any size and includes primary tumors and secondary neoplasms. A solid tumor is an abnormal growth or mass of tissue that usually does not contain cysts or liquid areas. Examples of solid tumors are sarcomas, carcinomas, and lymphomas. Leukaemia's (cancers of the blood) generally do not form solid tumors (National Cancer Institute, Dictionary of Cancer Terms).

"Tumor burden" or "tumor load', refers to the total amount of tumorous material distributed throughout the body. Tumor burden refers to the total number of cancer cells or the total size of tumor(s), throughout the body, including lymph nodes and bone marrow. Tumor burden can be determined by a variety of methods known in the art, such as, e.g., using callipers, or while in the body using imaging techniques, e.g., ultrasound, bone scan, computed tomography (CT), or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using callipers, or while in the body using imaging techniques, e.g., bone scan, ultrasound, CR or MRI scans.

As used herein, "subject" refers to a human or animal subject. In certain preferred embodiments, the subject is a human.

The term "treat" or "treating" a cancer as used herein means to administer a compound of the present invention to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

For the purposes of this invention, beneficial or desired clinical results include, but are not limited to, one or more of the following: reducing the proliferation of (or destroying) neoplastic or cancerous cell; inhibiting metastasis or neoplastic cells; shrinking or decreasing the size of a tumor; remission of the cancer; decreasing symptoms resulting from the cancer; increasing the quality of life of those suffering from the cancer; decreasing the dose of other medications required to treat the cancer; delaying the progression of the cancer; curing the cancer; overcoming one or more resistance mechanisms of the cancer; and/or prolonging survival of patients the cancer. Positive therapeutic effects in cancer can be measured in a number of ways (see, for example, W. A. Weber, Assessing tumor response to therapy, J. Nucl. Med. 50 Suppl. 1:1S-10S (2009). For example, with respect to tumor growth inhibition (T/C), according to the National Cancer Institute (NCI) standards, a T/C less than or equal to 42% is the minimum level of anti-tumor activity. A T/C<10% is considered a high anti-tumor activity level, with T/C (%)=median tumor volume of the treated/median tumor volume of the control×100.

In some embodiments, the treatment achieved by a compound of the invention is defined by reference to any of the following: partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow and includes the amount of time patients have experienced a CR or PR, as well as the amount of time patients have experienced stable disease (SD). DFS refers to the length of time during and after treatment that the patient remains free of disease. OS refers to a prolongation in life expectancy as compared to naïve or untreated subjects or patients. In some embodiments, response to a combination of the invention is any of PR, CR, PFS, DFS, OR or OS that is assessed using Response Evaluation Criteria in Solid Tumors (RECIST) 1.1 response criteria.

The treatment regimen for a compound of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrattesty and the Wilcon on-test.

The terms "treatment regimen", "dosing protocol" and "dosing regimen" are used interchangeably to refer to the dose and timing of administration of each compound of the invention, alone or in combination with another therapeutic agent.

"Ameliorating" means a lessening or improvement of one or more symptoms upon treatment with a combination described herein, as compared to not administering the combination. "Ameliorating" also includes shortening or reduction in duration of a symptom.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

Abnormal cell growth includes the abnormal growth of: (1) tumor cells (tumors) that show increased expression of CDK2; (2) tumors that proliferate by aberrant CDK2 activation; (3) tumors characterized by amplification or overexpression of CCNE1 and/or CCNE2; and (4) tumors that are resistant to endocrine therapy, HER2 antagonists or CDK4/6 inhibition.

The term "additional anticancer therapeutic agent" as used herein means any one or more therapeutic agent, other than a compound of the invention, that is or can be used in the treatment of cancer. In some embodiments, such additional anticancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, immuno-oncology agents, and the like.

In some embodiments, the additional anticancer agent is an endocrine agent, such as an aromatase inhibitor, a SERD or a SERM.

In other embodiments, a compound of the invention may be administered in combination with a standard of care agent. In some embodiments, a compound of the invention may be administered in combination with endocrine therapy, e.g., agents such as letrozole, fulvestrant, tamoxifen, exemestane, or anastrozole. In some embodiments, a compound of the invention may be administered in combination with a chemotherapeutic agent, e.g., docetaxel, paclitaxel, cisplatin, carboplatin, capecitabine, gemcitabine or vinorelbine. In other embodiments, a compound of the invention may be administered in combination with an anti-HER2 agent, e.g., trastuzumab or pertuzumab.

In some embodiments, the additional anticancer agent is an anti-angiogenesis agent, including for example VEGF inhibitors, VEGFR inhibitors, TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™), bevacizumab (Avastin™), axitinib (AG 13736), SU 14813 (Pfizer), and AG 13958 (Pfizer). Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™). Yet further anti-angiogenesis agents include ABT 510 (Abbott), apratastat (TMI 005), AZD 8955 (AstraZeneca), incyclinide (Metastat™), and PCK 3145 (*Procyon*). Yet further anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In other embodiments, the additional anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors. Additional examples of signal transduction inhibitors which may be used in conjunction with a compound of the invention and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38).

Other examples of signal transduction inhibitors include gefitinib (Iressa™), cetuximab (Erbitux™), erlotinib (Tarceva™), trastuzumab (Herceptin™), sunitinib (Sutent™), imatinib (Gleevec™), crizotinib (Pfizer), lorlatinib (Pfizer), dacomitinib (Pfizer), bosutinib (Pfizer), gedatolisib (Pfizer), canertinib (CI 1033), pertuzumab (Omnitarg™), lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), ARRY 142886 (Array Biopharm), everolimus (Certican™), zotarolimus (Endeavor™), temsirolimus (Torisel™), AP 23573 (ARIAD), and VX 680 (Vertex), XL 647 (Exelixis), sorafenib (Nexavar™), LE-AON (Georgetown University), and GI-4000 (Globelmmune). Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), palbociclib (Pfizer), and AG 024322 (Pfizer).

In other embodiments, the additional anti-cancer agent is a so called classical antineoplastic agent. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, DNA methyltransferase inhibitors, silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor (such as, e.g., talazoparib, olapariv, rucaparib, niraparib, iniparib, veliparib), microtubulin inhibitors, antibiotics, plant derived spindle inhibitors, platinum-coordinated compounds, gene therapeutic agents, antisense oligonucleotides, vascular targeting agents (VTAs), and statins. Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi), Selective Estrogen-Receptor Downregulators (SERD's; such as fulvestrant), exemestane (Aromasin), anastrozole (Arimidex), atamestane, fadrozole, letrozole (Femara), formestane; gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), cyproterone, flutamide (Eulexin), megestrol, nilutamide (Nilandron), and osaterone, dutasteride, episteride, finasteride, Serenoa repens, PHL 00801, abarelix, goserelin, leuprorelin, triptorelin, bicalutamide; antiandrogen agents, such as enzalutamide, abiraterone acetate, bicalutamide (Casodex); and combinations thereof. Other examples of classical antineoplastic agents used in combination with a compound of the invention include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In still other embodiments, the additional anti-cancer agent is a so called dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy), bexarotene (Targretin™), Tesmilifene (DPPE—enhances efficacy of cytotoxics), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof. Further examples of classical antineoplastic agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

In other embodiments, the additional anti-cancer agent is an epigenetic modulator, for example an inhibitor or EZH2, SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX, IDH1/2 or BCL6.

In further embodiments, the additional anti-cancer agent is an immunomodulatory agent, such as an inhibitor of CTLA-4, PD-1 or PD-L1 (e.g., pembrolizumab, nivolumab or avelumab), LAG-3, TIM-3, TIGIT, 4-1BB, OX40, GITR, CD40, or a CAR-T-cell therapy.

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In some embodiments of the methods provided herein, the cancer is breast cancer, ovarian cancer, bladder cancer, uterine cancer, prostate cancer, lung cancer (including SCLC or NSCLC), esophageal cancer, liver cancer, pancreatic cancer or stomach cancer.

In some such embodiments, the cancer is characterized by amplification or overexpression of CCNE1 and/or CCNE2.

Dosage Forms and Regimens

Administration of the compounds of the invention may be affected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus, compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of lactose monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus, the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer agent), either sequentially or simultaneously.

As noted above, the compounds of the invention may be used in combination with one or more additional anti-cancer agents. The efficacy of the compounds of the invention in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 antagonists and the like.

When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates and polymorphs of said compound or pharmaceutically acceptable salts thereof), in combination with one or more (preferably one to three) additional anti-cancer therapeutic agents.

Synthetic Methods

Compounds of the invention are prepared according to the exemplary procedures provided herein and modifications thereof known to those of skill in the art.

The following abbreviations are used throughout the Examples: "Ac" means acetyl, "AcO" or "OAc" means acetoxy, "ACN" means acetonitrile, "aq" means aqueous, "atm" means atmosphere(s), "BOC", "Boc" or "boc" means N-tert-butoxycarbonyl, "Bn" means benzyl, "Bu" means butyl, "nBu" means normal-butyl, "tBu" means tert-butyl, "Cbz" means benzyloxycarbonyl, "DCM" ($CH_2Cl_2$) means methylene chloride/dichloromethane, "de" means diastereomeric excess, "DEA" means diethylamine, "DIPEA" means diisopropylethyl amine, "DMA" means N,N-dimethylacetamide, "DMAP" means 4-dimethylaminopyridine, "DMF" means N,N-dimethyl formamide, "DMSO" means dimethylsulfoxide, "ee" means enantiomeric excess, "Et" means ethyl, "EtOAc" means ethyl acetate, "EtOH" means ethanol, "HATU" means 1-[bis(dimethylamino)methylene]-1H-1,2,3-triazolo[4,5-b]pyridinium 3-oxid hexafluorophosphate, "HOAc" or "AcOH" means acetic acid, "i-Pr" or "ⁱPr" means isopropyl, "IPA" means isopropyl alcohol, "Me" means methyl, "MeOH" means methanol, "MS" means mass spectrometry, "MTBE" means methyl tert-butyl ether, "Ph" means phenyl, "sat." means saturated, "SFC" means supercritical fluid chromatography, "T3P" means propylphosphonic anhydride, "TFA" means trifluoroacetic acid, "THF" means tetrahydrofuran, "TLC" means thin layer chromatography, "Rf" means retention fraction, "~" means approximately, "rt" means retention time, "h" means hours, "min" means minutes.

EXAMPLES

Preparation of Synthetic Intermediates

Intermediate 1: benzyl {1-tert-butyl-3-[(1S,3R)-3-hydroxycyclopentyl]-1H-pyrazol-5-yl}carbamate Intermediate 2: benzyl {1-tert-butyl-3-[(1R,3S)-3-hydroxycyclopentyl]-1H-pyrazol-5-yl}carbamate

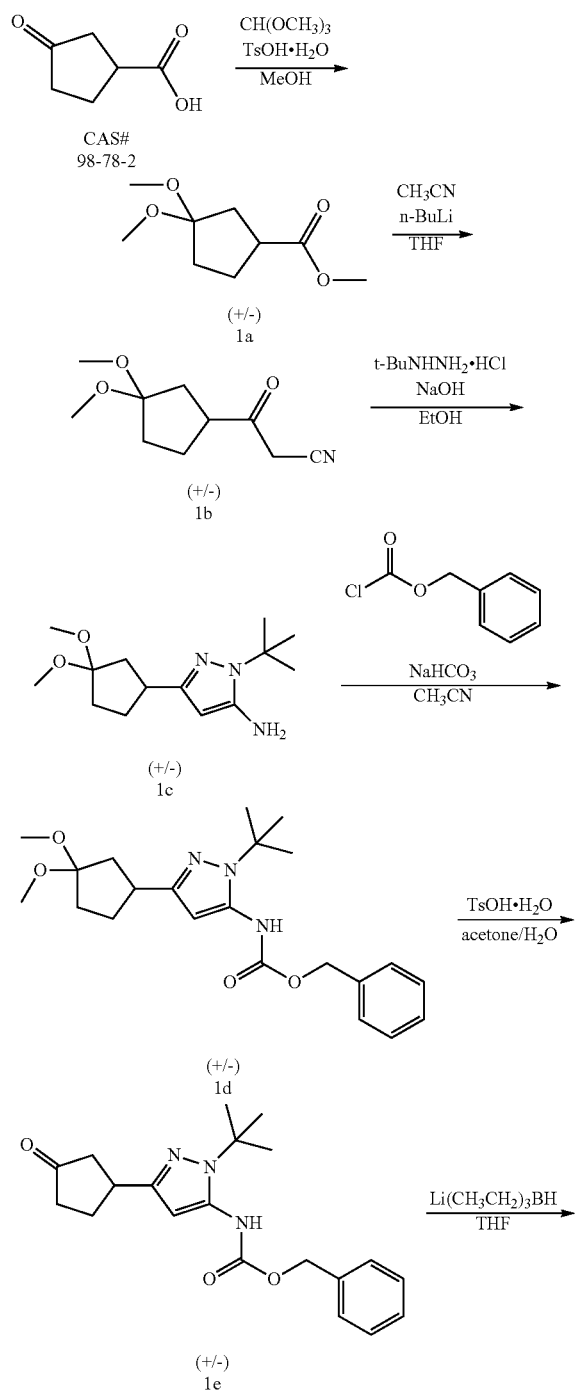

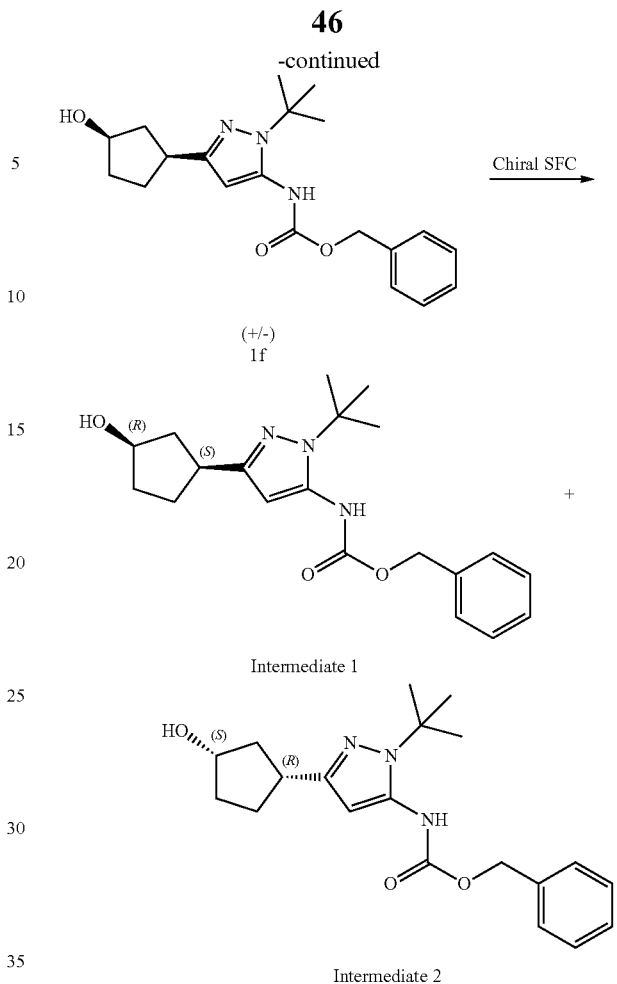

Two parallel reactions, each containing a solution of (±)-3-oxocyclopentanecarboxylic acid (CAS #98-78-2, 900 g, 7.02 mol) in methanol (5 L) at 13° C. were each treated with trimethyl orthoformate (4.47 kg, 42.15 mol, 4.62 L) and 4-toluenesulfonic acid monohydrate (26.72 g, 140.5 mmol). The mixtures were stirred at 13° C. for 25 hours. Each batch was quenched separately with sat. aq NaHCO₃ (1 L), then the two batches were combined and concentrated under vacuum to remove most of the methanol. The residue was diluted with ethyl acetate (4 L), and the layers separated. The aqueous layer was further extracted with ethyl acetate (2×1 L). The combined organic layers were washed with sat. aq NaCl (3×1 L), dried over magnesium sulfate, filtered, and concentrated under vacuum to give (±)-methyl 3,3-dimethoxycyclopentanecarboxylate (1a, 2.5 kg, 13.28 mol, 94%) as a light yellow oil. ¹H NMR (400 MHz, CHLOROFORM-d) δ=3.67 (s, 3H), 3.20 (s, 3H), 3.19 (s, 3H), 2.94-2.82 (m, 1H), 2.16-2.00 (m, 2H), 1.99-1.76 (m, 4H).

A solution of n-butyllithium (3.44 L of a 2.5 M solution in hexanes, 8.6 mol) was added to a reactor containing THF (3 L) at −65° C. Anhydrous acetonitrile (453 mL, 353 g, 8.61 mol) was added dropwise, slowly enough to maintain the internal temperature below −55° C. The mixture was stirred for an additional 1 hour at −65° C. A solution of (±)-methyl 3,3-dimethoxycyclopentanecarboxylate (1a, 810 g, 4.30 mol) in THF (1 L) was then added dropwise, slowly enough to maintain the internal temperature below −50° C. After stirring for an additional hour at −65° C., the reaction was quenched with water (4 L), neutralized with aq HCl (1 M)

to pH 7, and extracted with ethyl acetate (3×3 L). The combined organic layers were washed with sat. aq NaCl (2×3 L), dried over magnesium sulfate, filtered, and concentrated under vacuum to give crude (±)-3-(3,3-dimethoxycyclopentyl)-3-oxopropanenitrile (1b, 722 g, 3.66 mol, 85%) as a red oil, which was used without further purification.

Solid sodium hydroxide (131.4 g, 3.29 mol total) was added in portions to a suspension of tert-butylhydrazine hydrochloride (409.4 g, 3.29 mol) in ethanol (3 L) at 16-25° C. Stirring was continued at 25° C. for 1 hour. A solution of crude (±)-3-(3,3-dimethoxycyclopentyl)-3-oxopropanenitrile (1 b, 540 g, 2.74 mol) in ethanol was added at 25° C., then the mixture was heated to 75° C. internal and stirred for 30 hours. The reaction was filtered, and the filtrate concentrated under vacuum to give crude product as a red oil. This product was combined with crude from three more identically-prepared batches (each starting with 540 g 1b; 2.16 kg, 10.96 mol total for the 4 batches), and purified by silica gel chromatography (eluting with 0-35% ethyl acetate in petroleum ether), affording (±)-1-tert-butyl-3-(3,3-dimethoxycyclopentyl)-1H-pyrazol-5-amine (1c, 1.60 kg, 5.98 mol, 54% yield) as a red oil. $^1$H NMR (CHLOROFORM-d) δ=5.41 (s, 1H), 3.50 (br. s., 2H), 3.22 (s, 3H), 3.20 (s, 3H), 3.13 (tt, J=7.9, 9.6 Hz, 1H), 2.25 (dd, J=8.0, 13.3 Hz, 1H), 2.09-2.00 (m, 1H), 1.99-1.91 (m, 1H), 1.83 (dd, J=10.8, 12.8 Hz, 2H), 1.78-1.68 (m, 1H), 1.60 (s, 9H).

Benzyl chloroformate (563.6 mL, 676.3 g, 3.96 mol) was added to a chilled (0-5° C.) solution of (±)-1-tert-butyl-3-(3,3-dimethoxycyclopentyl)-1H-pyrazol-5-amine (1c, 530 g, 1.98 mol) in acetonitrile (3.5 L). The mixture was stirred at 23° C. for 2 hours, and then solid sodium hydrogen carbonate (532.9 g, 6.34 mol) was added in portions. Stirring was continued at 23° C. for 26 hours. The resulting suspension was filtered and the filtrate concentrated under vacuum to give crude (±)-benzyl [1-tert-butyl-3-(3,3-dimethoxycyclopentyl)-1H-pyrazol-5-yl]carbamate (1d, 980 g, 1.98 mol max) as a red oil, which was used in the next step without further purification.

A solution of the crude (±)-benzyl [1-tert-butyl-3-(3,3-dimethoxycyclopentyl)-1H-pyrazol-5-yl]carbamate (1d, 980 g, 1.98 mol max) in acetone (2 L) and water (2 L) at 18° C. was treated with 4-toluenesulfonic acid monohydrate (48.75 g, 256.3 mmol). The mixture was heated to 60° C. internal for 20 hours. After concentration under vacuum to remove most of the acetone, the aqueous residue was extracted with dichloromethane (3×3 L). The combined organic extracts were dried over sodium sulfate, filtered, and concentrated under vacuum to a crude red oil. This crude product was combined with crude from two other identically-prepared batches (each derived from 1.98 mol 1c, 5.94 mol total for the 3 batches), and purified by silica gel chromatography (eluting with 0-50% ethyl acetate in petroleum ether) to give (±)-benzyl [1-tert-butyl-3-(3-oxocyclopentyl)-1H-pyrazol-5-yl]carbamate (1e, 1.6 kg) as a yellow solid. This solid was stirred in 10:1 petroleum ether/ethyl acetate (1.5 L) at 20° C. for 18 hours. The resulting suspension was filtered, the filter cake washed with petroleum ether (2×500 mL), and the solids dried under vacuum to give (±)-benzyl [1-tert-butyl-3-(3-oxocyclopentyl)-1H-pyrazol-5-yl]carbamate (1e, 1.4 kg, 3.9 mol, 66% combined for the three batches). $^1$H NMR (DMSO-d$_6$) δ=9.12 (br. s., 1H), 7.56-7.13 (m, 5H), 6.03 (s, 1H), 5.12 (s, 2H), 3.41-3.27 (m, 1H), 2.48-2.39 (m, 1H), 2.34-2.10 (m, 4H), 1.98-1.81 (m, 1H), 1.48 (s, 9H).

A solution of (±)-benzyl [1-tert-butyl-3-(3-oxocyclopentyl)-1H-pyrazol-5-yl]carbamate (1e, 320 g, 0.900 mol) in THF (1.5 L) was degassed under vacuum and purged with dry nitrogen (3 cycles), then cooled to −65° C. internal. A solution of lithium triethylborohydride (1.0 M in THF, 1.80 L, 1.80 mol) was added dropwise at a rate which maintained the internal temperature below −55° C., then stirring was continued at −65° C. for 1.5 hours. The reaction mixture was quenched with sat. aq NaHCO$_3$ (1.5 L) at −40 to −30° C. Hydrogen peroxide (30% aqueous, 700 g) was added to the mixture dropwise, while the internal temperature was maintained at −10 to 0° C. The mixture was stirred at 10° C. for 1 hour, then extracted with ethyl acetate (3×2 L). The combined organic layers were washed with sat. aq Na$_2$SO$_3$ (2×1 L) and sat. aq NaCl (2×1 L). The organics were dried over magnesium sulfate, filtered, and concentrated under vacuum to a crude yellow oil. The crude product from this batch was combined with crude from three other, identically-prepared batches (each starting from 0.900 mol 1e, for a total of 3.60 mol) for purification. Before chromatography, the combined mixture showed ~3.3:1 cis/trans ratio by NMR. The combined crude product was purified twice by silica gel chromatography, eluting with 0-50% ethyl acetate in dichloromethane), affording (±)-trans-benzyl [1-tert-butyl-3-(3-hydroxycyclopentyl)-1H-pyrazol-5-yl]carbamate (if, 960 g) as a light yellow solid, which was further purified by trituration, as described below.

A previous batch of 1f had been obtained from smaller-scale reactions, starting from a total of 120 g 1e (0.34 mol). The columned product from this batch was combined with the columned product from the batch above (which had been derived from 3.60 mol 1e, for a total of 3.94 mol 1e used for all the combined batches), suspended in 10:1 dichloromethane/methanol (1.5 L), and stirred at 20° C. for 16 hours. The suspension was filtered, and the filter cake washed with petroleum ether (2×500 mL). The solids were dried under vacuum to give clean (±)-trans-benzyl [1-tert-butyl-3-(3-hydroxycyclopentyl)-1H-pyrazol-5-yl]carbamate (if, 840 g, 2.35 mol, 60% total yield for all the combined batches) as a white solid. $^1$H NMR (400 MHz, DMSO-d$_6$) δ=9.07 (br. s., 1H), 7.45-7.27 (m, 5H), 5.92 (s, 1H), 5.11 (s, 2H), 4.57 (d, J=4.5 Hz, 1H), 4.21-4.07 (m, 1H), 2.88 (quin, J=8.6 Hz, 1H), 2.24-2.13 (m, 1H), 1.92-1.78 (m, 1H), 1.78-1.62 (m, 2H), 1.61-1.53 (m, 1H), 1.47 (s, 9H), 1.52-1.43 (m, 1H). MS: 358 [M+H]$^+$.

The enantiomers of (±)-trans-benzyl [1-tert-butyl-3-(3-hydroxycyclopentyl)-1H-pyrazol-5-yl]carbamate (if, 700 g, 1.96 mol) were separated by chiral SFC.

The product from the first-eluting enantiomer peak (310 g solid) was suspended in methanol/petroleum ether (1:10, 1 L) and stirred at 25° C. for 1 hour. The suspension was filtered, the filter pad washed with petroleum ether (2×500 mL), and the solids dried under vacuum to give benzyl {1-tert-butyl-3-[(1 S,3R)-3-hydroxycyclopentyl]-1H-pyrazol-5-yl}carbamate (Intermediate 1, 255 g, 713 mmol, 36%, >99% ee) as a white solid. $^1$H NMR (400 MHz, DMSO-d$_6$) δ=9.08 (br. s., 1H), 7.58-7.20 (m, 5H), 5.92 (s, 1H), 5.11 (s, 2H), 4.57 (d, J=4.4 Hz, 1H), 4.19-4.09 (m, 1H), 2.88 (quin, J=8.6 Hz, 1H), 2.24-2.13 (m, 1H), 1.91-1.79 (m, 1H), 1.79-1.61 (m, 2H), 1.61-1.53 (m, 1H), 1.47 (s, 9H), 1.52-1.44 (m, 1H). MS: 358 [M+H]$^+$. Optical rotation [α]$_D$+ 3.76 (c 1.0, MeOH). Chiral purity: >99% ee, retention time 3.371 min. Chiral SFC analysis was performed on a ChiralPak AD-3 150×4.6 mm ID, 3 μm column heated to 40° C., eluted with a mobile phase of CO$_2$ and a gradient of 0-40% methanol+0.05% DEA over 5.5 min, then held at 40% for 3 min; flowing at 2.5 mL/min.

The product from the second-eluting enantiomer peak (300 g solid) was suspended in methanol/petroleum ether (1:10, 1 L) and stirred at 25° C. for 1 hour. The suspension was filtered, the filter pad washed with petroleum ether (2×500 mL), and the solids dried under vacuum to give benzyl {1-tert-butyl-3-[(1R,3S)-3-hydroxycyclopentyl]-1H-pyrazol-5-yl}carbamate (Intermediate 2, 255 g, 713 mmol, 36%, 94% ee) as a white solid. $^1$H NMR (400 MHz, DMSO-$d_6$) δ=9.08 (br. s., 1H), 7.55-7.19 (m, 5H), 5.92 (s, 1H), 5.11 (s, 2H), 4.57 (d, J=4.4 Hz, 1H), 4.23-4.07 (m, 1H), 2.88 (quin, J=8.7 Hz, 1H), 2.23-2.14 (m, 1H), 1.90-1.79 (m, 1H), 1.77-1.61 (m, 2H), 1.61-1.53 (m, 1H), 1.47 (s, 9H), 1.52-1.44 (m, 1H). MS: 358 [M+H]$^+$. Optical rotation [α]$_D$-2.43 (c 1.0, MeOH). Chiral purity: 94% ee, retention time 3.608 min. Chiral SFC analysis was performed on a ChiralPak AD-3 150×4.6 mm ID, 3 μm column heated to 40° C., eluted with a mobile phase of $CO_2$ and a gradient of 0-40% methanol+0.05% DEA over 5.5 min, then held at 40% for 3 min; flowing at 2.5 mL/min.

A sample of the second-eluting enantiomer from a previous batch with [α]$_D$-3.1 (c 1.1, MeOH) and 96% ee was crystalized from dichloroethane/pentane. A crystal structure was obtained by small-molecule X-ray crystallography, which showed (1R,3S) geometry. The absolute stereochemistry of Intermediate 2 was thus assigned (1R,3S) based on its comparable optical rotation and order of elution in the analytical method. Intermediate 1, the enantiomer of Intermediate 2, was thus assigned (1S,3R) stereochemistry.

Intermediate 3: (5-methyl-1,3-oxazol-2-yl)acetic Acid

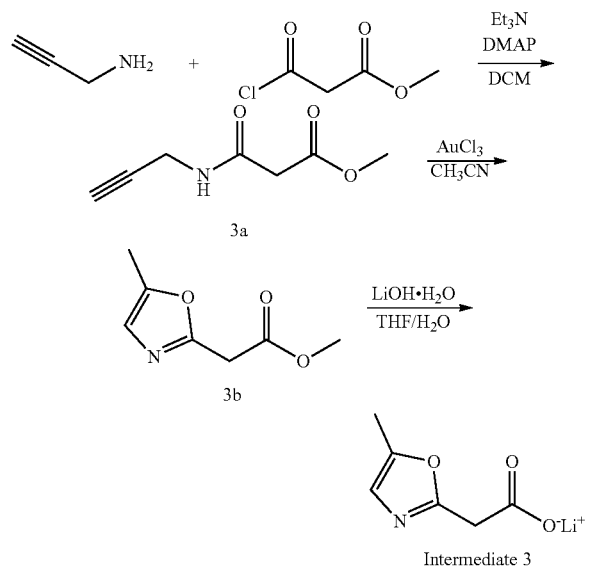

A solution of prop-2-yl-1-amine (25.0 g, 450 mmol) in dichloromethane (500 mL) at 15° C. was treated with triethylamine (138 g, 1360 mmol) and DMAP (5.55 g, 45.4 mmol). The mixture was cooled to 0° C. and methyl 3-chloro-3-oxopropanoate (74.4 g, 545 mmol) was added dropwise over 30 minutes. The resulting solution was stirred at 15° C. for 16 hours, then allowed to stand at that temperature for 2 days. The resulting suspension was filtered, the filtrate concentrated under vacuum, and the residue purified by silica gel chromatography (eluting with 60% EtOAc/petroleum ether) to give methyl 3-oxo-3-(prop-2-yn-1-ylamino)propanoate (3a, 47 g, 67%, 90% pure by NMR) as a light yellow oil. $^1$H NMR (400 MHz, CHLOROFORM-d) δ=7.43 (br s, 1H), 4.09 (dd, J=2.6, 5.3 Hz, 2H), 3.76 (s, 3H), 3.36 (s, 2H), 2.25 (s, 1H).

Two parallel batches were run according to the following procedure: A solution of methyl 3-oxo-3-(prop-2-yn-1-ylamino)propanoate (3a, 23.5 g, 151 mmol) in acetonitrile (300 mL) was treated with gold trichloride (2.50 g, 8.24 mmol) at room temperature (20° C.). The resulting mixture was heated to 70° C. for 16 hours in the dark. The two batches were then combined, filtered to remove the catalyst, and the filtrate concentrated to dryness. The residue was purified by silica gel chromatography (eluting with 40% EtOAc/petroleum ether) to give to give methyl (5-methyl-1,3-oxazol-2-yl)acetate (3b, 26.5 g, 56.5% for the combined batches) as a light yellow oil. $^1$H NMR (400 MHz, CHLOROFORM-d) δ=6.68 (d, J=1.0 Hz, 1H), 3.80 (s, 2H), 3.75 (s, 3H), 2.30 (d, J=1.3 Hz, 3H).

A solution of methyl (5-methyl-1,3-oxazol-2-yl)acetate (3b, 26.5 g, 170.8 mmol) in THF (80 mL) and water (20 mL) was treated with lithium hydroxide monohydrate (7.17 g, 171 mmol) and stirred at room temperature (25° C.) for 2 hours. The mixture was concentrated to remove most of the THF, then the residue diluted with water (25 mL) and extracted with dichloromethane (2×30 mL). The aqueous layer was concentrated to give crude product (~26 g), which was further purified by trituration with EtOAc/MeOH (v/v 10/1) to give lithium (5-methyl-1,3-oxazol-2-yl)acetate (Intermediate 3, 21.7 g, 90%) as a light yellow solid. $^1$H NMR (400 MHz, DEUTERIUM OXIDE) δ=6.63 (d, J=1.0 Hz, 1H), 3.59 (s, 2H), 2.22 (d, J=1.0 Hz, 3H).

Intermediate 4: Lithium (5-methoxypyrazin-2-yl)acetate

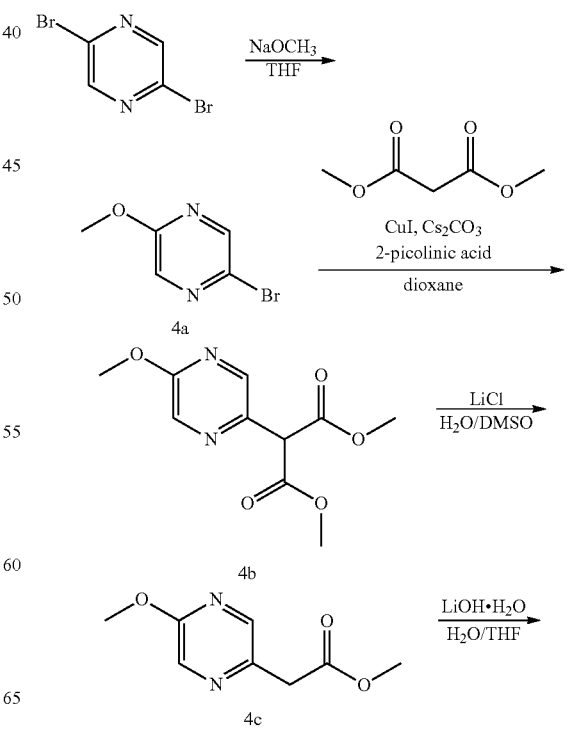

-continued

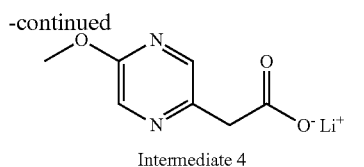

Intermediate 4

A solution of 2,5-dibromopyrazine (30.0 g, 126 mmol) in THF (252 mL) was cooled to 0° C. Sodium methoxide (25 wt % solution in methanol, 29.0 mL, 27.3 g, 126 mmol) was added dropwise over 18 minutes. The solution was allowed to warm to room temperature and stirred for 37 hours. The suspension was filtered, the flask and filter cake rinsed with a small amount of THF, and the filtrate concentrated under vacuum to give 2-bromo-5-methoxypyrazine (4a, 23.80 g, 100%) as a solid. $^1$H NMR (400 MHz, CHLOROFORM-d) δ=8.20 (d, J=1.2 Hz, 1H), 8.03 (d, J=1.2 Hz, 1H), 3.97 (s, 3H).

A nitrogen-purged flask was charged with copper(I) iodide (2.82 g, 14.8 mmol), 2-picolinic acid (3.65 g, 29.6 mmol), cesium carbonate (36.2 g, 111 mmol), and 2-bromo-5-methoxypyrazine (4a, 7.00 g, 37.03 mmol). The flask was again purged with nitrogen, then dry dioxane (250 mL) and dimethyl malonate (22 mL, 192 mmol) were introduced by syringe. Nitrogen was bubbled through the solution for 10 minutes. The mixture was heated at 100° C. for 36 hours. After cooling to room temperature, the suspension was filtered, and the filtrate concentrated to an oil. The solids remaining in the filter cake were suspended in water (150 mL) and the solution slowly acidified with 4M HCl (~17 mL). This solution was extracted with ethyl acetate (2×150 mL). The ethyl acetate extracts were combined with the crude oil obtained from the filtrate, and all were washed with sat. aq NH$_4$Cl (50 mL), dried over sodium sulfate, filtered, and concentrated. The residue was purified by silica gel chromatography (eluting with 0-50% ethyl acetate in heptane) to give dimethyl (5-methoxypyrazin-2-yl)propanedioate (4b, 5.94 g, 67%) as an oil which solidifies on standing. $^1$H NMR (400 MHz, CHLOROFORM-d) δ=8.23 (d, J=1.3 Hz, 1H), 8.18 (d, J=1.3 Hz, 1H), 4.90 (s, 1H), 3.97 (s, 3H), 3.79 (s, 6H).

A solution of dimethyl (5-methoxypyrazin-2-yl)propanedioate (4b, 7.30 g, 30.4 mmol) in DMSO (51 mL) and water (3.4 mL) was cooled to 0° C. Solid lithium chloride (5.15 g, 122 mmol) was added and the mixture heated to 100° C. for 17 hours. The dark red solution was partitioned between ethyl acetate (150 mL) and water (300 mL). The aqueous layer was further extracted with ethyl acetate (3×50 mL). The combined organics were washed with half-saturated aq NaCl and sat. aq NaCl, dried over sodium sulfate, filtered, and concentrated. The crude product was purified by silica gel chromatography (eluting with 0-60% ethyl acetate in heptane), affording methyl (5-methoxypyrazin-2-yl)acetate (4c, 3.86 g, 70%) as an oil. $^1$H NMR (400 MHz, CHLOROFORM-d) δ=8.18 (d, J=1.3 Hz, 1H), 8.06 (d, J=1.2 Hz, 1H), 3.96 (s, 3H), 3.79 (s, 2H), 3.73 (s, 3H).

A suspension of methyl (5-methoxypyrazin-2-yl)acetate (4c, 3.86 g, 21.2 mmol) and lithium hydroxide monohydrate (889 mg, 21.2 mmol) in THF (42 mL) and water (42 mL) was stirred at 25° C. for 14 hours. Unreacted ester was still present by LCMS, so additional lithium hydroxide monohydrate (50 mg, 1.2 mmol) was added and stirring continued at 25° C. for 6 hours. Conversion was still not complete, so even more lithium hydroxide monohydrate (110 mg, 2.62 mmol; total 1.049 g, 25 mmol) was added and the mixture heated to 30° C. for 2 hours. The THF was removed under vacuum, and the aqueous residue lyophilized to dryness, leaving lithium (5-methoxypyrazin-2-yl)acetate (Intermediate 4, 4.272 g, 115% of the theoretical mass of 3.71 g), as a mixture with lithium hydroxide. $^1$H NMR (400 MHz, DEUTERIUM OXIDE) δ=8.14 (d, J=1.3 Hz, 1H), 8.01 (d, J=1.2 Hz, 1H), 3.93 (s, 3H), 3.64 (s, 2H).

Intermediate 5: Lithium 3-(methoxymethyl)-1-methyl-1H-pyrazole-5-carboxylate

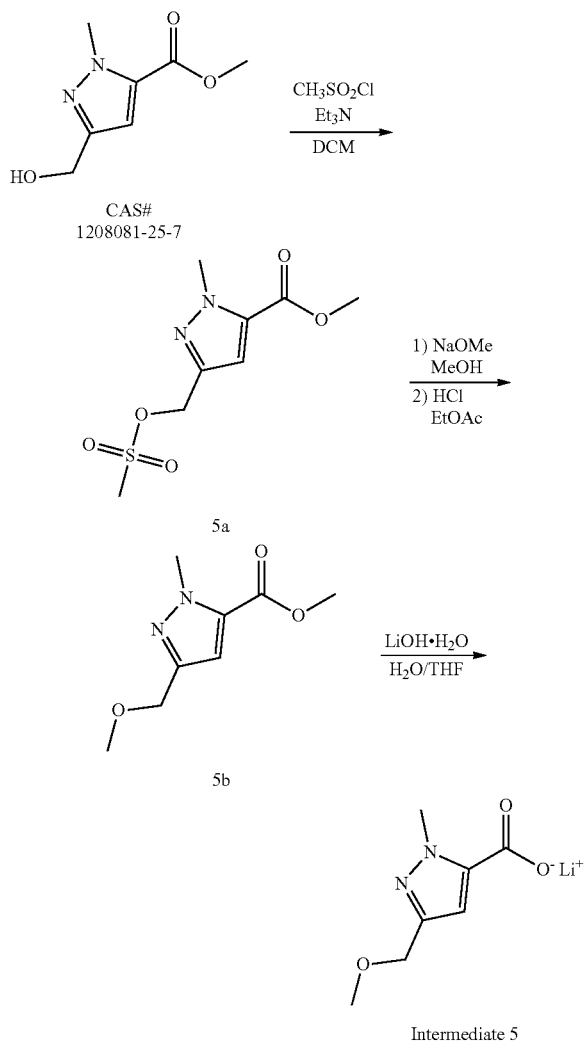

Intermediate 5

A solution of methanesulfonyl chloride (11.32 g, 98.8 mmol) in dichloromethane (50 mL) was added dropwise to a cooled (0° C.) mixture of methyl 3-(hydroxymethyl)-1-methyl-1H-pyrazole-5-carboxylate (CAS #1208081-25-7, 15.0 g, 88.1 mmol) and diisopropylethyl amine (14.8 g, 115 mmol) in dichloromethane (250 mL). The mixture was stirred at 0° C. for 45 minutes after the addition was complete. The reaction mixture was washed with sat. aq NH$_4$Cl, and the organic layer dried over sodium sulfate, filtered, and concentrated to give methyl 1-methyl-3-{[(methylsulfonyl)oxy]methyl}-1H-pyrazole-5-carboxylate (5a, 22.6 g, >99%) as a yellow oil, which was used without further purification. $^1$H NMR (400 MHz, CHLOROFORM-d) δ=6.98 (s, 1H), 5.26 (s, 2H), 4.20 (s, 3H), 3.91 (s, 3H), 3.03 (s, 3H).

A solution of methyl 1-methyl-3-{[(methylsulfonyl)oxy]methyl}-1H-pyrazole-5-carboxylate (5a, 22.6 g, 91.0 mmol) in methanol (200 mL) at room temperature was treated with solid sodium methoxide (9.84 g, 182 mmol) in small portions. The reaction was heated to 70° C. for 30 minutes. TLC suggested partial hydrolysis of the ester, so to re-esterify, the cloudy mixture was acidified with 4M HCl in ethyl acetate (40 mL, 160 mmol), and heating continued at 70° C. for 5 hours. The mixture was concentrated to dryness, leaving a white solid. This solid was extracted with ethyl acetate/petroleum ether (1/3, 3×200 mL). The combined extracts were concentrated to dryness, then the residual solid re-extracted with ethyl acetate/petroleum ether (1/3, 100 mL), dried over sodium sulfate, filtered, and concentrated to give methyl 3-(methoxymethyl)-1-methyl-1H-pyrazole-5-carboxylate (5b, 14.5 g, 86%, 80% pure by NMR) as a light yellow liquid which solidified on standing. Major component only: $^1$H NMR (400 MHz, CHLOROFORM-d) δ=6.83 (s, 1H), 4.45 (s, 2H), 4.16 (s, 3H), 3.88 (s, 3H), 3.39 (s, 3H).

A solution of methyl 3-(methoxymethyl)-1-methyl-1H-pyrazole-5-carboxylate (5b, 14.5 g, 78.7 mmol) and lithium hydroxide monohydrate (3.47 g, 82.7 mmol) in THF (150 mL) and water (50 mL) was stirred at room temperature for 16 hours. The THF was removed under vacuum, and the residue dissolved in water (100 mL) and extracted with dichloromethane (3×30 mL). The organic layers were discarded. The aqueous layer was concentrated and dried under vacuum to give lithium 3-(methoxymethyl)-1-methyl-1H-pyrazole-5-carboxylate (Intermediate 5, 12.85 g, 92%) as a yellow solid. $^1$H NMR (400 MHz, DMSO-$d_6$) δ=6.37 (s, 1H), 4.24 (s, 2H), 4.01 (s, 3H), 3.20 (s, 3H). MS: 171 [M+H]$^+$.

General Methods and Representative Examples

Method A

Example 1: (1R,3S)-3-(3-{[(2-methoxypyridin-4-yl)acetyl]amino}-1H-pyrazol-5-yl)cyclopentyl propylcarbamate

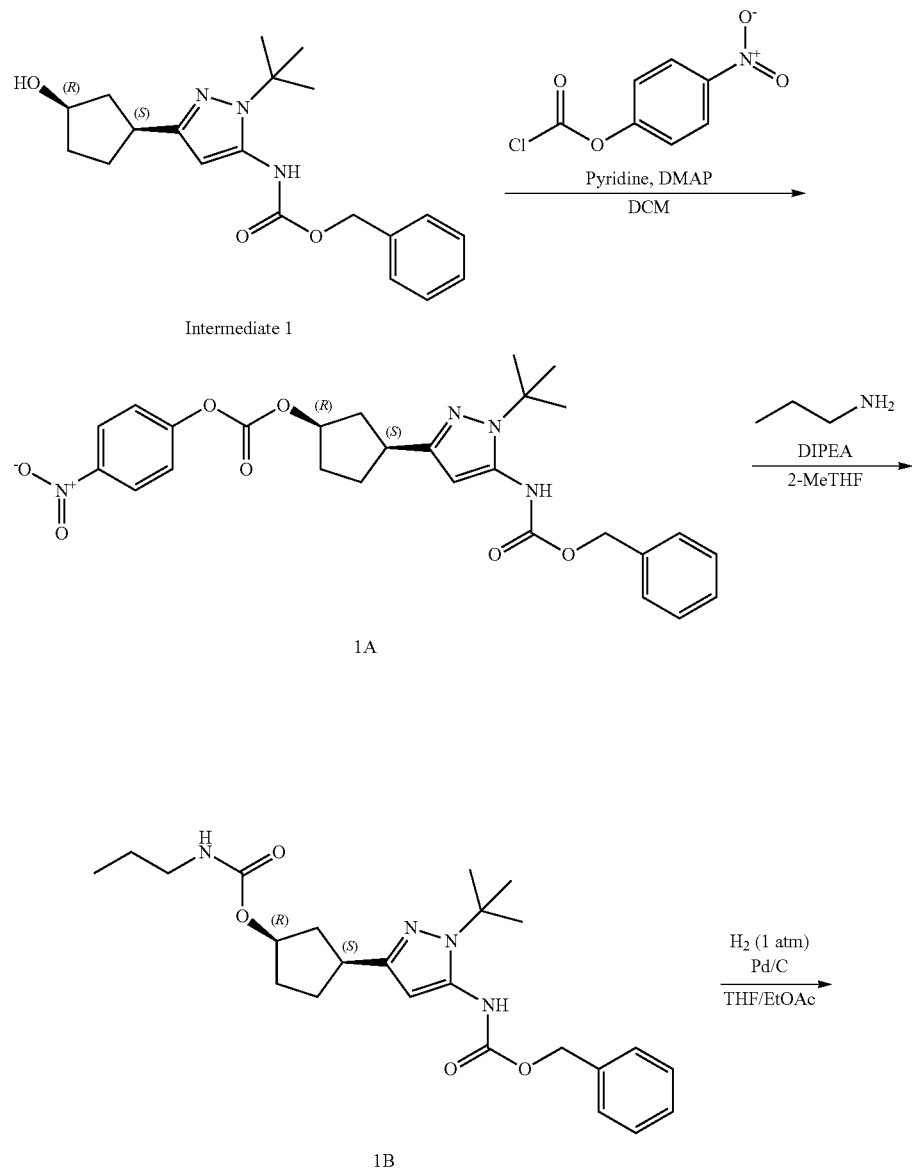

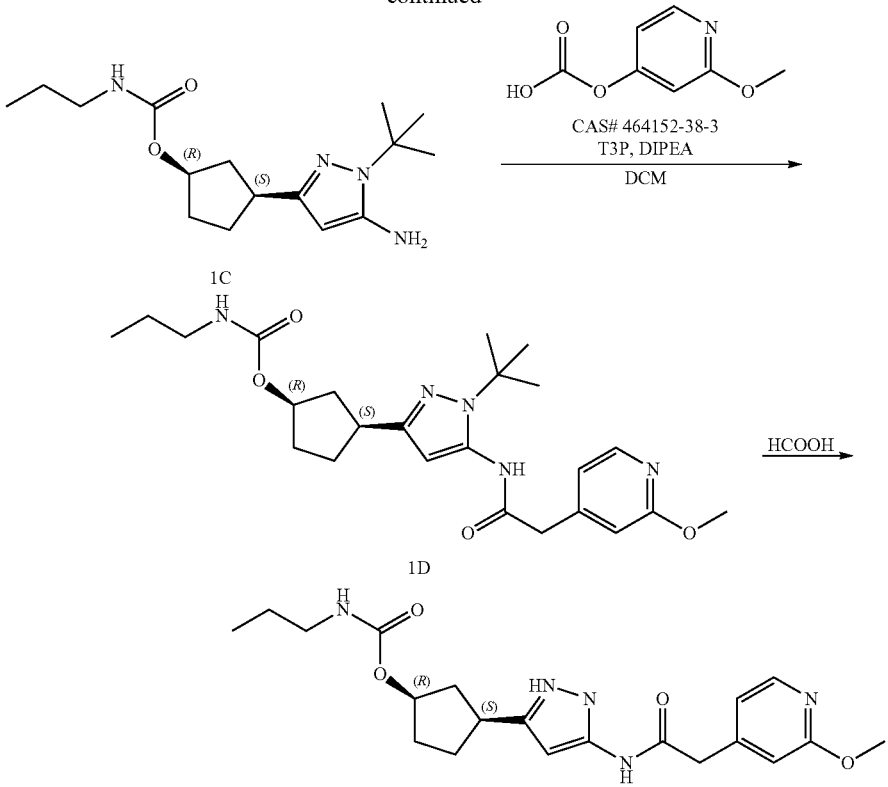

Example 1

A room-temperature solution of benzyl {1-tert-butyl-3-[(1S,3R)-3-hydroxycyclopentyl]-1H-pyrazol-5-yl}carbamate (Intermediate 1, 5.00 g, 14.0 mmol) and 4-nitrophenyl chloroformate (4.23 g, 21.0 mmol) in anhydrous dichloromethane (50 mL) was treated with pyridine (3.40 mL, 42.0 mmol) and 4-(dimethylamino)pyridine (170 mg, 1.4 mmol). After stirring at room temperature overnight, the solution was concentrated and purified by silica gel chromatography (eluting with 0-100% ethyl acetate in n-heptane) to give (1R,3S)-3-(5-{[(benzyloxy)carbonyl]amino}-1-tert-butyl-1H-pyrazol-3-yl)cyclopentyl 4-nitrophenyl carbonate (1A, 7.30 g, 100%) as a solid foam. $^1$H NMR (400 MHz, CHLOROFORM-d) δ=8.24-8.14 (m, 2H), 7.36-7.22 (m, 7H), 6.21 (br. s., 1H), 6.06 (br. s., 1H), 5.25-5.15 (m, 1H), 5.12 (s, 2H), 3.15-2.97 (m, 1H), 2.58-2.47 (m, 1H), 2.09-1.78 (m, 5H), 1.51 (s, 9H). MS: 523 [M+H]$^+$.

A solution of (1R,3S)-3-(5-{[(benzyloxy)carbonyl]amino}-1-tert-butyl-1H-pyrazol-3-yl)cyclopentyl 4-nitrophenyl carbonate (1A, 36 g, 69 mmol) in 2-methyltetrahydrofuran (300 mL) was cooled to 10° C. Diisopropylethyl amine (26.7 g, 36 mL, 207 mmol) and propan-1-amine (6.11 g, 8.52 mL, 103 mmol) were added, and the solution stirred at 10° C. for 16 hours. After concentrating to dryness, the residue was diluted with ethyl acetate (600 mL), washed with 1M NaOH (4×200 mL), and then with sat. aq NaCl (100 mL). The organic layer was dried over sodium sulfate, filtered, and concentrated to give crude benzyl (1-tert-butyl-3-{(1S,3R)-3-[(propylcarbamoyl)oxy]cyclopentyl}-1H-pyrazol-5-yl)carbamate (1B, 30 g, 98%), which was used without further purification.

A room-temperature (20-25° C.) suspension of Pd/C (50% H$_2$O, 8 g) and crude benzyl (1-tert-butyl-3-{(1S,3R)-3-[(propylcarbamoyl)oxy]cyclopentyl}-1H-pyrazol-5-yl)carbamate (1B, 30 g, 68 mmol) in ethyl acetate (300 mL) and THF (150 mL) was degassed and purged with hydrogen (3 cycles), then stirred at room temperature under a hydrogen balloon for 16 hours. The suspension was filtered, the filtrate concentrated under vacuum, and the residue crystallized from ethyl acetate (50 mL) and petroleum ether (300 mL), affording (1R,3S)-3-(5-amino-1-tert-butyl-1H-pyrazol-3-yl)cyclopentyl propylcarbamate (1C, 17.65 g, 84%) as a white solid. $^1$H NMR (400 MHz, DMSO-d$_6$) δ=7.00 (br t, J=5.6 Hz, 1H), 5.23 (s, 1H), 4.95 (br s, 1H), 4.82-4.58 (m, 2H), 2.91 (q, J=6.6 Hz, 2H), 2.85-2.73 (m, 1H), 2.37-2.21 (m, 1H), 1.92-1.76 (m, 2H), 1.72-1.52 (m, 3H), 1.48 (s, 9H), 1.44-1.32 (m, 2H), 0.82 (t, J=7.4 Hz, 3H). MS: 309 [M+H]$^+$.]$^+$. Optical rotation [α]$_D$–4.04 (c 0.89, MeOH). Chiral purity: 98% ee by chiral analytical SFC.

A cooled (10° C.) mixture of (1R,3S)-3-(5-amino-1-tert-butyl-1H-pyrazol-3-yl)cyclopentyl propylcarbamate (1C, 8.65 g, 28.05 mmol), (2-methoxypyridin-4-yl)acetic acid (CAS #464152-38-3, 5.86 g, 33.7 mmol) diisopropylethyl amine (14.7 mL, 84.1 mmol) and propylphosphonic anhydride (T3β ®, 50 wt % solution in EtOAc, 53.5 g, 84.1 mmol) in dichloromethane (250 mL) was stirred for 16 hours. The reaction was quenched with sat. aq Na$_2$CO$_3$ (20 mL) and extracted with dichloromethane (100 mL). The organic layer was washed with more sat. aq Na$_2$CO$_3$ (2×200 mL) and sat. aq NaCl (100 mL), dried over anhydrous sodium sulfate, filtered, and concentrated to dryness. For purification, this batch was combined with two other similarly-prepared batches derived from 1.0 g and 8.0 g 1C (total SM for the three batches=17.65 g, 57.23 mmol 1C). Silica gel chromatography (eluting with 0-60% EtOAc/petroleum ether) gave (1R,3S)-3-(1-tert-butyl-5-{[(2-methoxypyridin-4-yl)acetyl]amino}-1H-pyrazol-3-yl)cyclopentyl propylcarbamate (1D, 25 g, 95% yield for the combined batches). MS: 458 [M+H]$^+$.

A solution of (1R,3S)-3-(1-tert-butyl-5-{[(2-methoxypyridin-4-yl)acetyl]amino}-1H-pyrazol-3-yl)cyclopentyl propylcarbamate (1D, 20.5 g, 44.8 mmol) in formic acid (50 mL) was stirred at 75° C. for 20 hours. For purification, this batch was combined with a smaller batch (derived from 4.50 g, 9.84 mmol 1D, for a total of 25.0 g, 54.6 mmol), concentrated to dryness, and purified by preparative HPLC [Phenomenex Gemini C18 250×50 mm×10 μm column; eluting with a gradient of water (0.05% ammonium hydroxide v/v) in ACN over 15 minutes; flowing at 110 mL/min].

Pure (1R,3S)-3-(3-{[(2-methoxypyridin-4-yl)acetyl]amino}-1H-pyrazol-5-yl)cyclopentyl propylcarbamate (Example 1, 16.61 g, 76% yield for the combined batches) as a pale yellow solid. $^1$H NMR (400 MHz, CHLOROFORM-d) δ=11.62-9.81 (m, 1H), 9.06 (br s, 1H), 8.06 (d, J=5.3 Hz, 1H), 6.79 (d, J=5.3 Hz, 1H), 6.66 (s, 1H), 6.50 (s, 1H), 5.24-4.94 (m, 2H), 3.88 (s, 3H), 3.58 (s, 2H), 3.19-2.83 (m, 3H), 2.54-2.28 (m, 1H), 2.04 (br s, 1H), 1.97-1.70 (m, 4H), 1.54-1.34 (m, 2H), 0.85 (br t, J=7.0 Hz, 3H). MS: 402 [M+H]$^+$. Optical rotation [α]$_D$+17.1 (c 1.06, MeOH). Chiral purity: 96% ee by chiral analytical SFC.

Example 2: (1R,3S)-3-(3-{[(2-methyl-1,3-thiazol-5-yl)acetyl]amino}-1H-pyrazol-5-yl)cyclopentyl propan-2-ylcarbamate

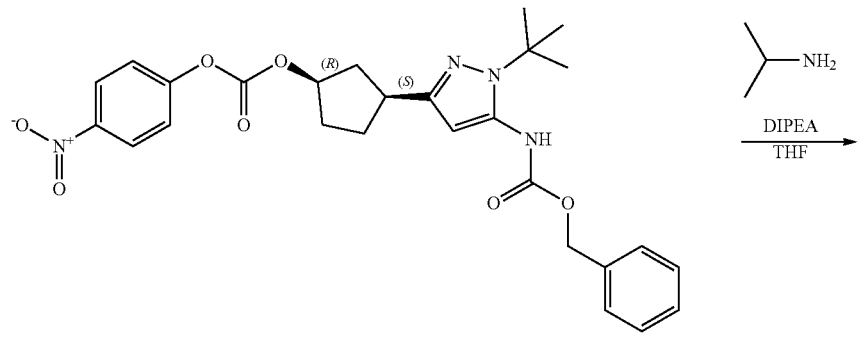

1A

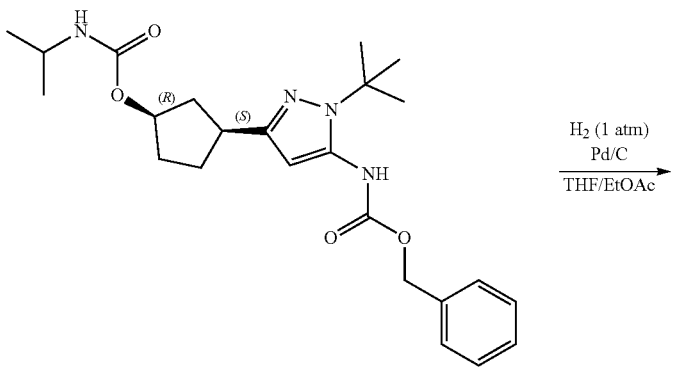

2A

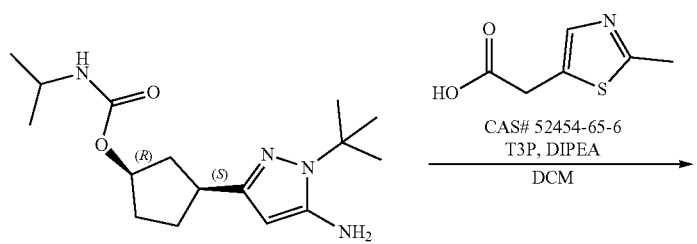

2B

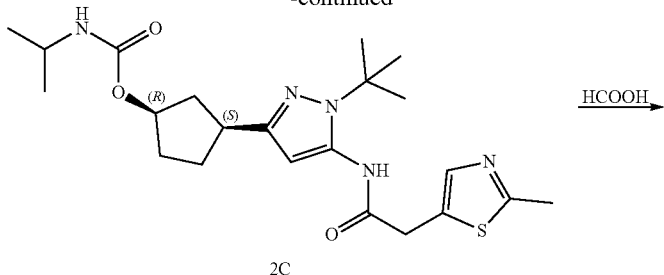

2C

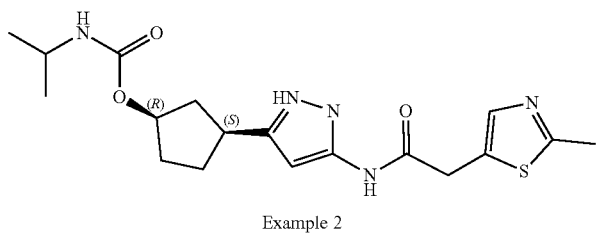

Example 2

A solution of (1R,3S)-3-(5-{[(benzyloxy)carbonyl]amino}-1-tert-butyl-1H-pyrazol-3-yl)cyclopentyl 4-nitrophenyl carbonate (1A, 2.00 g, 3.83 mmol), isopropyl amine (294 mg, 4.98 mmol), and diisopropylethyl amine (3.33 mL, 19.1 mmol) in THF (20 mL) was stirred at 10° C. for 4 hours. After concentrating to dryness, the residue was diluted with ethyl acetate (100 mL), and the solution washed with 1M sodium hydroxide (4×50 mL) and sat. aq NaCl (30 mL). The organic layer was dried over sodium sulfate, filtered, and concentrated to give crude benzyl (1-tert-butyl-3-{(1S,3R)-3-[(propan-2-ylcarbamoyl)oxy]cyclopentyl}-1H-pyrazol-5-yl)carbamate (2A, 1.8 g, 100% crude).

A room temperature (10° C.) suspension of the crude benzyl (1-tert-butyl-3-{(1 S,3R)-3-[(propan-2-ylcarbamoyl)oxy]cyclopentyl}-1H-pyrazol-5-yl)carbamate (2A, 1.8 g, 3.83 mmol) and Pd/C (wet, 200 mg) in ethyl acetate (10 mL) and THF (5 mL) was degassed and purged with hydrogen, then stirred under a hydrogen balloon at 10° C. for 16 hours. The catalyst was removed by filtration, and the filtrate concentrated to dryness. The residue was purified by preparative HPLC on a Phenomenex Gemini C18 250*50 mm*10 μm column, eluting with 25-45% water (0.05% ammonium hydroxide v/v) in acetonitrile. Lyophilization of the product-containing fractions afforded (1R,3S)-3-(5-amino-1-tert-butyl-1H-pyrazol-3-yl)cyclopentyl propan-2-ylcarbamate (2B, 1.0 g, 85%) as a yellow oil. MS: 309 [M+H]⁺.

Propylphosphonic anhydride (T3β ®, 50 wt % solution in EtOAc, 457, g. 0.718 mmol) was added to a cooled (0° C.) solution of (1R,3S)-3-(5-amino-1-tert-butyl-1H-pyrazol-3-yl)cyclopentyl propan-2-ylcarbamate (2B, 80 mg, 0.26 mmol), diisopropylethyl amine (92.7 mg, 0.718 mmol) and (2-methyl-1,3-thiazol-5-yl)acetic acid (CAS #52454-65-6, 45.1 mg, 0.287 mmol) in dichloromethane (3 mL). The mixture was allowed to stir at room temperature (10° C.) for 16 hours, then partitioned between dichloromethane (20 mL) and sat. aq Na₂CO₃ (10 mL). The organic layer was washed with sat. aq NaCl (10 mL), dried over sodium sulfate, filtered, and concentrated to give crude (1R,3S)-3-(1-tert-butyl-5-{[(2-methyl-1,3-thiazol-5-yl)acetyl]amino}-1H-pyrazol-3-yl)cyclopentyl propan-2-ylcarbamate (2C, 120 mg, 100% crude) as a yellow gum.

The crude (1R,3S)-3-(1-tert-butyl-5-{[(2-methyl-1,3-thiazol-5-yl)acetyl]amino}-1H-pyrazol-3-yl)cyclopentyl propan-2-ylcarbamate (2C, 120 mg, 0.26 mmol) was dissolved in formic acid (5 mL) and stirred at 75° C. for 20 hours. Volatiles were removed under vacuum, and the residue purified by preparative HPLC on a Xtimate C18 150*25 mm*5 μm column, eluting with 12-52% water (0.05% ammonium hydroxide v/v) in acetonitrile. Lyophilization of the product-containing fractions afforded (1R,3S)-3-(3-{[(2-methyl-1,3-thiazol-5-yl)acetyl]amino}-1H-pyrazol-5-yl)cyclopentyl propan-2-ylcarbamate (Example 2, 60.35 mg, 58%) as a white solid. ¹H NMR (400 MHz, DMSO-d6) δ=12.10 (s, 1H), 10.58 (s, 1H), 7.41 (s, 1H), 6.95 (br d, J=6.3 Hz, 1H), 6.29 (s, 1H), 4.98 (br s, 1H), 3.81 (s, 2H), 3.57 (br d, J=6.5 Hz, 1H), 3.03 (br s, 1H), 2.59 (s, 3H), 2.45 (br s, 1H), 2.07-1.81 (m, 2H), 1.78-1.44 (m, 3H), 1.03 (br d, J=6.5 Hz, 6H). MS: 392 [M+H]⁺. Chiral purity: 99% ee by chiral analytical SFC.

Example 3: (1R,3S)-3-(3-{[(1-methyl-1H-indazol-5-yl)acetyl]amino}-1H-pyrazol-5-yl)cyclopentyl ethylcarbamate

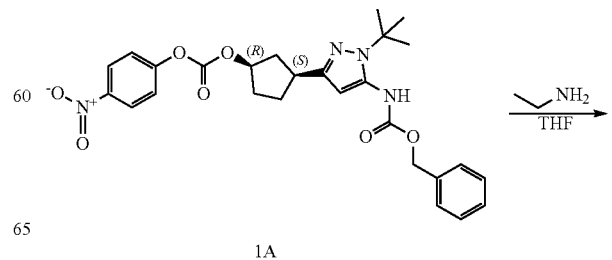

1A

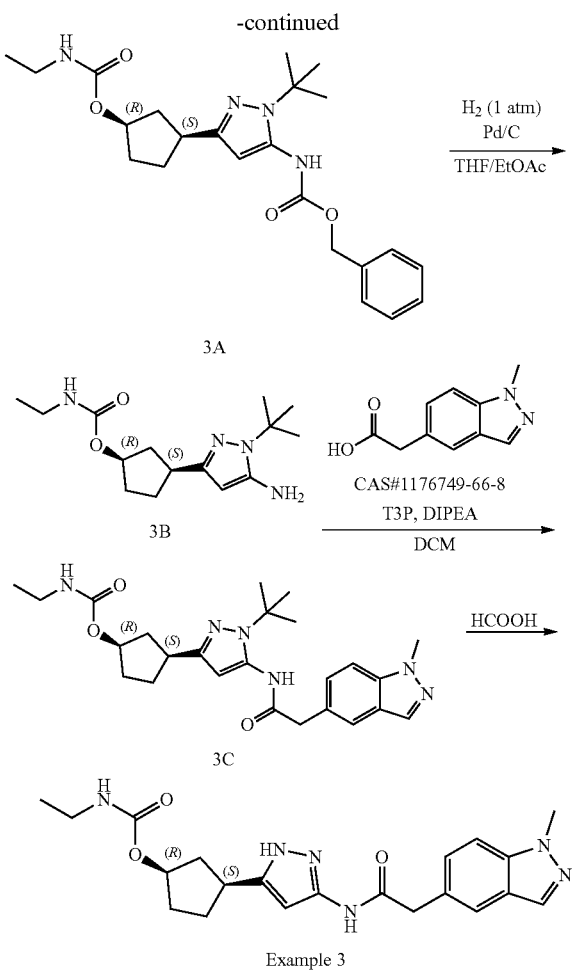

A solution of (1R,3S)-3-(5-{[(benzyloxy)carbonyl]amino}-1-tert-butyl-1H-pyrazol-3-yl)cyclopentyl 4-nitrophenyl carbonate (1A, 2.5 g, 4.8 mmol) and ethylamine (1.08 g, 23.9 mmol) in THF (20 mL) was stirred at 30° C. for 3 hours, concentrated to dryness, and the residue dissolved in dichloromethane (30 mL). The solution was washed with aq NaOH until the organic layer was colorless (5×5 mL), then washed with water (5 mL) and sat. aq NaCl (5 mL), dried over sodium sulfate, filtered, and concentrated to give crude benzyl (1-tert-butyl-3-{(1 S,3R)-3-[(ethylcarbamoyl)oxy]cyclopentyl}-1H-pyrazol-5-yl)carbamate (3A, 2.0 g, 97%, >80% pure by LCMS) as a colorless oil. MS: 429 [M+H]+, 451 [M+Na]+.

The crude benzyl (1-tert-butyl-3-{(1 S,3R)-3-[(ethylcarbamoyl)oxy]cyclopentyl}-1H-pyrazol-5-yl)carbamate (3A, 2.0 g, 4.7 mmol) was dissolved in ethyl acetate (30 mL) and THF (10 mL), the solution degassed, and 10% Pd/C catalyst (wet, 200 mg) was added. The suspension was stirred under a hydrogen balloon at room temperature (10° C.) for 2 hours. The catalyst was removed by filtration, the filtrate concentrated to dryness, and the residue purified by silica gel chromatography (eluting with 0-60% ethyl acetate in petroleum ether) to give (1R,3S)-3-(5-amino-1-tert-butyl-1H-pyrazol-3-yl)cyclopentyl ethylcarbamate (3B, 1.15 g, 84%) as a light yellow gum which solidified on standing to a light yellow solid. MS: 295 [M+H]+. 1H NMR (400 MHz, CHLOROFORM-d) δ=5.43 (s, 1H), 5.13 (br s, 1H), 4.58 (br s, 1H), 3.50 (br s, 2H), 3.31-3.13 (m, 2H), 2.99 (quin, J=8.5 Hz, 1H), 2.53-2.39 (m, 1H), 2.04-1.96 (m, 1H), 1.95-1.87 (m, 1H), 1.87-1.68 (m, 3H), 1.62 (s, 9H), 1.14 (t, J=7.2 Hz, 3H). Chiral purity: >98% ee by chiral analytical SFC.

Propylphosphonic anhydride (T3β ®, 50 wt % solution in EtOAc, 0.485 mL, 0.815 mmol) was added to a room-temperature (10° C.) solution of (1R,3S)-3-(5-amino-1-tert-butyl-1H-pyrazol-3-yl)cyclopentyl ethylcarbamate (3B, 80.0 mg, 0.272 mmol), 2-(1-methyl-1H-indazol-5-yl)acetic acid (CAS #1176749-66-8, 59.1 mg, 0.311 mmol), and diisopropylethyl amine (0.142 mL, 0.815 mmol) in dichloromethane (5 mL). The mixture was stirred for 3 hours, then partitioned between dichloromethane (5 mL) and water (3 mL). The organic layer was washed with sat. aq Na2CO3 (2×3 mL), sat. aq NH4Cl (2×3 mL), water (2 mL), and sat. aq NaCl (2 mL), then dried over sodium sulfate, filtered, and concentrated to give crude (1R,3S)-3-(1-tert-butyl-5-{[(1-methyl-1H-indazol-5-yl)acetyl]amino}-1H-pyrazol-3-yl)cyclopentyl ethylcarbamate (3C, 127 mg, 100% crude) as a light yellow gum. MS: 489 [M+Na]+.

A solution of the crude (1R,3S)-3-(1-tert-butyl-5-{[(1-methyl-1H-indazol-5-yl)acetyl]amino}-1H-pyrazol-3-yl)cyclopentyl ethylcarbamate (3C, 127 mg, 0.272 mmol) in formic acid (6 mL) was heated at 75° C. for 18 hours. The reaction mixture was concentrated to dryness, then purified by preparative HPLC on a DuraShell 150*25 mm*5 μm column, eluting with 24-44% water (0.05% ammonium hydroxide v/v) in acetonitrile. After lyophilization of the product-containing fractions, (1R,3S)-3-(3-{[(1-methyl-1H-indazol-5-yl)acetyl]amino}-1H-pyrazol-5-yl)cyclopentyl ethylcarbamate (Example 3, 52.39 mg, 47%) was obtained as a white solid. MS: 411 [M+H]+. 1H NMR (400 MHz, DMSO-d6) δ=12.05 (brs, 1H), 10.51 (s, 1H), 8.06-7.95 (m, 1H), 7.64 (s, 1H), 7.56 (d, J=8.5 Hz, 1H), 7.35 (dd, J=1.4, 8.7 Hz, 1H), 7.02 (br t, J=5.5 Hz, 1H), 6.27 (br s, 1H), 4.97 (brs, 1H), 4.04-3.95 (m, 3H), 3.66 (s, 2H), 3.10-2.85 (m, 3H), 2.43 (td, J=6.9, 14.0 Hz, 1H), 2.04-1.92 (m, 1H), 1.91-1.80 (m, 1H), 1.74-1.49 (m, 3H), 0.97 (t, J=7.2 Hz, 3H). Chiral purity: 99% ee by chiral analytical SFC.

Example 4: (1R,3S)-3-(3-{[(1-methyl-1H-1,2,3-triazol-5-yl)carbonyl]amino}-1H-pyrazol-5-yl)cyclopentyl (2S)-butan-2-ylcarbamate

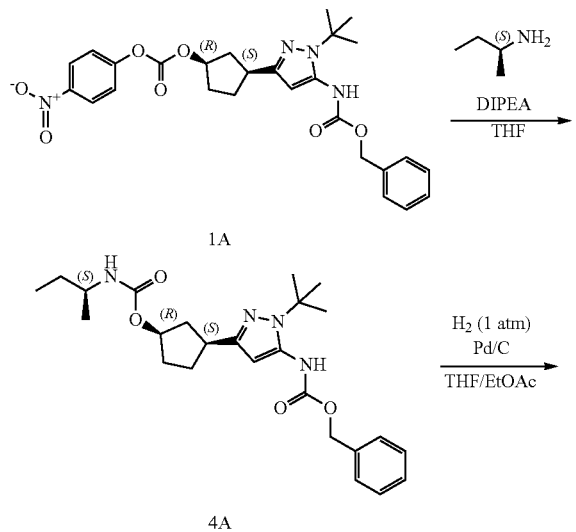

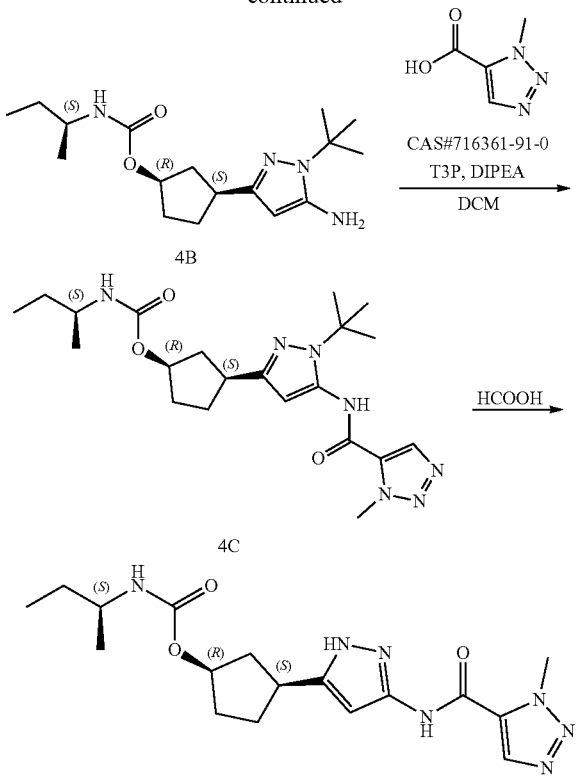

Example 4

A solution of (1R,3S)-3-(5-{[(benzyloxy)carbonyl] amino}-1-tert-butyl-1H-pyrazol-3-yl)cyclopentyl 4-nitrophenyl carbonate (1A, 22.0 g, 42.1 mmol), (S)-(+)-sec-butylamine (4.00 g, 54.7 mmol), and diisopropylethyl amine (36.7 mL, 211 mmol) in THF (300 mL) was stirred at 10° C. for 16 hours. The mixture was concentrated to dryness, and the residue diluted with ethyl acetate (500 mL). The solution was washed with 1M aq NaOH (4×200 mL) and sat. aq NaCl (100 mL). The organic layer was dried over sodium sulfate, filtered, and concentrated to give crude benzyl {3-[(1 S,3R)-3-{[(2S)-butan-2-ylcarbamoyl]oxy}cyclopentyl]-1-tert-butyl-1H-pyrazol-5-yl}carbamate (4A, 18 g, 94%, ~80% pure by LCMS). MS: 479 [M+Na]⁺.

A room temperature (10° C.) solution of the crude benzyl {3-[(1 S,3R)-3-{[(2S)-butan-2-ylcarbamoyl]oxy}cyclopentyl]-1-tert-butyl-1H-pyrazol-5-yl}carbamate (4A, 18 g, 39 mmol) in ethyl acetate (200 mL) and THF (100 mL) was degassed and treated with Pd/C catalyst (wet, 5 g). The suspension was stirred under a hydrogen balloon for 16 hours. The mixture was filtered to remove the catalyst, the filtrate was concentrated to dryness. For purification, this batch was combined with a second batch of crude derived by the same method from 20 g 4A (total for both batches: 38 g, 83 mmol) and purified by preparative HPLC on a Phenomenex Gemini C18 250*50 mm*10 μm column, eluting with 30-50% water (0.05% ammonium hydroxide v/v) in acetonitrile. After lyophilization, (1R,3S)-3-(5-amino-1-tert-butyl-1H-pyrazol-3-yl)cyclopentyl (2S)-butan-2-ylcarbamate (4B, 20.1 g, 75% for the combined batches). MS: 323 [M+H]⁺. ¹H NMR (400 MHz, DMSO-d₆) δ=6.86 (br d, J=8.3 Hz, 1H), 5.22 (s, 1H), 4.94 (br s, 1H), 4.82-4.49 (m, 2H), 3.46-3.36 (m, 1H), 2.90-2.71 (m, 1H), 2.38-2.24 (m, 1H), 1.91-1.75 (m, 2H), 1.74-1.53 (m, 3H), 1.52-1.46 (m, 9H), 1.43-1.27 (m, 2H), 1.01 (d, J=6.5 Hz, 3H), 0.81 (t, J=7.4 Hz, 3H). Optical rotation [α]_D +4.0 (c 1.3, MeOH). Chiral purity: 98% de by chiral analytical SFC.

Propylphosphonic anhydride (T3β ®, 50 wt % solution in EtOAc, 592 mg, 0.93 mmol) was added to a cooled (0° C.) solution of (1R,3S)-3-(5-amino-1-tert-butyl-1H-pyrazol-3-yl)cyclopentyl (2S)-butan-2-ylcarbamate (4B, 100 mg, 0.310 mmol), 1-methyl-1H-1,2,3-triazole-5-carboxylic acid (CAS #716361-91-0, 59.1 mg, 0.465 mmol), and diisopropylethyl amine (120 mg, 0.93 mmol) in dichloromethane (5 mL). The mixture was stirred at 10° C. for 18 hours, then washed with sat. aq Na₂CO₃ and sat. aq NaCl, dried over sodium sulfate, filtered, and concentrated to give crude (1R,3S)-3-(1-tert-butyl-5-{[(1-methyl-1H-1,2,3-triazol-5-yl)carbonyl]amino}-1H-pyrazol-3-yl)cyclopentyl (2S)-butan-2-ylcarbamate (4C, 130 mg, 97%) as a yellow gum. MS: 432 [M+H]⁺, 454 [M+Na]⁺.

A solution of crude (1R,3S)-3-(1-tert-butyl-5-{[(1-methyl-1H-1,2,3-triazol-5-yl)carbonyl]amino}-1H-pyrazol-3-yl)cyclopentyl (2S)-butan-2-ylcarbamate (4C, 130 mg, 0.301 mmol) in formic acid (3 mL) was stirred at 75° C. for 6 days. The mixture was concentrated to dryness, and the residue was purified by preparative HPLC on a DuraShell 150*25 mm*5 μm column, eluting with 10-51% water (0.05% ammonium hydroxide v/v) in acetonitrile. After lyophilization, (1R,3S)-3-(3-{[(1-methyl-1H-1,2,3-triazol-5-yl)carbonyl]amino}-1H-pyrazol-5-yl)cyclopentyl (2S)-butan-2-ylcarbamate (Example 4, 27.67 mg, 24%) was obtained as a pale yellow solid. MS: 376 [M+H]⁺. ¹H NMR (400 MHz, DMSO-d₆) δ=12.32 (br s, 1H), 11.14 (s, 1H), 8.46 (s, 1H), 6.90 (br d, J=8.0 Hz, 1H), 6.45 (br s, 1H), 5.00 (br d, J=3.8 Hz, 1H), 4.25 (s, 3H), 3.36 (br s, 2H), 3.29-2.99 (m, 1H), 2.09-2.01 (m, 1H), 1.95-1.84 (m, 1H), 1.81-1.56 (m, 3H), 1.44-1.27 (m, 2H), 1.01 (br d, J=6.5 Hz, 3H), 0.80 (br t, J=7.4 Hz, 3H). Chiral purity: >98% de by chiral analytical SFC.

Example 5: (1R,3S)-3-(3-{[(5-methyl-1,3-oxazol-2-yl)acetyl]amino}-1H-pyrazol-5-yl)cyclopentyl (1-methylcyclopropyl)carbamate

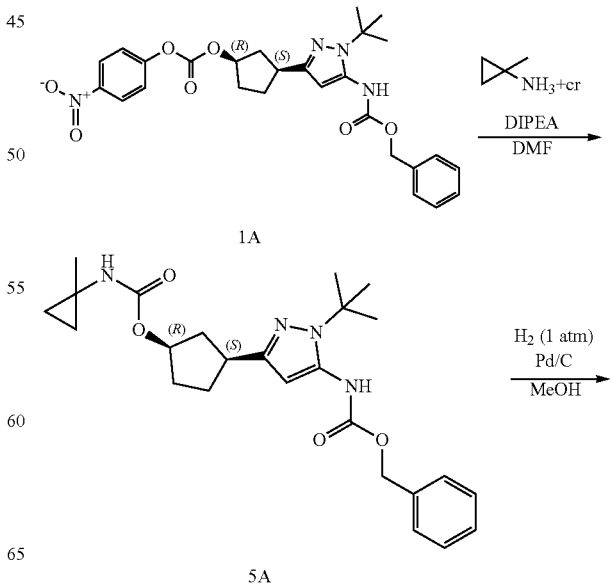

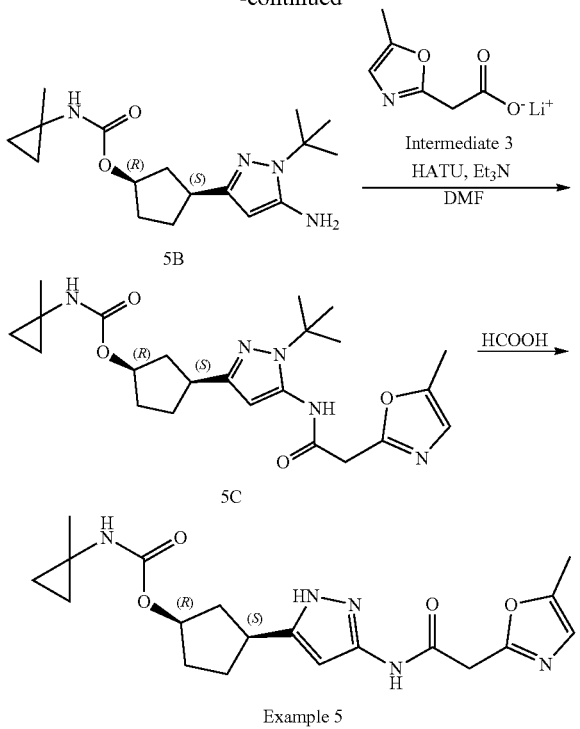

Example 5

A solution of (1R,3S)-3-(5-{[(benzyloxy)carbonyl]amino}-1-tert-butyl-1H-pyrazol-3-yl)cyclopentyl 4-nitrophenyl carbonate (1A, 9.50 g, 18.2 mmol), 1-methylcyclopropanamine hydrochloride (2.93 g, 27.2 mmol), and diisopropylethyl amine (10.0 mL, 58.2 mmol) in DMF (80 mL) was stirred at 60° C. for 2 hours. After cooling to room temperature, the mixture was partitioned between ethyl acetate (300 mL) and water (300 mL). The organic layer was washed with water (2×300 mL), 2M aq $Na_2CO_3$ (300 mL), and sat. aq NaCl (300 mL), then dried over sodium sulfate, filtered, concentrated, and purified by silica gel chromatography (eluting with 0-100% ethyl acetate in heptane) to give benzyl {1-tert-butyl-3-[(1 S,3R)-3-{[(1-methylcyclopropyl)-carbamoyl]oxy}cyclopentyl]-1H-pyrazol-5-yl}carbamate (5A, 6.28 g, 76%) as a solid. MS: 455 [M+H]$^+$. $^1$H NMR (400 MHz, CHLOROFORM-d) δ=7.45-7.30 (m, 5H), 6.30 (br. s., 1H), 6.10 (br. s., 1H), 5.20 (s, 2H), 5.15 (br. s., 1H), 5.06 (br. s., 1H), 3.08 (quin, J=8.3 Hz, 1H), 2.44 (br. s., 1H), 2.12-1.97 (m, 1H), 1.96-1.75 (m, 4H), 1.58 (s, 9H), 1.35 (br. s., 3H), 0.74 (br. s., 2H), 0.58 (br. s., 2H).

A mixture of benzyl {1-tert-butyl-3-[(1 S,3R)-3-{[(1-methylcyclopropyl)-carbamoyl]oxy}cyclopentyl]-1H-pyrazol-5-yl}carbamate (5A, 6.28 g, 13.8 mmol) and 10% Pd/C (620 mg) in methanol (200 mL) was stirred at room temperature (20° C.) a hydrogen balloon for 18 hours. The suspension was filtered through a Celite pad to remove the catalyst. The flask and filter pad were rinsed with additional methanol, then the combined filtrates concentrated to give (1R,3S)-3-(5-amino-1-tert-butyl-1H-pyrazol-3-yl)cyclopentyl (1-methylcyclopropyl)carbamate (5B, 4.42 g, 100% crude) as a foam-like solid. MS: 321 [M+H]$^+$. $^1$H NMR (400 MHz, METHANOL-d$_4$) δ=5.06 (br. s., 1H), 3.14-2.97 (m, 1H), 2.58-2.37 (m, 1H), 2.14-2.00 (m, 1H), 2.00-1.69 (m, 4H), 1.69-1.54 (m, 10H), 1.31 (s, 3H), 0.74-0.66 (m, 2H), 0.60-0.53 (m, 2H).

A solution of (1R,3S)-3-(5-amino-1-tert-butyl-1H-pyrazol-3-yl)cyclopentyl (1-methylcyclopropyl)carbamate (5B, 4.00 g, 12.5 mmol), lithium (5-methyl-1,3-oxazol-2-yl)acetate (Intermediate 3, 3.52 g, 24.9 mmol), 1-[bis(dimethylamino)methylene]-1H-1,2,3-triazolo[4,5-b]pyridinium 3-oxid hexafluorophosphate (HATU, 14.2 g, 37.3 mmol), and triethylamine (5.30 mL0, 38.0 mmol) in DMF (100 mL) was stirred at 60° C. for 2 hours. After cooling to room temperature, the reaction mixture was partitioned between ethyl acetate (200 mL) and water (200 mL). The organic phase was further washed with water (2×200 mL) and sat. aq NaCl (200 mL). The combined aqueous layers were extracted with ethyl acetate (200 mL). The combined organic extracts were dried over sodium sulfate, concentrated, and purified by silica gel chromatography (eluting with 10-100% ethyl acetate in heptane) to give impure product (5.50 g solid). This impure material was re-purified by silica gel chromatography (eluting with 100% ethyl acetate) to give pure (1R,3S)-3-(1-tert-butyl-5-{[(5-methyl-1,3-oxazol-2-yl)acetyl]amino}-1H-pyrazol-3-yl)cyclopentyl (1-methylcyclopropyl)carbamate (5C, 4.22 g, 76%) as a solid. MS: 444 [M+H]$^+$. $^1$H NMR (400 MHz, DMSO-d$_6$) δ=9.78 (s, 1H), 7.32 (br. s., 1H), 6.78 (d, J=1.1 Hz, 1H), 5.93 (s, 1H), 4.97 (br. s., 1H), 3.83 (s, 2H), 3.03-2.88 (m, 1H), 2.42-2.30 (m, 1H), 2.27 (d, J=1.1 Hz, 3H), 1.98-1.88 (m, 1H), 1.87-1.77 (m, 1H), 1.73-1.58 (m, 3H), 1.49 (s, 9H), 1.23 (s, 3H), 0.63-0.56 (m, 2H), 0.50-0.44 (m, 2H).

A solution of (1R,3S)-3-(1-tert-butyl-5-{[(5-methyl-1,3-oxazol-2-yl)acetyl]amino}-1H-pyrazol-3-yl)cyclopentyl (1-methylcyclopropyl)carbamate (5C, 4.20 g, 9.47 mmol) in formic acid (50 mL) was stirred at 100° C. for 1 hour. After cooling to room temperature, the reaction mixture was concentrated to remove most of formic acid. The residue was partitioned between ethyl acetate (200 mL) and sodium bicarbonate (200 mL). The aqueous layer was extracted with more ethyl acetate (200 mL). The combined organic extracts were dried over sodium sulfate, filtered, and concentrated to dryness. The solid residue was triturated twice with ethyl ether (30 mL) to give (1R,3S)-3-(3-{[(5-methyl-1,3-oxazol-2-yl)acetyl]amino}-1H-pyrazol-5-yl)cyclopentyl (1-methylcyclopropyl)carbamate (Example 5, 1.93 g, 53%) as a solid. MS: 388 [M+H]$^+$. $^1$H NMR (400 MHz, DMSO-d$_6$) δ=12.08 (br. s., 1H), 10.59 (br. s., 1H), 7.32 (br. s., 1H), 6.74 (d, J=1.0 Hz, 1H), 6.27 (br. s., 1H), 4.97 (br. s., 1H), 3.79 (s, 2H), 3.14-2.93 (m, 1H), 2.44 (dd, J=14.1, 7.0 Hz, 1H), 2.26 (d, J=0.7 Hz, 3H), 1.99 (t, J=3.4 Hz, 1H), 1.93-1.81 (m, 1H), 1.68 (d, J=8.2 Hz, 2H), 1.60-1.46 (m, 1H), 1.22 (s, 3H), 0.58 (br. s., 2H), 0.49-0.42 (m, 2H).

Example 6: (1R,3S)-3-(3-{[(5-methoxypyrazin-2-yl)acetyl]amino}-1H-pyrazol-5-yl)cyclopentyl (1-methylcyclopropyl)carbamate

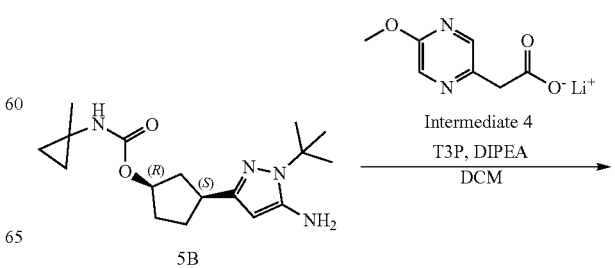

-continued

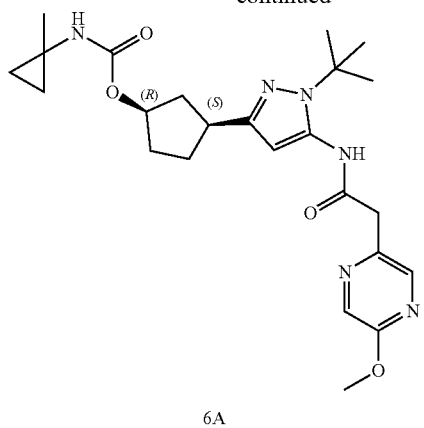

6A

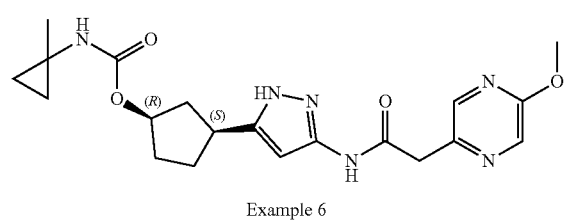

Example 6

A solution of (1R,3S)-3-(5-amino-1-tert-butyl-1H-pyrazol-3-yl)cyclopentyl (1-methylcyclopropyl)carbamate (5B, 150.0 mg, 0.468 mmol), lithium (5-methoxypyrazin-2-yl)acetate (Intermediate 4, 118 mg, 0.702 mmol), diisopropylethyl amine (182 mg, 1.40 mmol), and propylphosphonic anhydride (T3β ®, 50 wt % solution in EtOAc, 447 mg, 0.702 mmol) in dichloromethane (10.0 mL) was stirred at 40° C. for 30 hours. The reaction was quenched with sat. aq NaHCO₃ (8 mL) and extracted with dichloromethane (3×8 mL). The combined organic extracts were washed with sat. aq NaCl (15 mL), concentrated, and purified by silica gel chromatography (eluting with 50% ethyl acetate in petroleum ether) to give (1R,3S)-3-(1-tert-butyl-5-{[(5-methoxypyrazin-2-yl)acetyl]amino}-1H-pyrazol-3-yl)cyclopentyl (1-methylcyclopropyl)carbamate (6A, 100 mg, 45%, 81% pure by LCMS) as a light yellow gum. MS: 471 [M+H]⁺.

The (1R,3S)-3-(1-tert-butyl-5-{[(5-methoxypyrazin-2-yl)acetyl]amino}-1H-pyrazol-3-yl)cyclopentyl (1-methylcyclopropyl)carbamate (6A, 100 mg, 0.213 mmol) was dissolved in formic acid (5 mL) and stirred at 75° C. for 16 hours. The solution was concentrated under vacuum and the residue purified by preparative HPLC on a DuraShell 150*25 mm*5 μm column, eluting with 26-46% water (0.05% ammonium hydroxide v/v) in acetonitrile. After lyophilization, (1R,3S)-3-(3-{[(5-methoxypyrazin-2-yl)acetyl]amino}-1H-pyrazol-5-yl)cyclopentyl (1-methylcyclopropyl)carbamate (Example 6, 15.55 mg, 18%) was obtained as a white solid. MS: 415 [M+H]⁺. ¹H NMR (400 MHz, DMSO-d₆) δ=12.07 (br s, 1H), 10.54 (s, 1H), 8.23 (d, J=1.3 Hz, 1H), 8.16 (s, 1H), 7.35 (br s, 1H), 6.26 (br s, 1H), 4.96 (br s, 1H), 3.89 (s, 3H), 3.77 (s, 2H), 3.02 (br d, J=8.5 Hz, 1H), 2.47-2.39 (m, 1H), 1.97 (br d, J=9.3 Hz, 1H), 1.90-1.80 (m, 1H), 1.72-1.59 (m, 2H), 1.58-1.45 (m, 1H), 1.21 (s, 3H), 0.57 (br s, 2H), 0.48-0.40 (m, 2H). Chiral purity: 99% ee by chiral analytical SFC.

Example 7: (1R,3S)-3-(3-{[(5-methyl-1,2-oxazol-3-yl)acetyl]amino}-1H-pyrazol-5-yl)cyclopentyl (1-methylcyclopropyl)carbamate

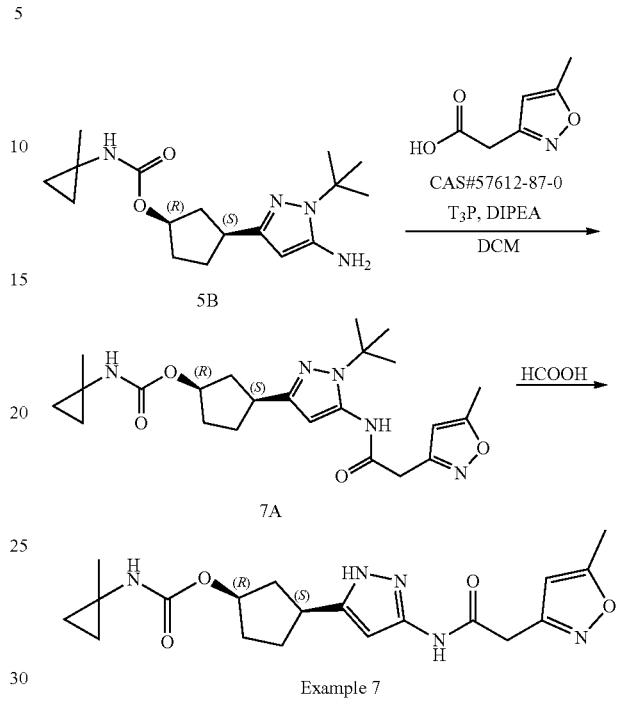

Example 7

A solution of (1R,3S)-3-(5-amino-1-tert-butyl-1H-pyrazol-3-yl)cyclopentyl (1-methylcyclopropyl)carbamate (5B, 78 mg, 0.24 mmol), (5-methyl-1,2-oxazol-3-yl)acetic acid (CAS #57612-87-0, 51.5 mg, 0.365 mmol), diisopropylethyl amine (0.130 mL, 0.730 mmol), and propylphosphonic anhydride (T3β ®, 50 wt % solution in EtOAc, 0.435 mL, 0.730 mmol) in dichloromethane (5.0 mL) was stirred at 30-35° C. for 18 hours. The solution was washed with satd. aq. NaHCO₃ (5 mL) and satd. aq. NaCl (5 mL), dried, filtered, and concentrated, to give crude (1R,3S)-3-(1-tert-butyl-5-{[(5-methyl-1,2-oxazol-3-yl)acetyl]amino}-1H-pyrazol-3-yl)cyclopentyl (1-methylcyclopropyl)carbamate (7A, 95 mg, 88%) as a gum. MS: 444 [M+H]⁺.

The crude (1R,3S)-3-(1-tert-butyl-5-{[(5-methyl-1,2-oxazol-3-yl)acetyl]amino}-1H-pyrazol-3-yl)cyclopentyl (1-methylcyclopropyl)carbamate (7A, 95 mg, 0.21 mmol) was dissolved in formic acid (5.0 mL) and heated to 75° C. for 15 hours. The sample was concentrated to dryness, the residue dissolved in ethyl acetate (30 mL), washed with satd. aq. NaHCO₃ (10 mL), dried, filtered, and concentrated. The crude product was purified by preparative HPLC on an Agela Durashell C18 150*25 mm 5μ column, eluting with 18-58% water (with 0.05% ammonium hydroxide) in acetonitrile, to give (1R,3S)-3-(3-{[(5-methyl-1,2-oxazol-3-yl)acetyl]amino}-1H-pyrazol-5-yl)cyclopentyl (1-methylcyclopropyl)carbamate (Example 7, 39.71 mg, 50%) as a beige solid. MS: 388 [M+H]⁺. ¹H NMR (400 MHz, DMSO-d6) δ=12.08 (br s, 1H), 10.59 (s, 1H), 7.34 (br s, 1H), 6.36-6.03 (m, 2H), 4.97 (br s, 1H), 3.64 (s, 2H), 3.15-2.87 (m, 1H), 2.46-2.40 (m, 1H), 2.37 (s, 3H), 1.98 (br d, J=9.0 Hz, 1H), 1.90-1.81 (m, 1H), 1.77-1.59 (m, 2H), 1.54 (br d, J=8.0 Hz, 1H), 1.22 (s, 3H), 0.58 (br s, 2H), 0.49-0.43 (m, 2H). Chiral purity: >99% ee by chiral analytical SFC.

Example 8: (1R,3S)-3-[3-({[3-(methoxymethyl)-1-methyl-1H-pyrazol-5-yl]carbonyl}amino)-1H-pyrazol-5-yl]cyclopentyl (1-methylcyclopropyl)carbamate

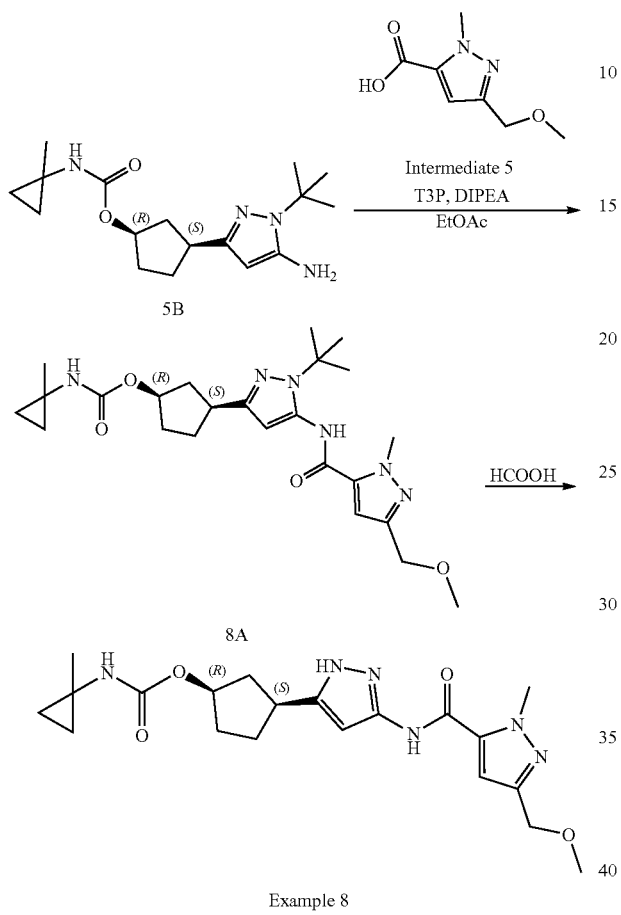

Example 8

A solution of (1R,3S)-3-(5-amino-1-tert-butyl-1H-pyrazol-3-yl)cyclopentyl (1-methylcyclopropyl)carbamate (5B, 5.47 g, 17.1 mmol) and 3-(methoxymethyl)-1-methyl-1H-pyrazole-5-carboxylic acid (Intermediate 5, 4.36 g, 25.6 mmol) in ethyl acetate (80 mL) was treated with diisopropylethyl amine (9.00 mL, 52.4 mmol) and propylphosphonic anhydride (T3β ®, 50 wt % solution in EtOAc, 10.9 g, 10.0 mL, 31.4 mmol) and stirred at room temperature overnight. Since LCMS showed the reaction was not complete, the mixture was heated to 50° C. for 3 hours, but LCMS still showed incomplete conversion. After cooling to room temperature, the solution was partitioned between ethyl acetate (100 mL) and deionized water (200 mL). The organic layer was dried over sodium sulfate, filtered, and concentrated. The residue was dissolved in ethyl acetate (80 mL). Additional 3-(methoxymethyl)-1-methyl-1H-pyrazole-5-carboxylic acid (Intermediate 5, 2.90 g, 17.1 mmol), diisopropylethyl amine (9.00 mL, 52.4 mmol), and T3β (10.0 mL, 33.6 mmol) were added, and the reaction stirred at room temperature for 4 hours. The solution was diluted with ethyl acetate (100 mL); washed with water (200 mL), sat. aq. NaHCO₃ (200 mL) and sat. aq. NaCl (200 mL); dried over sodium sulfate, filtered, and concentrated. The residue was purified by silica gel chromatography (eluting with a gradient of 0-100% ethyl acetate in heptane), to give (1R,3S)-3-[1-tert-butyl-5-({[3-(methoxymethyl)-1-methyl-1H-pyrazol-5-yl]carbonyl}amino)-1H-pyrazol-3-yl]cyclopentyl (1-methylcyclopropyl)carbamate (8A, 4.83 g, 60%) as a foam-like solid. MS: 473 [M+H]⁺. ¹H NMR (400 MHz, CHLOROFORM-d) δ=7.71 (br. s., 1H), 6.68 (br. s., 1H), 6.23 (br. s., 1H), 5.12 (br. s., 2H), 4.47 (s, 2H), 4.18 (s, 3H), 3.43 (s, 3H), 3.03-3.16 (m, 1H), 2.41 (br. s., 1H), 1.97-2.11 (m, 1H), 1.87 (m, J=5.9 Hz, 4H), 1.63 (s, 9H), 1.33 (s, 3H), 0.73 (br. s., 2H), 0.52-0.61 (m, 2H).

A solution of (1R,3S)-3-[1-tert-butyl-5-({[3-(methoxymethyl)-1-methyl-1H-pyrazol-5-yl]carbonyl}amino)-1H-pyrazol-3-yl]cyclopentyl (1-methylcyclopropyl)carbamate (8A, 4.77 g, 10.1 mmol) in formic acid (50 mL) was stirred at 100° C. for 2 hours. After cooling to room temperature, most of the formic acid was removed undervacuum, and the residue partitioned between ethyl acetate (200 mL) and sat. aq. NaHCO₃ (200 mL). The aqueous layer was extracted with ethyl acetate (200 mL). The combined organic extracts were dried over sodium sulfate, filtered, concentrated, and purified by silica gel chromatography (eluting with 0-10% methanol in ethyl acetate) to give a white solid (3.15 g). This solid was recrystallized from ethyl acetate/heptane to give (1R,3S)-3-[3-({[3-(methoxymethyl)-1-methyl-1H-pyrazol-5-yl]carbonyl}amino)-1H-pyrazol-5-yl]cyclopentyl (1-methylcyclopropyl)carbamate (Example 8, 2.90 g, 69%) as a crystalline solid. MS: 417 [M+H]⁺. ¹H NMR (400 MHz, DMSO-d6) δ=12.20 (br. s., 1H), 10.69 (s, 1H), 7.33 (br. s., 1H), 7.11 (s, 1H), 6.41 (br. s., 1H), 4.99 (br. s., 1H), 4.33 (s, 2H), 4.05 (s, 3H), 3.27 (s, 3H), 3.00-3.13 (m, 1H), 2.41-2.49 (m, 1H), 1.97-2.10 (m, 1H), 1.83-1.95 (m, 1H), 1.72 (br. s., 2H), 1.59 (br. s., 1H), 1.24 (s, 3H), 0.60 (br. s., 2H), 0.47 (br. s., 2H)

Example 9: (1R,3S)-3-[3-({[3-(methoxymethyl)-1-methyl-1H-pyrazol-5-yl]carbonyl}-amino)-1H-pyrazol-5-yl]cyclopentyl [(2ξ)-4,4,4-trifluorobutan-2-yl]carbamate—Isomer A

Example 10: (1R,3S)-3-[3-({[3-(methoxymethyl)-1-methyl-1H-pyrazol-5-yl]carbonyl}-amino)-1H-pyrazol-5-yl]cyclopentyl [(2ξ)-4,4,4-trifluorobutan-2-yl]carbamate—Isomer B

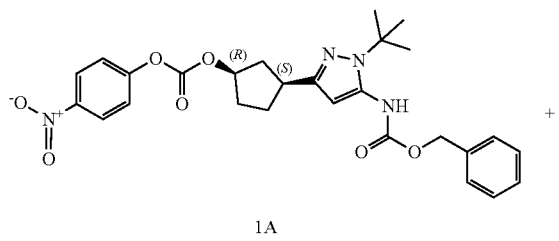

1A

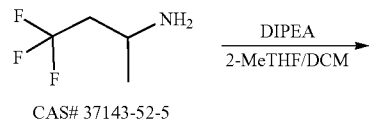

CAS# 37143-52-5

71

-continued

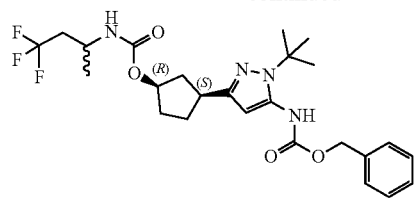

9A
mixture of diastereomers

H₂ (1 atm)
Pd/C
―――――→
THF/EtOAc

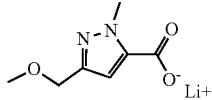

Intermediate 5
T3P, DIPEA
―――――→
DCM

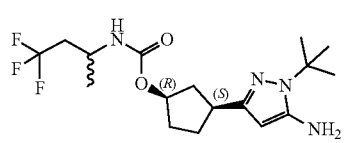

9B
mixture of diastereomers

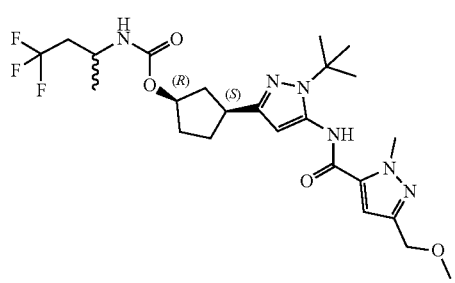

9C
mixture of diastereomers

HCOOH
―――――→

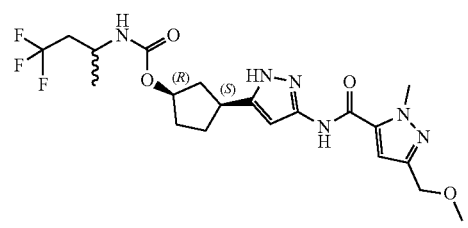

9D
mixture of diastereomers

Chiral
SFC
―――――→

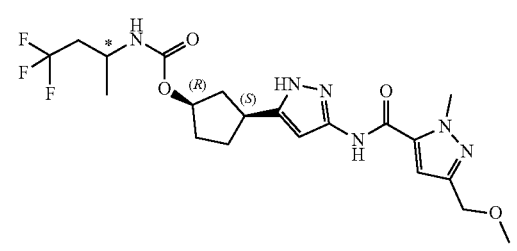

Example 9
Isomer A

+

72

-continued

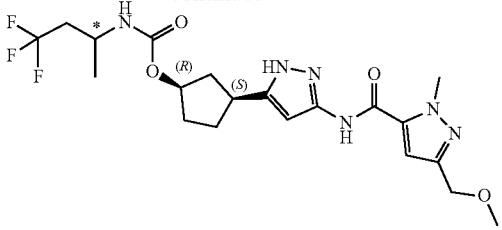

Example 10
Isomer b

A solution of (1R,3S)-3-(5-{[(benzyloxy)carbonyl]amino}-1-tert-butyl-1H-pyrazol-3-yl)cyclopentyl 4-nitrophenyl carbonate (1A, 2.5 g, 4.8 mmol), 4,4,4-trifluorobutan-2-amine (CAS #37143-52-5, 900 mg, 5.5 mmol), and diisopropylethyl amine (4.17 mL, 23.9 mmol) in 2-methyltetrahydrofuran (40 mL) and dichloromethane (20 mL) was stirred at 40-50° C. for 15 hours. The solvents were removed under vacuum, and the residue partitioned between ethyl acetate (150 mL) and 1N aq sodium hydroxide (2×50 m). The organic layer was washed with sat. aq NaCl (60 mL), dried over sodium sulfate, filtered, concentrated, and purified by silica gel chromatography (eluting with 15-30% ethyl acetate in petroleum ether), to give benzyl {1-tert-butyl-3-[(1S,3R)-3-{[(4,4,4-trifluorobutan-2-yl)carbamoyl]oxy}cyclopentyl]-1H-pyrazol-5-yl}carbamate (9A, mixture of diastereomers, 2.0 g, 82%, 79% pure by LCMS), as a yellow oil. MS: 511 [M+H]⁺.

The benzyl {1-tert-butyl-3-[(1 S,3R)-3-{[(4,4,4-trifluorobutan-2-yl)carbamoyl]oxy}-cyclopentyl]-1H-pyrazol-5-yl}carbamate mixture (9A, 2.0 g, 3.9 mmol) was dissolved in ethyl acetate (20 mL) and THF (20 mL), and 10% Pd/C catalyst (50% wet, 650 mg) was added. The suspension was degassed, filled with hydrogen from a balloon, and stirred at 20-25° C. under a hydrogen balloon for 16 hours. The catalyst was removed by filtration, and the filtrated concentrated to give crude (1R,3S)-3-(5-amino-1-tert-butyl-1H-pyrazol-3-yl)cyclopentyl (4,4,4-trifluorobutan-2-yl)carbamate (9B, mixture of diastereomers, 1.4 g, 95%, 76% pure by LCMS) as a yellow oil. MS: 377 [M+H]⁺.

A cooled (0° C.) solution of crude (1R,3S)-3-(5-amino-1-tert-butyl-1H-pyrazol-3-yl)cyclopentyl (4,4,4-trifluorobutan-2-yl)carbamate (9B, 225 mg, 0.598 mmol), 3-(methoxymethyl)-1-methyl-1H-pyrazole-5-carboxylate (Intermediate 5, 173 mg, 0.897 mmol), and diisopropylethyl amine (232 mg, 1.79 mmol) in dichloromethane (10 mL) was treated with propylphosphonic anhydride (T3β ®, 50 wt % solution in EtOAc, 1.14 g, 1.79 mmol). The mixture was warmed to 20° C. and stirred for 36 hours, then warmed to 40° C. for 90 hours. The mixture was partitioned between dichloromethane and half-saturated Na₂CO₃. The organic layer was dried over sodium sulfate, filtered, and concentrated to give crude (1R,3S)-3-[1-tert-butyl-5-({[3-(methoxymethyl)-1-methyl-1H-pyrazol-5-yl]carbonyl}amino)-1H-pyrazol-3-yl]cyclopentyl (4,4,4-trifluorobutan-2-yl)carbamate (9C, mixture of diastereomers, 300 mg, 95%) as a yellow gum. MS: 529 [M+H]⁺.

A solution of the crude (1R,3S)-3-[1-tert-butyl-5-({[3-(methoxymethyl)-1-methyl-1H-pyrazol-5-yl]carbonyl}amino)-1H-pyrazol-3-yl]cyclopentyl (4,4,4-trifluorobutan-2-yl)carbamate (9C, 300 mg, 0.57 mmol) in formic acid (10 mL) was stirred at 80° C. for 2 hours. The mixture was concentrated to dryness and the residue purified by preparative HPLC on a DuraShell 150*25 mm*5 μm column, eluting with 32% water (0.05% ammonium hydroxide v/v) in acetonitrile. After lyophilization, (1R,3S)-3-[3-({[3-(methoxymethyl)-1-methyl-1H-pyrazol-5-yl]carbonyl} amino)-1H-pyrazol-5-yl]cyclopentyl (4,4,4-trifluoro-butan-2-yl)carbamate (9D, mixture of diastereomers, 45 mg, 17%) was obtained as a white solid. MS: 473 [M+H]$^+$.

The diastereomeric mixture 9D was separated by chiral preparative SFC on a Phenomenex-Amylose-1 250 mm*30 mm 5 μm column, eluting with 40% ethanol (+0.1% NH$_3$H$_2$O) in CO$_2$, affording Example 9 (Peak 1, 12.26 mg, 27%, 99% de) and Example 10 (Peak 2, 11.53 mg, 26%, 98% de) as white solids. The absolute stereochemistry of the chiral center in the 4,4,4-trifluorobutan-2-yl]carbamate of each molecule was not determined.

Example 9: (1R,3S)-3-[3-({[3-(methoxymethyl)-1-methyl-1H-pyrazol-5-yl]carbonyl}amino)-1H-pyrazol-5-yl] cyclopentyl [(2ξ)-4,4,4-trifluorobutan-2-yl]carbamate—Isomer A. $^1$H NMR (400 MHz, DMSO-d6) δ=12.25 (br s, 1H), 10.74 (s, 1H), 7.22 (br d, J=8.4 Hz, 1H), 7.12 (s, 1H), 6.43 (br s, 1H), 5.10-4.96 (m, 1H), 4.34 (s, 2H), 4.05 (s, 3H), 3.92-3.79 (m, 1H), 3.27 (s, 3H), 3.17-3.03 (m, 1H), 2.46 (brd, J=6.1 Hz, 1H), 2.43-2.31 (m, 2H), 2.12-1.85 (m, 2H), 1.80-1.57 (m, 3H), 1.13 (d, J=6.7 Hz, 3H). $^{19}$F NMR (377 MHz, DMSO-d6) δ=−62.57 (s, 3F). MS: 473 [M+H]$^+$. Optical rotation: [α]D−2 (c 0.1, MeOH).

Chiral purity: 99% de. Chiral SFC/MS analysis was performed on a Chiralpak AD-3 (150×4.6 mm I.D., 3 μm) column, eluted with 40% ethanol (+0.05% DEA) in CO2, flowing at 2.5 mL/min, at 35° C., with pressure set at 1500 psi. Under these conditions, this peak had a retention time of 3.372 minutes.

Example 10: (1R,3S)-3-[3-({[3-(methoxymethyl)-1-methyl-1H-pyrazol-5-yl]carbonyl}amino)-1H-pyrazol-5-yl] cyclopentyl [(2ξ)-4,4,4-trifluorobutan-2-yl]carbamate—Isomer B. $^1$H NMR (400 MHz, DMSO-d6) δ=12.25 (br s, 1H), 10.74 (s, 1H), 7.24 (br d, J=8.3 Hz, 1H), 7.12 (s, 1H), 6.42 (brs, 1H), 5.16-4.91 (m, 1H), 4.34 (s, 2H), 4.05 (s, 3H), 3.84 (td, J=7.0, 13.8 Hz, 1H), 3.27 (s, 3H), 3.16-3.01 (m, 1H), 2.50-2.46 (m, 1H), 2.45-2.29 (m, 2H), 2.12-1.99 (m, 1H), 1.95-1.85 (m, 1H), 1.80-1.53 (m, 3H), 1.13 (d, J=6.7 Hz, 3H). $^{19}$F NMR (377 MHz, DMSO-d6) δ=−62.56 (s, 3F). MS: 473 [M+H]$^+$. Optical rotation: [α]$_D$+10 (c 0.1, MeOH). Chiral purity: 98% de. Chiral SFC/MS analysis was performed on a Chiralpak AD-3 (150×4.6 mm I.D., 3 μm) column, eluted with 40% ethanol (+0.05% DEA) in CO2, flowing at 2.5 mL/min, at 35° C., with pressure set at 1500 psi. Under these conditions, this peak had a retention time of 4.123 minutes.

Method B

Example 11: (1R,3S)-3-(3-{[(5-methyl-1,3-oxazol-2-yl)acetyl]amino}-1H-pyrazol-5-yl)cyclopentyl tert-butylcarbamate

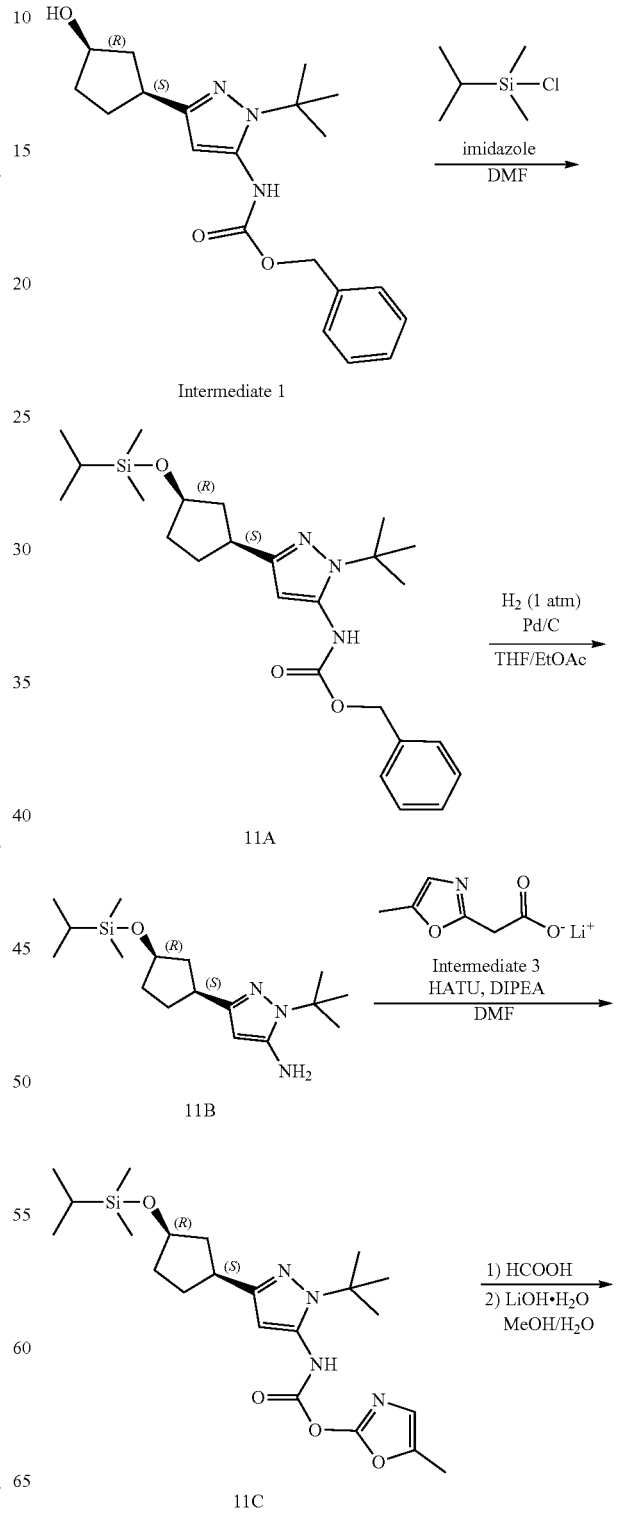

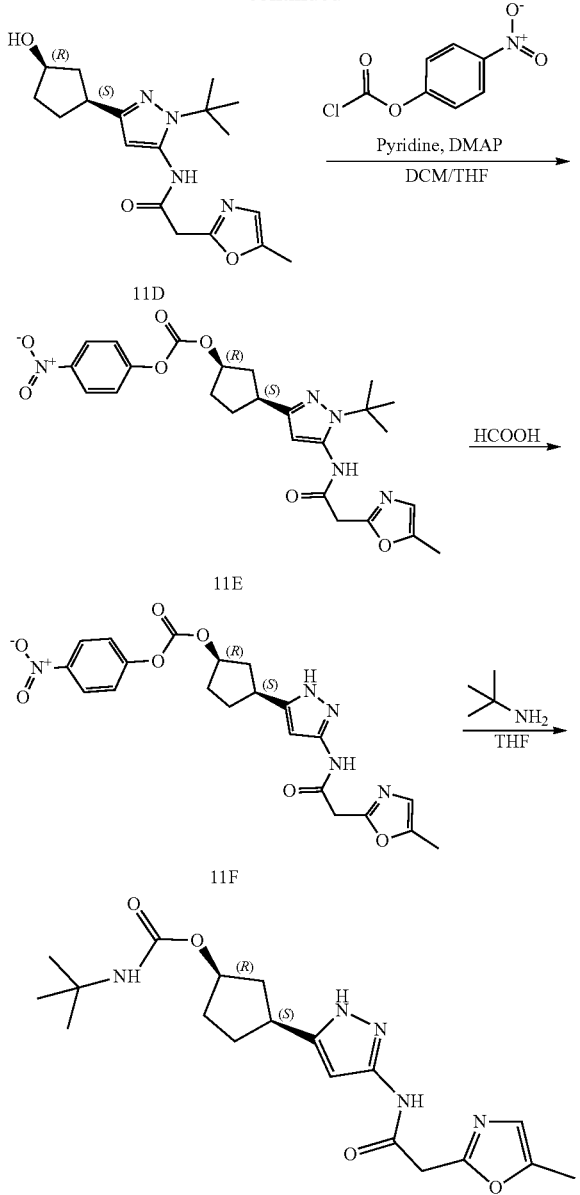

Example 11

Benzyl {1-tert-butyl-3-[(1 S,3R)-3-hydroxycyclopentyl]-1H-pyrazol-5-yl}carbamate (Intermediate 1, 20 g, 56 mmol) and imidazole (5.71 g, 83.9 mmol) were dissolved in DMF (200 mL) with sonication. While the solution was at room temperature, tert-butyldimethylsilyl chloride (11.0 g, 72.7 mmol) was added in portions. After the addition was complete, the clear solution was stirred at 25° C. for 1 hour. The solvents were removed under vacuum and the residue partitioned between ethyl acetate (500 mL) and sat. aq NaCl (200 mL). The organic layer was dried over sodium sulfate, filtered, and concentrated to give crude benzyl {1-tert-butyl-3-[(1S,3R)-3-{[tert-butyl(dimethyl)silyl]-oxy}cyclopentyl]-1H-pyrazol-5-yl}carbamate (11A, 26 g, 99%) as a colorless oil. MS: 472 [M+H]$^+$.

Crude benzyl {1-tert-butyl-3-[(1 S,3R)-3-{[tert-butyl(dimethyl)silyl]oxy}cyclopentyl]-1H-pyrazol-5-yl}carbamate (11A, 26 g, 55 mmol) was dissolved in ethyl acetate (100 mL) and THF (100 mL). Added Pd/C (50% wet, 4 g), degassed the solution, and stirred at 25° C. under a hydrogen balloon for 2 hours. The mixture was then filtered, and the filtrate concentrated under vacuum to give crude 1-tert-butyl-3-[(1 S,3R)-3-{[tert-butyl(dimethyl)-silyl]oxy}cyclopentyl]-1H-pyrazol-5-amine (11B, 19 g, >99%) as a light yellow oil. MS: 338 [M+H]$^+$.

To a room temperature (25° C.) solution of crude 1-tert-butyl-3-[(1 S,3R)-3-{[tert-butyl(dimethyl)silyl]oxy}cyclopentyl]-1H-pyrazol-5-amine (11B, 5.00 g, 14.8 mmol), lithium (5-methyl-1,3-oxazol-2-yl)acetate (Intermediate 3, 3.14 g, 21.3 mmol) and diisopropylethyl amine (5.74 g, 44.4 mmol) in DMF (150 mL) was added 1-[bis(dimethylamino)methylene]-1H-1,2,3-triazolo[4,5-b]pyridinium 3-oxid hexafluorophosphate (HATU, 8.45 g, 22.2 mmol). The mixture was heated to 40° C. for 1 hour, then diluted with ethyl acetate (300 mL) and washed sequentially with water (150 mL) and sat. aq NaCl. The organic layer was dried over sodium sulfate, filtered, and concentrated. The residue was purified by silica gel chromatography (eluting with 30% ethyl acetate in petroleum ether) to give N-{1-tert-butyl-3-[(1 S,3R)-3-{[tert-butyl(dimethyl)silyl]oxy}cyclopentyl]-1H-pyrazol-5-yl}-2-(5-methyl-1,3-oxazol-2-yl)acetamide (11C, 5.5 g, 81%, 77% pure by LCMS) as a yellow oil. MS: 461 [M+H]$^+$.

A solution of N-{1-tert-butyl-3-[(1 S,3R)-3-{[tert-butyl(dimethyl)silyl]oxy}-cyclopentyl]-1H-pyrazol-5-yl}-2-(5-methyl-1,3-oxazol-2-yl)acetamide (11C, 5.5 g, 11.9 mmol) in formic acid (50 mL) was stirred at 25° C. for 14 hours. The solution was concentrated to dryness and the light yellow oily residue was dissolved in methanol (20 mL). To this was added a solution of lithium hydroxide monohydrate (2.50 g, 59.7 mmol) in water (10 mL), and the mixture was stirred for 30 minutes at 25° C. The solution was concentrated to dryness. The residue was dissolved in dichloromethane (30 mL), washed with water (10 mL) and sat. aq NaCl (10 mL), dried over sodium sulfate, filtered, concentrated, and purified by silica gel chromatography (eluting with 3% methanol in dichloromethane) to give N-{1-tert-butyl-3-[(1 S,3R)-3-hydroxycyclopentyl]-1H-pyrazol-5-yl}-2-(5-methyl-1,3-oxazol-2-yl)acetamide (11D, 3.8 g, 92%, 79% pure by LCMS) as a light yellow oil. MS: 347 [M+H]$^+$.

A suspension of N-{1-tert-butyl-3-[(1S,3R)-3-hydroxycyclopentyl]-1H-pyrazol-5-yl}-2-(5-methyl-1,3-oxazol-2-yl)acetamide (11D, 3.8 g, 11 mmol), DMAP (134 mg, 1.10 mmol), pyridine (2.60 g, 32.9 mmol) and 4-nitrophenyl chloroformate (4.42 g, 21.9 mmol) in dichloromethane (40 mL) and THF (40 mL) was stirred at 25° C. for 2 hours. The solvents were removed under vacuum. The residue was dissolved in ethyl acetate (200 mL), washed with sat. aq NH$_4$Cl (100 mL) and sat. aq NaCl, dried over sodium sulfate, filtered, concentrated, and purified by silica gel chromatography (eluting with 50% ethyl acetate in petroleum ether) to afford (1R,3S)-3-(1-tert-butyl-5-{[(5-methyl-1,3-oxazol-2-yl)acetyl]amino}-1H-pyrazol-3-yl)cyclopentyl 4-nitrophenyl carbonate (11E, 5.0 g, 89%, 89% pure by LCMS) as a yellow oil. MS: 512 [M+H]$^+$.

A solution of (1R,3S)-3-(1-tert-butyl-5-{[(5-methyl-1,3-oxazol-2-yl)acetyl]amino}-1H-pyrazol-3-yl)cyclopentyl 4-nitrophenyl carbonate (11E, 5.0 g, 9.8 mmol) in formic acid (30 mL) was stirred at 75° C. for 16 hours. The mixture was concentrated to remove most of the formic acid, then the residue was dissolved in dichloromethane (30 mL) and washed with sat. aq NaHCO$_3$ (2×15 mL), water (15 mL), and sat. aq NaCl (15 mL). The organic layer was dried over sodium sulfate, filtered, concentrated, and purified by silica gel chromatography (eluting with 80% ethyl acetate in petroleum ether) to give (1R,3S)-3-(3-{[(5-methyl-1,3-oxazol-2-yl)acetyl]amino}-1H-pyrazol-5-yl)cyclopentyl 4-nitrophenyl carbonate (11F, 1.7 g, 38%) as a light yellow solid. MS: 456 [M+H]⁺.

A solution of (1R,3S)-3-(3-{[(5-methyl-1,3-oxazol-2-yl)acetyl]amino}-1H-pyrazol-5-yl)cyclopentyl 4-nitrophenyl carbonate (11F, 4.00 g, 8.78 mmol) and tert-butylamine (6.42 g, 87.8 mmol) in THF (30 mL) was stirred at 25° C. for 1 hour. The mixture was concentrated to dryness, the residue dissolved in dichloromethane (80 mL), washed with 1M NaOH (2×20 mL) and sat. aq NaCl (20 mL), dried over sodium sulfate, filtered, concentrated and purified by silica gel chromatography (eluting with 3% methanol in dichloromethane to give impure (1R,3S)-3-(3-{[(5-methyl-1,3-oxazol-2-yl)acetyl]amino}-1H-pyrazol-5-yl)cyclopentyl tert-butylcarbamate (Example 11, 2.3 g, 67%, 73% pure by HPLC). A second batch of (1R,3S)-3-(3-{[(5-methyl-1,3-oxazol-2-yl)acetyl]amino}-1H-pyrazol-5-yl)cyclopentyl 4-nitrophenyl carbonate (11F, 1.50 g, 3.29 mmol) was dissolved in tert-butylamine (10 mL) and stirred at 40° C. for 1 hour. That reaction mixture was concentrated to dryness, and the crude product thus obtained was combined with the 2.3 g of impure product from the first batch, above, (total 12.08 mmol 11F consumed in both batches) and further purified by preparative HPLC on a Phenomenex Gemimi C18 250×50 mm, 10 μm column, eluting with 3-45% water (+0.05% NH₄OH) in ACN. Pure (1R,3S)-3-(3-{[(5-methyl-1,3-oxazol-2-yl)acetyl]amino}-1H-pyrazol-5-yl)cyclopentyl tert-butylcarbamate (Example 11, 2.23 g, 47% for the combined batches) was obtained as a white solid. ¹H NMR (400 MHz, DMSO-d₆) δ=12.10 (s, 1H), 10.62 (s, 1H), 6.87-6.63 (m, 2H), 6.29 (d, J=1.8 Hz, 1H), 4.96 (br s, 1H), 3.79 (s, 2H), 3.03 (quin, J=8.6 Hz, 1H), 2.48-2.40 (m, 1H), 2.25 (d, J=1.1 Hz, 3H), 2.04-1.94 (m, 1H), 1.92-1.80 (m, 1H), 1.75-1.63 (m, 2H), 1.55 (br s, 1H), 1.19 (s, 9H). MS: 390 [M+H]⁺. Optical rotation [α]_D+3.5 (c 0.8, MeOH). Chiral purity: 98% ee by chiral analytical SFC.

Example 12: (1R,3S)-3-(3-{[(3-methyl-1,2-oxazol-5-yl)acetyl]amino}-1H-pyrazol-5-yl)cyclopentyl 2,2-dimethylazetidine-1-carboxylate

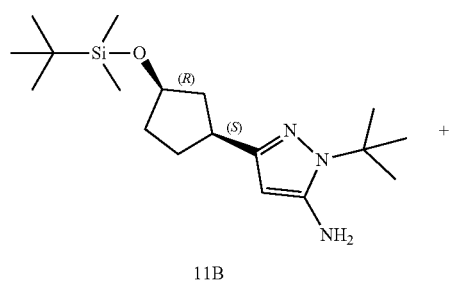

11B

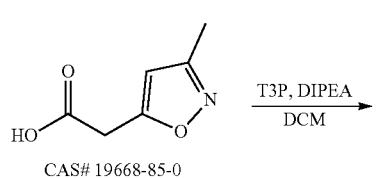

CAS# 19668-85-0

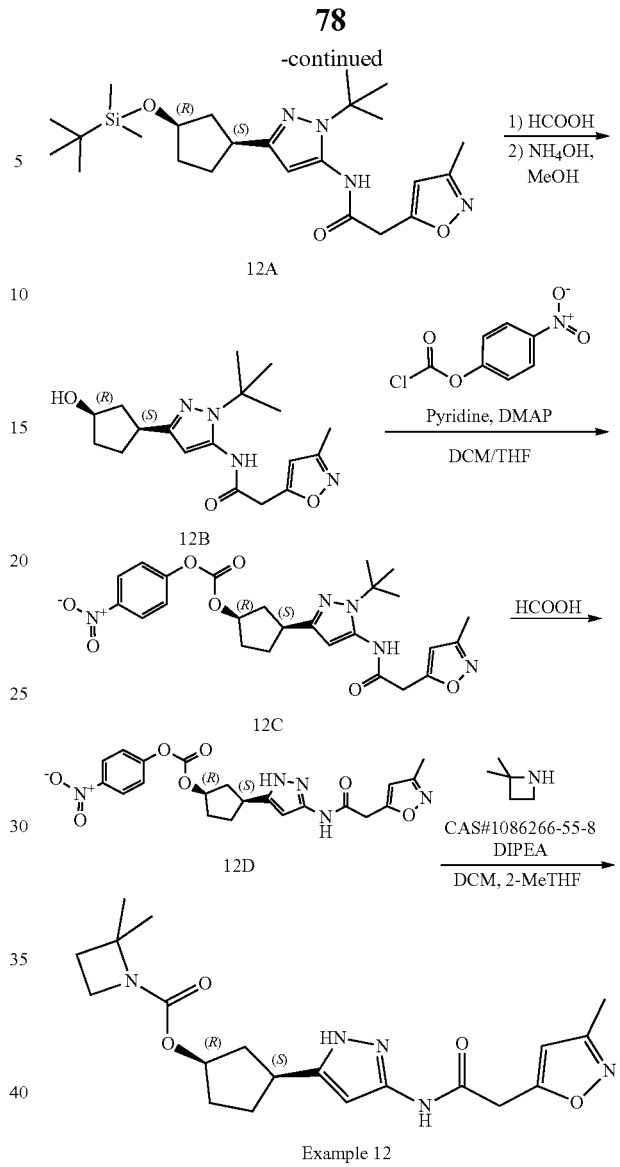

Example 12

Propylphosphonic anhydride (T3β ®, 50 wt % solution in EtOAc, 4.41 g, 6.93 mmol) was added to a cooled (0° C.) solution of 1-tert-butyl-3-[(1 S,3R)-3-{[tert-butyl(dimethyl)silyl]oxy}cyclopentyl]-1H-pyrazol-5-amine (11B, 780 mg, 2.31 mmol), 3-methyl-5-isoxazoleacetic acid (CAS #19668-85-0, 489 mg, 3.47 mmol) and diisopropylethyl amine (1.23 mL, 6.93 mmol) in dichloromethane (10 mL). The mixture was stirred at 30° C. for 1 hour, then partitioned between dichloromethane and semi-saturated Na₂CO₃. The organic layer was washed with sat. aq NaCl, dried over sodium sulfate, filtered, concentrated, and purified by silica gel chromatography (eluting with 10-50% ethyl acetate in petroleum ether) to give N-{1-tert-butyl-3-[(1 S,3R)-3-{[tert-butyl(dimethyl)silyl]oxy}cyclopentyl]-1H-pyrazol-5-yl}-2-(3-methyl-1,2-oxazol-5-yl)acetamide (12A, 1.1 g) as a colorless oil. MS: 461 [M+H]⁺.

A solution of N-{1-tert-butyl-3-[(1 S,3R)-3-{[tert-butyl(dimethyl)silyl]oxy}-cyclopentyl]-1H-pyrazol-5-yl}-2-(3-methyl-1,2-oxazol-5-yl)acetamide (12A, 1.1 g) in formic acid (15 mL) was stirred at 45° C. for 1 hour, then allowed to stand at room temperature overnight. The mixture was concentrated to dryness, the residue was dissolved in methanol (30 mL) and aqueous NH₄OH (10 mL), and the solution stirred at 20° C. for 1 hour. The mixture was concentrated and purified by silica gel chromatography (eluting with 1/10 methanol/dichloromethane) to give N-{1-tert-butyl-3-[(1S,3R)-3-hydroxycyclopentyl]-1H-pyrazol-5-yl}-2-(3-methyl-1,2-oxazol-5-yl)acetamide (12B, 1.0 g) as a light yellow oil. MS: 347 [M+H]⁺.

A solution of N-{1-tert-butyl-3-[(1 S,3R)-3-hydroxycyclopentyl]-1H-pyrazol-5-yl}-2-(3-methyl-1,2-oxazol-5-yl)acetamide (12B, 1.0 g) in dichloromethane (30 mL) and THF (30 mL) was treated with DMAP (70.5 mg, 0.577 mmol), pyridine (1.14 g, 14.4 mmol), and 4-nitrophenyl chloroformate (1.16 g, 5.77 mmol). The resulting suspension was stirred at 20° C. for 12 hours. Solvents were removed under vacuum, the residue was dissolved in dichloromethane (30 mL), and the solution was washed sequentially with sat. aq NH₄Cl (15 mL) and sat. aq NaCl (15 mL). The organic layer was dried, concentrated, and purified by silica gel chromatography (eluting with 50% ethyl acetate in petroleum ether) to give (1R,3S)-3-(1-tert-butyl-5-{[(3-methyl-1,2-oxazol-5-yl)acetyl]amino}-1H-pyrazol-3-yl)cyclopentyl 4-nitrophenyl carbonate (12C, 1.3 g). MS: 512 [M+H]⁺.

A solution of (1R,3S)-3-(1-tert-butyl-5-{[(3-methyl-1,2-oxazol-5-yl)acetyl]amino}-1H-pyrazol-3-yl)cyclopentyl 4-nitrophenyl carbonate (12C, 1.3 g) in formic acid (20 mL) was heated at 75° C. for 16 hours. Most of the formic acid was removed under vacuum, the residue was dissolved in dichloromethane (30 mL), and the solution washed sequentially with sat. aq NaHCO₃ (2×15 mL), water (15 mL), and sat. aq NaCl (15 mL). The organic layer was dried over sodium sulfate, filtered, concentrated, and purified by silica gel chromatography (eluting with 80% ethyl acetate in petroleum ether) to give (1R,3S)-3-(3-{[(3-methyl-1,2-oxazol-5-yl)acetyl]amino}-1H-pyrazol-5-yl)cyclopentyl 4-nitrophenyl carbonate (12D, 850 mg, 81% over 5 steps based on 11B) as a white solid. MS: 456 [M+H]⁺.

A solution of (1R,3S)-3-(3-{[(3-methyl-1,2-oxazol-5-yl)acetyl]amino}-1H-pyrazol-5-yl)cyclopentyl 4-nitrophenyl carbonate (12D, 60 mg, 0.13 mmol), 2,2-dimethylazetidine (CAS #1086266-55-8, 13.5 mg, 0.158 mmol), and diisopropylethyl amine (102 mg, 0.79 mmol) in dichloromethane (1 mL) and 2-methyltetrahydrofuran (1 mL) was stirred at 15° C. for 1 hour, then concentrated and the residue purified by preparative HPLC (on an Xbridge 150*30 mm*10 μm column, eluting with 17-57% water (0.05% ammonium hydroxide v/v) in acetonitrile). After lyophilization, (1R,3S)-3-(3-{[(3-methyl-1,2-oxazol-5-yl)acetyl]amino}-1H-pyrazol-5-yl)cyclopentyl 2,2-dimethylazetidine-1-carboxylate (Example 12, 28.21 mg, 53%) was obtained as a white solid. MS: 402 [M+H]⁺. ¹H NMR (400 MHz, DMSO-d₆) δ=12.13 (br d, J=8.2 Hz, 1H), 10.62 (br s, 1H), 6.29 (s, 1H), 6.21 (s, 1H), 5.03-4.91 (m, 1H), 3.82 (s, 2H), 3.71 (brt, J=8.4 Hz, 1H), 3.64 (t, J=7.5 Hz, 1H), 3.12-3.01 (m, 1H), 2.41 (dt, J=6.7, 15.5 Hz, 1H), 2.19 (s, 3H), 2.04-1.97 (m, 1H), 1.96-1.89 (m, 2H), 1.87-1.79 (m, 1H), 1.77-1.57 (m, 3H), 1.37-1.27 (m, 6H). Chiral purity: 99% ee by chiral analytical SFC.

Example 13: (1R,3S)-3-[3-({[3-(methoxymethyl)-1-methyl-1H-pyrazol-5-yl]carbonyl}-amino)-1H-pyrazol-5-yl]cyclopentyl propan-2-ylcarbamate

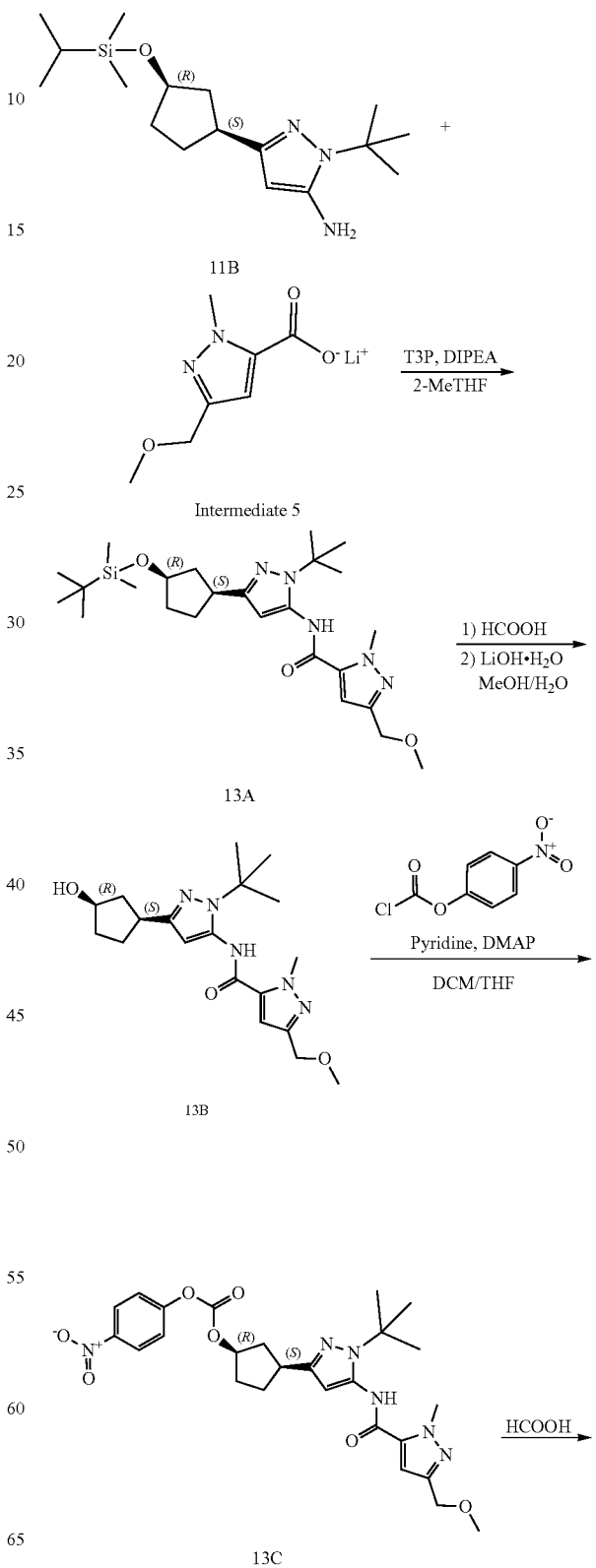

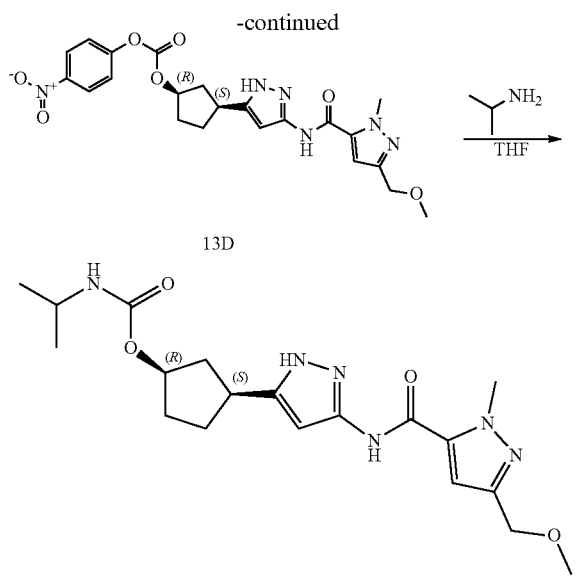

13D

Example 13

Propylphosphonic anhydride (T3β ®, 50 wt % solution in EtOAc, 50.3 g, 79.1 mmol) was added to a room temperature (26° C.) solution of 1-tert-butyl-3-[(1 S,3R)-3-{[tert-butyl(dimethyl)silyl]oxy}cyclopentyl]-1H-pyrazol-5-amine (11B, 8.90 g, 26.4 mmol), lithium 3-(methoxymethyl)-1-methyl-1H-pyrazole-5-carboxylate (Intermediate 5, 5.83 g, 34.3 mmol), and diisopropylethyl amine (10.2 g, 79.1 mmol) in 2-methyltetrahydrofuran (100.0 mL). The resulting mixture was stirred at this temperature for 18 hours. After concentrating the mixture to dryness, the residue was dissolved in dichloromethane (150 mL), and the solution washed sequentially with water (2×30 mL), sat. aq NaHCO₃ (2×30 mL) and sat. aq NaCl (30 mL). The organic layer was dried over sodium sulfate, filtered, and concentrated to give crude N-{1-tert-butyl-3-[(1 S,3R)-3-{[tert-butyl(dimethyl)silyl]oxy}cyclopentyl]-1H-pyrazol-5-yl}-3-(methoxymethyl)-1-methyl-1H-pyrazole-5-carboxamide (13A, 12.9 g, 100%) as an oil. MS: 490 [M+H]⁺.

The crude N-{1-tert-butyl-3-[(1 S,3R)-3-{[tert-butyl(dimethyl)silyl]oxy}cyclopentyl]-1H-pyrazol-5-yl}-3-(methoxymethyl)-1-methyl-1H-pyrazole-5-carboxamide (13A, 12.9 g, 26.3 mmol) was dissolved in formic acid (80 mL) and stirred at room temperature (27° C.) for 30 minutes. The mixture was concentrated to dryness, and the residue dissolved in methanol (80 mL). A solution of lithium hydroxide monohydrate (3.43 g, 81.8 mmol) in water (15 mL) was added, and the mixture stirred at room temperature (27° C.) for 1 hour. The mixture was concentrated to dryness, and the residue was purified by silica gel chromatography (eluting with 0-80% ethyl acetate in petroleum ether) to give N-{1-tert-butyl-3-[(1S,3R)-3-hydroxycyclopentyl]-1H-pyrazol-5-yl}-3-(methoxymethyl)-1-methyl-1H-pyrazole-5-carboxamide (13B, 8.0 g, 78%) as a yellow gum. MS: 376 [M+H]⁺.

A solution of N-{1-tert-butyl-3-[(1 S,3R)-3-hydroxycyclopentyl]-1H-pyrazol-5-yl}-3-(methoxymethyl)-1-methyl-1H-pyrazole-5-carboxamide (13B, 8.0 g, 21 mmol) in dichloromethane (80 mL) and THF (80 mL) was treated with DMAP (260 mg, 2.13 mmol), pyridine (5.06 g, 63.9 mmol), and 4-nitrophenyl chloroformate (8.59 g, 42.6 mmol). The resulting yellow suspension was stirred at room temperature for 18 hours. The reaction mixture was concentrated to dryness and purified by silica gel chromatography (eluting with 0-45% ethyl acetate in petroleum ether) to give (1R,3S)-3-[1-tert-butyl-5-({[3-(methoxymethyl)-1-methyl-1H-pyrazol-5-yl]carbonyl}amino)-1H-pyrazol-3-yl]cyclopentyl 4-nitrophenyl carbonate (13C, 10.6 g, 92%) as a light brown gum. MS: 541 [M+H]⁺.

A solution of (1R,3S)-3-[1-tert-butyl-5-({[3-(methoxymethyl)-1-methyl-1H-pyrazol-5-yl]carbonyl}amino)-1H-pyrazol-3-yl]cyclopentyl 4-nitrophenyl carbonate (13C, 10.6 g, 19.6 mmol) in formic acid (80 mL) was stirred at 70° C. for 18 hours. The solution was concentrated to dryness. The residue was dissolved in dichloromethane (150 mL) and the solution neutralized with sat. aq NaHCO₃. The organic layer was washed with water (30 mL) and sat. aq NaCl (30 mL), dried over sodium carbonate, filtered, and concentrated to give crude (1R,3S)-3-[3-({[3-(methoxymethyl)-1-methyl-1H-pyrazol-5-yl]carbonyl}amino)-1H-pyrazol-5-yl]cyclopentyl 4-nitrophenyl carbonate (13D, 8.5 g, 90%, 86% pure by LCMS) as a light yellow glass. MS: 485 [M+H]⁺.

A room temperature (27° C.) solution of crude (1R,3S)-3-[3-({[3-(methoxymethyl)-1-methyl-1H-pyrazol-5-yl]carbonyl}amino)-1H-pyrazol-5-yl]cyclopentyl 4-nitrophenyl carbonate (13D, 1.7 g, 3.5 mmol) and 2-propylamine (1.04 g, 17.5 mmol) in THF (30 mL) was stirred for 6 hours. The solution was concentrated to dryness, and the residue was combined with the residue from a second batch which had been derived from 1.7 g, 3.5 mmol 13D (total 6.27 mmol 13D consumed for the combined two batches) to give 3.2 g crude product. This product was purified by preparative HPLC on a Phenomenex Gemini C18 250*50 mm*10 μm column, eluting with 15-45% water (0.05% ammonium hydroxide v/v) in acetonitrile. After lyophilization, (1R,3S)-3-[3-({[3-(methoxymethyl)-1-methyl-1H-pyrazol-5-yl]carbonyl}amino)-1H-pyrazol-5-yl]cyclopentyl propan-2-yl-carbamate (Example 13, 2.06 g, 78%) was obtained as a white crystalline solid found to be a monohydrate (Form 1) based on elemental analysis. MS: 405 [M+H]⁺. ¹H NMR (400 MHz, DMSO-d6) δ=12.23 (br s, 1H), 10.73 (br s, 1H), 7.11 (s, 1H), 6.96 (br d, J=7.0 Hz, 1H), 6.41 (br s, 1H), 5.00 (br s, 1H), 4.33 (s, 2H), 4.04 (s, 3H), 3.57 (qd, J=6.6, 13.4 Hz, 1H), 3.26 (s, 3H), 3.17-2.96 (m, 1H), 2.48-2.39 (m, 1H), 2.03 (brd, J=6.8 Hz, 1H), 1.95-1.83 (m, 1H), 1.73 (br d, J=8.5 Hz, 2H), 1.61 (br s, 1H), 1.03 (br d, J=6.3 Hz, 6H). Optical rotation [α]_D+4.8 (c 1.0, MeOH). Chiral purity: >99% ee by chiral analytical SFC. Anal. Calcd for C₁₉H₂₈N₆O₄—H₂O: C, 54.02; H, 7.16; N, 19.89. Found: C, 53.94; H, 7.22; N, 19.81. The white crystalline solid from above (500 mg) was recrystallized from 9:1 H₂O/CH₃CN (2 mL) by heating until dissolved and then allowing the resulting solution to stand at room temperature for 18 h. During the 18 h time period, larger crystals of monohydrate (Form 1) formed. Single crystal X-ray diffraction of a selected crystal from this material provided the structure in FIG. 1.

The crystalline solid prepared above as monohydrate (Form 1) was further characterized by powder X-ray diffraction (PXRD).

Instrumentation Powder X-Ray Diffraction:

Powder X-ray diffraction analysis was conducted using a Bruker AXS D8 Advance diffractometer equipped with a Cu radiation source. Diffracted radiation was detected by a LYNXEYE_EX detector with motorized slits. Both primary and secondary equipped with 2.5 soller slits. The X-ray tube voltage and amperage were set at 40 kV and 40 mA respectively. Data was collected in the Theta-Theta goniometer in a locked couple scan at Cu K-alpha wavelength from 3.0 to 40.0 degrees 2-Theta with an increment of 0.01 degrees, using a scan speed of 1.0 seconds per step. Samples were prepared by placement in a silicon low background sample. Data were collected and analyzed using Bruker DIFFRAC Plus software. The PXRD data file was not processed prior to peak searching. The peak search algorithm in the EVA software was applied to make preliminary peak assignments using a threshold value of 1. To ensure validity, adjustments were manually made; the output of automated assignments was visually checked, and peak positions were adjusted to the peak maximum. Peaks with relative intensity of ≥3% were generally chosen. The peaks which were not resolved or were consistent with noise were not selected. A typical error associated with the peak position from PXRD stated in USP is up to +/−0.2° 2-Theta (USP-941).

The PXRD pattern of Example 13, Form 1 monohydrate, is shown in FIG. 2. A PXRD peak list and relative intensity data for the compound of Example 13, Form 1 monohydrate (2-Theta°) is provided in Table 1 below:

TABLE 1

| Angle (2-theta °) ±0.2 °2θ | Relative Intensity (%) |
|---|---|
| 3.9 | 19.5% |
| 9.1 | 18.3% |
| 10.4 | 96.5% |
| 11.7 | 64.3% |
| 12.9 | 41.4% |
| 16.0 | 15.5% |
| 18.2 | 100.0% |
| 18.6 | 14.4% |
| 19.4 | 38.1% |
| 19.6 | 20.3% |
| 20.0 | 10.5% |
| 20.3 | 20.6% |
| 20.6 | 43.0% |
| 20.8 | 26.1% |
| 21.0 | 23.7% |
| 22.2 | 20.6% |
| 22.7 | 3.4% |
| 23.5 | 22.9% |
| 24.2 | 64.0% |
| 25.0 | 25.9% |
| 25.7 | 8.3% |
| 26.0 | 10.1% |
| 26.3 | 15.1% |
| 26.6 | 8.4% |
| 27.0 | 5.0% |
| 27.6 | 21.3% |
| 28.2 | 31.7% |
| 28.9 | 5.2% |
| 30.4 | 6.8% |
| 31.1 | 7.8% |
| 31.5 | 9.9% |
| 33.9 | 11.6% |
| 35.1 | 3.3% |
| 35.8 | 3.0% |
| 36.6 | 7.1% |
| 37.6 | 3.9% |
| 38.3 | 5.2% |

Example 14: (1R,3S)-3-[3-({[3-(methoxymethyl)-1-methyl-1H-pyrazol-5-yl]carbonyl}-amino)-1H-pyrazol-5-yl]cyclopentyl (2S)-butan-2-ylcarbamate

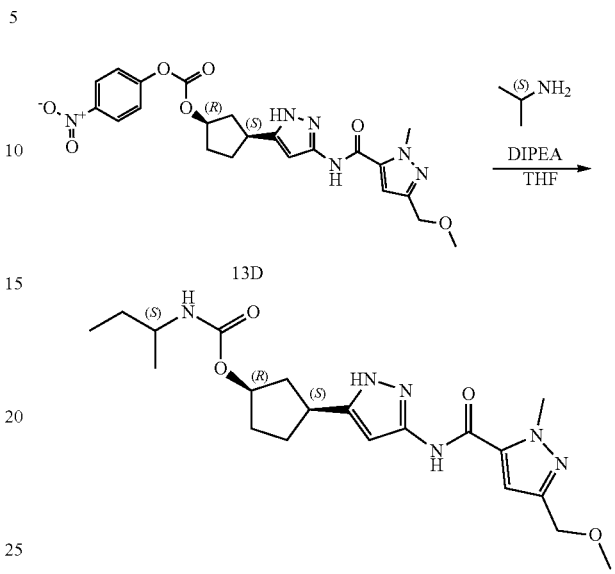

Example 14

A solution of crude (1R,3S)-3-[3-({[3-(methoxymethyl)-1-methyl-1H-pyrazol-5-yl]carbonyl}amino)-1H-pyrazol-5-yl]cyclopentyl 4-nitrophenyl carbonate (13D, 5.5 g, 11 mmol), (S)-(+)-sec-butylamine (1.49 g, 13.6 mmol), and diisopropylethyl amine (4.40 g, 34.1 mmol) in THF (100 mL) was stirred at room temperature (30° C.) for 18 hours. The reaction mixture was concentrated to dryness, and the residue purified by preparative HPLC on a Phenomenex Gemini C18 250*50 mm*10 μm column, eluting with 25-45% water (0.05% ammonium hydroxide v/v) in acetonitrile, to afford (1R,3S)-3-[3-({[3-(methoxymethyl)-1-methyl-1H-pyrazol-5-yl]carbonyl}amino)-1H-pyrazol-5-yl]cyclopentyl (2S)-butan-2-ylcarbamate (Example 14, 3.50 g, 74%) as a light yellow solid. MS: 419 [M+H]$^+$. $^1$H NMR (400 MHz, DMSO-d6) δ=12.23 (br s, 1H), 10.72 (s, 1H), 7.11 (s, 1H), 6.90 (br d, J=8.2 Hz, 1H), 6.42 (br s, 1H), 5.00 (br s, 1H), 4.33 (s, 2H), 4.04 (s, 3H), 3.43-3.37 (m, 1H), 3.26 (s, 3H), 3.14-2.98 (m, 1H), 2.45 (brs, 1H), 2.08-1.97 (m, 1H), 1.95-1.82 (m, 1H), 1.80-1.68 (m, 2H), 1.67-1.52 (m, 1H), 1.42-1.26 (m, 2H), 1.00 (d, J=6.5 Hz, 3H), 0.80 (t, J=7.4 Hz, 3H). Optical rotation [α]$_D$+16.6 (c 2.05, MeOH). Chiral purity: >99% ee by chiral analytical SFC.

Example 15: (1R,3S)-3-(3-{[(3-methyl-1,2-oxazol-5-yl)acetyl]amino}-1H-pyrazol-5-yl)cyclopentyl (1-methylcyclopropyl)carbamate

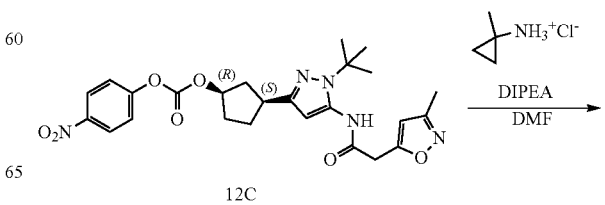

12C

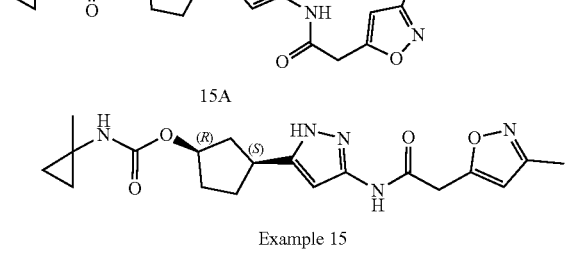

15A

Example 15

A solution of (1R,3S)-3-(1-tert-butyl-5-{[(3-methyl-1,2-oxazol-5-yl)acetyl]amino}-1H-pyrazol-3-yl)cyclopentyl 4-nitrophenyl carbonate (12C, 1.64 g, 3.2 mmol) in DMF (10.7 mL) was treated with 1-methylcyclopropan-1-amine hydrochloride (516 mg, 4.8 mmol) and diisopropylethyl amine (1.7 mL, 9.6 mmol). The mixture was stirred under nitrogen for 2 hours at 60° C., then at room temperature overnight. After diluting with ethyl acetate (150 mL), the solution was washed with deionized water (20 mL), with 2 M aq. Na₂CO₃ (20 mL), and with sat. aq. NaCl (20 mL). The combined aqueous layers were back-extracted with ethyl acetate (30 mL). The combined organic extracts were dried over sodium sulfate, filtered, concentrated and purified by silica gel chromatography (eluting with 0-100% ethyl acetate in heptane) to give (1R,3S)-3-(1-tert-butyl-5-{[(3-methyl-1,2-oxazol-5-yl)acetyl]amino}-1H-pyrazol-3-yl)cyclopentyl (1-methylcyclopropyl)carbamate (15A, 1.58 g, 82%) as an oil.

A solution of 1R,3S)-3-(1-tert-butyl-5-{[(3-methyl-1,2-oxazol-5-yl)acetyl]amino}-1H-pyrazol-3-yl)cyclopentyl (1-methylcyclopropyl)carbamate (15A, 1.50 g, 3.4 mmol) in formic acid (10 mL) was heated in a 100° C. oil bath for 1 hour. Most of the formic acid was removed under vacuum. The residue was treated with sat. aq. NaHCO3 (30 mL), then extracted with ethyl acetate (150 mL, then 50 mL). The combined organics were dried over magnesium sulfate, filtered, concentrated, and purified by silica gel chromatography (eluting with 0-40% isopropanol in heptane) to give a white solid (960 mg). This solid was dissolved in acetonitrile (20 mL) and water (10 mL), and the solution lyophilized overnight to give a white solid (796 mg). The lyophilized material was suspended in ethyl acetate (28 mL), stirred in a 60° C. oil bath for 1 hour, and allowed to cool to room temperature with stirring for 3 more hours. The solid was collected by filtration and dried (50° C., 10 mmHg) to give (1R,3S)-3-(3-{[(3-methyl-1,2-oxazol-5-yl)acetyl]amino}-1H-pyrazol-5-yl)cyclopentyl (1-methylcyclopropyl)carbamate (Example 15 565 mg, 41%) as a white solid. MS: 388 [M+H]⁺. ¹H NMR (400 MHz, DMSO-d6) δ=12.10 (brs, 1H), 10.61 (s, 1H), 7.34 (brs, 1H), 6.28 (brs, 1H), 6.21 (s, 1H), 4.97 (brs, 1H), 3.82 (s, 2H), 3.14-2.94 (m, 1H), 2.48-2.39 (m, 1H), 2.20 (s, 3H), 1.99 (s, 1H), 1.93-1.80 (m, 1H), 1.78-1.60 (m, 2H), 1.54 (br s, 1H), 1.22 (s, 3H), 0.58 (br s, 2H), 0.49-0.42 (m, 2H). Optical rotation [α]$_D$+10.0° (c 0.2, MeOH).

Method C

Example 16: (1R,3S)-3-{3-[(1,2-oxazol-5-ylacetyl)amino]-1H-pyrazol-5-yl}cyclopentyl (2S)-butan-2-ylcarbamate

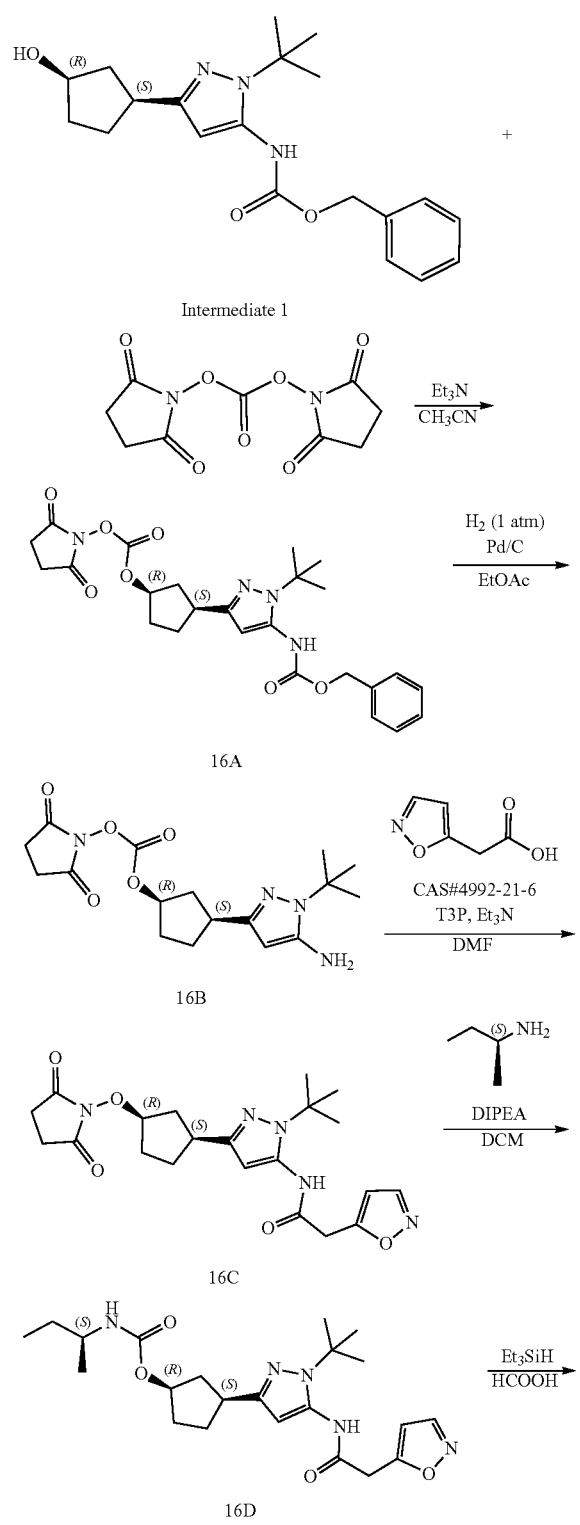

-continued

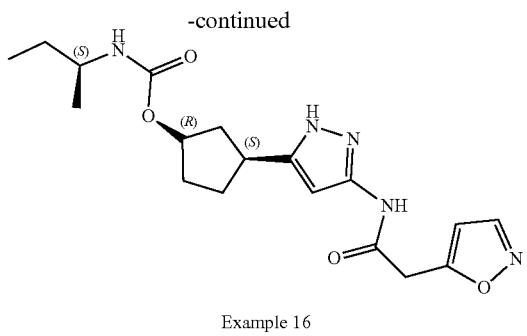

Example 16

Triethylamine (4.7 mL, 33.4 mmol) was added to a suspension of benzyl {1-tert-butyl-3-[(1 S,3R)-3-hydroxycyclopentyl]-1H-pyrazol-5-yl}carbamate (Intermediate 1, 5.97 g, 16.7 mmol) in anhydrous acetonitrile (50 mL). The solution was cooled to 0° C., then N,N'-disuccinimidyl carbonate (8.56 g, 33.4 mmol) was added. After stirring at 0° C. for 10 minutes, the cooling bath was removed and the mixture stirred at room temperature (23° C.) for 24 hours. LCMS showed unreacted starting alcohol was still present, so additional N,N'-disuccinimidyl carbonate (2.36 g; total 10.92 g, 42.63 mmol) and triethyl amine ((2.8 mL; total 7.5 mL, 54 mmol) were added, and stirring continued at room temperature for 5 more hours. The solvents were removed under vacuum, and the residue diluted with ethyl acetate (150 mL) and deionized water (100 mL). The resulting emulsion was suction-filtered to remove a white solid. The layers of the filtrate were separated. The filter cake was rinsed with ethyl acetate (2×100 mL), and those rinsed used to further extract the aqueous layer. The combined organic extracts were dried over magnesium sulfate, filtered, and concentrated. The residue was purified by silica gel chromatography (eluting with 20-70% ethyl acetate in heptane), affording benzyl {1-tert-butyl-3-[(1 S,3R)-3-({[(2,5-dioxopyrrolidin-1-yl)oxy]carbonyl}oxy)cyclopentyl]-1H-pyrazol-5-yl}carbamate (16A, 4.5 g, 54%) as a solid. $^1$H NMR (400 MHz, CHLOROFORM-d) δ=7.42-7.34 (m, 5H), 6.24 (br. s., 1H), 6.13 (br. s., 1H), 5.30-5.22 (m, 1H), 5.20 (s, 2H), 3.21-3.12 (m, 1H), 2.82 (s, 4H), 2.57 (ddd, J=6.7, 8.4, 14.8 Hz, 1H), 2.15-2.05 (m, 2H), 2.04-1.87 (m, 3H), 1.59 (s, 9H). MS: 499 [M+H]$^+$.

A solution of benzyl {1-tert-butyl-3-[(1 S,3R)-3-({[(2,5-dioxopyrrolidin-1-yl)oxy]carbonyl}oxy)cyclopentyl]-1H-pyrazol-5-yl}carbamate (16A, 3.5 g, 7.0 mmol) and 10% Pd/C (1.2 g) in ethyl acetate (150 mL) was stirred under a hydrogen balloon at room temperature (23° C.) overnight. The mixture was filtered through a Celite pad, the filter pad rinsed with ethyl acetate (3×30 mL), and the combined filtrates concentrated to give crude 1-[({[(1R,3S)-3-(5-amino-1-tert-butyl-1H-pyrazol-3-yl)cyclopentyl]oxy}-carbonyl)oxy]pyrrolidine-2,5-dione (16B), which was used immediately in the next step. MS: 365 [M+H]$^+$.

The crude 1-[({[(1R,3S)-3-(5-amino-1-tert-butyl-1H-pyrazol-3-yl)cyclopentyl]oxy}-carbonyl)oxy]pyrrolidine-2,5-dione (16B, 7.0 mmol max) was dissolved in DMF (20 mL), 1,2-oxazol-5-ylacetic acid (CAS #4992-21-6, 1.4 g, 11 mmol) and propylphosphonic anhydride (T3β ®, 11 mL of a 50 wt % solution in EtOAc, 14 mmol) were added, and the solution cooled to 0° C. under nitrogen. Triethyl amine (3.5 ml, 25 mmol) was added dropwise over 10 minutes, slowly enough to keep the internal temperature below 20° C. The cooling bath was removed and the mixture stirred at room temperature for 1 hour. The reaction was quenched with sat. aq NaHCO$_3$ and extracted with ethyl acetate (3×). The combined organic layers were washed with sat. aq NaHCO$_3$ (2×) and sat. aq NaCl (1×), dried over magnesium sulfate, filtered, concentrated, and purified by silica gel chromatography (eluting with 30-100% ethyl acetate in heptane, yielding N-(1-tert-butyl-3-{(1 S,3R)-3-[(2,5-dioxopyrrolidin-1-yl)oxy]cyclopentyl}-1H-pyrazol-5-yl)-2-(1,2-oxazol-5-yl)acetamide (16C, 2.46 g, 74%) as a white foam. $^1$H NMR (400 MHz, METHANOL-d$_4$) δ=8.35 (d, J=1.7 Hz, 1H), 6.42-6.37 (m, 1H), 6.05 (s, 1H), 5.33-5.23 (m, 1H), 3.98 (s, 2H), 3.16 (td, J=8.8, 17.2 Hz, 1H), 2.82 (s, 4H), 2.63-2.51 (m, 1H), 2.16-2.02 (m, 3H), 2.00-1.80 (m, 3H), 1.56 (s, 9H). MS: 474 [M+H]$^+$.

A solution of N-(1-tert-butyl-3-{(1S,3R)-3-[(2,5-dioxopyrrolidin-1-yl)oxy]-cyclopentyl}-1H-pyrazol-5-yl)-2-(1,2-oxazol-5-yl)acetamide (16C, 158 mg, 0.334 mmol), diisopropylethyl amine (0.15 mL, 0.91 mmol), and (S)-(+)-sec-butylamine (50 µL, 0.50 mmol) in dichloromethane (3.5 mL) was stirred at 20° C. for 3 hours. The reaction mixture was diluted with dichloromethane (10 mL) and washed with sat. aq NaHCO$_3$ (2×3 mL), deionized water (3 mL), sat. aq NH$_4$Cl (3 mL) and sat. aq NaCl (3 mL). The organic layer was dried over magnesium sulfate, filtered, and concentrated to dryness, leaving crude (1R,3S)-3-{1-tert-butyl-5-[(1,2-oxazol-5-ylacetyl)amino]-1H-pyrazol-3-yl}cyclopentyl (2S)-butan-2-ylcarbamate (16D, 115.0 mg, 80%) as a yellow gel. $^1$H NMR (400 MHz, DMSO-de) δ=9.79 (s, 1H), 8.50 (d, J=1.7 Hz, 1H), 6.85 (d, J=8.1 Hz, 1H), 6.40 (d, J=1.6 Hz, 1H), 5.93 (s, 1H), 4.97 (br. s., 1H), 3.95 (s, 2H), 3.43-3.33 (m, 1H), 2.95 (quin, J=8.5 Hz, 1H), 2.40-2.31 (m, 1H), 1.99-1.77 (m, 2H), 1.76-1.57 (m, 3H), 1.47 (s, 9H), 1.39-1.30 (m, 2H), 1.00 (d, J=6.6 Hz, 3H), 0.79 (t, J=7.4 Hz, 3H). MS: 432 [M+H]$^+$.

The crude (1R,3S)-3-{1-tert-butyl-5-[(1,2-oxazol-5-ylacetyl)amino]-1H-pyrazol-3-yl}cyclopentyl (2S)-butan-2-ylcarbamate (16D, 115.0 mg, 0.2665 mmol) was dissolved in formic acid (6.0 mL) and triethylsilane (1.5 mL) and stirred at 70° C. for 18 hours. The layers of the resulting biphasic mixture were separated. The upper, triethylsilane layer was discarded. The lower, acid layer was concentrated to dryness, dissolved in acetonitrile, and concentrated to dryness again. The residue was dried further under vacuum to obtain crude product as a waxy brown solid (109.9 mg). Acetonitrile (5 mL) was added, and the suspension stirred at room temperature for 1 hour. The resulting precipitate was collected by suction filtration, and air-dried to give (1R,3S)-3-{3-[(1,2-oxazol-5-ylacetyl)amino]-1H-pyrazol-5-yl}cyclopentyl (2S)-butan-2-ylcarbamate (Example 16, 42.1 mg, 42%) as an off-white solid. $^1$H NMR (400 MHz, DMSO-d$_6$) δ=12.11 (br. s., 1H), 10.65 (s, 1H), 8.48 (d, J=1.7 Hz, 1H), 6.87 (d, J=8.1 Hz, 1H), 6.37 (d, J=1.5 Hz, 1H), 6.29 (br. s., 1H), 4.98 (br. s., 1H), 3.91 (s, 2H), 3.43-3.33 (m, 1H), 3.11-2.97 (m, 1H), 2.48-2.38 (m, 1H), 2.05-1.94 (m, 1H), 1.94-1.81 (m, 1H), 1.78-1.62 (m, 2H), 1.61-1.50 (m, 1H), 1.41-1.27 (m, 2H), 0.99 (d, J=6.6 Hz, 3H), 0.79 (t, J=7.4 Hz, 3H). MS: 376 [M+H]$^+$.

Method D

Example 17: (1R,3S)-3-{3-[(1,2-oxazol-3-ylacetyl)amino]-1H-pyrazol-5-yl}cyclopentyl tert-butylcarbamate

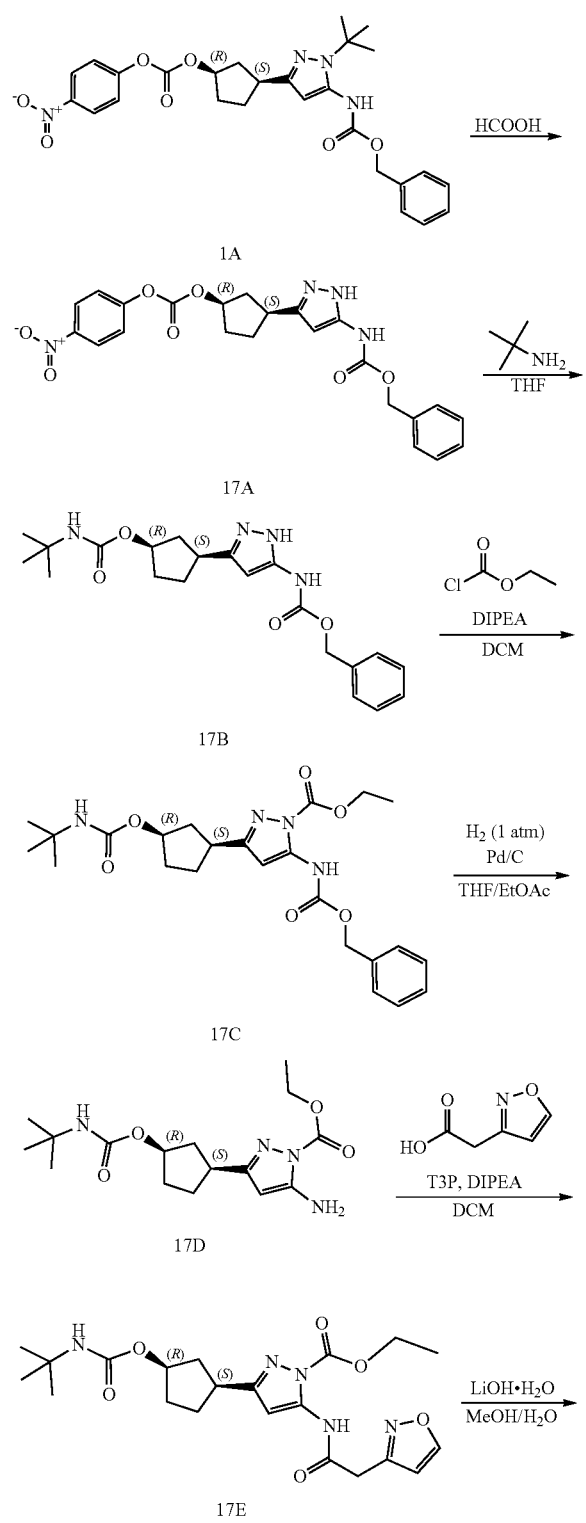

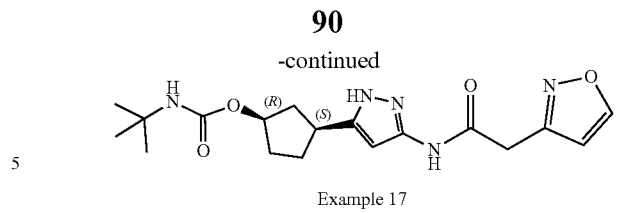

Example 17

A solution of (1R,3S)-3-(5-{[(benzyloxy)carbonyl]amino}-1-tert-butyl-1H-pyrazol-3-yl)cyclopentyl 4-nitrophenyl carbonate (1A, 5.00 g, 9.57 mmol) in formic acid (30 mL) was stirred at 75° C. for 20 hours. The mixture was concentrated to dryness and the residue purified by silica gel chromatography (eluting with 50-70% ethyl acetate in petroleum ether) to give (1R,3S)-3-(5-{[(benzyloxy)carbonyl]amino}-1H-pyrazol-3-yl)cyclopentyl 4-nitrophenyl carbonate (17A, 3.6 g, 81%, 82% pure by LCMS) as a light yellow solid. MS: 467 [M+H]$^+$.

A mixture of (1R,3S)-3-(5-{[(benzyloxy)carbonyl]amino}-1H-pyrazol-3-yl)cyclopentyl 4-nitrophenyl carbonate (17A, 2.2 g, 4.7 mmol) and tert-butylamine (1.38 g, 18.9 mmol) in THF (40 mL) was stirred at room temperature (29° C.) for 18 hours. Solvents were removed under vacuum, and the residue purified by silica gel chromatography (eluting with 0-90% ethyl acetate in petroleum ether) to give benzyl (3-{(1 S,3R)-3-[(tert-butylcarbamoyl)oxy]cyclopentyl}-1H-pyrazol-5-yl)carbamate (17B, 1.5 g, 79%) as a light yellow glass. MS: 401 [M+H]$^+$.

Ethyl chloroformate (970 mg, 8.94 mmol) was added in portions to a room temperature (29° C.) solution of benzyl (3-{(1 S,3R)-3-[(tert-butylcarbamoyl)oxy]-cyclopentyl}-1H-pyrazol-5-yl)carbamate (17B, 1.50 g, 3.75 mmol) and diisopropylethyl amine (1.45 g, 11.2 mmol) in dichloromethane (30 mL), then the mixture stirred at room temperature for 18 hours. The solution was washed with sat. aq NH$_4$Cl (3×5 mL) and sat. aq NaCl (5 mL), dried over sodium sulfate, filtered, and concentrated to give crude ethyl 5-{[(benzyloxy)carbonyl]amino}-3-{(1 S,3R)-3-[(tert-butylcarbamoyl)oxy]-cyclopentyl}-1H-pyrazole-1-carboxylate (17C, 2.0 g, >99%) as a light yellow gum, which was used without further purification. MS: 473 [M+H]$^+$.

The crude ethyl 5-{[(benzyloxy)carbonyl]amino}-3-{(1 S,3R)-3-[(tert-butylcarbamoyl)oxy]cyclopentyl}-1H-pyrazole-1-carboxylate (17C, 2.0 g, 4.2 mmol if pure) was dissolved in ethyl acetate (15 mL) and THF (15 mL). Added 10% Pd/C catalyst (200 mg), degassed, and stirred under a hydrogen balloon at room temperature (29° C.) for 1.5 hours. The suspension was filtered to remove the catalyst, the filtrate concentrated to dryness, and the residue purified by silica gel chromatography (eluting with 0-100% ethyl acetate in petroleum ether, then with 0-30% ethyl acetate in dichloromethane) to give ethyl 5-amino-3-{(1 S,3R)-3-[(tert-butylcarbamoyl)oxy]cyclopentyl}-1H-pyrazole-1-carboxylate (17D, 900 mg, 63%, 56% from 17A) as a light yellow gum. MS: 339 [M+H]$^+$.

A solution of ethyl 5-amino-3-{(1 S,3R)-3-[(tert-butylcarbamoyl)oxy]cyclopentyl}-1H-pyrazole-1-carboxylate (17D, 250 mg, 0.739 mmol), diisopropylethyl amine (286 mg, 2.22 mmol), and 1,2-oxazol-3-ylacetic acid (CAS #57612-86-9, 113 mg, 0.887 mmol) in dichloromethane (10 mL) at room temperature (29° C.) was treated with propylphosphonic anhydride (T3β ®, 50 wt % solution in EtOAc, 1.41 g, 2.22 mmol), then stirred at room temperature for 6 hours. The solution was diluted with dichloromethane (10 mL), then washed with water (5 mL), sat. aq NaHCO$_3$ (2×5 mL), sat. aq NH4Cl (5 mL) and sat. aq NaCl (5 mL). The organic layer was dried over sodium sulfate, filtered, and concentrated to give crude ethyl 3-{(1 S,3R)-3-[(tert-butylcarbamoyl)oxy] cyclopentyl}-5-[(1,2-oxazol-3-ylacetyl)amino]-1H-pyrazole-1-carboxylate (17E, 331 mg, 100%) as a brown gum. MS: 448 [M+H]+.

This crude ethyl 3-{(1 S,3R)-3-[(tert-butylcarbamoyl) oxy]cyclopentyl}-5-[(1,2-oxazol-3-ylacetyl)amino]-1H-pyrazole-1-carboxylate (17E, 331 mg, 0.739 mmol) was dissolved in methanol (5 mL), a solution of lithium hydroxide monohydrate (93.1 mg, 2.22 mmol) in water (1 mL) was added, and the mixture stirred at room temperature (30° C.) for 1 hour. The mixture was allowed to stand overnight, then concentrated to dryness.

The residue was dissolved in methanol (3 mL), filtered, and the filtrate purified by preparative HPLC on a YMC-Actus Triart C18 150*30 5μ column, eluting with 20-50% water (0.05% ammonium hydroxide v/v) in acetonitrile. After lyophilization of the product-containing fractions, (1R,3S)-3-{3-[(1,2-oxazol-3-ylacetyl)amino]-1H-pyrazol-5-yl}cyclopentyl tert-butylcarbamate (Example 17, 74.84 mg, 27%, 99% ee by chiral analytical SFC) was obtained as a white solid. $^1$H NMR (500 MHz, DMSO-d6) δ=12.09 (br s, 1H), 10.63 (s, 1H), 8.83 (s, 1H), 6.76 (br s, 1H), 6.53 (s, 1H), 6.29 (s, 1H), 4.96 (br s, 1H), 3.75 (s, 2H), 3.02 (quin, J=8.7 Hz, 1H), 2.47-2.41 (m, 1H), 2.04-1.93 (m, 1H), 1.92-1.79 (m, 1H), 1.78-1.61 (m, 2H), 1.55 (br s, 1H), 1.19 (s, 9H). MS: 376 [M+H]+.

Method E

Example 18: (1R,3S)-3-(3-{[(5-methyl-1,3,4-thiadiazol-2-yl)acetyl]amino}-1H-pyrazol-5-yl)cyclopentyl (1-methylcyclobutyl)carbamate

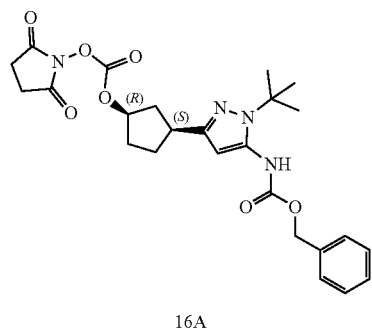

16A

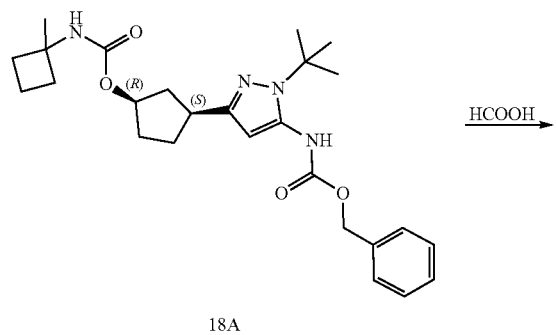

18A

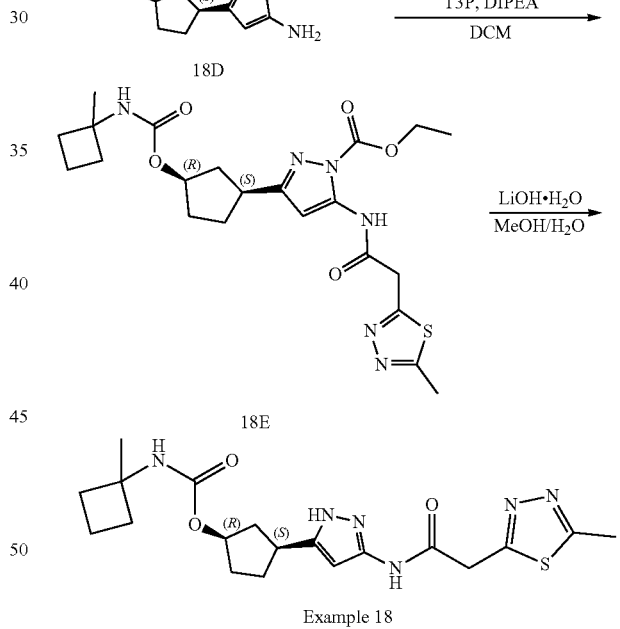

Example 18

A solution of benzyl {1-tert-butyl-3-[(1 S,3R)-3-({[(2,5-dioxopyrrolidin-1-yl)oxy]carbonyl}oxy)cyclopentyl]-1H-pyrazol-5-yl}carbamate (16A, 1.20 g, 2.41 mmol), 1-methylcyclobutylamine hydrochloride (CAS #174886-05-6, 439 mg, 3.61 mmol), and diisopropylethyl amine (1.56 g, 12.0 mmol) in THF (15 mL) was stirred at room temperature (32° C.) for 18 hours. The mixture was concentrated under vacuum and the residue dissolved in dichloromethane (25 mL). The solution washed with water (2×5 mL), sat. aq NH4Cl (5 mL) and sat. aq NaCl (5 mL). The organic layer was dried over sodium sulfate, filtered, concentrated. The crude product was purified by silica gel chromatography (eluting with 0-30% ethyl acetate in petroleum ether) to give benzyl {1-tert-butyl-3-[(1 S,3R)-3-{[(1-methylcyclobutyl)carbamoyl]oxy}cyclopentyl]-1H-pyrazol-5-yl}carbamate (18A, 920 mg, 82%) as a light yellow gum. MS: 469 [M+H]$^+$.

The benzyl {1-tert-butyl-3-[(1S,3R)-3-{[(1-methylcyclobutyl)carbamoyl]-oxy}cyclopentyl]-1H-pyrazol-5-yl}carbamate (18A, 920 mg, 1.96 mmol) was stirred in formic acid (10 mL) at 75° C. for 18 hours. The volatiles were removed under vacuum, and the residue partitioned between dichloromethane (20 mL) and sat. aq NaHCO$_3$. The organic layer was dried over sodium sulfate, filtered, concentrated, and purified by silica gel chromatography (eluting with 0-80% ethyl acetate in petroleum ether) to give benzyl {3-[(1 S,3R)-3-{[(1-methylcyclobutyl)carbamoyl]oxy}cyclopentyl]-1H-pyrazol-5-yl}carbamate (18B, 500 mg, 62%) as a light yellow gum. MS: 435 [M+Na]$^+$.

Ethyl chloroformate (197 mg, 1.82 mmol) was added in portions to a solution of give benzyl {3-[(1S,3R)-3-{[(1-methylcyclobutyl)carbamoyl]oxy}cyclopentyl]-1H-pyrazol-5-yl}carbamate (18B, 500 mg, 1.21 mmol) and diisopropylethyl amine (470 mg, 3.64 mmol) in dichloromethane (15 mL). The mixture was stirred at room temperature (35° C.) for 4 hours, then washed with sat. aq NH4Cl (2×5 mL) and sat. aq NaCl (5 mL). The organic layer was dried over sodium sulfate, filtered, and concentrated to give crude ethyl 5-{[(benzyloxy)carbonyl]amino}-3-[(1 S,3R)-3-{[(1-methylcyclobutyl)carbamoyl]-oxy}cyclopentyl]-1H-pyrazole-1-carboxylate (18C, 560 mg, 95%, 80% pure by NMR) as a light yellow glass. $^1$H NMR (400 MHz, CHLOROFORM-d) δ=9.50 (s, 1H), 7.44-7.32 (m, 5H), 7.33-7.32 (m, 1H), 6.62 (br. s., 1H), 5.22 (s, 2H), 5.17 (br. s., 1H), 4.51 (q, J=7.0 Hz, 2H), 3.25-3.13 (m, 1H), 2.51-2.30 (m, 2H), 2.14-2.03 (m, 1H), 2.00-1.73 (m, 8H), 1.47 (t, J=7.2 Hz, 4H), 1.44 (s, 3H). MS: 485 [M+H]$^+$; 507 [M+Na]$^+$.

A suspension of crude ethyl 5-{[(benzyloxy)carbonyl]amino}-3-[(1 S,3R)-3-{[(1-methylcyclobutyl)carbamoyl]oxy}cyclopentyl]-1H-pyrazole-1-carboxylate (18C, 560 mg, 1.16 mmol) and Pd/C catalyst (wet, 50 wt %, 150 mg) in ethyl acetate (10 mL) and THF (10 mL) was degassed, backfilled with hydrogen, then stirred und a hydrogen balloon at room temperature for 1 hour. The catalyst was removed by filtration, and the filtrate concentrated to give crude ethyl 5-amino-3-[(1 S,3R)-3-{[(1-methylcyclobutyl)-carbamoyl]oxy}cyclopentyl]-1H-pyrazole-1-carboxylate (18D, 430 mg, 100% crude) as a light yellow gum. MS: 351 [M+H]$^+$; 373 [M+Na]$^+$.

Crude ethyl 5-amino-3-[(1 S,3R)-3-{[(1-methylcyclobutyl)carbamoyl]oxy}-cyclopentyl]-1H-pyrazole-1-carboxylate (18D, 100.0 mg, 0.285 mmol) and sodium 2-(5-methyl-1,3,4-thiadiazol-2-yl)acetate (CAS #1909316-87-5, 77.6 mg, 0.428 mmol) were suspended in dichloromethane (10 mL) at room temperature (35° C.). Diisopropylethyl amine (184 mg, 1.43 mmol) and propylphosphonic anhydride (T3β ®, 50 wt % solution in EtOAc, 545 mg, 0.856 mmol) were added and the resulting solution stirred at 35° C. for 3 hours. The reaction mixture was washed with water (3 mL), sat. aq NH$_4$Cl (2×3 mL) and sat. aq NaCl (3 mL). The organic layer was dried over sodium sulfate, filtered, and concentrated to give crude ethyl 3-[(1S,3R)-3-{[(1-methylcyclobutyl)carbamoyl]oxy}-cyclopentyl]-5-{[(5-methyl-1,3,4-thiadiazol-2-yl)acetyl]amino}-1H-pyrazole-1-carboxylate (18E, 140 mg, 100% crude) as a light yellow gum. MS: 513 [M+Na]$^+$.

A mixture of crude ethyl 3-[(1S,3R)-3-{[(1-methylcyclobutyl)carbamoyl]oxy}-cyclopentyl]-5-{[(5-methyl-1,3,4-thiadiazol-2-yl)acetyl]amino}-1H-pyrazole-1-carboxylate (18E, 140 mg, 0.285 mmol) and lithium hydroxide monohydrate (35.9 mg, 0.856 mmol) in methanol (5 mL) and water (1 mL) was stirred at room temperature (35° C.) for 30 minutes, then let stand overnight. The suspension was concentrated to ~3 mL, the solids removed by filtration, and the filtrate purified by preparative HPLC on a DuraShell 150*25 mm*5 μm column, eluting with 27-47% water (0.05% ammonium hydroxide v/v) in acetonitrile. After lyophilization of the product-containing fractions, (1R,3S)-3-(3-{[(5-methyl-1,3,4-thiadiazol-2-yl)acetyl]amino}-1H-pyrazol-5-yl)cyclopentyl (1-methylcyclo-butyl)carbamate (Example 18, 30.89 mg, 26%, >99% ee by chiral analytical SFC) was obtained as a white solid. $^1$H NMR (500 MHz, DMSO-d6) δ=12.14 (br s, 1H), 10.78 (s, 1H), 7.18 (br s, 1H), 6.30 (br s, 1H), 4.97 (br s, 1H), 4.19 (s, 2H), 3.13-2.95 (m, 1H), 2.69 (s, 3H), 2.48-2.40 (m, 1H), 2.21 (br s, 2H), 1.99 (br d, J=8.9 Hz, 1H), 1.92-1.83 (m, 1H), 1.82-1.75 (m, 2H), 1.74-1.63 (m, 4H), 1.57 (br s, 1H), 1.34-1.23 (m, 3H). MS: 419 [M+H]$^+$.

Additional compounds of the invention were prepared by modifications of the methods exemplified herein. When chiral starting reactants were available, compounds were prepared and isolated as single stereoisomers having a known absolute configuration, as indicated by (R) and (S) labels on their structures. When racemic starting reactants were used, compounds were carried through synthesis as a mixture of diastereomers and then separated into single stereoisomers by an appropriate chiral preparative HPLC or SFC method before characterization and testing. In these cases, the known stereocenters are drawn with wedge bonds and annotated with (R) and (S) labels; the unknown stereocenters are drawn as starred flat bonds, and an explanation is included in Table 2. Where relative but not absolute stereochemistry is known, structures are drawn with starred wedge bonds, without (R) and/or (S) labels, and an explanation is included in Table 2.

Selected compounds and their corresponding characterization data are presented in Table 2 below.

TABLE 2

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 19 (A) | 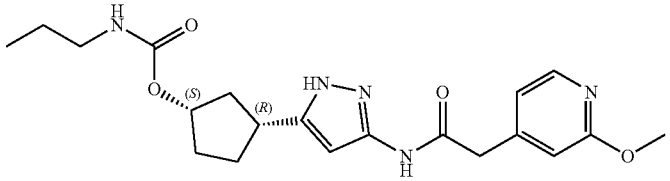<br>(1S,3R)-3-(3-{[(2-methoxypyridin-4-yl)acetyl]amino}-1H-pyrazol-5-yl)cyclopentyl propylcarbamate<br>All stereocenters known | 402.3 | 1H NMR (400 MHz, CHLOROFORM-d) δ = 11.32-10.73 (m, 1H), 9.43 (br s, 1H), 8.03 (d, J = 5.3 Hz, 1H), 6.77 (d, J = 4.8 Hz, 1H), 6.65 (s, 1H), 6.47 (br s, 1H), 5.17 (br t, J = 5.8 Hz, 1H), 5.09 (br s, 1H), 3.86 (s, 3H), 3.57 (s, 2H), 3.11-2.97 (m, 3H), 2.45-2.31 (m, 1H), 2.00 (br d, J = 4.8 Hz, 1H), 1.91-1.68 (m, 4H), 1.50-1.36 (m, 2H), 0.84 (br t, J = 7.3 Hz, 3H) |
| 20 (A) | 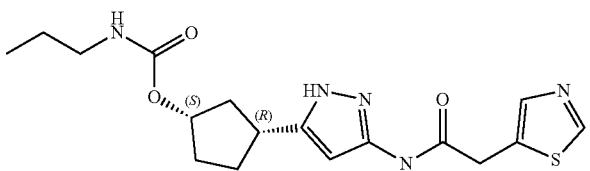<br>(1S,3R)-3-{3-[(1,3-thiazol-5-ylacetyl)amino]-1H-pyrazol-5-yl}cyclopentyl propylcarbamate<br>All stereocenters known | 378.3 | 1H NMR (400 MHz, DMSO-d6) δ = 12.10 (s, 1H), 10.62 (s, 1H), 8.97 (s, 1H), 7.73 (s, 1H), 7.04 (br t, J = 5.3 Hz, 1H), 6.30 (s, 1H), 5.03-4.95 (m, 1H), 3.92 (s, 2H), 3.11-2.98 (m, 1H), 2.91 (q, J = 6.4 Hz, 2H), 2.47-2.40 (m, 1H), 2.08-1.95 (m, 1H), 1.94-1.82 (m, 1H), 1.77-1.53 (m, 3H), 1.44-1.31 (m, 2H), 0.81 (t, J = 7.4 Hz, 3H) |
| 21 (A) | 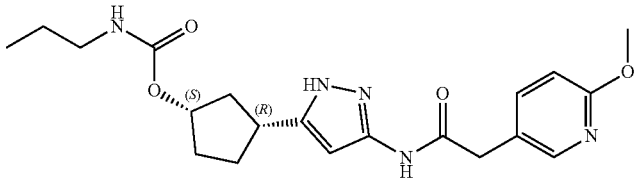<br>(1S,3R)-3-(3-{[(6-methoxypyridin-3-yl)acetyl]amino}-1H-pyrazol-5-yl)cyclopentyl propylcarbamate<br>All stereocenters known | 402.3 | 1H NMR (400 MHz, CHLOROFORM-d) δ = 9.93 (s, 1H), 8.21-8.12 (m, 1H), 8.09 (d, J = 2.3 Hz, 1H), 7.56 (dd, J = 2.5, 8.5 Hz, 1H), 6.74 (d, J = 8.3 Hz, 1H), 6.62-6.49 (m, 1H), 5.21-5.14 (m, 1H), 4.90-4.82 (m, 1H), 3.93 (s, 3H), 3.62 (s, 2H), 3.20-3.01 (m, 3H), 2.46 (ddd, J = 6.8, 8.7, 14.9 Hz, 1H), 2.15-2.06 (m, 1H), 1.98-1.76 (m, 4H), 1.56-1.42 (m, 2H), 0.93-0.85 (m, 3H) |
| 22 (A) | 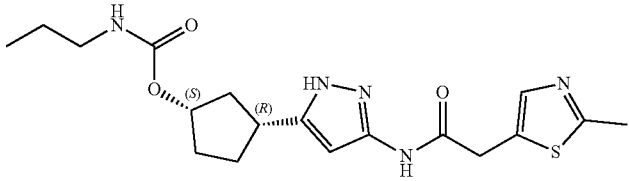<br>(1S,3R)-3-(3-{[(2-methyl-1,3-thiazol-5-yl)acetyl]amino}-1H-pyrazol-5-yl)cyclopentyl propylcarbamate<br>All stereocenters known | 392.3 | 1H NMR (400 MHz, CHLOROFORM-d) δ = 10.24 (br s, 1H), 8.55 (s, 1H), 7.49 (s, 1H), 6.64-6.50 (m, 1H), 5.22-5.13 (m, 1H), 4.98-4.87 (m, 1H), 3.88 (s, 2H), 3.21-3.00 (m, 3H), 2.68 (s, 3H), 2.57-2.43 (m, 1H), 2.17-2.04 (m, 1H), 1.99-1.77 (m, 4H), 1.57-1.41 (m, 2H), 0.90 (t, J = 7.4 Hz, 3H) |
| 23 (A) | 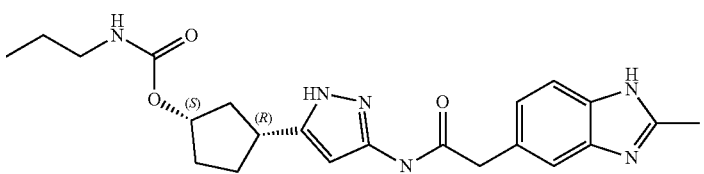<br>(1S,3R)-3-(3-{[(2-methyl-1H-benzimidazol-5-yl)acetyl]amino}-1H-pyrazol-5-yl)cyclopentyl propylcarbamate<br>All stereocenters known | 425.3 | 1H NMR (400 MHz, DMSO-d6) δ = 12.34-11.82 (m, 2H), 10.46 (br s, 1H), 7.62-7.27 (m, 2H), 7.20-6.92 (m, 2H), 6.41-6.13 (m, 1H), 5.16-4.78 (m, 1H), 3.63 (s, 2H), 3.11-2.96 (m, 1H), 2.90 (q, J = 6.5 Hz, 2H), 2.49-2.36 (m, 4H), 2.05-1.81 (m, 2H), 1.76-1.50 (m, 3H), 1.44-1.27 (m, 2H), 0.90-0.69 (m, 3H) |

TABLE 2-continued

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 24 (A) | (1S,3R)-3-(3-{[(3ξ)-2,3-dihydro-1-benzofuran-3-ylcarbonyl]amino}-1H-pyrazol-5-yl)cyclopentyl propylcarbamate—Isomer A<br>Single stereoisomer; absolute configuration of the chiral center in the dihydrobenzofuran was not determined | 399.3 | ¹H NMR (400 MHz, DMSO-d6) δ = 12.12 (br s, 1H), 10.81 (s, 1H), 7.30 (d, J = 7.3 Hz, 1H), 7.14 (t, J = 7.7 Hz, 1H), 7.02 (br t, J = 5.6 Hz, 1H), 6.83 (t, J = 7.4 Hz, 1H), 6.78 (d, J = 8.0 Hz, 1H), 6.28 (s, 1H), 4.98 (br s, 1H), 4.78 (dd, J = 6.3, 8.8 Hz, 1H), 4.64 (t, J = 9.2 Hz, 1H), 4.45 (dd, J = 6.4, 9.2 Hz, 1H), 3.12-2.96 (m, 1H), 2.89 (q, J = 6.7 Hz, 2H), 2.47-2.37 (m, 1H), 2.06-1.94 (m, 1H), 1.93-1.79 (m, 1H), 1.77-1.62 (m, 2H), 1.60-1.48 (m, 1H), 1.44-1.27 (m, 2H), 0.79 (t, J = 7.4 Hz, 3H) [α]$_D^{25}$ −42.0 (c 0.1, MeOH) Peak 1 of 2: Column: SS WHELK-O1 (250 mm*50 mm, 10 μm); Mobile phase: 40% IPA (0.1% NH3.H2O) in CO₂; Flow rate: 6.5 mL/min Column temp 40° C. |
| 25 (A) | (1S,3R)-3-(3-{[(3ξ)-2,3-dihydro-1-benzofuran-3-ylcarbonyl]amino}-1H-pyrazol-5-yl)cyclopentyl propylcarbamate—Isomer B<br>Single stereoisomer; absolute configuration of the chiral center in the dihydrobenzofuran was not determined | 399.3 | ¹H NMR (400 MHz, DMSO-d6)ä = 12.12 (br s, 1H), 10.80 (s, 1H), 7.30 (d, J = 7.5 Hz, 1H), 7.14 (t, J = 7.7 Hz, 1H), 7.03 (br t, J = 5.4 Hz, 1H), 6.83 (t, J = 7.2 Hz, 1H), 6.78 (d, J = 8.0 Hz, 1H), 6.28 (br s, 1H), 4.98 (br s, 1H), 4.78 (dd, J = 6.3, 8.8 Hz, 1H), 4.64 (t, J = 9.2 Hz, 1H), 4.45 (dd, J = 6.3, 9.3 Hz, 1H), 3.11-2.97 (m, 1H), 2.89 (q, J = 6.6 Hz, 2H), 2.48-2.37 (m, 1H), 2.04-1.93 (m, 1H), 1.92-1.79 (m, 1H), 1.76-1.62 (m, 2H), 1.61-1.51 (m, 1H), 1.44-1.29 (m, 2H), 0.80 (t, J = 7.4 Hz, 3H) [α]$_D^{25}$ +39.3 (c 0.1, MeOH) Peak 2 of 2: Column: SS WHELK-O1 (250 mm*50 mm, 10 μm); Mobile phase: 40% IPA (0.1% NH3.H2O) in CO₂; Flow rate: 6.5 mL/min Column temp 40° C. |
| 26 (A) | (1S,3R)-3-(3-{[(2-methyl-1,3-thiazol-5-yl)acetyl]amino}-1H-pyrazol-5-yl)cyclopentyl propan-2-yl carbamate<br>All stereocenters known | 392.3 | ¹H NMR (400 MHz, DMSO-d6) δ = 12.09 (s, 1H), 10.58 (s, 1H), 7.40 (s, 1H), 6.95 (br d, J = 7.8 Hz, 1H), 6.28 (s, 1H), 4.98 (br s, 1H), 3.81 (s, 2H), 3.65-3.48 (m, 1H), 3.16-2.93 (m, 1H), 2.58 (s, 3H), 2.47-2.37 (m, 1H), 2.05-1.94 (m, 1H), 1.91-1.78 (m, 1H), 1.77-1.63 (m, 2H), 1.55 (br t, J = 13.7 Hz, 1H), 1.02 (br d, J = 6.3 Hz, 6H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 27 (B) | 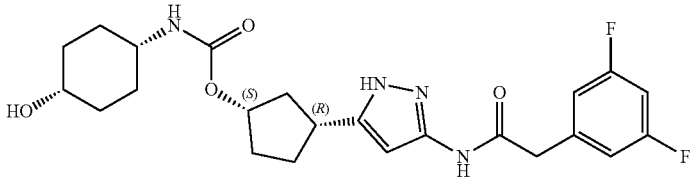 (1S,3R)-3-(3-{[(3,5-difluorophenyl)acetyl]amino}-1H-pyrazol-5-yl)cyclopentyl (cis-4-hydroxycyclohexyl)carbamate All stereocenters known; cyclohexyl ring is meso-N,O-cis. | 463.4 | 1H NMR (400 MHz, DMSO-d6) δ = 12.08 (br s, 1H), 10.57 (s, 1H), 7.15-7.08 (m, 1H), 7.02 (br d, J = 6.3 Hz, 2H), 6.97 (br d, J = 7.3 Hz, 1H), 6.27 (br s, 1H), 4.96 (br d, J = 1.8 Hz, 1H), 4.31 (br s, 1H), 3.63 (s, 3H), 3.30-3.19 (m, 1H), 3.07-2.96 (m, 1H), 2.46-2.38 (m, 1H), 1.98 (br d, J = 8.5 Hz, 1H), 1.91-1.81 (m, 1H), 1.74-1.63 (m, 2H), 1.61-1.48 (m, 5H), 1.41 (br d, J = 10.3 Hz, 4H) |
| 28 (B) | 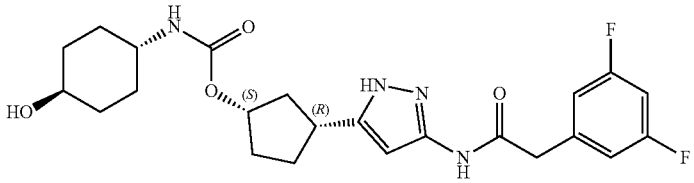 (1S,3R)-3-(3-{[(3,5-difluorophenyl)acetyl]amino}-1H-pyrazol-5-yl)cyclopentyl (trans-4-hydroxycyclohexyl)carbamate All stereocenters known; cyclohexyl ring is meso-N,O-trans. | 463.4 | 1H NMR (400 MHz, DMSO-d6) δ = 12.09 (s, 1H), 10.56 (s, 1H), 7.16-7.07 (m, 1H), 7.06-6.98 (m, 2H), 6.92 (br d, J = 7.5 Hz, 1H), 6.27 (s, 1H), 5.01-4.91 (m, 1H), 4.53 (d, J = 4.3 Hz, 1H), 3.63 (s, 2H), 3.22-3.13 (m, 1H), 3.04-2.95 (m, 1H), 2.43-2.37 (m, 1H), 2.01-1.93 (m, 1H), 1.86 (ddd, J = 2.8, 6.7, 9.9 Hz, 1H), 1.81-1.61 (m, 7H), 1.59-1.50 (m, 1H), 1.20-1.07 (m, 4H) |
| 29 (C) | 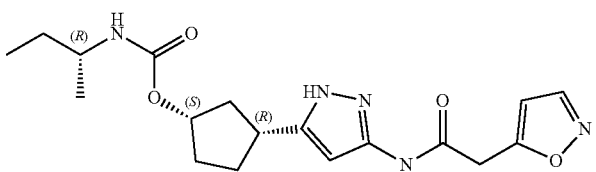 (1S,3R)-3-{3-[(1,2-oxazol-5-ylacetyl)amino]-1H-pyrazol-5-yl}cyclopentyl (2R)-butan-2-ylcarbamate All stereocenters known | 376.2 | 1H NMR (400 MHz, DMSO-d6) δ = 12.13 (s, 1H), 10.66 (s, 1H), 8.49 (d, J = 1.5 Hz, 1H), 6.88 (br d, J = 8.0 Hz, 1H), 6.38 (s, 1H), 6.30 (s, 1H), 4.99 (br s, 1H), 3.92 (s, 2H), 3.39-3.36 (m, 1H), 3.12-2.94 (m, 1H), 2.49-2.40 (m, 1H), 2.05-1.95 (m, 1H), 1.94-1.82 (m, 1H), 1.79-1.50 (m, 3H), 1.46-1.27 (m, 2H), 1.00 (d, J = 6.8 Hz, 3H), 0.80 (br t, J = 7.4 Hz, 3H) $[\alpha]_D^{25}$ +3.6 (c 0.11, MeOH) |
| 30 (C) | 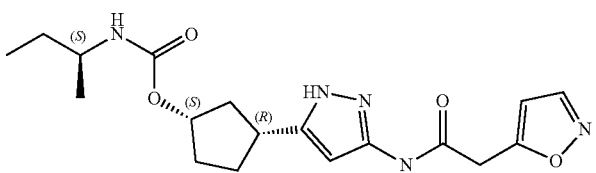 (1S,3R)-3-{3-[(1,2-oxazol-5-ylacetyl)amino]-1H-pyrazol-5-yl}cyclopentyl (2S)-butan-2-ylcarbamate All stereocenters known | 376.2 | 1H NMR (400 MHz, DMSO-d6) δ = 12.13 (s, 1H), 10.66 (s, 1H), 8.49 (d, J = 1.5 Hz, 1H), 6.88 (br d, J = 8.0 Hz, 1H), 6.38 (s, 1H), 6.30 (s, 1H), 4.99 (br s, 1H), 3.92 (s, 2H), 3.36 (d, J = 2.8 Hz, 1H), 3.12-2.98 (m, 1H), 2.49-2.41 (m, 1H), 2.05-1.95 (m, 1H), 1.94-1.79 (m, 1H), 1.77-1.51 (m, 3H), 1.41-1.29 (m, 2H), 1.00 (d, J = 6.5 Hz, 3H), 0.79 (t, J = 7.4 Hz, 3H) $[\alpha]_D^{25}$ −15.0 (c 0.11, MeOH) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 31 (A) | (1S,3R)-3-(3-{[(1-methyl-1H-1,2,3-triazol-5-yl)carbonyl]amino}-1H-pyrazol-5-yl)cyclopentyl (2S)-butan-2-ylcarbamate<br>All stereocenters known | 376.4 | 1H NMR (400 MHz, DMSO-d6) δ = 12.33 (br s, 1H), 11.15 (br s, 1H), 8.46 (s, 1H), 6.91 (br d, J = 8.3 Hz, 1H), 6.44 (s, 1H), 5.00 (br s, 1H), 4.24 (s, 3H), 3.43-3.37 (m, 1H), 3.13-3.01 (m, 1H), 2.49-2.40 (m, 1H), 2.08-1.98 (m, 1H), 1.96-1.83 (m, 1H), 1.79-1.68 (m, 2H), 1.67-1.56 (m, 1H), 1.40-1.28 (m, 2H), 1.00 (d, J = 6.5 Hz, 3H), 0.81 (t, J = 7.3 Hz, 3H). |
| 32 (A) | (1R,3S)-3-(3-{[(3-methyl-1,2-oxazol-5-yl)acetyl]amino}-1H-pyrazol-5-yl)cyclopentyl (2S)-butan-2-ylcarbamate<br>All stereocenters known | 390.3 | 1H NMR (400 MHz, DMSO-d6) δ = 12.12 (s, 1H), 10.64 (s, 1H), 6.89 (br d, J = 8.3 Hz, 1H), 6.30 (br s, 1H), 6.22 (s, 1H), 4.99 (br s, 1H), 3.83 (s, 2H), 3.35-3.30 (m, 1H), 3.10-2.99 (m, 1H), 2.48-2.40 (m, 1H), 2.20 (s, 3H), 2.06-1.82 (m, 2H), 1.77-1.51 (m, 3H), 1.41-1.27 (m, 2H), 1.00 (d, J = 6.5 Hz, 3H), 0.80 (t, J = 7.4 Hz, 3H) |
| 33 (A) | (1R,3S)-3-(3-{[(2-methyl-1,3-thiazol-5-yl)acetyl]amino}-1H-pyrazol-5-yl)cyclopentyl (2S)-butan-2-ylcarbamate<br>All stereocenters known | 406.2 | 1H NMR (400 MHz, DMSO-d6) δ = 12.08 (s, 1H), 10.56 (s, 1H), 7.41 (s, 1H), 6.86 (br d, J = 8.0 Hz, 1H), 6.29 (br s, 1H), 4.99 (br s, 1H), 3.82 (s, 2H), 3.34 (br s, 1H), 3.12-2.97 (m, 1H), 2.59 (s, 3H), 2.48-2.39 (m, 1H), 2.05-1.95 (m, 1H), 1.94-1.82 (m, 1H), 1.77-1.65 (m, 2H), 1.63-1.52 (m, 1H), 1.43-1.27 (m, 2H), 1.00 (d, J = 6.5 Hz, 3H), 0.80 (t, J = 7.4 Hz, 3H) |
| 34 (A) | (1R,3S)-3-(3-{[(5-methylpyrazin-2-yl)acetyl]amino}-1H-pyrazol-5-yl)cyclopentyl (2S)-butan-2-ylcarbamate<br>All stereocenters known | 401.4 | 1H NMR (400 MHz, DMSO-d6) δ = 12.08 (br s, 1H), 10.60 (s, 1H), 8.47 (d, J = 13.6 Hz, 2H), 6.88 (br d, J = 8.3 Hz, 1H), 6.28 (s, 1H), 4.99 (br s, 1H), 3.83 (s, 2H), 3.42-3.37 (m, 1H), 3.11-2.97 (m, 1H), 2.47 (s, 3H), 2.45 (br d, J = 6.0 Hz, 1H), 2.07-1.80 (m, 2H), 1.78-1.49 (m, 3H), 1.40-1.26 (m, 2H), 0.99 (d, J = 6.5 Hz, 3H), 0.78 (t, J = 7.3 Hz, 3H) |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 35 (A) | (1R,3S)-3-(3-{[(6-methylpyrazin-3-yl)acetyl]amino}-1H-pyrazol-5-yl)cyclopentyl (2S)-butan-2-ylcarbamate<br>All stereocenters known | 400.4 | ¹H NMR (400 MHz, DMSO-d6) δ = 12.06 (s, 1H), 10.54 (s, 1H), 8.34 (d, J = 2.0 Hz, 1H), 7.58 (dd, J = 2.3, 8.0 Hz, 1H), 7.18 (d, J = 8.0 Hz, 1H), 6.86 (br d, J = 8.0 Hz, 1H), 6.27 (s, 1H), 4.97 (br s, 1H), 3.56 (s, 2H), 3.34-3.31 (m, 1H), 3.10-2.93 (m, 1H), 2.47-2.39 (m, 4H), 2.03-1.93 (m, 1H), 1.91-1.80 (m, 1H), 1.75-1.61 (m, 2H), 1.60-1.50 (m, 1H), 1.32 (td, J = 7.1, 11.1 Hz, 2H), 0.99 (d, J = 6.5 Hz, 3H), 0.78 (t, J = 7.4 Hz, 3H) |
| 36 (A) | (1R,3S)-3-{3-[(1,3-thiazol-5-ylacetyl)amino]-1H-pyrazol-5-yl}cyclopentyl (2S)-butan-2-ylcarbamate<br>All stereocenters known | 392.3 | ¹H NMR (400 MHz, DMSO-d6) δ = 12.11 (br s, 1H), 10.63 (s, 1H), 8.97 (s, 1H), 7.73 (s, 1H), 6.88 (br d, J = 8.3 Hz, 1H), 6.30 (br s, 1H), 4.99 (br s, 1H), 4.05-3.79 (m, 2H), 3.36-3.31 (m, 1H), 3.12-2.98 (m, 1H), 2.49-2.41 (m, 1H), 2.07-1.81 (m, 2H), 1.77-1.52 (m, 3H), 1.42-1.26 (m, 2H), 1.00 (d, J = 6.5 Hz, 3H), 0.79 (t, J = 7.4 Hz, 3H) |
| 37 (A) | (1R,3S)-3-(3-{[(2-methoxypyridin-4-yl)acetyl]amino}-1H-pyrazol-5-yl)cyclopentyl (2S)-butan-2-ylcarbamate<br>All stereocenters known | 416.3 | ¹H NMR (400 MHz, DMSO-d6) δ = 12.09 (s, 1H), 10.58 (s, 1H), 8.08 (d, J = 5.3 Hz, 1H), 6.98-6.81 (m, 2H), 6.74 (s, 1H), 6.28 (br s, 1H), 4.98 (br s, 1H), 3.83 (s, 3H), 3.59 (s, 2H), 3.35 (br s, 1H), 3.10-2.96 (m, 1H), 2.49-2.40 (m, 1H), 2.04-1.81 (m, 2H), 1.78-1.52 (m, 3H), 1.42-1.25 (m, 2H), 1.00 (d, J = 6.5 Hz, 3H), 0.79 (t, J = 7.4 Hz, 3H) |
| 38 (A) | (1R,3S)-3-{3-[(phenylacetyl)amino]-1H-pyrazol-5-yl}cyclopentyl (2S)-butan-2-ylcarbamate<br>All stereocenters known | 385.4 | ¹H NMR (400 MHz, DMSO-d6) δ = 12.06 (s, 1H), 10.51 (br s, 1H), 7.34-7.27 (m, 4H), 7.27-7.20 (m, 1H), 6.87 (br d, J = 8.3 Hz, 1H), 6.29 (br s, 1H), 4.98 (br s, 1H), 3.58 (s, 2H), 3.36-3.30 (m, 1H), 3.09-2.96 (m, 1H), 2.45 (td, J = 7.2, 14.0 Hz, 1H), 2.05-1.80 (m, 2H), 1.77-1.50 (m, 3H), 1.40-1.26 (m, 2H), 1.00 (d, J = 6.5 Hz, 3H), 0.79 (t, J = 7.4 Hz, 3H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 39 (A) | (1R,3S)-3-{3-[([1,2,4]triazolo[1,5-a]pyrimidin-6-ylacetyl)amino]-1H-pyrazol-5-yl}cyclopentyl (2S)-butan-2-ylcarbamate<br>All stereocenters known | 427.2 | 1H NMR (400 MHz, DMSO-d6) δ = 12.11 (br s, 1H), 10.66 (s, 1H), 9.33 (d, J = 2.0 Hz, 1H), 8.84 (d, J = 2.3 Hz, 1H), 8.71-8.56 (m, 1H), 6.94-6.72 (m, 1H), 6.28 (br s, 1H), 4.98 (br s, 1H), 3.86 (s, 2H), 3.42 (br d, J = 4.8 Hz, 1H), 3.15-2.91 (m, 1H), 2.48-2.39 (m, 1H), 2.07-1.80 (m, 2H), 1.78-1.50 (m, 3H), 1.45-1.22 (m, 2H), 1.06-0.89 (m, 3H), 0.85-0.68 (m, 3H) |
| 40 (A) | (1R,3S)-3-[3-({[2-(ethylsulfonyl)phenyl]acetyl}amino)-1H-pyrazol-5-yl]cyclopentyl (2S)-butan-2-ylcarbamate<br>All stereocenters known | 477.3 | 1H NMR (400 MHz, DMSO-d6) δ = 12.09 (br s, 1H), 10.59 (s, 1H), 8.04-7.85 (m, 1H), 7.70 (dt, J = 1.1, 7.5 Hz, 1H), 7.59-7.48 (m, 2H), 6.87 (br d, J = 8.3 Hz, 1H), 6.26 (br s, 1H), 4.98 (br s, 1H), 4.17 (s, 2H), 3.37-3.29 (m, 3H), 3.10-2.96 (m, 1H), 2.49-2.39 (m, 1H), 2.07-1.79 (m, 2H), 1.77-1.48 (m, 3H), 1.42-1.24 (m, 2H), 1.12 (t, J = 7.4 Hz, 3H), 0.99 (br d, J = 6.5 Hz, 3H), 0.78 (t, J = 7.4 Hz, 3H) |
| 41 (A) | (1R,3S)-3-(3-{[(3-methoxy-1-methyl-1H-pyrazol-5-yl)carbonyl]amino}-1H-pyrazol-5-yl)cyclopentyl (2S)-butan-2-ylcarbamate<br>All stereocenters known | 405.3 | 1H NMR (400 MHz, DMSO-d6) δ = 12.24 (s, 1H), 10.66 (s, 1H), 6.89 (br d, J = 8.3 Hz, 1H), 6.59 (s, 1H), 6.42 (br s, 1H), 5.00 (br d, J = 4.1 Hz, 1H), 3.94 (s, 3H), 3.78 (s, 3H), 3.43-3.36 (m, 1H), 3.13-3.02 (m, 1H), 2.56-2.52 (m, 1H), 2.09-1.99 (m, 1H), 1.97-1.86 (m, 1H), 1.80-1.69 (m, 2H), 1.67-1.57 (m, 1H), 1.43-1.31 (m, 2H), 1.01 (d, J = 6.6 Hz, 3H), 0.81 (t, J = 7.4 Hz, 3H) |
| 42 (A) | (1R,3S)-3-(3-{[(1-methyl-1H-pyrazol-5-yl)carbonyl]amino}-1H-pyrazol-5-yl)cyclopentyl (2S)-butan-2-ylcarbamate<br>All stereocenters known | 375.3 | 1H NMR (400 MHz, DMSO-d6) δ = 11.39 (s, 1H), 9.88 (s, 1H), 6.64 (d, J = 1.9 Hz, 1H), 6.31 (s, 1H), 6.05 (br d, J = 8.3 Hz, 1H), 5.59 (br s, 1H), 4.16 (br s, 1H), 3.24 (s, 3H), 2.61-2.54 (m, 1H), 2.32-2.18 (m, 1H), 1.72-1.68 (m, 1H), 1.27-1.14 (m, 1H), 1.12-1.00 (m, 1H), 0.97-0.84 (m, 2H), 0.82-0.72 (m, 1H), 0.58-0.44 (m, 2H), 0.16 (d, J = 6.6 Hz, 3H), −0.04 (t, J = 7.4 Hz, 3H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 43 (A) | (1R,3S)-3-{3-[([1,3]thiazolo[4,5-b]pyridin-7-ylcarbonyl)amino]-1H-pyrazol-5-yl}cyclopentyl (2S)-butan-2-ylcarbamate<br>All stereocenters known | 429.3 | 1H NMR (400 MHz, DMSO-d6) δ = 12.40 (s, 1H), 11.49 (br s, 1H), 9.81 (s, 1H), 8.93 (d, J = 5.0 Hz, 1H), 8.37 (d, J = 5.0 Hz, 1H), 6.92 (br d, J = 8.3 Hz, 1H), 6.56 (br s, 1H), 5.03 (br s, 1H), 3.34-3.31 (m, 1H), 3.20-3.08 (m, 1H), 2.48 (br s, 1H), 2.12-2.03 (m, 1H), 1.97-1.85 (m, 1H), 1.77 (br d, J = 9.8 Hz, 2H), 1.66 (br t, J = 14.1 Hz, 1H), 1.44-1.30 (m, 2H), 1.02 (d, J = 6.8 Hz, 3H), 0.81 (t, J = 7.4 Hz, 3H) |
| 44 (A) | (1R,3S)-3-[3-({[4-methoxy-2-(methylsulfonyl)phenyl]acetyl}amino)-1H-pyrazol-5-yl]cyclopentyl (2S)-butan-2-ylcarbamate<br>All stereocenters known | 493.4 | 1H NMR (400 MHz, DMSO-d6) δ = 12.06 (br s, 1H), 10.53 (br s, 1H), 7.45-7.38 (m, 2H), 7.25 (dd, J = 2.6, 8.4 Hz, 1H), 6.86 (br d, J = 8.0 Hz, 1H), 6.25 (br s, 1H), 4.97 (br s, 1H), 4.08 (s, 2H), 3.83 (s, 3H), 3.37 (br s, 1H), 3.28 (s, 3H), 3.08-2.95 (m, 1H), 2.45-2.37 (m, 1H), 2.03-1.93 (m, 1H), 1.91-1.80 (m, 1H), 1.76-1.62 (m, 2H), 1.59-1.48 (m, 1H), 1.38-1.26 (m, 2H), 0.98 (br d, J = 6.5 Hz, 3H), 0.77 (br t, J = 7.3 Hz, 3H) |
| 45 (A) | (1R,3S)-3-[3-({[4-methyl-2-(methylsulfonyl)phenyl]acetyl}amino)-1H-pyrazol-5-yl]cyclopentyl (2S)-butan-2-ylcarbamate<br>All stereocenters known | 477.1 | 1H NMR (400 MHz, DMSO-d6) δ = 12.08 (s, 1H), 10.56 (s, 1H), 7.77 (s, 1H), 7.49 (d, J = 6.5 Hz, 1H), 7.38 (d, J = 7.8 Hz, 1H), 6.88 (br d, J = 8.5 Hz, 1H), 6.26 (s, 1H), 4.98 (br s, 1H), 4.13 (s, 2H), 3.31-3.23 (m, 4H), 3.11-2.96 (m, 1H), 2.48-2.44 (m, 1H), 2.39 (s, 3H), 1.99 (br d, J = 8.3 Hz, 1H), 1.93-1.83 (m, 1H), 1.76-1.63 (m, 2H), 1.62-1.50 (m, 1H), 1.33 (br dd, J = 6.9, 11.2 Hz, 2H), 0.99 (d, J = 6.5 Hz, 3H), 0.78 (t, J = 7.3 Hz, 3H) |
| 46 (A) | (1R,3S)-3-(3-{[(3-methylimidazo[1,2-b]pyridazin-6-yl)acetyl]amino}-1H-pyrazol-5-yl)cyclopentyl (2S)-butan-2-ylcarbamate<br>All stereocenters known | 440.4 | 1H NMR (400 MHz, CHLOROFORM-d) δ = 10.72 (br s, 1H), 10.11 (br s, 1H), 7.84 (d, J = 9.3 Hz, 1H), 7.56 (d, J = 0.7 Hz, 1H), 7.07 (d, J = 9.3 Hz, 1H), 6.62 (br s, 1H), 5.17 (br s, 1H), 4.66 (br d, J = 7.9 Hz, 1H), 3.91 (s, 2H), 3.65-3.53 (m, 1H), 3.19 (quin, J = 8.2 Hz, 1H), 2.56-2.43 (m, 4H), 2.18-2.06 (m, 1H), 1.98-1.84 (m, 4H), 1.47-1.34 (m, 2H), 1.15-1.01 (m, 3H), 0.85 (t, J = 7.4 Hz, 3H) |

TABLE 2-continued

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 47 (A) | (1R,3S)-3-(3-{[(2-methylimidazo[1,2-b]pyridazin-6-yl)acetyl]amino}-1H-pyrazol-5-yl)cyclopentyl (2S)-butan-2-ylcarbamate<br>All stereocenters known | 440.4 | $^1$H NMR (400 MHz, DMSO-d6) δ = 12.11 (br s, 1H), 10.69 (s, 1H), 7.99 (s, 1H), 7.93 (d, J = 9.3 Hz, 1H), 7.15 (d, J = 9.3 Hz, 1H), 6.87 (br d, J = 8.3 Hz, 1H), 6.29 (br s, 1H), 4.98 (br s, 1H), 3.87 (s, 2H), 3.38 (br s, 1H), 3.10-2.97 (m, 1H), 2.48-2.40 (m, 1H), 2.38 (s, 3H), 2.06-1.80 (m, 2H), 1.78-1.49 (m, 3H), 1.42-1.24 (m, 2H), 0.99 (br d, J = 6.5 Hz, 3H), 0.78 (br t, J = 7.3 Hz, 3H) |
| 48 (A) | (1R,3S)-3-(3-{[(1-methyl-1H-indazol-5-yl)acetyl]amino}-1H-pyrazol-5-yl)cyclopentyl (2S)-butan-2-ylcarbamate<br>All stereocenters known | 439.4 | $^1$H NMR (400 MHz, DMSO-d6) δ = 12.05 (br s, 1H), 10.51 (br s, 1H), 7.99 (s, 1H), 7.65 (s, 1H), 7.56 (br d, J = 8.5 Hz, 1H), 7.35 (br d, J = 8.5 Hz, 1H), 6.86 (br d, J = 8.0 Hz, 1H), 6.28 (br s, 1H), 4.97 (br s, 1H), 4.01 (s, 3H), 3.67 (s, 2H), 3.30 (br s, 1H), 3.11-2.92 (m, 1H), 2.46-2.37 (m, 1H), 2.04-1.91 (m, 1H), 1.85 (br d, J = 5.8 Hz, 1H), 1.76-1.61 (m, 2H), 1.54 (br s, 1H), 1.43-1.15 (m, 2H), 0.98 (br d, J = 6.5 Hz, 3H), 0.77 (br t, J = 7.2 Hz, 3H) |
| 49 (A) | (1R,3S)-3-(3-{[(2-sulfamoylphenyl)acetyl]amino}-1H-pyrazol-5-yl)cyclopentyl (2S)-butan-2-ylcarbamate<br>All stereocenters known | 463.8 | $^1$H NMR (400 MHz, DMSO-d6) δ = 12.25-11.99 (m, 1H), 10.67-10.42 (m, 1H), 7.91 (br d, J = 6.6 Hz, 1H), 7.56 (br d, J = 6.0 Hz, 1H), 7.46 (br s, 4H), 6.88 (br d, J = 6.1 Hz, 1H), 6.28 (br s, 1H), 4.98 (br s, 1H), 4.12 (br s, 2H), 3.47-3.42 (m, 1H), 3.03 (br s, 1H), 2.46-2.39 (m, 1H), 1.98 (br s, 1H), 1.87 (br s, 1H), 1.69 (br s, 2H), 1.56 (br s, 1H), 1.34 (br s, 2H), 0.99 (br s, 3H), 0.79 (br s, 3H) |
| 50 (A) | (1R,3S)-3-[3-({[5-methoxy-2-(methylsulfonyl)phenyl]acetyl}amino)-1H-pyrazol-5-yl]cyclopentyl (2S)-butan-2-ylcarbamate<br>All stereocenters known | 492.9 | $^1$H NMR (400 MHz, DMSO-d6) δ = 12.08 (s, 1H), 10.56 (s, 1H), 7.89 (d, J = 8.5 Hz, 1H), 7.17-6.99 (m, 2H), 6.87 (br d, J = 7.8 Hz, 1H), 6.27 (s, 1H), 4.97 (br s, 1H), 4.13 (s, 2H), 3.84 (s, 3H), 3.39 (br s, 1H), 3.22 (s, 2H), 3.27-3.15 (m, 1H), 3.08-2.99 (m, 1H), 2.44 (br d, J = 6.5 Hz, 1H), 2.08-1.79 (m, 2H), 1.78-1.47 (m, 3H), 1.42-1.24 (m, 2H), 0.99 (br d, J = 6.5 Hz, 3H), 0.82-0.73 (m, 1H), 0.78 (br t, J = 7.4 Hz, 2H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 51 (A) | 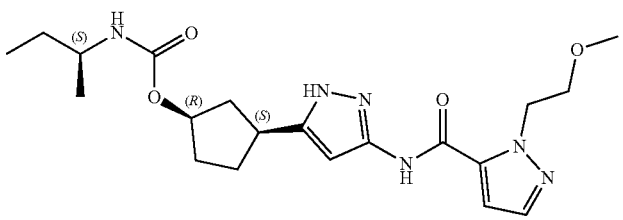<br>(1R,3S)-3-[3-({[1-(2-methoxyethyl)-1H-pyrazol-5-yl]carbonyl}amino)-1H-pyrazol-5-yl]cyclopentyl (2S)-butan-2-ylcarbamate<br>All stereocenters known | 419.3 | 1H NMR (400 MHz, DMSO-d6) δ = 12.24 (br s, 1H), 10.74 (br s, 1H), 7.52 (s, 1H), 7.12 (br s, 1H), 6.90 (br d, J = 8.0 Hz, 1H), 6.42 (br s, 1H), 5.00 (br s, 1H), 4.69 (br t, J = 5.6 Hz, 2H), 3.66 (br t, J = 5.6 Hz, 2H), 3.46 (br s, 1H), 3.18 (s, 3H), 3.12-3.00 (m, 1H), 2.46-2.36 (m, 1H), 2.03 (br d, J = 7.0 Hz, 1H), 1.94-1.82 (m, 1H), 1.79-1.68 (m, 2H), 1.65-1.55 (m, 1H), 1.44-1.22 (m, 2H), 1.00 (br d, J = 6.5 Hz, 3H), 0.80 (t, J = 7.3 Hz, 3H) |
| 52 (A) | 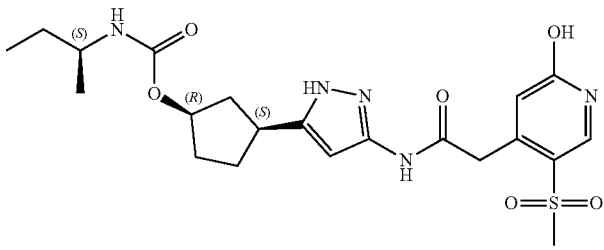<br>(1R,3S)-3-[3-({[2-hydroxy-5-(methylsulfonyl)pyridin-4-yl]acetyl}amino)-1H-pyrazol-5-yl]cyclopentyl (2S)-butan-2-ylcarbamate<br>All stereocenters known | 479.9 | 1H NMR (400 MHz, DMSO-d6) δ = 12.52-11.80 (m, 2H), 10.60 (s, 1H), 7.94 (s, 1H), 6.89 (br d, J = 8.3 Hz, 1H), 6.37 (s, 1H), 6.27 (br s, 1H), 4.98 (br s, 1H), 3.89 (s, 2H), 3.39 (br s, 1H), 3.25 (s, 3H), 3.09-2.98 (m, 1H), 2.49-2.41 (m, 1H), 2.09-1.95 (m, 1H), 1.87 (br d, J = 8.3 Hz, 1H), 1.78-1.64 (m, 2H), 1.63-1.50 (m, 1H), 1.34 (br dd, J = 6.9, 11.4 Hz, 2H), 1.00 (d, J = 6.8 Hz, 3H), 0.79 (t, J = 7.4 Hz, 3H) |
| 53 (A) | 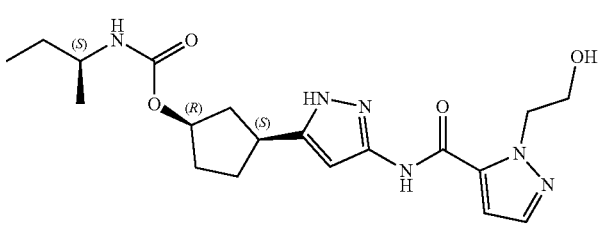<br>(1R,3S)-3-[3-({[1-(2-hydroxyethyl)-1H-pyrazol-5-yl]carbonyl}amino)-1H-pyrazol-5-yl]cyclopentyl (2S)-butan-2-ylcarbamate<br>All stereocenters known | 405.3 | 1H NMR (400 MHz, DMSO-d6) δ = 12.25 (s, 1H), 10.76 (s, 1H), 7.51 (d, J = 1.8 Hz, 1H), 7.11 (d, J = 1.8 Hz, 1H), 6.92 (br d, J = 8.0 Hz, 1H), 6.44 (s, 1H), 5.01 (br s, 1H), 4.87 (t, J = 5.5 Hz, 1H), 4.58 (t, J = 6.3 Hz, 2H), 3.70 (q, J = 5.9 Hz, 2H), 3.44-3.37 (m, 1H), 3.13-3.02 (m, 1H), 2.50-2.44 (m, 1H), 2.07-1.99 (m, 1H), 1.96-1.85 (m, 1H), 1.80-1.70 (m, 2H), 1.67-1.56 (m, 1H), 1.41-1.30 (m, 2H), 1.01 (d, J = 6.8 Hz, 3H), 0.81 (t, J = 7.4 Hz, 3H) |
| 54 (A) | 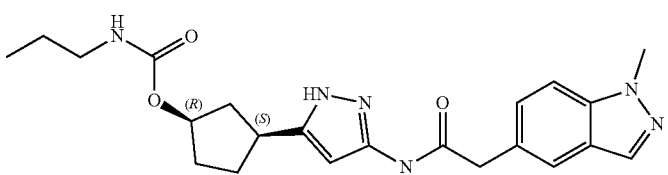<br>(1R,3S)-3-(3-{[(1-methyl-1H-indazol-5-yl)acetyl]amino}-1H-pyrazol-5-yl)cyclopentyl propylcarbamate<br>All stereocenters known | 425.4 | 1H NMR (400 MHz, DMSO-d6) δ = 12.05 (br s, 1H), 10.51 (br s, 1H), 7.99 (s, 1H), 7.64 (s, 1H), 7.56 (d, J = 8.8 Hz, 1H), 7.35 (d, J = 8.3 Hz, 1H), 7.03 (br s, 1H), 6.27 (br s, 1H), 4.97 (br s, 1H), 4.01 (s, 3H), 3.66 (s, 2H), 3.09-2.95 (m, 1H), 2.88 (q, J = 6.6 Hz, 2H), 2.44-2.35 (m, 1H), 1.97 (br d, J = 8.0 Hz, 1H), 1.91-1.78 (m, 1H), 1.74-1.61 (m, 2H), 1.54 (br s, 1H), 1.42-1.29 (m, 2H), 0.79 (t, J = 7.4 Hz, 3H) |

TABLE 2-continued

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 55 (A) | (1R,3S)-3-(3-{[(1-methyl-1H-indazol-5-yl)acetyl]amino}-1H-pyrazol-5-yl)cyclopentyl propan-2-ylcarbamate<br>All stereocenters known | 425.4 | ¹H NMR (400 MHz, DMSO-d6) δ = 12.13 (br s, 1H), 10.53 (s, 1H), 8.00 (s, 1H), 7.66 (s, 1H), 7.56 (d, J = 8.5 Hz, 1H), 7.37 (dd, J = 1.4, 8.7 Hz, 1H), 6.93 (br d, J = 7.8 Hz, 1H), 6.28 (s, 1H), 4.98 (br s, 1H), 4.06-3.99 (m, 3H), 3.68 (s, 2H), 3.61-3.54 (m, 1H), 3.09-2.97 (m, 1H), 2.44 (td, J = 7.2, 13.9 Hz, 1H), 2.05-1.93 (m, 1H), 1.91-1.81 (m, 1H), 1.75-1.63 (m, 2H), 1.61-1.50 (m, 1H), 1.08-0.96 (m, 6H) |
| 56 (A) | (1R,3S)-3-(3-{[(3ξ)-2,3-dihydro-1-benzofuran-3-ylcarbonyl]amino}-1H-pyrazol-5-yl)cyclopentyl propan-2-ylcarbamate—Isomer A<br>Single stereoisomer; absolute configuration of the chiral center in the dihydrobenzofuran was not determined | 399.3 | ¹H NMR (400 MHz, DMSO-d6) δ = 12.12 (br s, 1H), 10.81 (s, 1H), 7.30 (d, J = 7.5 Hz, 1H), 7.14 (t, J = 7.5 Hz, 1H), 6.93 (br d, J = 7.5 Hz, 1H), 6.87-6.74 (m, 2H), 6.29 (br s, 1H), 4.98 (br s, 1H), 4.79 (dd, J = 6.1, 8.7 Hz, 1H), 4.65 (t, J = 9.2 Hz, 1H), 4.46 (dd, J = 6.1, 9.4 Hz, 1H), 3.56 (br dd, J = 6.8, 13.3 Hz, 1H), 3.04 (br d, J = 7.5 Hz, 1H), 2.48-2.38 (m, 1H), 2.07-1.79 (m, 2H), 1.77-1.49 (m, 3H), 1.02 (br d, J = 5.8 Hz, 6H)<br>[α]$_D^{25}$ −50 (c 0.12, MeOH)<br>Peak 1 of 2: Column: Chiralpak AD-3 150 × 4.6 mm I.D., 3 μm; Mobile phase: 40% IPA (0.05% DEA) in CO₂; Flow rate: 2.5 mL/min; Column temp 35° C. |
| 57 (A) | (1R,3S)-3-(3-{[(3ξ)-2,3-dihydro-1-benzofuran-3-ylcarbonyl]amino}-1H-pyrazol-5-yl)cyclopentyl propan-2-ylcarbamate—Isomer B<br>Single stereoisomer; absolute configuration of the chiral center in the dihydrobenzofuran was not determined | 399.3 | ¹H NMR (400 MHz, DMSO-d6) δ = 12.12 (br s, 1H), 10.81 (s, 1H), 7.30 (d, J = 7.3 Hz, 1H), 7.14 (t, J = 7.8 Hz, 1H), 6.93 (br d, J = 8.3 Hz, 1H), 6.87-6.74 (m, 2H), 6.29 (br s, 1H), 4.98 (br s, 1H), 4.79 (dd, J = 6.0, 8.8 Hz, 1H), 4.65 (t, J = 9.0 Hz, 1H), 4.46 (dd, J = 6.4, 9.4 Hz, 1H), 3.65-3.47 (m, 1H), 3.04 (br d, J = 8.0Hz, 1H), 2.44 (br d, J = 7.0 Hz, 1H), 2.08-1.80 (m, 2H), 1.79-1.47 (m, 3H), 1.11-0.88 (m, 6H)<br>[α]$_D^{25}$ +47 (c 0.4, MeOH)<br>Peak 2 of 2: Column: Chiralpak AD-3 150 × 4.6 mm I.D., 3 μm; Mobile phase: 40% IPA (0.05% DEA) in CO₂; Flow rate: 2.5 mL/min; Column temp 35° C. |
| 58 (B) | (1R,3S)-3-(3-{[(2-methoxypyridin-4-yl)acetyl]amino}-1H-pyrazol-5-yl)cyclopentyl methyl(propan-2-yl)carbamate<br>All stereocenters known | 416.4 | ¹H NMR (400 MHz, DMSO-d6) δ = 12.09 (br s, 1H), 10.56 (s, 1H), 8.07 (d, J = 5.3 Hz, 1H), 6.91 (dd, J = 1.3, 5.3 Hz, 1H), 6.74 (s, 1H), 6.29 (br s, 1H), 5.01 (br s, 1H), 4.37-4.01 (m, 1H), 3.89-3.79 (m, 3H), 3.58 (s, 2H), 3.16-2.98 (m, 1H), 2.61 (br s, 3H), 2.46-2.26 (m, 1H), 2.05-1.94 (m, 1H), 1.93-1.81 (m, 1H), 1.79-1.60 (m, 3H), 0.99 (br d, J = 6.5 Hz, 6H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 59 (B) | 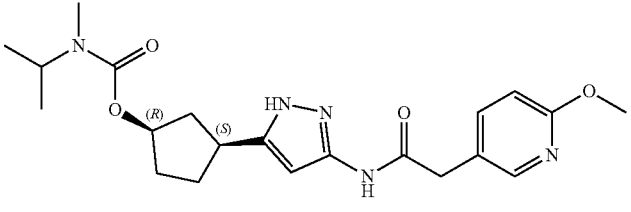<br>(1R,3S)-3-(3-{[(6-methoxypyridin-3-yl)acetyl]amino}-1H-pyrazol-5-yl)cyclopentyl methyl(propan-2-yl)carbamate<br>All stereocenters known | 416.3 | 1H NMR (400 MHz, DMSO-d6) δ = 12.07 (br s, 1H), 10.52 (s, 1H), 8.06 (d, J = 2.3 Hz, 1H), 7.63 (dd, J = 2.5, 8.5 Hz, 1H), 6.77 (d, J = 8.5 Hz, 1H), 6.28 (br s, 1H), 5.01 (br s, 1H), 4.31-4.00 (m, 1H), 3.85-3.77 (m, 3H), 3.53 (s, 2H), 3.08 (quin, J = 7.9 Hz, 1H), 2.61 (br s, 3H), 2.44-2.33 (m, 1H), 2.05-1.96 (m, 1H), 1.93-1.81 (m, 1H), 1.79-1.61 (m, 3H), 0.99 (br d, J = 6.6 Hz, 6H) |
| 60 (A) | 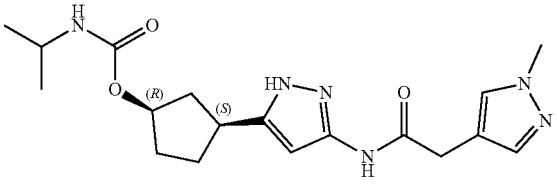<br>(1R,3S)-3-(3-{[(1-methyl-1H-pyrazol-4-yl)acetyl]amino}-1H-pyrazol-5-yl)cyclopentyl propan-2-ylcarbamate<br>All stereocenters known | 375.3 | 1H NMR (400 MHz, DMSO-d6) δ = 12.04 (br s, 1H), 10.35 (br s, 1H), 7.54 (s, 1H), 7.29 (s, 1H), 6.95 (br d, J = 7.6 Hz, 1H), 6.29 (br s, 1H), 4.98 (br s, 1H), 3.78 (s, 3H), 3.57 (br dd, J = 6.7, 13.4 Hz, 1H), 3.39 (s, 2H), 3.11-2.97 (m, 1H), 2.48-2.38 (m, 1H), 2.09-1.79 (m, 2H), 1.78-1.50 (m, 3H), 1.02 (br d, J = 6.5 Hz, 6H) |
| 61 (B) | 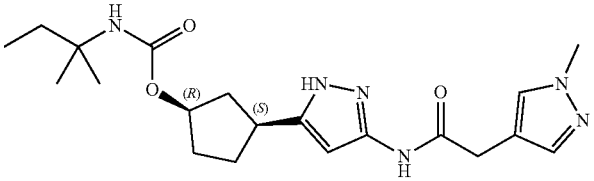<br>(1R,3S)-3-(3-{[(1-methyl-1H-pyrazol-4-yl)acetyl]amino}-1H-pyrazol-5-yl)cyclopentyl (2-methylbutan-2-yl)carbamate<br>All stereocenters known | [M + Na]+ 424.8 | 1H NMR (400 MHz, DMSO-d6) δ = 12.03 (br s, 1H), 10.34 (s, 1H), 7.53 (s, 1H), 7.28 (s, 1H), 6.62 (br s, 1H), 6.27 (br s, 1H), 4.95 (br s, 1H), 3.77 (s, 3H), 3.38 (br s, 2H), 3.10-2.91 (m, 1H), 2.47-2.37 (m, 1H), 2.04-1.93 (m, 1H), 1.91-1.78 (m, 1H), 1.76-1.62 (m, 2H), 1.56 (br d, J = 7.5 Hz, 3H), 1.13 (s, 6H), 0.74 (t, J = 7.4 Hz, 3H) |
| 62 (B) | 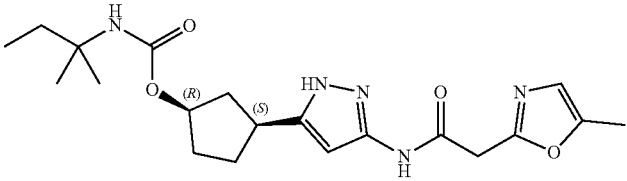<br>(1R,3S)-3-(3-{[(5-methyl-1,3-oxazol-2-yl)acetyl]amino}-1H-pyrazol-5-yl)cyclopentyl (2-methylbutan-2-yl)carbamate<br>All stereocenters known | 404.4 | 1H NMR (400 MHz, DMSO-d6) δ = 12.10 (br s, 1H), 10.62 (s, 1H), 6.74 (d, J = 1.1 Hz, 1H), 6.62 (br s, 1H), 6.28 (s, 1H), 4.95 (br s, 1H), 3.79 (s, 2H), 3.03 (quin, J = 8.6 Hz, 1H), 2.47-2.40 (m, 1H), 2.25 (d, J = 0.9 Hz, 3H), 2.04-1.94 (m, 1H), 1.92-1.82 (m, 1H), 1.74-1.64 (m, 2H), 1.56 (q, J = 7.2 Hz, 3H), 1.13 (s, 6H), 0.73 (t, J = 7.5 Hz, 3H) |

TABLE 2-continued

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 63 (A) | (1R,3S)-3-{3-[(1,2-oxazol-3-ylacetyl)amino]-1H-pyrazol-5-yl}cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 430.2 | ¹H NMR (400 MHz, DMSO-d6) δ = 12.12 (s, 1H), 10.65 (br s, 1H), 8.83 (s, 1H), 7.19 (br d, J = 8.3 Hz, 1H), 6.53 (s, 1H), 6.29 (br s, 1H), 4.99 (br d, J = 2.5 Hz, 1H), 3.89-3.78 (m, 1H), 3.75 (s, 2H), 3.09-2.97 (m, 1H), 2.45-2.29 (m, 3H), 2.04-1.95 (m, 1H), 1.92-1.84 (m, 1H), 1.77-1.63 (m, 2H), 1.61-1.52 (m, 1H), 1.10 (br d, J = 6.5 Hz, 3H)<br>[α]$_D^{20}$ −2.85 (c 0.117, MeOH)<br>Peak 1 of 2: Column: Xtimate C18 150*25 mm*5 μm; Mobile phase: From 22-52% CH3CN in water (0.05% ammonia hydroxide v/v); Flow rate: 25 mL/min |
| 64 (A) | (1R,3S)-3-{3-[(1,2-oxazol-3-ylacetyl)amino]-1H-pyrazol-5-yl}cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 430.4 | ¹H NMR (400 MHz, DMSO-d6) δ = 12.11 (s, 1H), 10.63 (s, 1H), 8.83 (d, J = 1.0 Hz, 1H), 7.20 (br d, J = 8.0 Hz, 1H), 6.53 (s, 1H), 6.29 (s, 1H), 5.04-4.95 (m, 1H), 3.84-3.77 (m, 1H), 3.75 (s, 2H), 3.07-2.98 (m, 1H), 2.46-2.32 (m, 3H), 2.04-1.95 (m, 1H), 1.94-1.84 (m, 1H), 1.77-1.64 (m, 2H), 1.61-1.50 (m, 1H), 1.11 (br d, J = 6.8 Hz, 3H)<br>[α]$_D^{25}$ +8.12 (c 0.197, MeOH)<br>Peak 2 of 2: Column: Xtimate C18 150*25 mm*5 μm; Mobile phase: From 22-52% CH3CN in water (0.05% ammonia hydroxide v/v); Flow rate: 25 mL/min |
| 65 (A) | (1R,3S)-3-(3-{[(1-methyl-1H-pyrazol-3-yl)acetyl]amino}-1H-pyrazol-5-yl)cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 443.3 | ¹H NMR (400 MHz, DMSO-d6) δ = 12.04 (s, 1H), 10.35 (s, 1H), 7.55 (d, J = 2.0 Hz, 1H), 7.19 (br d, J = 8.3 Hz, 1H), 6.29 (s, 1H), 6.10 (d, J = 2.3 Hz, 1H), 4.99 (br d, J = 2.0 Hz, 1H), 3.88-3.79 (m, 1H), 3.76 (s, 3H), 3.52 (s, 2H), 3.07-2.98 (m, 1H), 2.48-2.30 (m, 3H), 2.05-1.95 (m, 1H), 1.92-1.83 (m, 1H), 1.77-1.63 (m, 2H), 1.61-1.52 (m, 1H), 1.10 (d, J = 6.5 Hz, 3H)<br>[α]$_D^{25}$ −3.56 (c 0.15, MeOH)<br>Peak 1 of 2: Column: Chiralpak AD-3 150 × 4.6 mm × 3 μm; Mobile phase: 40% EtOH (0.05% DEA) in CO₂; Flow rate: 2.5 mL/min |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 66 (A) | 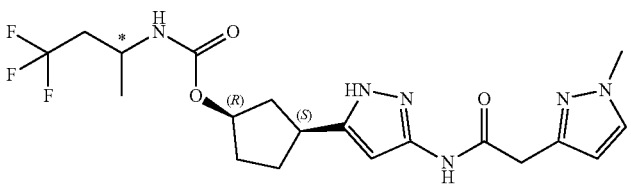<br>(1R,3S)-3-(3-{[(1-methyl-1H-pyrazol-3-yl)acetyl]amino}-1H-pyrazol-5-yl)cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 443.3 | 1H NMR (400 MHz, DMSO-d6) δ = 12.04 (br dd, J = 5.9, 9.4 Hz, 1H), 10.36 (br s, 1H), 7.55 (d, J = 2.0 Hz, 1H), 7.24-7.16 (m, 1H), 6.31-6.22 (m, 1H), 6.10 (d, J = 2.0 Hz, 1H), 5.04-4.94 (m, 1H), 3.86-3.78 (m, 1H), 3.76 (s, 3H), 3.52 (s, 2H), 3.08-2.97 (m, 1H), 2.47-2.29 (m, 3H), 2.05-1.94 (m, 1H), 1.93-1.83 (m, 1H), 1.77-1.62 (m, 2H), 1.60-1.49 (m, 1H), 1.11 (d, J = 6.5 Hz, 3H)<br>$[\alpha]_D^{25}$ +2.73 (c 0.22, MeOH), Peak 2 of 2: Column: Chiralpak AD-3 150 × 4.6 mm × 3 μm; Mobile phase: 40% EtOH (0.05% DEA) in CO2; Flow rate: 2.5 mL/min |
| 67 (A) | 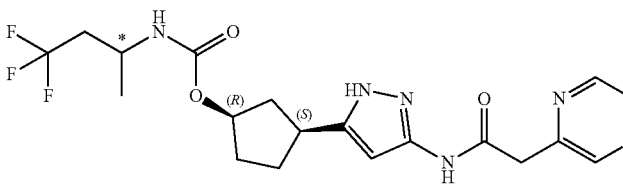<br>(1R,3S)-3-(3-{[(5-methoxypyrazin-2-yl)acetyl]amino}-1H-pyrazol-5-yl)cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 471.3 | 1H NMR (400 MHz, DMSO-d6) δ = 12.07 (s, 1H), 10.54 (s, 1H), 8.23 (d, J = 1.3 Hz, 1H), 8.16 (s, 1H), 7.17 (br d, J = 8.3 Hz, 1H), 6.27 (s, 1H), 5.02-4.95 (m, 1H), 3.89 (s, 3H), 3.85-3.79 (m, 1H), 3.77 (s, 2H), 3.07-2.99 (m, 1H), 2.47-2.29 (m, 3H), 2.03-1.94 (m, 1H), 1.91-1.83 (m, 1H), 1.73-1.62 (m, 2H), 1.60-1.52 (m, 1H), 1.12-1.07 (m, 3H)<br>$[\alpha]_D^{25}$ −1.67 (c 0.12, MeOH), Peak 1 of 2: Column: Chiralpak AD-3 150 × 4.6 mm × 3 μm; Mobile phase: 40% IPA (0.05% DEA) in CO2, Flow rate: 2.5 mL/min |
| 68 (A) | 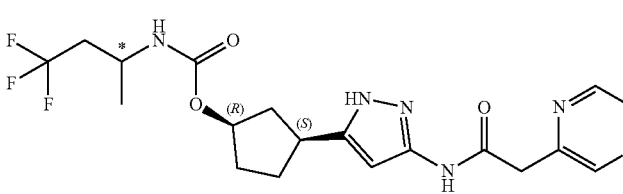<br>(1R,3S)-3-(3-{[(5-methoxypyrazin-2-yl)acetyl]amino}-1H-pyrazol-5-yl)cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 471.3 | 1H NMR (400 MHz, DMSO-d6) δ = 12.07 (s, 1H), 10.54 (s, 1H), 8.22 (d, J = 1.0 Hz, 1H), 8.16 (s, 1H), 6.27 (s, 1H), 5.05-4.94 (m, 1H), 3.89 (s, 3H), 3.85-3.78 (m, 1H), 3.77 (s, 2H), 3.02 (dt, J = 1.3, 8.3 Hz, 1H), 2.47-2.30 (m, 3H), 2.04-1.93 (m, 1H), 1.91-1.83 (m, 1H), 1.73-1.62 (m, 2H), 1.58-1.48 (m, 1H), 1.14-1.07 (m, 3H)<br>$[\alpha]_D^{25}$ +6.67 (c 0.11, MeOH), Peak 2 of 2: Column: Chiralpak AD-3 150 × 4.6 mm × 3 μm; Mobile phase: 40% IPA (0.05% DEA) in CO2, Flow rate: 2.5 mL/min |

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 69 (A) | 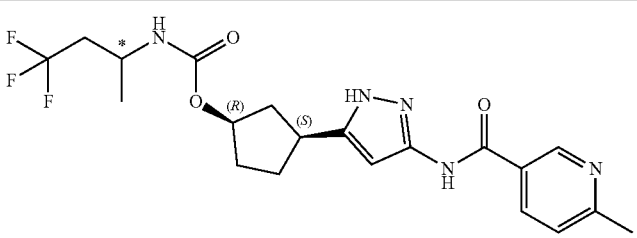<br>(1R,3S)-3-(3-{[(6-methylpyridin-3-yl)carbonyl]amino}-1H-pyrazol-5-yl)cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 440.3 | 1H NMR (400 MHz, DMSO-d6) ä = 12.23 (s, 1H), 10.87 (s, 1H), 8.99 (d, J = 1.8 Hz, 1H), 8.20 (dd, J = 2.3, 8.0 Hz, 1H), 7.36 (d, J = 7.8 Hz, 1H), 7.22 (br d, J = 8.3Hz, 1H), 6.46 (s, 1H), 5.02 (br d, J = 5.5 Hz, 1H), 3.90-3.77 (m, 1H), 3.14-3.01 (m, 1H), 2.53 (s, 3H), 2.49-2.44 (m, 1H), 2.43-2.31 (m, 2H), 2.08-1.99 (m, 1H), 1.96-1.84 (m, 1H), 1.78-1.69 (m, 2H), 1.67-1.57 (m, 1H), 1.12 (d, J = 6.5 Hz, 3H)<br>$[\alpha]_D^{25}$ −2 (c 0.1, MeOH)<br>Peak 1 of 2: Column: ChiralPak AD-3 150 × 4.6 mm × 3 μm; Gradient: 40% IPA (0.1% Ethanolamine) in CO2; Flow rate: 2.5 mL/min Column temp 40° C. |
| 70 (A) | 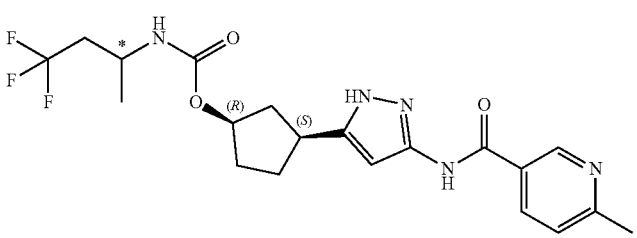<br>(1R,3S)-3-(3-{[(6-methylpyridin-3-yl)carbonyl]amino}-1H-pyrazol-5-yl)cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 440.4 | 1H NMR (400 MHz, DMSO-d6) δ = 12.23 (s, 1H), 10.87 (s, 1H), 8.99 (d, J = 1.8 Hz, 1H), 8.20 (dd, J = 2.3, 8.0 Hz, 1H), 7.36 (d J = 8.3 Hz, 1H), 7.23 (br d, J = 8.5 Hz, 1H), 6.46 (s, 1H), 5.02 (br d, J = 5.0 Hz, 1H), 3.83 (td, J = 7.0, 14.2 Hz, 1H), 3.15-3.01 (m, 1H), 2.53 (s, 3H), 2.47 (br s, 1H), 2.45-2.29 (m, 2H), 2.04 (br d, J = 7.8 Hz, 1H), 1.96-1.85 (m, 1H), 1.80-1.67 (m, 2H), 1.66-1.55 (m, 1H), 1.13 (d, J = 6.5 Hz, 3H)<br>$[\alpha]_D^{25}$ +8 (c 0.1, MeOH)<br>Peak 2 of 2: Column: ChiralPak AD-3 150 × 4.6 mm × 3 μm; Gradient: 40% IPA (0.1% Ethanolamine) in CO2; Flow rate: 2.5 mL/min Column temp 40° C. |
| 71 (B) | 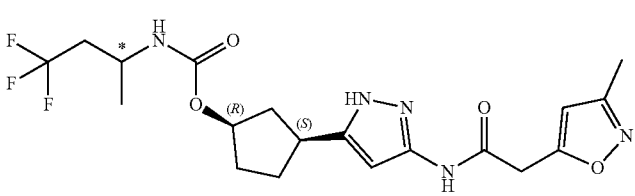<br>(1R,3S)-3-(3-{[(3-methyl-1,2-oxazol-5-yl)acetyl]amino}-1H-pyrazol-5-yl)cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 444.3 | 1H NMR (400 MHz, DMSO-d6) δ = 12.14 (s, 1H), 10.64 (s, 1H), 7.18 (d, J = 8.5 Hz, 1H), 6.29 (br s, 1H), 6.22 (s, 1H), 5.06-4.93 (m, 1H), 3.94-3.69 (m, 3H), 3.14-2.93 (m, 1H), 2.48-2.29 (m, 3H), 2.20 (s, 3H), 2.07-1.80 (m, 2H), 1.77-1.52 (m, 3H), 1.12 (d, J = 6.8 Hz, 3H)<br>$[\alpha]_D^{25}$ −1.0 (c 0.2, MeOH)<br>Peak 1 of 2: Column: SS WHELK-O1 (250 mm*50 mm, 10 μm); Mobile phase: 35% IPA (0.1% NH3.H2O) in CO2; Flow rate: 7 mL/min Column temp 40° C. |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 72 (B) | 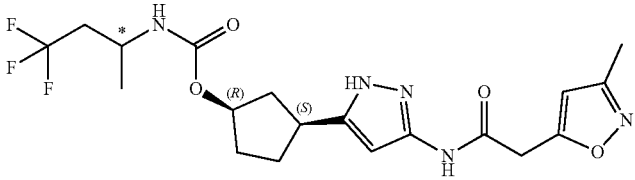<br>(1R,3S)-3-(3-{[(3-methyl-1,2-oxazol-5-yl)acetyl]amino}-1H-pyrazol-5-yl)cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 444.3 | 1H NMR (400 MHz, DMSO-d6) δ = 12.13 (br s, 1H), 10.64 (s, 1H), 7.20 (d, J = 8.5 Hz, 1H), 6.28 (s, 1H), 6.22 (s, 1H), 5.07-4.90 (m, 1H), 3.89-3.77 (m, 3H), 3.13-2.98 (m, 1H), 2.48-2.26 (m, 3H), 2.20 (s, 3H), 2.06-1.83 (m, 2H), 1.79-1.51 (m, 3H), 1.12 (d, J = 6.5 Hz, 3H) [α]$_D^{25}$ +1.0 (c 0.2, MeOH) Peak 2 of 2; Column: SS WHELK-O1 (250 mm*50 mm, 10 μm), Mobile phase: 35% IPA (0.1% NH3.H20) in CO2; Flow rate: 7 mL/min Column temp 40° C. |
| 73 (B) | 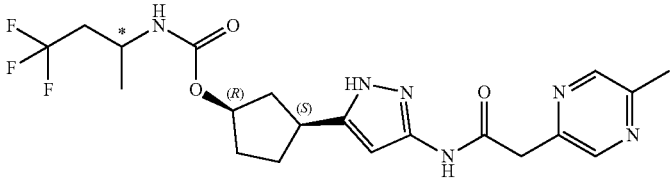<br>(1R,3S)-3-(3-{[(5-methylpyrazin-2-yl)acetyl]amino}-1H-pyrazol-5-yl)cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 455.4 | 1H NMR (400 MHz, DMSO-d6) δ = 12.09 (br s, 1H), 10.64-10.53 (m, 1H), 8.50-8.42 (m, 2H), 7.18 (d, J = 8.3 Hz, 1H), 6.27 (br s, 1H), 5.02-4.94 (m, 1H), 3.85-3.78 (m, 3H), 3.07-2.96 (m, 1H), 2.46 (s, 3H), 2.44-2.26 (m, 3H), 2.03-1.95 (m, 1H), 1.91-1.82 (m, 1H), 1.72-1.62 (m, 2H), 1.57 (dt, J = 5.0, 9.0 Hz, 1H), 1.09 (d, J = 6.8 Hz, 3H) [α]$_D^{25}$ −1.82° (c 0.11, MeOH) Peak 1 of 2; Column: Chiralpak AD-3 50 × 3 mm × 3 μm; Mobile phase: 40% EtOH (0.05% DEA) in CO2; Flow rate: 2 mL/min Column temp 40° C. |
| 74 (B) | 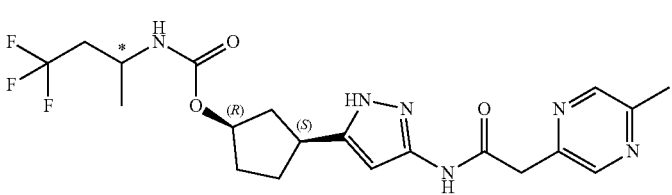<br>(1R,3S)-3-(3-{[(5-methylpyrazin-2-yl)acetyl]amino}-1H-pyrazol-5-yl)cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 455.4 | 1H NMR (400 MHz, DMSO-d6) δ = 12.09 (s, 1H), 10.60 (s, 1H), 8.46 (d, J = 13.6 Hz, 2H), 7.20 (br d, J = 8.3 Hz, 1H), 6.27 (s, 1H), 5.02-4.94 (m, 1H), 3.84-3.76 (m, 3H), 3.02 (quin, J = 8.4 Hz, 1H), 2.46 (s, 3H), 2.45-2.25 (m, 3H), 2.03-1.94 (m, 1H), 1.92-1.83 (m, 1H), 1.75-1.63 (m, 2H), 1.60-1.49 (m, 1H), 1.10 (d, J = 6.8 Hz, 3H) [α]$_D^{25}$ +6.67 (c 0.12, MeOH) Peak 2 of 2; Column: Chiralpak AD-3 50 × 3 mm × 3 μm; Mobile phase 40% EtOH (0.05% DEA) in CO2, Flow rate: 2 mL/min Column temp 40° C. |

TABLE 2-continued

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 75 (B) | (1R,3S)-3-(3-{[(6-methylpyridin-3-yl)acetyl]amino}-1H-pyrazol-5-yl)cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 454.4 | ¹H NMR (400 MHz, DMSO-d6) δ = 12.17-11.90 (m, 1H), 10.62-10.49 (m, 1H), 8.35 (d, J = 2.0 Hz, 1H), 7.58 (dd, J = 2.1, 7.9 Hz, 1H), 7.22-7.13 (m, 2H), 6.25 (s, 1H), 5.02-4.94 (m, 1H), 3.87-3.76 (m, 1H), 3.57 (s, 2H), 3.08-2.96 (m, 1H), 2.46-2.28 (m, 6H), 2.03-1.93 (m, 1H), 1.92-1.81 (m, 1H), 1.76-1.61 (m, 2H), 1.55 (dt, J = 4.8, 9.3 Hz, 1H), 1.10 (d, J = 6.8 Hz, 3H)<br>[α]$_D^{25}$ +4.44 (c 0.120, MeOH)<br>Peak 1 of 2: Column: SS WHELK-O1 (250 mm*50 mm, 10 μm); Mobile phase: 35% EtOH (0.1% NH3.H2O) in CO₂; Flow rate: 7 mL/min; Column temp 40° C. |
| 76 (B) | (1R,3S)-3-(3-{[(6-methylpyridin-3-yl)acetyl]amino}-1H-pyrazol-5-yl)cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 454.4 | ¹H NMR (400 MHz, DMSO-d6) δ = 12.25-11.76 (m, 1H), 10.73-10.48 (m, 1H), 8.35 (s, 1H), 7.62-7.54 (m, 1H), 7.18 (br d, J = 8.0 Hz, 2H), 6.29-6.21 (m, 1H), 5.05-4.91 (m, 1H), 3.88-3.75 (m, 1H), 3.57 (s, 2H), 3.08-2.94 (m, 1H), 2.45-2.25 (m, 6H), 2.06-1.93 (m, 1H), 1.91-1.83 (m, 1H), 1.76-1.61 (m, 2H), 1.59-1.48 (m, 1H), 1.15-1.06 (m, 3H)<br>[α]$_D^{25}$ +5.56 (c 0.108, MeOH)<br>Peak 2 of 2: Column: SS WHELK-O1 (250 mm*50 mm, 10μm); Mobile phase: 35% EtOH (0.1% NH3.H2O) in CO₂, Flow rate: 7 mL/min; Column temp 40° C. |
| 77 (B) | (1R,3S)-3-(3-{[(2-methoxypyridin-4-yl)acetyl]amino}-1H-pyrazol-5-yl)cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 470.4 | ¹H NMR (400 MHz, DMSO-d6) δ = 12.10 (br s, 1H), 10.59 (s, 1H), 8.08 (d, J = 5.3 Hz, 1H), 7.17 (br d, J = 8.5 Hz, 1H), 6.92 (dd, J = 1.3, 5.3 Hz, 1H), 6.74 (s, 1H), 6.27 (s, 1H), 5.07-4.92 (m, 1H), 3.90-3.76 (m, 4H), 3.59 (s, 2H), 3.11-2.97 (m, 1H), 2.48-2.27 (m, 3H), 2.05-1.94 (m, 1H), 1.92-1.80 (m, 1H), 1.75-1.52 (m, 3H), 1.11 (d, J = 6.8 Hz, 3H)<br>[α]$_D^{25}$ +2.98 (c 0.134, MeOH)<br>Peak 1 of 2: Column: SS WHELK-O1 (250 mm*50 mm, 10 μm), Mobile phase: 35% IPA (0.1% NH3.H2O) in CO₂, Flow rate: 6.5 mL/min, Column temp 40° C. |

TABLE 2-continued

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 78 (B) | 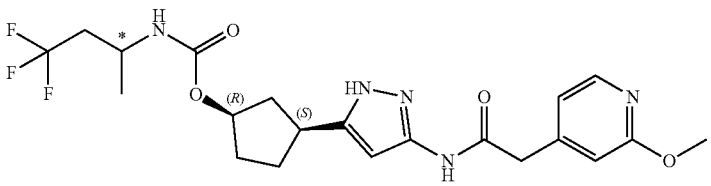<br>(1R,3S)-3-(3-{[(2-methoxypyridin-4-yl)acetyl]amino}-1H-pyrazol-5-yl)cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 470.4 | ¹H NMR (400 MHz, DMSO-d6) δ = 12.10 (br s, 1H), 10.59 (s, 1H), 8.08 (d, J = 5.0 Hz, 1H), 7.19 (br d, J = 8.5 Hz, 1H), 6.98-6.88 (m, 1H), 6.74 (s, 1H), 6.27 (s, 1H), 5.00 (br s, 1H), 3.91-3.75 (m, 4H), 3.59 (s, 2H), 3.12-2.97 (m, 1H), 2.49-2.27 (m, 3H), 2.07-1.80 (m, 2H), 1.77-1.62 (m, 2H), 1.61-1.49 (m, 1H), 1.12 (d, J = 6.8 Hz, 3H) [α]$_D^{25}$ +8.0 (c 0.1, MeOH) Peak 2 of 2: Column: SS WHELK-O1 (250 mm*50 mm, 10 μm); Mobile phase: 35% IPA (0.1% NH3.H2O) in CO₂; Flow rate: 6.5 mL/min, Column temp 40° C. |
| 79 (B) | 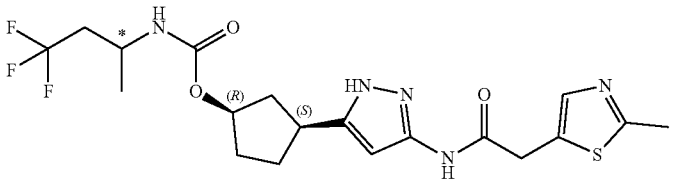<br>(1R,3S)-3-(3-{[(2-methyl-1,3-thiazol-5-yl)acetyl]amino}-1H-pyrazol-5-yl)cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 460.2 | ¹H NMR (400 MHz, DMSO-d6) δ = 12.10 (br s, 1H), 10.58 (s, 1H), 7.40 (s, 1H), 7.18 (br d, J = 8.5 Hz, 1H), 6.27 (br s, 1H), 4.99 (br s, 1H), 3.86-3.73 (m, 3H), 3.10-2.95 (m, 1H), 2.58 (s, 3H), 2.47-2.28 (m, 3H), 2.04-1.95 (m, 1H), 1.92-1.81 (m, 1H), 1.75-1.63 (m, 2H), 1.61-1.52 (m, 1H), 1.11 (d, J = 6.8 Hz, 3H)<br>¹⁹F NMR (376 MHz, DMSO-d6) δ = -62.57 (br s, 3F); [α]$_D^{25}$ +3 (c 0.2, MeOH) Peak 1 of 2: Column: SS WHELK-O1 (250 mm*50 mm, 10 μm); Mobile phase: 35% EtOH (0.1% NH3.H2O) in CO₂; Flow rate: 7 mL/min; Column temp 40 C. |
| 80 (B) | 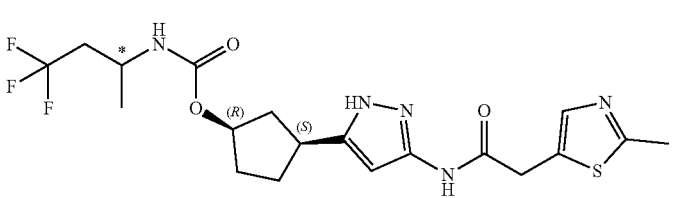<br>(1R,3S)-3-(3-{[(2-methyl-1,3-thiazol-5-yl)acetyl]amino}-1H-pyrazol-5-yl)cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 460.3 | ¹H NMR (400 MHz, DMSO-d6) δ = 12.09 (br s, 1H), 10.58 (s, 1H), 7.40 (s, 1H), 7.19 (d, J = 8.3 Hz, 1H), 6.27 (s, 1H), 4.99 (br s, 1H), 3.87-3.79 (m, 3H), 3.08-2.97 (m, 1H), 2.58 (s, 3H), 2.47-2.28 (m, 3H), 2.04-1.95 (m, 1H), 1.93-1.82 (m, 1H), 1.76-1.62 (m, 2H), 1.60-1.49 (m, 1H), 1.12 (d, J = 6.8 Hz, 3H)<br>¹⁹F NMR (376 MHz, DMSO-d6) δ = -62.55 (br s, 3F); [α]$_D^{25}$ +12 (c 0.2, MeOH) Peak 2 of 2: Column: SS WHELK-O1 (250 mm*50 mm, 10 μm); Mobile phase: 35% EtOH (0.1% NH3.H2O) in CO₂; Flow rate: 7 mL/min; Column temp 40° C. |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 81 (A) | (1R,3S)-3-(3-{[(5-methyl-1,3-oxazol-2-yl)acetyl]amino}-1H-pyrazol-5-yl)cyclopentyl [(2Ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 444.3 | ¹H NMR (400 MHz, DMSO-d6) δ = 12.12 (s, 1H), 10.62 (br s, 1H), 7.18 (br d, J = 8.6 Hz, 1H), 6.74 (s, 1H), 6.28 (br s, 1H), 4.99 (br d, J = 2.0 Hz, 1H), 3.83 (br d, J = 6.2 Hz, 1H), 3.79 (s, 2H), 3.08-2.98 (m, 1H), 2.46-2.32 (m, 3H), 2.25 (s, 3H), 2.04-1.95 (m, 1H), 1.93-1.83 (m, 1H), 1.74-1.54 (m, 3H), 1.10 (br d, J = 6.6 Hz, 3H)<br>$[\alpha]_D^{25}$ −1.91 (c 0.115, MeOH)<br>Peak 1 of 2: Column: Chiralpak AD-3 150 × 4.6 mm I.D., 3 μm; Mobile phase: 40% EtOH (0.05% DEA) in CO₂; Flow rate: 2.5 mL/min; Column temp 35° C. |
| 82 (A) | (1R,3S)-3-(3-{[(5-methyl-1,3-oxazol-2-yl)acetyl]amino}-1H-pyrazol-5-yl)cyclopentyl [(2Ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 444.3 | ¹H NMR (400 MHz, DMSO-d6) δ = 12.11 (s, 1H), 10.62 (br s, 1H), 7.20 (br d, J = 8.3 Hz, 1H), 6.74 (d, J = 1.1 Hz, 1H), 6.28 (br s, 1H), 5.05-4.94 (m, 1H), 3.88-3.80 (m, 1H), 3.79 (s, 2H), 3.09-2.99 (m, 1H), 2.47-2.31 (m, 3H), 2.25 (d, J = 1.0 Hz, 3H), 2.06-1.95 (m, 1H), 1.95-1.85 (m, 1H), 1.75-1.64 (m, 2H), 1.61-1.51 (m, 1H), 1.11 (d, J = 6.7 Hz, 3H)<br>$[\alpha]_D^{25}$ +1.74 (c 0.115, MeOH)<br>Peak 2 of 2: Column: Chiralpak AD-3 150 × 4.6 mm I.D., 3 μm; Mobile phase: 40% EtOH (0.05% DEA) in CO₂; Flow rate: 2.5 mL/min; Column temp 35° C. |
| 83 (A) | (1R,3S)-3-{3-[(1,3-oxazol-5-ylacetyl)amino]-1H-pyrazol-5-yl}cyclopentyl [(2Ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 430.4 | ¹H NMR (400 MHz, DMSO-d6) δ = 12.09 (s, 1H), 10.56 (s, 1H), 8.25 (s, 1H), 7.17 (br d, J = 8.2 Hz, 1H), 7.00 (s, 1H), 6.28 (s, 1H), 5.05-4.94 (m, 1H), 3.89-3.80 (m, 1H), 3.78 (s, 2H), 3.09-3.00 (m, 1H), 2.46-2.34 (m, 3H), 2.00 (br d, J = 9.3 Hz, 1H), 1.88 (dt, J = 2.9, 6.5 Hz, 1H), 1.75-1.64 (m, 2H), 1.62-1.53 (m, 1H), 1.11 (d, J = 6.7 Hz, 3H)<br>$[\alpha]_D^{25}$ −1.82 (c 0.11, MeOH)<br>Peak 1 of 2: Column: Chiralpak AD-3 150 × 4.6 mm × 3 μm; Mobile phase: 40% EtOH (0.05% DEA) in CO₂; Flow rate: 2.5 mL/min; Column temp 35° C. |

| Example No. (Method) | Structure; IUPAC name; stereochemistry. notes | LCMS [M + H]$^+$ | $^1$H NMR (ppm); $^{19}$F NMR (ppm); optical rotation; Chiral HPLC/SFC conditions |
|---|---|---|---|
| 84 (A) | 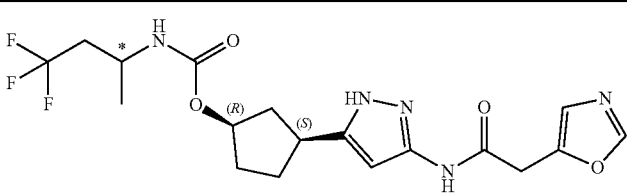<br>(1R,3S)-3-{3-[(1,3-oxazol-5-ylacetyl)amino]-1H-pyrazol-5-yl}cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 430.4 | $^1$H NMR (400 MHz, DMSO-d6) δ = 12.09 (br s, 1H), 10.56 (s, 1H), 8.25 (s, 1H), 7.18 (br d, J = 8.8 Hz, 1H), 7.00 (s, 1H), 6.28 (br s, 1H), 5.00 (br d, J = 2.0 Hz, 1H), 3.87-3.79 (m, 1H), 3.78 (s, 2H), 3.03 (br t, J = 8.7 Hz, 1H), 2.47-2.34 (m, 3H), 2.05-1.96 (m, 1H), 1.89 (ddd, J = 2.9, 6.6, 9.7 Hz, 1H), 1.75-1.64 (m, 2H), 1.61-1.50 (m, 1H), 1.12 (br d, J = 6.6 Hz, 3H)<br>[α]$_D^{25}$ +8.60 (c 0.31, MeOH)<br>Peak 2 of 2: Column: Chiralpak AD-3 150 × 4.6 mm × 3 μm; Mobile phase: 40% EtOH (0.05% DEA) in CO$_2$; Flow rate: 2.5 mL/min; Column temp 35° C. |
| 85 (A) | 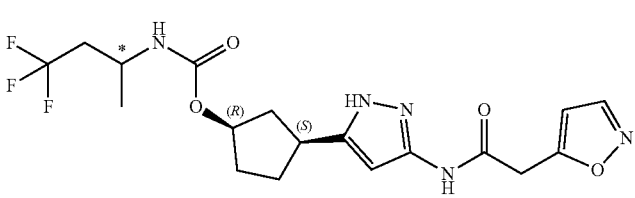<br>(1R,3S)-3-{3-[(1,2-oxazol-5-ylacetyl)amino]-1H-pyrazol-5-yl}cyclopentyl [(2ξ)-4,4,4-trifluorobutan-2-yl]carbamate—Isomer A<br>Single stereoisomer; absolute configuration of the chiral center in the 4,4,4-trifluorobutan-2-yl]carbamate was not determined | 430.3 | $^1$H NMR (400 MHz, DMSO-d6) δ = 12.14 (s, 1H), 10.68 (s, 1H), 8.49 (d, J = 1.5 Hz, 1H), 7.20 (d, J = 8.5 Hz, 1H), 6.37 (s, 1H), 6.29 (s, 1H), 5.00 (br s, 1H), 3.91 (s, 2H), 3.82 (td, J = 7.1, 13.7 Hz, 1H), 3.10-2.98 (m, 1H), 2.48-2.28 (m, 3H), 2.06-1.95 (m, 1H), 1.95-1.83 (m, 1H), 1.77-1.52 (m, 3H), 1.10 (d, J = 6.8 Hz, 3H)<br>[α]$_D^{25}$ −4 (c 0.1, MeOH)<br>Peak 1 of 2; Column: Chiralpak AD-3 150 × 4.6 mm I.D., 3 μm; Mobile phase: 40% EtOH (0.05% DEA) in CO$_2$; Flow rate: 2.5 mL/min; Column temp 35° C. |
| 86 (A) | 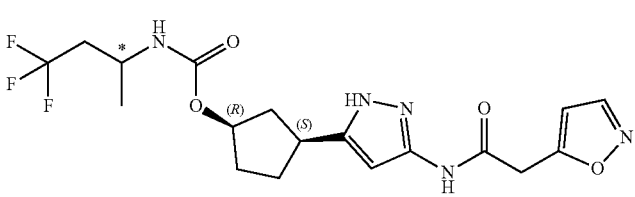<br>(1R,3S)-3-{3-[(1,2-oxazol-5-ylacetyl)amino]-1H-pyrazol-5-yl}cyclopentyl [(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 430.4 | $^1$H NMR (400 MHz, DMSO-d6) δ = 12.14 (s, 1H), 10.67 (s, 1H), 8.49 (d, J = 1.5 Hz, 1H), 7.21 (br d, J = 8.5 Hz, 1H), 6.37 (s, 1H), 6.29 (s, 1H), 5.00 (br s, 1H), 3.91 (s, 2H), 3.87-3.77 (m, 1H), 3.08-2.98 (m, 1H), 2.47-2.27 (m, 3H), 2.00 (br d, J = 8.3 Hz, 1H), 1.94-1.83 (m, 1H), 1.75-1.63 (m, 2H), 1.60-1.48 (m, 1H), 1.11 (d, J = 6.5 Hz, 3H)<br>[α]$_D^{25}$ +12 (c 0.1, MeOH)<br>Peak 2 of 2; Column: Chiralpak AD-3 150 × 4.6 mm I.D., 3 μm; Mobile phase: 40% EtOH (0.05% DEA) in CO$_2$; Flow rate: 2.5 mL/min; Column temp 35° C. |

TABLE 2-continued

| Example No. (Method) | Structure; IUPAC name; stereochemistry. notes | LCMS [M + H]+ | $^1$H NMR (ppm); $^{19}$F NMR (ppm); optical rotation; Chiral HPLC/SFC conditions |
|---|---|---|---|
| 87 (A) | (1R,3S)-3-[3-({[1-(2-methoxyethyl)-1H-pyrazol-5-yl]carbonyl}amino)-1H-pyrazol-5-yl]cyclopentyl [(2ξ)-4,4,4-trifluorobutan-2-yl]carbamate— Isomer A<br>Single stereoisomer; absolute configuration of the chiral center in the 4,4,4-trifluorobutan-2-yl]carbamate was not determined | 473.4 | $^1$H NMR (400 MHz, DMSO-d6) δ = 12.26 (d, J = 1.5 Hz, 1H), 10.75 (s, 1H), 7.51 (d, J = 1.8 Hz, 1H), 7.22 (br d, J = 8.5 Hz, 1H), 7.13 (d, J = 1.8 Hz, 1H), 6.42 (s, 1H), 5.06-4.97 (m, 1H), 4.69 (t, J = 5.6 Hz, 2H), 3.84 (quind, J = 6.7, 13.7 Hz, 1H), 3.66 (t, J = 5.6 Hz, 2H), 3.18 (s, 3H), 3.13-3.02 (m, 1H), 2.47-2.30 (m, 3H), 2.08-1.99 (m, 1H), 1.96-1.84 (m, 1H), 1.78-1.69 (m, 2H), 1.63 (ddd, J = 4.5, 9.3, 13.8 Hz, 1H), 1.12 (d, J = 6.8 Hz, 3H) $[α]_D^{25}$ −7.27 (c 0.11, MeOH) Peak 1 of 2: Column: ChiralPak AD-3 150 × 4.6 mm I.D., 3 μm; Mobile phase: 40% EtOH (0.1% Ethanolamine) in CO$_2$; Flow rate: 2.5 mL/min Column temp 40° C. |
| 88 (A) | (1R,3S)-3-[3-({[1-(2-methoxyethyl)-1H-pyrazol-5-yl]carbonyl}amino)-1H-pyrazol-5-yl]cyclopentyl [(2ξ)-4,4,4-trifluorobutan-2-yl]carbamate— Isomer B<br>Single stereoisomer; absolute configuration of the chiral center in the 4,4,4-trifluorobutan-2-yl]carbamate was not determined | 473.3 | $^1$H NMR (400MHz, DMSO-d6) δ = 12.26 (s, 1H), 10.75 (s, 1H), 7.51 (d, J = 2.0 Hz, 1H), 7.23 (br d, J = 8.3 Hz, 1H), 7.13 (d, J = 1.8 Hz, 1H), 6.42 (s, 1H), 5.01 (br d, J = 4.5 Hz, 1H), 4.69 (t, J = 5.6 Hz, 2H), 3.83 (td, J = 7.1, 13.6 Hz, 1H), 3.66 (t, J = 5.6 Hz, 2H), 3.18 (s, 3H), 3.14-3.00 (m, 1H), 2.49-2.25 (m, 3H), 2.09-1.98 (m, 1H), 1.98-1.83 (m, 1H), 1.81-1.67 (m, 2H), 1.65-1.53 (m, 1H), 1.12 (d, J = 6.5 Hz, 3H) $[α]_D^{25}$ +7.22 (c 0.12, MeOH), Peak 2 of 2: Column: ChiralPak AD-3 150 × 4.6 mm I.D., 3 μm; Mobile phase: 40% EtOH (0.1% Ethanolamine) in CO$_2$; Flow rate: 2.5 mL/min Column temp 40° C. |
| 89 (A) | (1R,3S)-3-{3-[(1,2-oxazol-5-ylacetyl)amino]-1H-pyrazol-5-yl}cyclopentyl methyl[(2ξ)-4,4,4-trifluorobutan-2-yl]carbamate— Isomer A<br>Single stereoisomer; absolute configuration of the chiral center in the 4,4,4-trifluorobutan-2-yl]carbamate was not determined | 444.3 | $^1$H NMR (400 MHz, DMSO-d6) δ = 12.13 (br s, 1H), 10.65 (s, 1H), 8.48 (d, J = 1.5 Hz, 1H), 6.36 (s, 1H), 6.30 (s, 1H), 5.00 (br s, 1H), 4.52-4.31 (m, 1H), 3.90 (s, 2H), 3.13-3.01 (m, 1H), 2.68-2.56 (m, 4H), 2.45-2.30 (m, 2H), 2.01 (br d, J = 7.8 Hz, 1H), 1.88 (br d, J = 5.8 Hz, 1H), 1.79-1.62 (m, 3H), 1.10 (d, J = 7.0Hz, 3H) $[α]_D^{25}$ −10 (c 0.1, MeOH) Peak 1 of 2: Column: Chiralpak AD-3 150 × 4.6 mm I.D., 3 μm; Mobile phase: 40% EtOH (0.05% DEA) in CO$_2$; Flow rate: 2.5 mL/min; Column temp 35° C. |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 90 (A) | 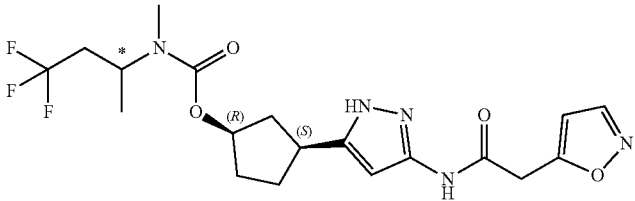<br>(1R,3S)-3-{3-[(1,2-oxazol-5-ylacetyl)amino]-1H- pyrazol-5-yl}cyclopentyl methyl[(2ξ)-4,4,4-trifluorobutan-2-yl]carbamate—Isomer B<br>Single stereoisomer; absolute configuration of the chiral center in the 4,4,4-trifluorobutan-2-yl]carbamate was not determined | 444.3 | 1H NMR (400 MHz, DMSO-d6) δ = 12.13 (br s, 1H), 10.65 (s, 1H), 8.48 (d, J = 1.5 Hz, 1H), 6.36 (s, 1H), 6.30 (s, 1H), 5.04 (br d, J = 9.8 Hz, 1H), 4.42 (br s, 1H), 3.90 (s, 2H), 3.08 (br t, J = 7.9 Hz, 1H), 2.65 (s, 3H), 2.62-2.53 (m, 1H), 2.45-2.38 (m, 1H), 2.38-2.24 (m, 1H), 2.01 (br d, J = 7.5 Hz, 1H), 1.86 (br d, J = 4.8 Hz, 1H), 1.78-1.57 (m, 3H), 1.10 (br dd, J = 6.9, 15.2 Hz, 3H)<br>$[\alpha]_D^{25}$ −4 (c 0.1, MeOH)<br>Peak 2 of 2: Column: Chiralpak AD-3 150 × 4.6 mm I.D., 3 µm; Mobile phase: 40% EtOH (0.05% DEA) in CO2; Flow rate: 2.5 mL/min; Column temp 35° C. |
| 91 (B) | 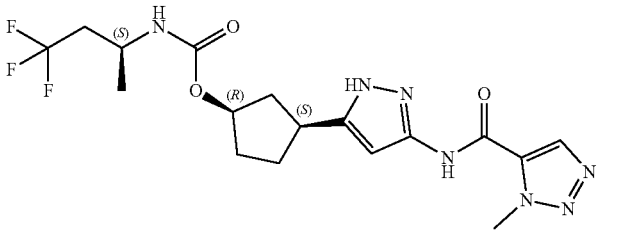<br>(1R,3S)-3-(3-{[(1-methyl-1H-1,2,3-triazol-5-yl)carbonyl]amino}-1H-pyrazol-5-yl)cyclopentyl [(2S)-4,4,4-trifluorobutan-2-yl]carbamate<br>All stereocenters known | 430.2 | 1H NMR (400MHz, DMSO-d6) δ = 12.31 (br. s., 1H), 11.12 (s, 1H), 8.46 (s, 1H), 7.21 (d, J = 8.4 Hz, 1H), 6.44 (br. s., 1H), 5.02 (br. s., 1H), 4.24 (s, 3H), 3.92-3.75 (m, 1H), 3.15-3.00 (m, 1H), 2.47-2.24 (m, 3H), 2.04 (d, J = 7.8 Hz, 1H), 1.89 (d, J = 5.4 Hz, 1H), 1.73 (t, J = 8.1 Hz, 2H), 1.60 (br s., 1H), 1.13 (d, J = 6.6 Hz, 3H)<br>19F NMR (376 MHz, DMSO-d6) δ = −62.58 (s, 3F) |
| 92 (A) | 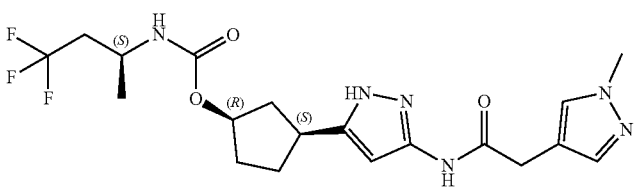<br>(1R,3S)-3-(3-{[(1-methyl-1H-pyrazol-4-yl)acetyl]amino}-1H-pyrazol-5-yl)cyclopentyl [(2S)-4,4,4-trifluorobutan-2-yl]carbamate<br>All stereocenters known | 443.4 | 1H NMR (400 MHz, METHANOL-d4) d 7.54 (s, 1H), 7.42 (s, 1H), 6.35 (br. s., 1H), 5.09 (br. s., 1H), 3.89-4.02 (m, 1H), 3.86 (s, 3H), 3.53 (s, 2H), 3.07-3.22 (m, 1H), 2.45-2.54 (m, 1H), 2.17-2.44 (m, 2H), 2.10 (d, J = 6.97 Hz, 1H), 1.72-2.01 (m, 4H), 1.21 (d, J = 6.60 Hz, 3H)<br>$[\alpha]_D^{22}$ +10.0 (c 0.3, MeOH) |
| 93 (A) | 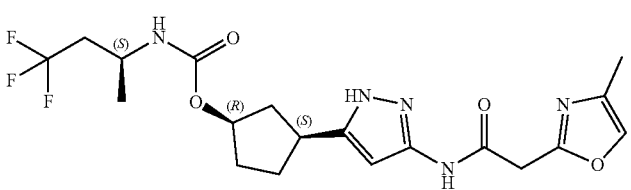<br>(1R,3S)-3-(3-{[(4-methyl-1,3-oxazol-2-yl)acetyl]amino}-1H-pyrazol-5-yl)cyclopentyl [(2S)-4,4,4-trifluorobutan-2-yl]carbamate<br>All stereocenters known | 444.1 | 1H NMR (400 MHz, DMSO-d6) δ = 12.12 (s, 1H), 10.63 (s, 1H), 7.71 (s, 1H), 7.21 (br d, J = 8.3 Hz, 1H), 6.28 (s, 1H), 4.99 (br s, 1H), 3.86-3.81 (m, 1H), 3.80 (s, 2H), 3.08-2.99 (m, 1H), 2.47-2.34 (m, 3H), 2.05 (d, J = 1.0 Hz, 3H), 2.00 (br d, J = 8.3 Hz, 1H), 1.88 (br s, 1H), 1.69 (br dd, J = 10.8, 15.6 Hz, 2H), 1.55 (br s, 1H), 1.11 (d, J = 6.8 Hz, 3H)<br>$[\alpha]_D^{25}$ +12.41 (c 0.145, MeOH); |

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 94 (A) | 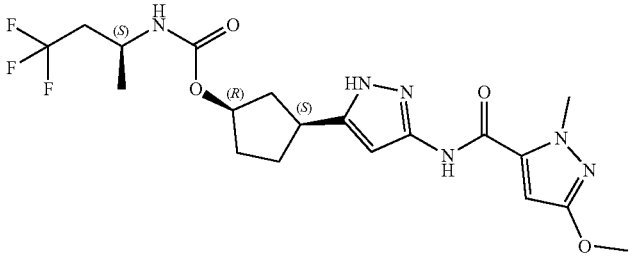 (1R,3S)-3-(3-{[(3-methoxy-1-methyl-1H-pyrazol-5-yl)carbonyl]amino}-1H-pyrazol-5-yl)cyclopentyl [(2S)-4,4,4-trifluorobutan-2-yl]carbamate<br>All stereocenters known | 459.3 | ¹H NMR (500 MHz, DMSO-d6) δ = 12.25 (s, 1H), 10.66 (s, 1H), 7.22 (br d, J = 8.4 Hz, 1H), 6.58 (s, 1H), 6.41 (s, 1H), 5.01 (br s, 1H), 3.93 (s, 3H), 3.83 (td, J = 6.9, 13.9 Hz, 1H), 3.77 (s, 3H), 3.12-3.03 (m, 1H), 2.54-2.51 (m, 1H), 2.44-2.29 (m, 2H), 2.08-1.99 (m, 1H), 1.94-1.84 (m, 1H), 1.79-1.66 (m, 2H), 1.64-1.54 (m, 1H), 1.12 (d, J = 6.7 Hz, 3H) |
| 95 (B) | 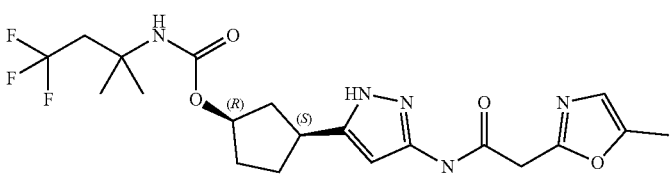 (1R,3S)-3-(3-{[(5-methyl-1,3-oxazol-2-yl)acetyl]amino}-1H-pyrazol-5-yl)cyclopentyl (4,4,4-trifluoro-2-methylbutan-2-yl)carbamate<br>All stereocenters known | 458.4 | ¹H NMR (400 MHz, DMSO-d6) δ = 12.10 (s, 1H), 10.62 (s, 1H), 7.12 (br s, 1H), 6.74 (d, J = 1.3 Hz, 1H), 6.29 (d, J = 2.0 Hz, 1H), 4.98 (br s, 1H), 3.79 (s, 2H), 3.11-2.95 (m, 1H), 2.79-2.61 (m, 2H), 2.48-2.41 (m, 1H), 2.25 (d, J = 1.0 Hz, 3H), 2.04-1.95 (m, 1H), 1.92-1.82 (m, 1H), 1.75-1.62 (m, 2H), 1.55 (br s, 1H), 1.27 (s, 6H) |
| 96 (B) | 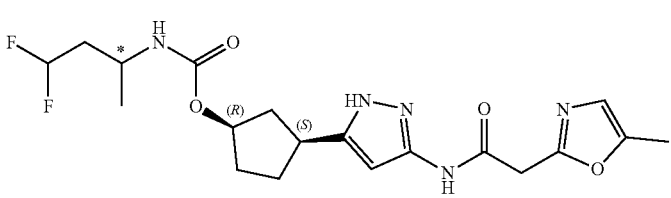 (1R,3S)-3-(3-{[(5-methyl-1,3-oxazol-2-yl)acetyl]amino}-1H-pyrazol-5-yl)cyclopentyl [(2ξ)-4,4-difluorobutan-2-yl]carbamate—Isomer A<br>Single stereoisomer; absolute configuration of the chiral center in the 4,4-difluorobutan-2-yl]carbamate was not determined | 426.3 | ¹H NMR (400 MHz, DMSO-d6) δ = 12.11 (s, 1H), 10.61 (s, 1H), 7.12 (br d, J = 8.3 Hz, 1H), 6.74 (d, J = 1.0 Hz, 1H), 6.29 (s, 1H), 6.18-5.84 (m, 1H), 4.99 (br s, 1H), 3.79 (s, 2H), 3.73-3.60 (m, 1H), 3.10-2.98 (m, 1H), 2.48-2.39 (m, 1H), 2.25 (d, J = 1.0 Hz, 3H), 2.06-1.82 (m, 4H), 1.78-1.51 (m, 3H), 1.07 (d, J = 6.8 Hz, 3H)<br>[α]$_D^{25}$ −4 (c 0.1, MeOH)<br>Peak 1 of 2: Column: Chiralpak AD-3 50 × 3 mm × 3 μm; Mobile phase: 40% EtOH (0.05% DEA) in CO$_2$; Flow rate: 2 mL/min Column temp 40° C. |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 97 (B) | 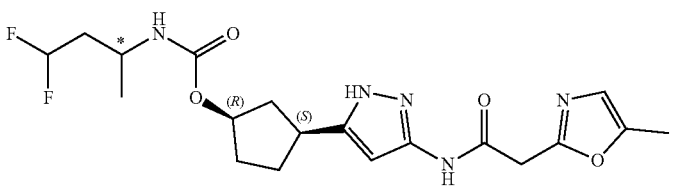<br>(1R,3S)-3-(3-{[(5-methyl-1,3-oxazol-2-yl)acetyl]amino}-1H-pyrazol-5-yl)cyclopentyl [(2ξ)-4,4-difluorobutan-2-yl]carbamate—Isomer B<br>Single stereoisomer; absolute configuration of the chiral center in the 4,4-difluorobutan-2-yl]carbamate was not determined | 426.3 | ¹H NMR (400 MHz, DMSO-d6) δ = 12.11 (s, 1H), 10.61 (s, 1H), 7.13 (br d, J = 8.3 Hz, 1H), 6.74 (d, J = 1.0 Hz, 1H), 6.29 (d, J = 1.5 Hz, 1H), 6.18-5.83 (m, 1H), 4.99 (br s, 1H), 3.79 (s, 2H), 3.72-3.59 (m, 1H), 3.11-2.97 (m, 1H), 2.48-2.39 (m, 1H), 2.25 (d, J = 1.3 Hz, 3H), 2.06-1.81 (m, 4H), 1.78-1.52 (m, 3H), 1.08 (br d, J = 6.8 Hz, 3H)<br>[α]$_D^{25}$ +18 (c 0.1, MeOH)<br>Peak 2 of 2: Column: Chiralpak AD-3 50 × 3 mm × 3 μm; Mobile phase: 40% EtOH (0.05% DEA) in CO₂; Flow rate: 2 mL/min Column temp 40° C. |
| 98 (B) | 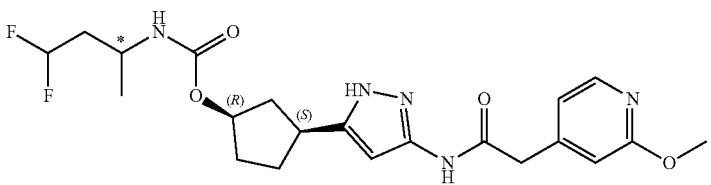<br>(1R,3S)-3-(3-{[(2-methoxypyridin-4-yl)acetyl]amino}-1H-pyrazol-5-yl)cyclopentyl [(2ξ)-4,4-difluorobutan-2-yl]carbamate—Isomer A<br>Single stereoisomer; absolute configuration of the chiral center in the 4,4-difluorobutan-2-yl]carbamate was not determined | 452.4 | ¹H NMR (400 MHz, DMSO-d6) δ = 12.09 (s, 1H), 10.57 (s, 1H), 8.07 (d, J = 5.0 Hz, 1H), 7.11 (br d, J = 8.0 Hz, 1H), 6.91 (dd, J = 1.1, 5.1 Hz, 1H), 6.73 (s, 1H), 6.27 (s, 1H), 6.18-5.83 (m, 1H), 4.98 (br s, 1H), 3.82 (s, 3H), 3.74-3.63 (m, 1H), 3.58 (s, 2H), 3.08-2.96 (m, 1H), 2.48-2.39 (m, 1H), 2.04-1.80 (m, 4H), 1.77-1.49 (m, 3H), 1.07 (br d, J = 6.8 Hz, 3H)<br>[α]$_D^{25}$ −4° (c 0.1, MeOH)<br>Peak 1 of 2: Column: Chiralpak AD-3 150 × 4.6 mm I.D., 3 μm; Mobile phase: 40% EtOH (0.05% DEA) in CO₂; Flow rate: 2.5 mL/min; Column temp 35° C. |
| 99 (B) | 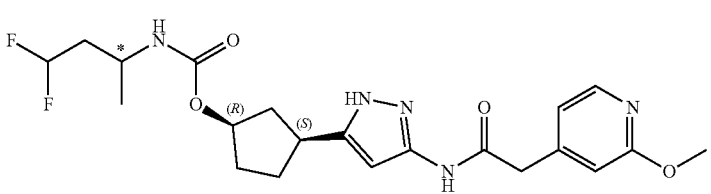<br>(1R,3S)-3-(3-{[(2-methoxypyridin-4-yl)acetyl]amino}-1H-pyrazol-5-yl)cyclopentyl [(2ξ)-4,4-difluorobutan-2-yl]carbamate—Isomer B<br>Single stereoisomer; absolute configuration of the chiral center in the 4,4-difluorobutan-2-yl]carbamate was not determined | 452.3 | ¹H NMR (400 MHz, DMSO-d6) δ = 12.09 (s, 1H), 10.57 (s, 1H), 8.07 (d, J = 5.3 Hz, 1H), 7.12 (br d, J = 8.0 Hz, 1H), 6.91 (dd, J = 1.1, 5.1 Hz, 1H), 6.73 (s, 1H), 6.28 (s, 1H), 6.17-5.84 (m, 1H), 4.99 (br s, 1H), 3.82 (s, 3H), 3.67 (td, J = 6.8, 13.4 Hz, 1H), 3.58 (s, 2H), 3.09-2.96 (m, 1H), 2.47-2.38 (m, 1H), 2.05-1.80 (m, 4H), 1.76-1.51 (m, 3H), 1.07 (br d, J = 6.8 Hz, 3H)<br>[α]$_D^{25}$ +18 (c 0.1, MeOH)<br>Peak 2 of 2: Column: Chiralpak AD-3 150 × 4.6 mm I.D., 3 μm; Mobile phase: 40% EtOH (0.05% DEA) in CO₂; Flow rate: 2.5 mL/min; Column temp 35° C. |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 100 (B) | 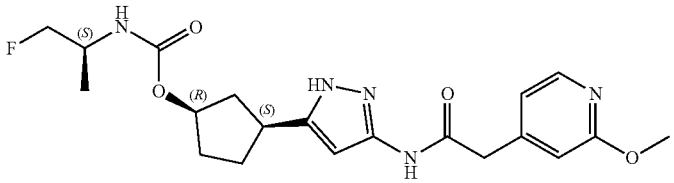<br>(1R,3S)-3-(3-{[(2-methoxypyridin-4-yl)acetyl]amino}-1H-pyrazol-5-yl)cyclopentyl [(2S)-1-fluoropropan-2-yl]carbamate<br>All stereocenters known | 420.3 | 1H NMR (400 MHz, DMSO-d6) δ = 12.08 (br s, 1H), 10.57 (s, 1H), 8.07 (d, J = 5.5 Hz, 1H), 7.15 (br d, J = 7.9 Hz, 1H), 6.91 (dd, J = 1.3, 5.3 Hz, 1H), 6.73 (s, 1H), 6.27 (br s, 1H), 4.99 (br s, 1H), 4.30 (br d, J = 5.5 Hz, 1H), 4.18 (d, J = 5.5 Hz, 1H), 3.83 (s, 3H), 3.80-3.67 (m, 1H), 3.58 (s, 2H), 3.09-2.96 (m, 1H), 2.48-2.39 (m, 1H), 2.03-1.94 (m, 1H), 1.92-1.82 (m, 1H), 1.75-1.63 (m, 2H), 1.62-1.52 (m, 1H), 1.02 (br d, J = 6.7 Hz, 3H) |
| 101 (B) | 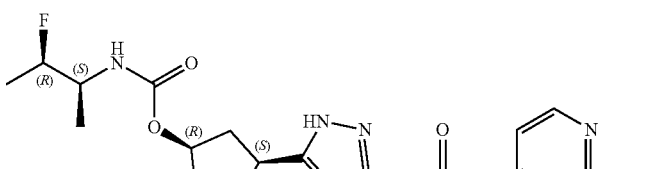<br>(1R,3S)-3-(3-{[(2-methoxypyridin-4-yl)acetyl]amino}-1H-pyrazol-5-yl)cyclopentyl [(2S,3R)-3-fluorobutan-2-yl]carbamate<br>All stereocenters known | 434.4 | 1H NMR (400 MHz, DMSO-d6) δ = 12.09 (s, 1H), 10.58 (s, 1H), 8.08 (d, J = 5.3 Hz, 1H), 7.17 (br d, J = 8.6 Hz, 1H), 6.92 (dd, J = 1.2, 5.2 Hz, 1H), 6.74 (s, 1H), 6.28 (d, J = 1.5 Hz, 1H), 4.99 (br d, J = 1.8 Hz, 1H), 4.66-4.30 (m, 1H), 3.83 (s, 3H), 3.66-3.48 (m, 3H), 3.16-2.93 (m, 1H), 2.48-2.42 (m, 1H), 2.08-1.81 (m, 2H), 1.78-1.48 (m, 3H), 1.31-1.09 (m, 3H), 1.04 (br d, J = 6.6 Hz, 3H) |
| 102 (B) | 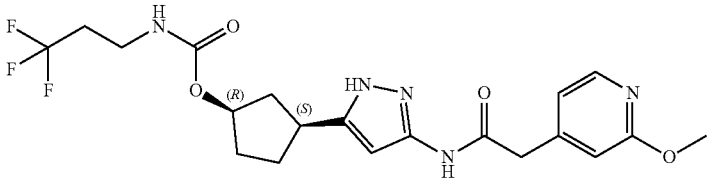<br>(1R,3S)-3-(3-{[(2-methoxypyridin-4-yl)acetyl]amino}-1H-pyrazol-5-yl)cyclopentyl (3,3,3-trifluoropropyl)carbamate<br>All stereocenters known | 456.3 | 1H NMR (400 MHz, DMSO-d6) δ = 12.10 (s, 1H), 10.59 (s, 1H), 8.07 (d, J = 5.0 Hz, 1H), 7.28 (t, J = 5.8 Hz, 1H), 6.91 (d, J = 5.3 Hz, 1H), 6.73 (s, 1H), 6.27 (s, 1H), 4.99 (br s, 1H), 3.82 (s, 3H), 3.58 (s, 2H), 3.23-3.15 (m, 2H), 3.08-2.97 (m, 1H), 2.47-2.34 (m, 3H), 2.03-1.94 (m, 1H), 1.91-1.82 (m, 1H), 1.75-1.63 (m, 2H), 1.61-1.51 (m, 1H) |
| 103 (B) | 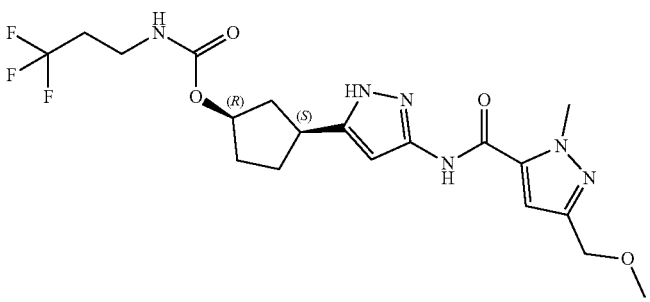<br>(1R,3S)-3-[3-({[3-(methoxymethyl)-1-methyl-1H-pyrazol-5-yl]carbonyl}amino)-1H-pyrazol-5-yl]cyclopentyl (3,3,3-trifluoropropyl)carbamate<br>All stereocenters known | 459.3 | 1H NMR (400 MHz, DMSO-d6) δ = 12.25 (d, J = 1.3 Hz, 1H), 10.74 (s, 1H), 7.31 (br t, J = 5.5 Hz, 1H), 7.13 (s, 1H), 6.43 (s, 1H), 5.15-4.92 (m, 1H), 4.34 (s, 2H), 4.05 (s, 3H), 3.27 (s, 3H), 3.25-3.17 (m, 2H), 3.15-3.03 (m, 1H), 2.49-2.32 (m, 3H), 2.13-1.84 (m, 2H), 1.82-1.57 (m, 3H) |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 104 (B) | (1R,3S)-3-[3-({[3-(methoxymethyl)-1-methyl-1H-pyrazol-5-yl]carbonyl}amino)-1H-pyrazol-5-yl]cyclopentyl [(1S)-1-cyclopropylethyl]carbamate<br>All stereocenters known | 431.4 | ¹H NMR (500 MHz, DMSO-d6) δ = 12.23 (s, 1H), 10.73 (s, 1H), 7.12 (s, 1H), 7.02 (br d, J = 8.1 Hz, 1H), 6.43 (s, 1H), 4.99 (br s, 1H), 4.33 (s, 2H), 4.05 (s, 3H), 3.26 (s, 3H), 3.13-3.02 (m, 1H), 3.02-2.93 (m, 1H), 2.52 (br d, J = 1.7 Hz, 1H), 2.10-1.99 (m, 1H), 1.95-1.84 (m, 1H), 1.73 (br d, J = 7.6 Hz, 2H), 1.61 (br s, 1H), 1.08 (d, J = 6.7 Hz, 3H), 0.81 (br d, J = 7.8 Hz, 1H), 0.40-0.28 (m, 2H), 0.24 (br dd, J = 4.2, 8.8 Hz, 1H), 0.09 (qd, J = 4.8, 9.3 Hz, 1H) |
| 105 (B) | (1R,3S)-3-[3-({[3-(methoxymethyl)-1-methyl-1H-pyrazol-5-yl]carbonyl}amino)-1H-pyrazol-5-yl]cyclopentyl [(1R)-1-cyclopropylethyl]carbamate<br>All stereocenters known | 431.4 | ¹H NMR (400 MHz, DMSO-d6) δ = 12.23 (s, 1H), 10.85-10.66 (m, 1H), 7.12 (s, 1H), 7.02 (br d, J = 8.1 Hz, 1H), 6.42 (br s, 1H), 5.00 (br s, 1H), 4.33 (s, 2H), 4.05 (s, 3H), 3.26 (s, 3H), 3.14-2.88 (m, 2H), 2.48-2.38 (m, 1H), 2.02 (td, J = 7.3, 15.1 Hz, 1H), 1.95-1.84 (m, 1H), 1.82-1.69 (m, 2H), 1.61 (br s, 1H), 1.12-1.03 (m, 3H), 0.89-0.72 (m, 1H), 0.42-0.19 (m, 3H), 0.14-0.00 (m, 1H) |
| 106 (B) | (1R,3S)-3-(3-{[(5-methoxypyrazin-2-yl)acetyl]amino}-1H-pyrazol-5-yl)cyclopentyl [(1S)-1-cyclopropylethyl]carbamate<br>All stereocenters known | 429.3 | ¹H NMR (500 MHz, DMSO-d6) δ = 12.07 (br s, 1H), 10.54 (s, 1H), 8.23 (s, 1H), 8.16 (s, 1H), 7.00 (br d, J = 8.4 Hz, 1H), 6.28 (s, 1H), 4.96 (br s, 1H), 3.89 (s, 3H), 3.77 (s, 2H), 3.08-2.92 (m, 2H), 2.47-2.39 (m, 1H), 1.98 (br d, J = 8.7 Hz, 1H), 1.93-1.82 (m, 1H), 1.75-1.62 (m, 2H), 1.55 (br s, 1H), 1.07 (br d, J = 6.4 Hz, 3H), 0.77 (br s, 1H), 0.34 (br d, J = 4.0 Hz, 1H), 0.31-0.25 (m, 1H), 0.22 (br d, J = 4.6 Hz, 1H), 0.11-0.00 (m, 1H) |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 107 (D) | (1R,3S)-3-(3-{[(3-methyl-1,2-oxazol-5-yl)acetyl]amino}-1H-pyrazol-5-yl)cyclopentyl tert-butylcarbamate<br>All stereocenters known | 389.9 | ¹H NMR (400 MHz, DMSO-d6) δ = 12.12 (br s, 1H), 10.68-10.62 (m, 1H), 6.78 (br s, 1H), 6.29 (br s, 1H), 6.22 (s, 1H), 4.96 (br d, J = 2.3 Hz, 1H), 3.82 (s, 2H), 3.11-2.95 (m, 1H), 2.47-2.41 (m, 1H), 2.20 (s, 3H), 2.04-1.95 (m, 1H), 1.92-1.83 (m, 1H), 1.68 (br t, J = 8.1 Hz, 2H), 1.60-1.50 (m, 1H), 1.19 (s, 9H) |
| 108 (D) | (1R,3S)-3-{3-[(1,2-oxazol-5-ylacetyl)amino]-1H-pyrazol-5-yl}cyclopentyl tert-butylcarbamate<br>All stereocenters known | 376.4 | ¹H NMR (400 MHz, DMSO-d6) δ = 12.12 (br s, 1H), 10.67 (s, 1H), 8.49 (s, 1H), 6.77 (br s, 1H), 6.37 (s, 1H), 6.29 (s, 1H), 4.96 (br s, 1H), 3.91 (s, 2H), 3.03 (quin, J = 8.5 Hz, 1H), 2.47-2.42 (m, 1H), 2.03-1.94 (m, 1H), 1.93-1.80 (m, 1H), 1.74-1.60 (m, 2H), 1.55 (br s, 1H), 1.19 (s, 9H)<br>$[\alpha]_D^{25}$ +8.20 (c 0.13, MeOH); |
| 109 (D) | (1R,3S)-3-(3-{[(5-methoxypyrazin-2-yl)acetyl]amino}-1H-pyrazol-5-yl)cyclopentyl tert-butylcarbamate<br>All stereocenters known | M + Na+ 438.9 | ¹H NMR (400 MHz, DMSO-d6) δ = 12.06 (br s, 1H), 10.56 (s, 1H), 8.23 (s, 1H), 8.16 (s, 1H), 6.76 (br s, 1H), 6.26 (br s, 1H), 4.95 (br s, 1H), 3.89 (s, 3H), 3.77 (s, 2H), 3.01 (br t, J = 8.2 Hz, 1H), 2.47-2.40 (m, 1H), 2.01-1.83 (m, 2H), 1.74-1.62 (m, 2H), 1.54 (br s, 1H), 1.18 (s, 9H) |
| 110 (D) | (1R,3S)-3-(3-{[(2-methyl-2H-1,2,3-triazol-4-yl)acetyl]amino}-1H-pyrazol-5-yl)cyclopentyl tert-butylcarbamate<br>All stereocenters known | 390.4 | ¹H NMR (500 MHz, DMSO-d6) δ = 12.07 (br s, 1H), 10.53 (br s, 1H), 7.59 (s, 1H), 6.77 (br s, 1H), 6.28 (br s, 1H), 4.95 (br s, 1H), 4.08 (s, 3H), 3.68 (s, 2H), 3.07-2.96 (m, 1H), 2.47-2.42 (m, 1H), 2.02-1.94 (m, 1H), 1.91-1.81 (m, 1H), 1.75-1.61 (m, 2H), 1.54 (br s, 1H), 1.19 (s, 9H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 111 (B) | 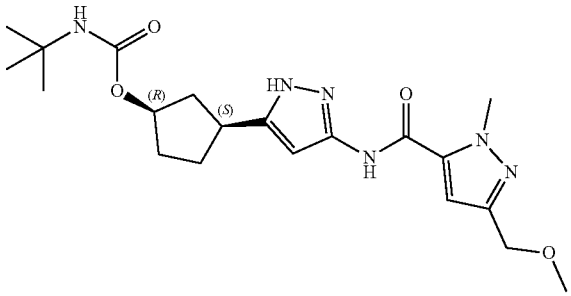<br>(1R,3S)-3-[3-({[3-(methoxymethyl)-1-methyl-1H-pyrazol-5-yl]carbonyl}amino)-1H-pyrazol-5-yl]cyclopentyl tert-butylcarbamate<br>All stereocenters known | 419.4 | 1H NMR (400 MHz, DMSO-d6) δ = 12.23 (s, 1H), 10.74 (s, 1H), 7.12 (s, 1H), 6.79 (br s, 1H), 6.42 (d, J = 1.5 Hz, 1H), 4.98 (br s, 1H), 4.33 (s, 2H), 4.05 (s, 3H), 3.26 (s, 3H), 3.11-3.00 (m, 1H), 2.49-2.41 (m, 1H), 2.06-1.97 (m, 1H), 1.94-1.82 (m, 1H), 1.77-1.67 (m, 2H), 1.60 (br s, 1H), 1.21 (s, 9H) |
| 112 (B) | 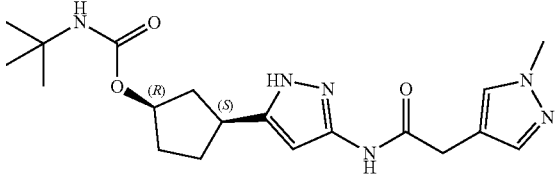<br>(1R,3S)-3-(3-{[(1-methyl-1H-pyrazol-4-yl)acetyl]amino}-1H-pyrazol-5-yl)cyclopentyl tert-butylcarbamate<br>All stereocenters known | M + Na+ 410.9 | 1H NMR (400 MHz, DMSO-d6) δ = 12.03 (br s, 1H), 10.35 (br s, 1H), 7.53 (s, 1H), 7.28 (s, 1H), 6.77 (br s, 1H), 6.28 (br s, 1H), 4.95 (br s, 1H), 3.77 (s, 3H), 3.38 (s, 2H), 3.08-2.93 (m, 1H), 2.44 (br s, 1H), 2.05-1.93 (m, 1H), 1.86 (br s, 1H), 1.75-1.61 (m, 2H), 1.54 (br s, 1H), 1.19 (s, 9H) |
| 113 (B) | 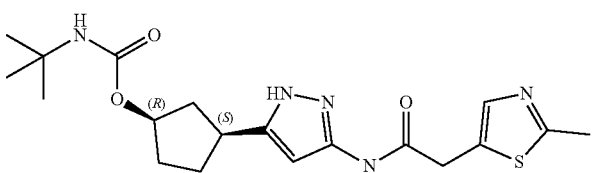<br>(1R,3S)-3-(3-{[(2-methyl-1,3-thiazol-5-yl)acetyl]amino}-1H-pyrazol-5-yl)cyclopentyl tert-butylcarbamate<br>All stereocenters known | 406.4 | 1H NMR (400 MHz, DMSO-d6) ä = 12.09 (s, 1H), 10.58 (s, 1H), 7.40 (s, 1H), 6.77 (br s, 1H), 6.28 (s, 1H), 4.95 (br d, J = 2.5 Hz, 1H), 3.81 (s, 2H), 3.07-2.97 (m, 1H), 2.58 (s, 3H), 2.47-2.40 (m, 1H), 2.01-1.93 (m, 1H), 1.91-1.82 (m, 1H), 1.73-1.63 (m, 2H), 1.55 (br t, J = 13.2 Hz, 1H), 1.19 (s, 9H) |
| 114 (B) | 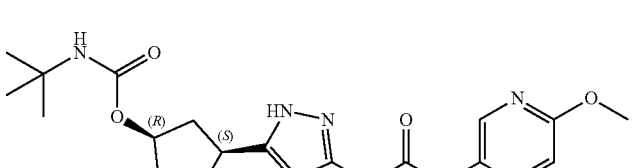<br>(1R,3S)-3-(3-{[(6-methoxypyridin-3-yl)acetyl]amino}-1H-pyrazol-5-yl)cyclopentyl tert-butylcarbamate<br>All stereocenters known | 416.4 | 1H NMR (400 MHz, DMSO-d6) δ = 12.06 (s, 1H), 10.53 (s, 1H), 8.06 (d, J = 2.0 Hz, 1H), 7.62 (dd, J = 2.3, 8.5 Hz, 1H), 6.77 (d, J = 8.5 Hz, 2H), 6.27 (d, J = 1.5 Hz, 1H), 4.99-4.90 (m, 1H), 3.81 (s, 3H), 3.52 (s, 2H), 3.05-2.96 (m, 1H), 2.44 (td, J = 7.3, 14.1 Hz, 1H), 2.01-1.91 (m, 1H), 1.89-1.80 (m, 1H), 1.73-1.61 (m, 2H), 1.58-1.48 (m, 1H), 1.18 (s, 9H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 115 (D) | 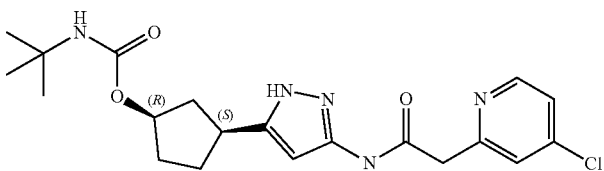<br>(1R,3S)-3-(3-{[(4-chloropyridin-2-yl)acetyl]amino}-1H-pyrazol-5-yl)cyclopentyl tert-butylcarbamate<br>All stereocenters known | 420.3 | 1H NMR (400 MHz, DMSO-d6) δ = 12.04 (br s, 1H), 10.67-10.48 (m, 1H), 8.46 (d, J = 5.3 Hz, 1H), 7.58-7.48 (m, 1H), 7.42 (dd, J = 2.0, 5.3 Hz, 1H), 6.73 (br s, 1H), 6.34-6.22 (m, 1H), 4.96 (br s, 1H), 3.83 (s, 2H), 3.11-2.95 (m, 1H), 2.48-2.38 (m, 1H), 2.04-1.94 (m, 1H), 1.92-1.80 (m, 1H), 1.75-1.62 (m, 2H), 1.55 (br s, 1H), 1.19 (s, 9H) |
| 116 (B) | 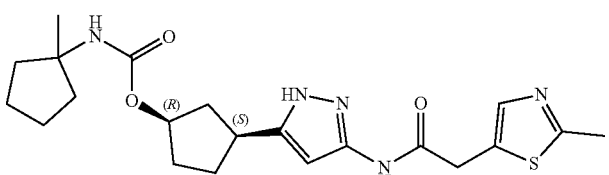<br>(1R,3S)-3-(3-{[(2-methyl-1,3-thiazol-5-yl)acetyl]amino}-1H-pyrazol-5-yl)cyclopentyl (1-methylcyclopentyl)carbamate<br>All stereocenters known | 432.3 | 1H NMR (400 MHz, DMSO-d6) δ = 12.08 (br s, 1H), 10.56 (s, 1H), 7.40 (s, 1H), 6.82 (br s, 1H), 6.28 (br s, 1H), 4.95 (br s, 1H), 3.80 (s, 2H), 3.10-2.94 (m, 1H), 2.58 (s, 3H), 2.47-2.38 (m, 1H), 2.04-1.79 (m, 4H), 1.68 (br t, J = 7.7 Hz, 2H), 1.63-1.48 (m, 5H), 1.42 (br dd, J = 6.3, 11.8 Hz, 2H), 1.24 (s, 3H) |
| 117 (B) | 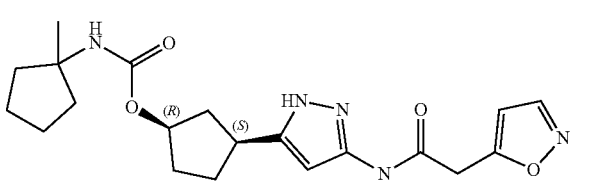<br>(1R,3S)-3-{3-[(1,2-oxazol-5-ylacetyl)amino]-1H-pyrazol-5-yl}cyclopentyl (1-methylcyclopentyl)carbamate<br>All stereocenters known | 402.1 | 1H NMR (400 MHz, DMSO-d6) δ = 12.11 (br s, 1H), 10.65 (br s, 1H), 8.48 (s, 1H), 6.83 (br s, 1H), 6.37 (s, 1H), 6.29 (br s, 1H), 4.96 (br s, 1H), 3.91 (s, 2H), 3.10-2.96 (m, 1H), 2.46-2.40 (m, 1H), 2.06-1.80 (m, 4H), 1.69 (br s, 2H), 1.55 (br d, J = 14.7 Hz, 5H), 1.41 (br s, 2H), 1.25 (s, 3H) |
| 118 (B) | 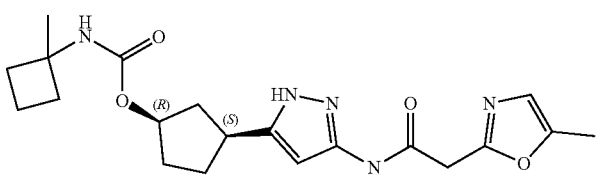<br>(1R,3S)-3-(3-{[(5-methyl-1,3-oxazol-2-yl)acetyl]amino}-1H-pyrazol-5-yl)cyclopentyl (1-methylcyclobutyl)carbamate<br>All stereocenters known | 402.3 | 1H NMR (400 MHz, DMSO-d6) δ = 12.10 (br s, 1H), 10.62 (s, 1H), 7.16 (br s, 1H), 6.74 (d, J = 1.1 Hz, 1H), 6.29 (s, 1H), 4.97 (br s, 1H), 3.79 (s, 2H), 3.11-2.97 (m, 1H), 2.45-2.41 (m, 1H), 2.25 (d, J = 1.0 Hz, 5H), 2.03-1.95 (m, 1H), 1.92-1.84 (m, 1H), 1.83-1.76 (m, 2H), 1.74-1.63 (m, 4H), 1.56 (br s, 1H), 1.30 (s, 3H) |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 119 (B) | (1R,3S)-3-(3-{[(1-methyl-1H-pyrazol-4-yl)acetyl]amino}-1H-pyrazol-5-yl)cyclopentyl (1-methylcyclobutyl)carbamate<br>All stereocenters known | M + Na+ 422.9 | ¹H NMR (400 MHz, DMSO-d6) δ = 12.03 (br s, 1H), 10.35 (br s, 1H), 7.53 (s, 1H), 7.28 (s, 1H), 7.17 (br s, 1H), 6.29 (br s, 1H), 4.97 (br s, 1H), 3.77 (s, 3H), 3.38 (br s, 2H), 3.09-2.95 (m, 1H), 2.43 (br s, 1H), 2.20 (br s, 2H), 1.98 (br d, J = 6.5 Hz, 1H), 1.92-1.75 (m, 3H), 1.70 (br d, J = 8.3 Hz, 4H), 1.56 (br s, 1H), 1.30 (s, 3H) |
| 120 (B) | (1R,3S)-3-(3-{[(3,5-difluorophenyl)acetyl]amino}-1H-pyrazol-5-yl)cyclopentyl [(3ξ)-3-methyltetrahydrofuran-3-yl]carbamate—Isomer A<br>Single stereoisomer; absolute configuration of the chiral center in the methyltetrahydrofuran was not determined | M + Na+ 470.9 | ¹H NMR (400 MHz, CHLOROFORM-d) δ = 8.23 (br s, 1H), 6.87 (br d, J = 5.9 Hz, 2H), 6.75 (dt, J = 2.2, 8.9 Hz, 1H), 6.52 (br s, 1H), 5.28 (br s, 1H), 5.16 (br s, 1H), 4.02-3.85 (m, 3H), 3.67 (s, 2H), 3.57 (d, J = 9.0 Hz, 1H), 3.17 (quin, J = 8.0 Hz, 1H), 2.42 (br s, 1H), 2.32-2.19 (m, 1H), 2.16-2.02 (m, 1H), 1.98-1.79 (m, 5H), 1.47 (s, 3H)<br>[α]_D²⁵ +16.67 (c 0.2, MeOH)<br>Peak 1 of 2: Column: Chiralpak IC-3 150 × 4.6 mm I.D., 3 μm; Mobile phase: 40% of IPA (0.05% DEA) in CO₂; Flow rate: 2.5 mL/min; Column temp 35° C. |
| 121 (B) | (1R,3S)-3-(3-{[(3,5-difluorophenyl)acetyl]amino}-1H-pyrazol-5-yl)cyclopentyl [(3ξ)-3-methyltetrahydrofuran-3-yl]carbamate—Isomer B<br>Single stereoisomer; absolute configuration of the chiral center in the methyltetrahydrofuran was not determined | M + Na+ 470.9 | ¹H NMR (400 MHz, CHLOROFORM-d) δ = 8.16 (br s, 1H), 6.87 (br d, J = 6.0 Hz, 2H), 6.50 (br s, 1H), 5.17 (br s, 1H), 5.29-5.10 (m, 1H), 4.00-3.84 (m, 3H), 3.67 (s, 2H), 3.57 (d, J = 9.0 Hz, 1H), 3.62-3.52 (m, 1H), 3.17 (quin, J = 7.9 Hz, 1H), 2.43 (br s, 1H), 2.24 (br d, J = 6.6 Hz, 1H), 2.16-2.04 (m, 1H), 1.98-1.78 (m, 5H), 1.48 (s, 3H)<br>[α]_D²⁰ +12 (c 0.2, MeOH)<br>Peak 2 of 2: Column: Chiralpak IC-3 150 × 4.6 mm I.D., 3 μm; Mobile phase: 40% of IPA (0.05% DEA) in CO₂; Flow rate: 2.5 mL/min; Column temp 35° C. |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 122 (B) | (1R,3S)-3-(3-{[(6-methoxypyridin-3-yl)acetyl]amino}-1H-pyrazol-5-yl)cyclopentyl [(3ξ)-3-methyltetrahydrofuran-3-yl]carbamate—Isomer A<br>Single stereoisomer; absolute configuration of the chiral center in the methyltetrahydrofuran was not determined | 444.4 | 1H NMR (400MHz, DMSO-d6) δ = 12.07 (br s, 1H), 10.53 (s, 1H), 8.06 (d, J = 2.1 Hz, 1H), 7.63 (dd, J = 2.4, 8.5 Hz, 1H), 7.22 (br s, 1H), 6.77 (d, J = 8.4 Hz, 1H), 6.27 (br s, 1H), 4.97 (br s, 1H), 3.87-3.78 (m, 4H), 3.72 (t, J = 7.1 Hz, 2H), 3.53 (s, 2H), 3.42 (d, J = 8.6 Hz, 1H), 3.02 (br t, J = 8.1 Hz, 1H), 2.48-2.39 (m, 1H), 2.19-2.08 (m, 1H), 2.04-1.93 (m, 1H), 1.92-1.82 (m, 1H), 1.79-1.62 (m, 3H), 1.56 (br s, 1H), 1.30 (s, 3H)<br>$[\alpha]_D^{25}$ +17 (c 0.2, MeOH)<br>Peak 1 of 2: Column: Chiralpak AD-3 150 × 4.6 mm I.D., 3 μm; Mobile phase: 40% of IPA (0.05% DEA) in CO2; Flow rate: 2.5 mL/min; Column temp 35° C. |
| 123 (B) | (1R,3S)-3-(3-{[(6-methoxypyridin-3-yl)acetyl]amino}-1H-pyrazol-5-yl)cyclopentyl [(3ξ)-3-methyltetrahydrofuran-3-yl]carbamate—Isomer B<br>Single stereoisomer; absolute configuration of the chiral center in the methyltetrahydrofuran was not determined | 444.4 | 1H NMR (400 MHz, CHLOROFORM-d) δ = 8.16 (br s, 1H), 8.09 (s, 1H), 7.62-7.50 (m, 1H), 6.75 (d, J = 8.6 Hz, 1H), 6.49 (s, 1H), 5.16 (br s, 2H), 4.04-3.83 (m, 6H), 3.62 (s, 2H), 3.57 (d, J = 9.0 Hz, 1H), 3.23-3.09 (m, 1H), 2.44 (br d, J = 7.1 Hz, 1H), 2.24 (br d, J = 5.4 Hz, 1H), 2.12 (br s, 1H), 1.95-1.80 (m, 5H), 1.47 (s, 3H)<br>$[\alpha]_D^{20}$ +17 (c 0.2, MeOH)<br>Peak 2 of 2: Column: Chiralpak AD-3 150 × 4.6 mm I.D., 3 μm; Mobile phase: 40% of IPA (0.05% DEA) in CO2; Flow rate: 2.5 mL/min; Column temp 35° C. |
| 124 (A) | (1R,3S)-3-{3-[(phenylacetyl)amino]-1H-pyrazol-5-yl}cyclopentyl [(3ξ)-3-methyltetrahydrofuran-3-yl]carbamate—Isomer A<br>Single stereoisomer; absolute configuration of the chiral center in the methyltetrahydrofuran was not determined | 413.3 | 1H NMR (400 MHz, DMSO-d6) δ = 12.06 (s, 1H), 10.52 (s, 1H), 7.30 (d, J = 4.3 Hz, 4H), 7.23 (qd, J = 4.2, 8.3 Hz, 2H), 6.28 (s, 1H), 4.97 (br s, 1H), 3.81 (br d, J = 8.5 Hz, 1H), 3.75-3.68 (m, 2H), 3.57 (s, 2H), 3.41 (d, J = 8.5 Hz, 1H), 3.07-2.95 (m, 1H), 2.48-2.40 (m, 1H), 2.18-2.09 (m, 1H), 2.03-1.93 (m, 1H), 1.92-1.81 (m, 1H), 1.77-1.62 (m, 3H), 1.61-1.49 (m, 1H), 1.30 (s, 3H)<br>Peak 1 of 2: Column: ChiralPak AD-3 150 × 4.6 mm I.D., 3 μm; Gradient: 40% of IPA (0.05% DEA) in CO2; Flow rate: 2.5 mL/min Column temp 40° C. |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 125 (A) | (1R,3S)-3-{3-[(phenylacetyl)amino]-1H-pyrazol-5-yl}cyclopentyl [(3ξ)-3-methyltetrahydrofuran-3-yl]carbamate—Isomer B<br>Single stereoisomer; absolute configuration of the chiral center in the methyltetrahydrofuran was not determined | 413.4 | 1H NMR (400 MHz, DMSO-d6) δ = 12.06 (br s, 1H), 10.52 (s, 1H), 7.38-7.13 (m, 6H), 6.28 (br s, 1H), 4.97 (br s, 1H), 3.80 (br d, J = 8.3 Hz, 1H), 3.71 (br t, J = 7.0 Hz, 2H), 3.57 (s, 2H), 3.42 (d, J = 8.5 Hz, 1H), 3.07-2.95 (m, 1H), 2.48-2.40 (m, 1H), 2.14 (br d, J = 6.5 Hz, 1H), 1.98 (br d, J = 8.3 Hz, 1H), 1.91-1.81 (m, 1H), 1.77-1.62 (m, 3H), 1.55 (br s, 1H), 1.30 (s, 3H)<br>Peak 2 of 2: Column: ChiralPak AD-3 150 × 4.6 mm I.D., 3 μm; Gradient: 40% of IPA (0.05% DEA) in CO2; Flow rate: 2.5 mL/min Column temp 40° C. |
| 126 (D) | (1R,3S)-3-(3-{[(2-methoxy-1,3-thiazol-5-yl)acetyl]amino}-1H-pyrazol-5-yl)cyclopentyl [(3ξ)-3-methyltetrahydrofuran-3-yl]carbamate—Isomer A<br>Single stereoisomer; absolute configuration of the chiral center in the methyltetrahydrofuran was not determined | 450.3 | 1H NMR (500 MHz, DMSO-d6) δ = 12.10 (br s, 1H), 10.58 (s, 1H), 7.24 (br s, 1H), 6.96 (s, 1H), 6.30 (br s, 1H), 4.98 (br s, 1H), 3.96 (s, 3H), 3.81 (br d, J = 7.6 Hz, 1H), 3.76-3.68 (m, 4H), 3.42 (d, J = 8.5 Hz, 1H), 3.08-2.97 (m, 1H), 2.48-2.42 (m, 1H), 2.19-2.10 (m, 1H), 1.99 (br d, J = 9.5 Hz, 1H), 1.87 (br dd, J = 6.4, 10.1 Hz, 1H), 1.77-1.64 (m, 3H), 1.57 (br s, 1H), 1.31 (s, 3H)<br>$[\alpha]_D^{25}$ +4 (c 0.1, MeOH)<br>Peak 1 of 2: Column: Chiralpak IC-3 150 × 4.6 mm I.D., 3 μm; Mobile phase: 40% IPA (0.05% DEA) in CO2; Flow rate: 2.5 mL/min; Column temp 35° C. |
| 127 (D) | (1R,3S)-3-(3-{[(2-methoxy-1,3-thiazol-5-yl)acetyl]amino}-1H-pyrazol-5-yl)cyclopentyl [(3ξ)-3-methyltetrahydrofuran-3-yl]carbamate—Isomer B<br>Single stereoisomer; absolute configuration of the chiral center in the methyltetrahydrofuran was not determined | 450.3 | 1H NMR (500 MHz, DMSO-d6) δ = 12.11 (br s, 1H), 10.58 (s, 1H), 7.24 (br s, 1H), 6.96 (s, 1H), 6.30 (s, 1H), 4.98 (br s, 1H), 3.96 (s, 3H), 3.80 (br d, J = 7.6 Hz, 1H), 3.75-3.67 (m, 4H), 3.42 (d, J = 8.5 Hz, 1H), 3.08-2.98 (m, 1H), 2.48-2.42 (m, 1H), 2.20-2.12 (m, 1H), 1.99 (br d, J = 9.3 Hz, 1H), 1.91-1.83 (m, 1H), 1.78-1.64 (m, 3H), 1.56 (br s, 1H), 1.31 (s, 3H)<br>$[\alpha]_D^{25}$ +6 (c 0.1, MeOH)<br>Peak 2 of 2: Column: Chiralpak IC-3 150 × 4.6 mm I.D., 3 μm; Mobile phase: 40% IPA (0.05% DEA) in CO2; Flow rate: 2.5 mL/min; Column temp 35° C. |
| 128 (A) | (1R,3S)-3-{3-[(1,2-oxazol-5-ylacetyl)amino]-1H-pyrazol-5-yl}cyclopentyl (1-methylcyclopropyl)carbamate<br>All stereocenters known | 374.4 | 1H NMR (400 MHz, DMSO-d6) δ = 12.11 (br s, 1H), 10.65 (s, 1H), 8.48 (s, 1H), 7.34 (br s, 1H), 6.37 (s, 1H), 6.28 (br s, 1H), 4.97 (br s, 1H), 3.91 (s, 2H), 3.14-2.96 (m, 1H), 2.46-2.41 (m, 1H), 1.98 (br d, J = 8.8 Hz, 1H), 1.92-1.79 (m, 1H), 1.72-1.59 (m, 2H), 1.53 (br s, 1H), 1.22 (s, 3H), 0.58 (br s, 2H), 0.50-0.41 (m, 2H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 129 (A) | 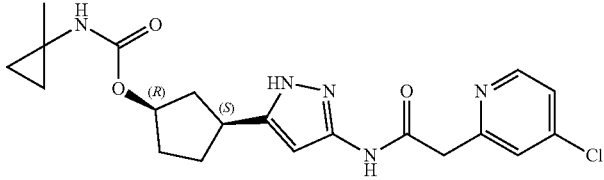<br>(1R,3S)-3-(3-{[(4-chloropyridin-2-yl)acetyl]amino}-1H-pyrazol-5-yl)cyclopentyl (1-methylcyclopropyl)carbamate<br>All stereocenters known | 418.4 | 1H NMR (400 MHz, DMSO-d6) δ = 12.07 (br s, 1H), 10.56 (br s, 1H), 8.46 (d, J = 5.4 Hz, 1H), 7.52 (d, J = 1.8 Hz, 1H), 7.42 (d, J = 5.5 Hz, 1H), 7.33 (br s, 1H), 6.27 (br s, 1H), 4.96 (br s, 1H), 3.83 (s, 2H), 3.02 (br d, J = 8.4 Hz, 1H), 2.48-2.39 (m, 1H), 1.97 (br d, J = 8.1 Hz, 1H), 1.91-1.80 (m, 1H), 1.74-1.57 (m, 2H), 1.57-1.47 (m, 1H), 1.22 (s, 3H), 0.57 (br s, 2H), 0.50-0.43 (m, 2H) |
| 130 (A) | 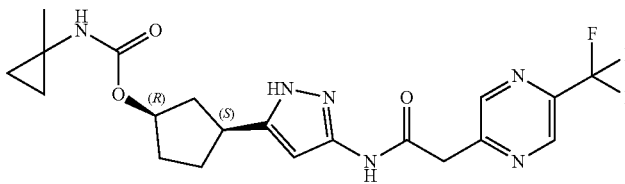<br>(1R,3S)-3-[3-({[5-(trifluoromethyl)pyrazin-2-yl]acetyl}amino)-1H-pyrazol-5-yl]cyclopentyl (1-methylcyclopropyl)carbamate<br>All stereocenters known | 453.3 | 1H NMR (500 MHz, DMSO-d6) δ = 12.11 (br s, 1H), 10.72 (s, 1H), 9.12 (s, 1H), 8.86 (s, 1H), 7.34 (s, 1H), 6.40-6.15 (m, 1H), 5.10-4.85 (m, 1H), 4.06 (s, 2H), 3.07-2.97 (m, 1H), 2.48-2.40 (m, 1H), 1.97 (br d, J = 8.1 Hz, 1H), 1.91-1.81 (m, 1H), 1.72-1.57 (m, 2H), 1.52 (br s, 1H), 1.21 (s, 3H), 0.56 (br s, 2H), 0.47-0.41 (m, 2H) |
| 131 (A) | 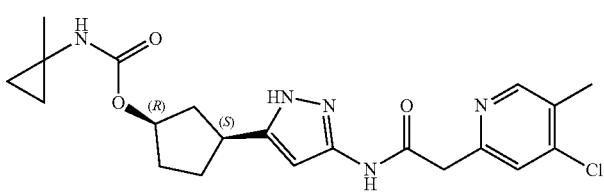<br>(1R,3S)-3-(3-{[(4-chloro-5-methylpyridin-2-yl)acetyl]amino}-1H-pyrazol-5-yl)cyclopentyl (1-methylcyclopropyl)carbamate<br>All stereocenters known | 432.3 | 1H NMR (400 MHz, DMSO-d6) δ = 12.05 (br s, 1H), 10.52 (s, 1H), 8.41 (s, 1H), 7.47 (s, 1H), 7.33 (br s, 1H), 6.26 (br s, 1H), 4.96 (br s, 1H), 3.77 (s, 2H), 3.02 (br d, J = 8.0 Hz, 1H), 2.46-2.37 (m, 1H), 2.32-2.25 (m, 3H), 1.97 (br d, J = 8.8 Hz, 1H), 1.90-1.77 (m, 1H), 1.77-1.58 (m, 2H), 1.57-1.44 (m, 1H), 1.21 (s, 3H), 0.57 (br s, 2H), 0.48-0.40 (m, 2H) |
| 132 (A) | 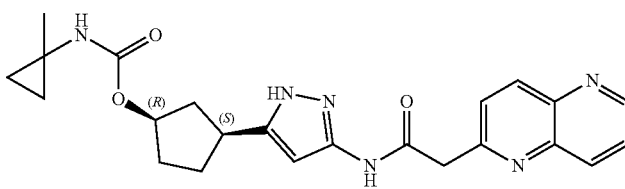<br>(1R,3S)-3-{3-[(1,5-naphthyridin-2-ylacetyl)amino]-1H-pyrazol-5-yl}cyclopentyl (1-methylcyclopropyl)carbamate<br>All stereocenters known | 435.3 | 1H NMR (400 MHz, DMSO-d6) δ = 12.09 (br s, 1H), 10.69 (s, 1H), 8.97 (d, J = 4.5 Hz, 1H), 8.37 (dd, J = 5.4, 8.4 Hz, 2H), 7.81-7.74 (m, 2H), 7.33 (br s, 1H), 6.28 (br s, 1H), 4.95 (br s, 1H), 4.07 (s, 2H), 3.01 (br s, 1H), 2.43-2.37 (m, 1H), 1.97 (br d, J = 7.5 Hz, 1H), 1.92-1.80 (m, 1H), 1.65 (br s, 2H), 1.52 (br s, 1H), 1.21 (s, 3H), 0.56 (br s, 2H), 0.43 (br s, 2H) |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 133 (A) | (1R,3S)-3-(3-{[(3-methyl-1,2-oxazol-5-yl)acetyl]amino}-1H-pyrazol-5-yl)cyclopentyl 2,2-dimethylpiperidine-1-carboxylate<br>All stereocenters known | 430.4 | ¹H NMR (400 MHz, DMSO-d6) δ = 12.13 (br s, 1H), 10.62 (s, 1H), 6.29 (br s, 1H), 6.21 (s, 1H), 5.02-4.95 (m, 1H), 3.82 (s, 2H), 3.30 (br d, J = 3.8 Hz, 2H), 3.07 (quin, J = 8.2 Hz, 1H), 2.44-2.37 (m, 1H), 2.19 (s, 3H), 2.05-1.97 (m, 1H), 1.90-1.82 (m, 1H), 1.78-1.68 (m, 2H), 1.64 (dt, J = 4.3, 8.9 Hz, 1H), 1.47 (s, 6H), 1.31 (s, 6H) |
| 134 (B) | (1R,3S)-3-(3-{[(3-methyl-1,2-oxazol-5-yl)acetyl]amino}-1H-pyrazol-5-yl)cyclopentyl 2,2-dimethylpyrrolidine-1-carboxylate<br>All stereocenters known | 416.4 | ¹H NMR (400 MHz, DMSO-d6) δ = 12.24-12.02 (m, 1H), 10.62 (s, 1H), 6.30 (br s, 1H), 6.22 (s, 1H), 5.09-4.94 (m, 1H), 3.83 (s, 2H), 3.35-3.26 (m, 2H), 3.09 (br d, J = 8.0 Hz, 1H), 2.48-2.33 (m, 1H), 2.20 (s, 3H), 2.08-1.97 (m, 1H), 1.94-1.81 (m, 1H), 1.80-1.61 (m, 7H), 1.33-1.22 (m, 6H) |
| 135 (A) | (1R,3S)-3-{3-[(1,2-oxazol-3-ylacetyl)amino]-1H-pyrazol-5-yl}cyclopentyl 2,2-dimethylpyrrolidine-1-carboxylate<br>All stereocenters known | 402.2 | ¹H NMR (400 MHz, DMSO-d6, T = 80 C) δ = 11.90 (br s, 1H), 10.30 (br s, 1H), 8.76 (d, J = 1.8 Hz, 1H), 6.51 (d, J = 1.5 Hz, 1H), 6.28 (br s, 1H), 5.04 (br s, 1H), 3.77 (s, 2H), 3.34 (br t, J = 6.5 Hz, 2H), 3.14 (br d, J = 3.3 Hz, 1H), 2.46 (br s, 1H), 2.11-1.98 (m, 1H), 1.96-1.86 (m, 1H), 1.84-1.62 (m, 7H), 1.31 (s, 6H) |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 136 (A) | (1R,3S)-3-(3-{[(1-methyl-1H-pyrazol-3-yl)acetyl]amino}-1H-pyrazol-5-yl)cyclopentyl 2,2-dimethylpyrrolidine-1-carboxylate<br>All stereocenters known | 415.2 | ¹H NMR (400 MHz, DMSO-d6) δ = 12.22-11.91 (m, 1H), 10.35 (br s, 1H), 7.54 (s, 1H), 7.29 (s, 1H), 6.30 (br s, 1H), 5.15-4.85 (m, 1H), 3.78 (s, 3H), 3.33-3.21 (m, 3H), 3.06 (br d, J = 6.5 Hz, 1H), 2.44-2.32 (m, 1H), 2.00 (br d, J = 6.8 Hz, 1H), 1.94-1.58 (m, 9H), 1.37-1.21 (m, 6H) |
| 137 (A) | (1R,3S)-3-{3-[([1,2,4]triazolo[1,5-a]pyrimidin-6-ylacetyl)amino]-1H-pyrazol-5-yl}cyclopentyl 2,2-dimethylpyrrolidine-1-carboxylate<br>All stereocenters known | 453.2 | ¹H NMR (400 MHz, DMSO-d6) δ = 12.11 (br s, 1H), 10.66 (s, 1H), 9.33 (d, J = 2.0 Hz, 1H), 8.84 (d, J = 2.3 Hz, 1H), 8.66 (s, 1H), 6.29 (br s, 1H), 5.13-4.89 (m, 1H), 3.85 (s, 2H), 3.33-3.29 (m, 1H), 3.26 (br t, J = 6.1 Hz, 1H), 3.13-3.02 (m, 1H), 2.44-2.32 (m, 1H), 2.06-1.96 (m, 1H), 1.93-1.82 (m, 1H), 1.80-1.57 (m, 7H), 1.35-1.19 (m, 6H) |
| 138 (A) | (1R,3S)-3-{3-[(1,3-oxazol-5-ylacetyl)amino]-1H-pyrazol-5-yl}cyclopentyl 2,2-dimethylpyrrolidine-1-carboxylate<br>All stereocenters known | 402.3 | ¹H NMR (400 MHz, DMSO-d6) δ = 12.23-12.01 (m, 1H), 10.57 (s, 1H), 8.26 (s, 1H), 6.99 (s, 1H), 6.29 (br s, 1H), 5.12-4.87 (m, 1H), 3.77 (s, 2H), 3.32-3.25 (m, 2H), 3.06 (br d, J = 7.0 Hz, 1H), 2.45-2.35 (m, 1H), 2.01 (br s, 1H), 1.85 (br s, 1H), 1.81-1.58 (m, 7H), 1.34-1.21 (m, 6H) |

TABLE 2-continued

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 139 (A) | 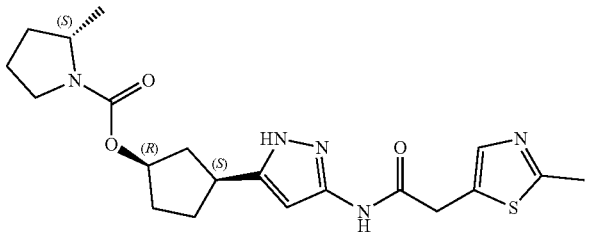<br>(1R,3S)-3-(3-{[(2-methyl-1,3-thiazol-5-yl)acetyl]amino}-1H-pyrazol-5-yl)cyclopentyl (2S)-2-methylpyrrolidine-1-carboxylate<br>All stereocenters known | 418.4 | ¹H NMR (400 MHz, DMSO-d6) δ = 12.11 (br s, 1H), 10.58 (s, 1H), 7.41 (s, 1H), 6.30 (s, 1H), 5.02 (br s, 1H), 3.81 (s, 3H), 3.24 (br s, 2H), 3.13-3.02 (m, 1H), 2.59 (s, 3H), 2.45-2.36 (m, 1H), 2.06-1.97 (m, 1H), 1.95-1.59 (m, 7H), 1.48 (br s, 1H), 1.14-0.98 (m, 3H) |
| 140 (A) | 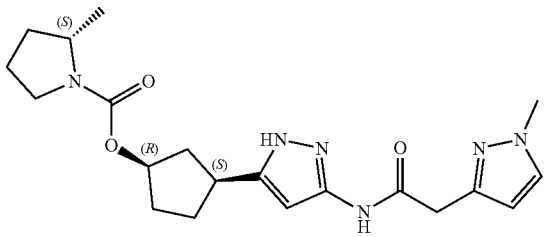<br>(1R,3S)-3-(3-{[(1-methyl-1H-pyrazol-3-yl)acetyl]amino}-1H-pyrazol-5-yl)cyclopentyl (2S)-2-methylpyrrolidine-1-carboxylate<br>All stereocenters known | 401.3 | ¹H NMR (400 MHz, DMSO-d6) δ = 12.05 (br s, 1H), 10.35 (br s, 1H), 7.54 (s, 1H), 7.29 (s, 1H), 6.29 (br s, 1H), 5.01 (br s, 1H), 3.78 (s, 4H), 3.38-3.34 (m, 2H), 3.24 (br s, 2H), 3.07 (quin, J = 8.2 Hz, 1H), 2.42 (br d, J = 8.3 Hz, 1H), 2.12-1.58 (m, 8H), 1.49 (br s, 1H), 1.13-0.98 (m, 3H) |
| 141 (A) | 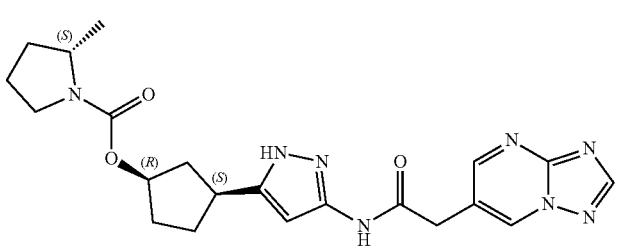<br>(1R,3S)-3-{3-[([1,2,4]triazolo[1,5-a]pyrimidin-6-ylacetyl)amino]-1H-pyrazol-5-yl}cyclopentyl (2S)-2-methylpyrrolidine-1-carboxylate<br>All stereocenters known | 438.9 | ¹H NMR (400 MHz, DMSO-d6) δ = 12.11 (br s, 1H), 10.65 (s, 1H), 9.33 (s, 1H), 8.84 (d, J = 2.0 Hz, 1H), 8.66 (s, 1H), 6.30 (s, 1H), 5.01 (br s, 1H), 3.90-3.68 (m, 3H), 3.29-3.15 (m, 2H), 3.14-3.02 (m, 1H), 2.44-2.36 (m, 1H), 2.01 (br d, J = 9.0 Hz, 1H), 1.95-1.58 (m, 7H), 1.45 (br s, 1H), 1.13-0.94 (m, 3H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 142 (B) | 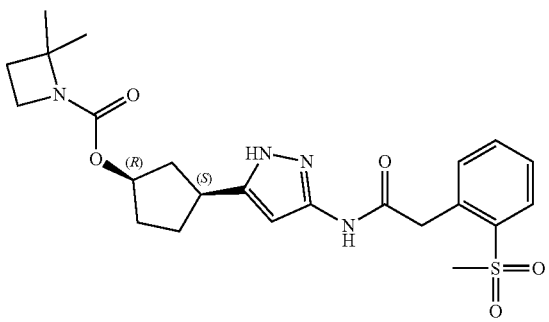<br>(1R,3S)-3-[3-({[2-(methylsulfonyl)phenyl]acetyl}amino)-1H-pyrazol-5-yl]cyclopentyl 2,2-dimethylazetidine-1-carboxylate<br>All stereocenters known | 475.4 | 1H NMR (400 MHz, DMSO-d6) δ = 12.10 (br d, J = 7.0 Hz, 1H), 10.59 (br s, 1H), 7.96 (dd, J = 1.3, 8.0 Hz, 1H), 7.72-7.64 (m, 1H), 7.58-7.52 (m, 1H), 7.50 (d, J = 7.5 Hz, 1H), 6.27 (s, 1H), 5.04-4.91 (m, 1H), 4.18 (s, 2H), 3.69 (br t, J = 8.3 Hz, 1H), 3.63 (t, J = 7.7 Hz, 1H), 3.28 (s, 3H), 3.06 (br d, J = 8.5 Hz, 1H), 2.48-2.34 (m, 1H), 2.04-1.96 (m, 1H), 1.96-1.79 (m, 3H), 1.77-1.56 (m, 3H), 1.37-1.25 (m, 6H) |
| 143 (B) | 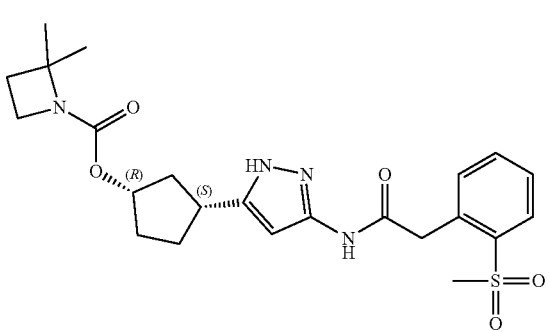<br>(1S,3R)-3-[3-({[2-(methylsulfonyl)phenyl]acetyl}amino)-1H-pyrazol-5-yl]cyclopentyl 2,2-dimethylazetidine-1-carboxylate<br>All stereocenters known | 475.4 | 1H NMR (400 MHz, DMSO-d6) δ = 12.09 (br d, J = 8.0 Hz, 1H), 10.58 (br s, 1H), 7.96 (dd, J = 1.1, 7.9 Hz, 1H), 7.71-7.64 (m, 1H), 7.57-7.52 (m, 1H), 7.50 (d, J = 7.8 Hz, 1H), 6.27 (s, 1H), 5.02-4.90 (m, 1H), 4.18 (s, 2H), 3.69 (br t, J = 7.8 Hz, 1H), 3.63 (t, J = 7.7 Hz, 1H), 3.28 (s, 3H), 3.11-3.00 (m, 1H), 2.46-2.32 (m, 1H), 2.04-1.96 (m, 1H), 1.94-1.88 (m, 2H), 1.87-1.79 (m, 1H), 1.76-1.65 (m, 2H), 1.64-1.55 (m, 1H), 1.34 (d, J = 5.8 Hz, 3H), 1.28 (d, J = 9.5 Hz, 3H) |
| 144 (B) | 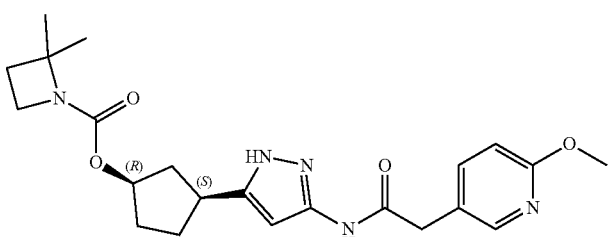<br>(1R,3S)-3-(3-{[(6-methoxypyridin-3-yl)acetyl]amino}-1H-pyrazol-5-yl)cyclopentyl 2,2-dimethylazetidine-1-carboxylate<br>All stereocenters known | 428.3 | 1H NMR (400 MHz, DMSO-d6) δ = 12.07 (br s, 1H), 10.51 (br s, 1H), 8.06 (br s, 1H), 7.62 (dd, J = 2.4, 8.4 Hz, 1H), 6.76 (br d, J = 8.5 Hz, 1H), 6.27 (br s, 1H), 5.07-4.85 (m, 1H), 3.87-3.77 (m, 3H), 3.73-3.59 (m, 2H), 3.52 (br s, 2H), 3.04 (br s, 1H), 2.46-2.32 (m, 1H), 1.99 (br s, 1H), 1.96-1.88 (m, 2H), 1.84 (br s, 1H), 1.76-1.54 (m, 3H), 1.37-1.25 (m, 6H) |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 145 (B) | 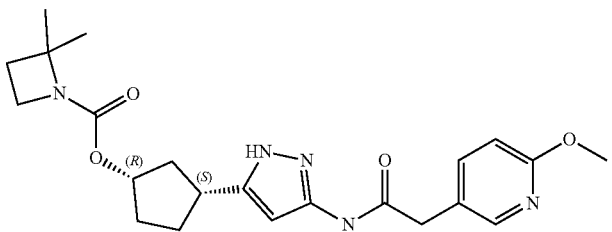<br>(1S,3R)-3-(3-{[(6-methoxypyridin-3-yl)acetyl]amino}-1H-pyrazol-5-yl)cyclopentyl 2,2-dimethylazetidine-1-carboxylate<br>All stereocenters known | 428.4 | 1H NMR (400 MHz, DMSO-d6) δ = 12.07 (br d, J = 7.0 Hz, 1H), 10.51 (br s, 1H), 8.06 (d, J = 2.0 Hz, 1H), 7.62 (dd, J = 2.5, 8.5 Hz, 1H), 6.77 (d, J = 8.3 Hz, 1H), 6.28 (br s, 1H), 5.06-4.90 (m, 1H), 3.81 (s, 3H), 3.72-3.66 (m, 1H), 3.63 (t, J = 7.7 Hz, 1H), 3.52 (s, 2H), 3.10-2.99 (m, 1H), 2.45-2.32 (m, 1H), 2.05-1.96 (m, 1H), 1.95-1.89 (m, 2H), 1.87-1.77 (m, 1H), 1.76-1.65 (m, 2H), 1.62 (br dd, J = 4.9, 9.2 Hz, 1H), 1.34 (d, J = 5.8 Hz, 3H), 1.28 (d, J = 8.3 Hz, 3H) |
| 146 (B) | 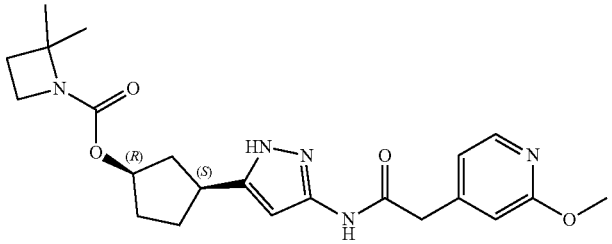<br>(1R,3S)-3-(3-{[(2-methoxypyridin-4-yl)acetyl]amino}-1H-pyrazol-5-yl)cyclopentyl 2,2-dimethylazetidine-1-carboxylate<br>All stereocenters known | 428.4 | 1H NMR (400 MHz, DMSO-d6) δ = 12.09 (br d, J = 7.3 Hz, 1H), 10.57 (br s, 1H), 8.07 (d, J = 5.3 Hz, 1H), 6.91 (d, J = 4.3 Hz, 1H), 6.73 (s, 1H), 6.28 (br s, 1H), 5.08-4.86 (m, 1H), 3.82 (s, 3H), 3.74-3.54 (m, 4H), 3.06 (br d, J = 7.3 Hz, 1H), 2.46-2.34 (m, 1H), 2.05-1.78 (m, 4H), 1.77-1.55 (m, 3H), 1.41-1.21 (m, 6H) |
| 147 (B) | 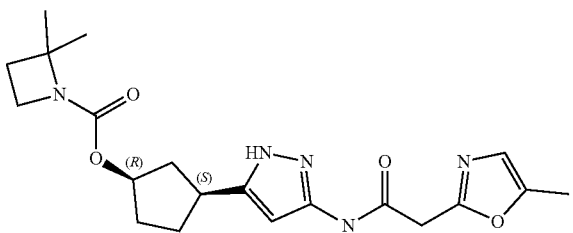<br>(1R,3S)-3-(3-{[(5-methyl-1,3-oxazol-2-yl)acetyl]amino}-1H-pyrazol-5-yl)cyclopentyl 2,2-dimethylazetidine-1-carboxylate<br>All stereocenters known | 402.3 | 1H NMR (400 MHz, DMSO-d6) δ = 12.13 (br s, 1H), 10.61 (br s, 1H), 6.74 (s, 1H), 6.28 (br s, 1H), 4.98 (br d, J = 19.1 Hz, 1H), 3.79 (s, 2H), 3.70 (br d, J = 6.8 Hz, 1H), 3.64 (br t, J = 7.4 Hz, 1H), 3.07 (br d, J = 6.8 Hz, 1H), 2.42 (br s, 1H), 2.25 (s, 3H), 2.12-1.81 (m, 4H), 1.79-1.52 (m, 3H), 1.45-1.22 (m, 6H) |
| 148 (B) | 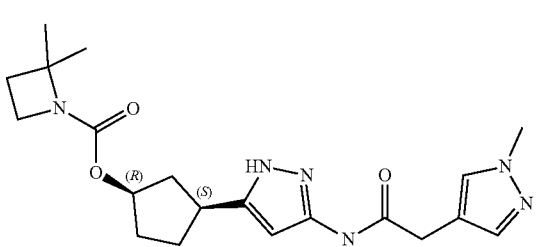<br>(1R,3S)-3-(3-{[(1-methyl-1H-pyrazol-4-yl)acetyl]amino}-1H-pyrazol-5-yl)cyclopentyl 2,2-dimethylazetidine-1-carboxylate<br>All stereocenters known | 401.4 | 1H NMR (400 MHz, DMSO-d6) δ = 12.02 (br d, J = 2.2 Hz, 1H), 10.34 (s, 1H), 7.53 (s, 1H), 7.28 (s, 1H), 6.27 (s, 1H), 5.04-4.90 (m, 1H), 3.77 (s, 3H), 3.72 (dt, J = 3.2, 7.5 Hz, 1H), 3.64 (t, J = 7.5 Hz, 1H), 3.38 (s, 2H), 3.10-2.98 (m, 1H), 2.42 (dt, J = 8.0, 15.1 Hz, 1H), 2.04-1.97 (m, 1H), 1.96-1.90 (m, 2H), 1.89-1.79 (m, 1H), 1.77-1.66 (m, 2H), 1.65-1.56 (m, 1H), 1.38-1.28 (m, 6H) |

TABLE 2-continued

| Example No. (Method) | Structure; IUPAC name; stereochemistry. notes | LCMS [M + H]⁺ | ¹H NMR (ppm); ¹⁹F NMR (ppm); optical rotation; Chiral HPLC/SFC conditions |
|---|---|---|---|
| 149 (B) | (1R,3S)-3-(3-{[(2-methoxypyridin-4-yl)acetyl]amino}-1H-pyrazol-5-yl)cyclopentyl (2S,4S)-2,4-dimethylazetidine-1-carboxylate<br>All stereocenters known | 428.3 | ¹H NMR (400 MHz, DMSO-d6) δ = 12.09 (s, 1H), 10.57 (s, 1H), 8.07 (d, J = 5.3 Hz, 1H), 6.91 (dd, J = 1.3, 5.3 Hz, 1H), 6.73 (s, 1H), 6.27 (s, 1H), 4.99-4.91 (m, 1H), 4.22-4.11 (m, 2H), 3.82 (s, 3H), 3.58 (s, 2H), 3.08-2.98 (m, 1H), 2.45-2.37 (m, 1H), 1.99 (br d, J = 8.5 Hz, 1H), 1.85 (t, J = 6.7 Hz, 3H), 1.76-1.64 (m, 2H), 1.59 (dt, J = 4.4, 9.0 Hz, 1H), 1.28 (d, J = 6.0 Hz, 3H), 1.20 (d, J = 6.3 Hz, 3H) |
| 150 (B) | (1R,3S)-3-(3-{[(3-methyl-1,2-oxazol-5-yl)acetyl]amino}-1H-pyrazol-5-yl)cyclopentyl (2S,4S)-2,4-dimethylazetidine-1-carboxylate<br>All stereocenters known | 401.9 | ¹H NMR (400 MHz, DMSO-d6) δ = 12.13 (s, 1H), 10.62 (s, 1H), 6.29 (d, J = 1.8 Hz, 1H), 6.21 (s, 1H), 5.02-4.95 (m, 1H), 4.25-4.15 (m, 2H), 3.82 (s, 2H), 3.06 (br s, 1H), 2.41 (br d, J = 7.8 Hz, 1H), 2.19 (s, 3H), 2.00 (br d, J = 8.5 Hz, 1H), 1.87 (t, J = 6.7 Hz, 3H), 1.76-1.65 (m, 2H), 1.59 (br s, 1H), 1.30-1.21 (m, 6H) |
| 151 (B) | (1R,3S)-3-(3-{[(6-methoxypyridin-3-yl)acetyl]amino}-1H-pyrazol-5-yl)cyclopentyl (2ξ)-2-methylazetidine-1-carboxylate—Isomer A<br>Single stereoisomer; absolute configuration of the chiral center in the 2-methylazetidine was not determined | 414.3 | ¹H NMR (400 MHz, DMSO-d6) δ = 12.08 (br s, 1H), 10.54 (br s, 1H), 8.06 (d, J = 2.0 Hz, 1H), 7.63 (dd, J = 2.4, 8.4 Hz, 1H), 6.78 (d, J = 8.5 Hz, 1H), 6.28 (br s, 1H), 5.06-4.88 (m, 1H), 4.30-4.14 (m, 1H), 3.82 (s, 3H), 3.72 (br t, J = 7.3 Hz, 2H), 3.53 (s, 2H), 3.06 (quin, J = 8.2 Hz, 1H), 2.43-2.34 (m, 1H), 2.29-2.18 (m, 1H), 2.04-1.94 (m, 1H), 1.92-1.80 (m, 1H), 1.78-1.58 (m, 4H), 1.24 (br s, 3H)<br>[α]$_D^{25}$ +15.0 (c 0.12, MeOH)<br>Peak 1 of 2 Column: Chiralpak AD-3 50 × 3 mm × 3 μm; Mobile phase: 40% EtOH (0.05% DEA) in CO₂; Flow rate: 2 mL/min Column temp 40° C. |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 152 (B) | (1R,3S)-3-(3-{[(6-methoxypyridin-3-yl)acetyl]amino}-1H-pyrazol-5-yl)cyclopentyl (2ξ)-2-methylazetidine-1-carboxylate—Isomer B<br>Single stereoisomer; absolute configuration of the chiral center in the 2-methylazetidine was not determined | 414.3 | 1H NMR (400 MHz, DMSO-d6) δ = 12.08 (br s, 1H), 10.54 (br s, 1H), 8.07 (d, J = 1.8 Hz, 1H), 7.63 (dd, J = 2.3, 8.5 Hz, 1H), 6.78 (d, J = 8.3 Hz, 1H), 6.28 (br s, 1H), 4.98 (br s, 1H), 4.20 (br d, J = 7.0 Hz, 1H), 3.82 (s, 3H), 3.72 (br s, 2H), 3.53 (s, 2H), 3.06 (br t, J = 8.3 Hz, 1H), 2.39 (br dd, J = 6.8, 14.1 Hz, 1H), 2.22 (br d, J = 7.8 Hz, 1H), 2.06-1.94 (m, 1H), 1.91-1.80 (m, 1H), 1.75-1.57 (m, 4H), 1.24 (br s, 3H)<br>[α]$_D^{25}$ −21.15° (c 0.104, MeOH)<br>Peak 2 of 2 Column: Chiralpak AD-3 50 × 3 mm × 3 μm; Mobile phase: 40% EtOH (0.05% DEA) in CO$_2$; Flow rate: 2 mL/min Column temp 40° C. |
| 153 (B) | (1R,3S)-3-(3-{[(2-methoxypyridin-4-yl)acetyl]amino}-1H-pyrazol-5-yl)cyclopentyl (2ξ)-2-methylazetidine-1-carboxylate—Isomer A<br>Single stereoisomer; absolute configuration of the chiral center in the 2-methylazetidine was not determined | 414.3 | 1H NMR (400 MHz, DMSO-d6) δ = 12.10 (br s, 1H), 10.58 (s, 1H), 8.07 (d, J = 5.3 Hz, 1H), 6.91 (dd, J = 1.0, 5.3 Hz, 1H), 6.74 (s, 1H), 6.28 (br s, 1H), 5.06-4.89 (m, 1H), 4.30-4.15 (m, 1H), 3.83 (s, 3H), 3.71 (br t, J = 7.5 Hz, 2H), 3.58 (s, 2H), 3.06 (quin, J = 8.3 Hz, 1H), 2.44-2.35 (m, 1H), 2.28-2.16 (m, 1H), 2.05-1.95 (m, 1H), 1.91-1.80 (m, 1H), 1.78-1.56 (m, 4H), 1.24 (br s, 3H)<br>[α]$_D^{25}$ +17.40 (c 0.1, MeOH)<br>Peak 1 of 2: Column: Chiralpak AD-3 50 × 3 mm × 3 μm; Mobile phase: 40% EtOH (0.05% DEA) in CO$_2$; Flow rate: 2 mL/min Column temp 40° C. |
| 154 (B) | (1R,3S)-3-(3-{[(2-methoxypyridin-4-yl)acetyl]amino}-1H-pyrazol-5-yl)cyclopentyl (2ξ)-2-methylazetidine-1-carboxylate—Isomer B<br>Single stereoisomer; absolute configuration of the chiral center in the 2-methylazetidine was not determined | 414.3 | 1H NMR (400 MHz, DMSO-d6) δ = 12.10 (br s, 1H), 10.59 (s, 1H), 8.07 (d, J = 5.3 Hz, 1H), 6.91 (dd, J = 1.0, 5.3 Hz, 1H), 6.74 (s, 1H), 6.28 (br s, 1H), 4.98 (br s, 1H), 4.26-4.12 (m, 1H), 3.83 (s, 3H), 3.72 (br s, 2H), 3.58 (s, 2H), 3.07 (quin, J = 8.1 Hz, 1H), 2.43-2.33 (m, 1H), 2.29-2.16 (m, 1H), 2.05-1.94 (m, 1H), 1.92-1.78 (m, 1H), 1.76-1.57 (m, 4H), 1.24 (br d, J = 4.3 Hz, 3H)<br>[α]$_D^{25}$ −33.15 (c 0.1, MeOH)<br>Peak 2 of 2: Column: Chiralpak AD-3 50 × 3 mm × 3 μm; Mobile phase: 40% EtOH (0.05% DEA) in CO$_2$; Flow rate: 2 mL/min Column temp 40° C. |

TABLE 2-continued

| Example No. (Method) | Structure; IUPAC name; stereochemistry. notes | LCMS [M + H]+ | ¹H NMR (ppm); ¹⁹F NMR (ppm); optical rotation; Chiral HPLC/SFC conditions |
|---|---|---|---|
| 155 (B) | (1R,3S)-3-(3-{[(2-methoxypyridin-4-yl)acetyl]amino}-1H-pyrazol-5-yl)cyclopentyl (2R*,3S*)-3-cyano-2-methylazetidine-1-carboxylate—Isomer A<br>Single stereoisomer; methyl and cyano groups on azetidine ring are trans, but absolute stereochemistry of those groups is undetermined | 439.4 | ¹H NMR (400 MHz, DMSO-d6) δ = 12.09 (s, 1H), 10.58 (s, 1H), 8.07 (d, J = 5.3 Hz, 1H), 6.91 (dd, J = 1.3, 5.3 Hz, 1H), 6.74 (s, 1H), 6.29 (s, 1H), 5.04-4.95 (m, 1H), 4.41 (quin, J = 6.3 Hz, 1H), 4.02-3.88 (m, 2H), 3.82 (s, 3H), 3.58 (s, 2H), 3.39-3.34 (m, 1H), 3.07 (br t, J = 8.0 Hz, 1H), 2.39 (td, J = 7.3, 14.4 Hz, 1H), 1.99 (br d, J = 7.8 Hz, 1H), 1.93-1.83 (m, 1H), 1.80-1.59 (m, 3H), 1.33 (br d, J = 4.0 Hz, 3H) $[[\alpha]_D^{25}$ −10 (c 0.1, MeOH) Peak 1 of 2: Column: Chiralpak AD-3 50 × 3 mm I.D., 3 μm; Mobile phase: 40% EtOH (0.05% DEA) in $CO_2$; Flow rate: 2 mL/min; Column temp 40° C. |
| 156 (B) | (1R,3S)-3-(3-{[(2-methoxypyridin-4-yl)acetyl]amino}-1H-pyrazol-5-yl)cyclopentyl (2R*,3S*)-3-cyano-2-methylazetidine-1-carboxylate—Isomer B<br>Single stereoisomer; methyl and cyano groups on azetidine ring are trans, but absolute stereochemistry of those groups is undetermined | 439.4 | ¹H NMR (400 MHz, DMSO-d6) δ = 12.10 (br s, 1H), 10.59 (s, 1H), 8.07 (d, J = 5.3 Hz, 1H), 6.92 (dd, J = 1.3, 5.3 Hz, 1H), 6.74 (s, 1H), 6.29 (br s, 1H), 5.01 (br s, 1H), 4.40 (quin, J = 6.3 Hz, 1H), 4.05-3.90 (m, 2H), 3.82 (s, 3H), 3.58 (s, 2H), 3.33-3.26 (m, 1H), 3.07 (br t, J = 8.2 Hz, 1H), 2.43-2.31 (m, 1H), 2.00 (q, J = 7.7 Hz, 1H), 1.91-1.81 (m, 1H), 1.80-1.62 (m, 3H), 1.33 (br d, J = 6.0 Hz, 3H) $[\alpha]_D^{25}$ −8 (c 0.1, MeOH) Peak 2 of 2: Column: Chiralpak AD-3 50 × 3 mm I.D., 3 μm; Mobile phase: 40% EtOH (0.05% DEA) in $CO_2$; Flow rate: 2 mL/min; Column temp 40° C. |
| 157 (B) | (1R,3S)-3-(3-{[(6-methoxypyridin-3-yl)acetyl]amino}-1H-pyrazol-5-yl)cyclopentyl (2R*,3S*)-3-cyano-2-methylazetidine-1-carboxylate—Isomer A<br>Single stereoisomer; methyl and cyano groups on azetidine ring are trans, but absolute stereochemistry of those groups is undetermined | 439.4 | ¹H NMR (400 MHz, DMSO-d6) δ = 12.08 (s, 1H), 10.54 (s, 1H), 8.06 (d, J = 2.0 Hz, 1H), 7.63 (dd, J = 2.4, 8.4 Hz, 1H), 6.77 (d, J = 8.5 Hz, 1H), 6.28 (br s, 1H), 5.01 (br s, 1H), 4.40 (quin, J = 6.3 Hz, 1H), 4.04-3.88 (m, 2H), 3.81 (s, 3H), 3.53 (s, 2H), 3.34-3.28 (m, 1H), 3.07 (quin, J = 8.2 Hz, 1H), 2.42-2.32 (m, 1H), 2.04-1.95 (m, 1H), 1.90-1.80 (m, 1H), 1.80-1.60 (m, 3H), 1.32 (br d, J = 5.8 Hz, 3H) $[\alpha]_D^{25}$ −8 (c 0.1, MeOH) Peak 1 of 2: Column: Chiralpak IC-3 150 × 4.6 mm I.D., 3 μm; Mobile phase: 40% IPA (0.05% DEA) in $CO_2$; Flow rate: 2.5 mL/min; Column temp 35° C. |

TABLE 2-continued

| Example No. (Method) | Structure; IUPAC name; stereochemistry. notes | LCMS [M + H]+ | $^1$H NMR (ppm); $^{19}$F NMR (ppm); optical rotation; Chiral HPLC/SFC conditions |
| --- | --- | --- | --- |
| 158 (B) | (1R,3S)-3-(3-{[(6-methoxypyridin-3-yl)acetyl]amino}-1H-pyrazol-5-yl)cyclopentyl (2R*,3S*)-3-cyano-2-methylazetidine-1-carboxylate—Isomer B Single stereoisomer; methyl and cyano groups on azetidine ring are trans, but absolute stereochemistry of those groups is undetermined | 439.4 | $^1$H NMR (400 MHz, DMSO-d6) δ = 12.08 (s, 1H), 10.53 (s, 1H), 8.06 (d, J = 2.3 Hz, 1H), 7.63 (dd, J = 2.4, 8.4 Hz, 1H), 6.77 (d, J = 8.5 Hz, 1H), 6.28 (s, 1H), 5.04-4.94 (m, 1H), 4.41 (quin, J = 6.3 Hz, 1H), 4.02-3.87 (m, 2H), 3.81 (s, 3H), 3.52 (s, 2H), 3.39-3.35 (m, 1H), 3.06 (quin, J = 8.0 Hz, 1H), 2.44-2.34 (m, 1H), 1.99 (br d, J = 7.5 Hz, 1H), 1.90-1.81 (m, 1H), 1.80-1.56 (m, 3H), 1.32 (br s, 3H) $[α]_D^{25}$ −10 (c 0.1, MeOH) Peak 2 of 2: Column: Chiralpak IC-3 150 × 4.6 mm I.D., 3 μm; Mobile phase: 40% IPA (0.05% DEA) in CO$_2$; Flow rate: 2.5 mL/min; Column temp 35° C. |
| 159 (B) | (1R,3S)-3-(3-{[(2-methyl-1,3-thiazol-5-yl)acetyl]amino}-1H-pyrazol-5-yl)cyclopentyl (2S*,3R*)-3-cyano-2-methylazetidine-1-carboxylate—Isomer A Single stereoisomer; methyl and cyano groups on azetidine ring are trans, but absolute stereochemistry of those groups is undetermined | 429.3 | $^1$H NMR (400 MHz, DMSO-d6) δ = 12.11 (s, 1H), 10.60 (s, 1H), 7.40 (s, 1H), 6.31 (s, 1H), 5.02 (br s, 1H), 4.41 (quin, J = 6.2 Hz, 1H), 4.09-3.87 (m, 2H), 3.81 (s, 2H), 3.39-3.35 (m, 1H), 3.08 (quin, J = 8.3 Hz, 1H), 2.58 (s, 3H), 2.43-2.31 (m, 1H), 2.04-1.96 (m, 1H), 1.92-1.82 (m, 1H), 1.79-1.61 (m, 3H), 1.34 (br d, J = 6.0 Hz, 3H) $[α]_D^{25}$ −6 (c 0.1, MeOH) Peak 1 of 2: Column: Chiralpak IC-3 150 × 4.6 mm I.D., 3 μm; Mobile phase: 40% IPA (0.05% DEA) in CO$_2$; Flow rate: 2.5 mL/min; Column temp 35° C. |
| 160 (B) | (1R,3S)-3-(3-{[(2-methyl-1,3-thiazol-5-yl)acetyl]amino}-1H-pyrazol-5-yl)cyclopentyl (2S*,3R*)-3-cyano-2-methylazetidine-1-carboxylate—Isomer B Single stereoisomer; methyl and cyano groups on azetidine ring are trans, but absolute stereochemistry of those groups is undetermined | 429.3 | $^1$H NMR (400 MHz, DMSO-d6) δ = 12.11 (s, 1H), 10.59 (s, 1H), 7.40 (s, 1H), 6.30 (br s, 1H), 5.06-4.95 (m, 1H), 4.42 (quin, J = 6.3 Hz, 1H), 4.04-3.89 (m, 2H), 3.80 (s, 2H), 3.40-3.35 (m, 1H), 3.08 (quin, J = 8.3 Hz, 1H), 2.58 (s, 3H), 2.40 (td, J = 7.3, 14.4 Hz, 1H), 2.00 (br d, J = 7.8 Hz, 1H), 1.91-1.82 (m, 1H), 1.81-1.60 (m, 3H), 1.40-1.39 (m, 1H), 1.34 (br d, J = 5.3 Hz, 2H) $[α]_D^{25}$ −10 (c 0.1, MeOH) Peak 2 of 2: Column: Chiralpak IC-3 150 × 4.6 mm I.D., 3 μm; Mobile phase: 40% IPA (0.05% DEA) in CO$_2$; Flow rate: 2.5 mL/min; Column temp 35° C. |

TABLE 2-continued

| Example No. (Method) | Structure; IUPAC name; stereochemistry. notes | LCMS [M + H]+ | 1H NMR (ppm); 19F NMR (ppm); optical rotation; Chiral HPLC/SFC conditions |
|---|---|---|---|
| 161 (B) | 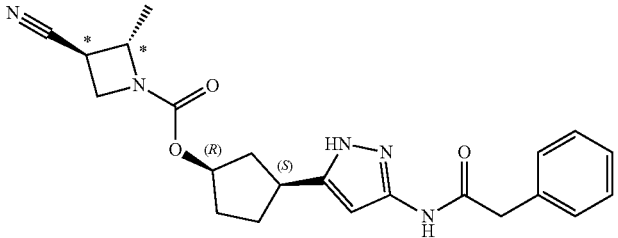<br>(1R,3S)-3-{3-[(phenylacetyl)amino]-1H-pyrazol-5-yl}cyclopentyl (2S*,3R*)-3-cyano-2-methylazetidine-1-carboxylate— Isomer A<br>Single stereoisomer; methyl and cyano groups on azetidine ring are trans, but absolute stereochemistry of those groups is undetermined | 408.3 | 1H NMR (400 MHz, DMSO-d6) δ = 12.06 (s, 1H), 10.50 (s, 1H), 7.34-7.21 (m, 5H), 6.29 (s, 1H), 4.99 (br d, J = 2.8 Hz, 1H), 4.41 (quin, J = 6.2 Hz, 1H), 4.02-3.88 (m, 2H), 3.57 (s, 2H), 3.40-3.35 (m, 1H), 3.06 (quin, J = 8.2 Hz, 1H), 2.47-2.32 (m, 1H), 1.99 (br d, J = 7.0 Hz, 1H), 1.89-1.80 (m, 1H), 1.79-1.59 (m, 3H), 1.32 (br s, 3H)<br>$[\alpha]_D^{25}$ −16.3 (c 0.11, MeOH)<br>Peak 1 of 2: Column: Chiralpak AD-3 50*4.6 mm I.D., 3μm: Mobile phase: 40% EtOH (0.05% DEA) in CO2; Flow rate: 4 mL/min; Column temp 40° C. |
| 162 (B) | 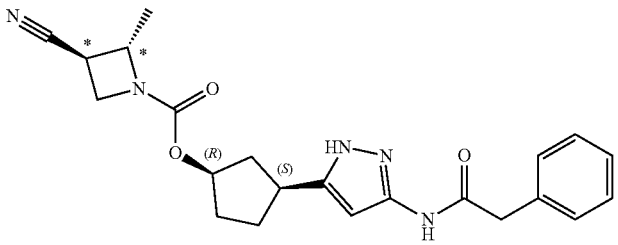<br>(1R,3S)-3-{3-[(phenylacetyl)amino]-1H-pyrazol-5-yl}cyclopentyl (2S*,3R*)-3-cyano-2-methylazetidine-1-carboxylate— Isomer B<br>Single stereoisomer; methyl and cyano groups on azetidine ring are trans, but absolute stereochemistry of those groups is undetermined | 408.3 | 1H NMR (400 MHz, DMSO-d6) δ = 12.06 (s, 1H), 10.51 (s, 1H), 7.33-7.21 (m, 5H), 6.29 (s, 1H), 5.01 (br s, 1H), 4.40 (quin, J = 6.3 Hz, 1H), 4.03-3.88 (m, 2H), 3.57 (s, 2H), 3.32-3.24 (m, 1H), 3.07 (quin, J = 8.3 Hz, 1H), 2.47-2.33 (m, 1H), 1.99 (br d, J = 7.5 Hz, 1H), 1.93-1.79 (m, 1H), 1.79-1.60 (m, 3H), 1.32 (br d, J = 5.8 Hz, 3H)<br>$[\alpha]_D^{25}$ −7.27 (c 0.12, MeOH)<br>Peak 2 of 2: Column: Chiralpak AD-3 50*4.6 mm I.D., 3 μm: Mobile phase: 40% EtOH (0.05% DEA) in CO2; Flow rate: 4 mL/min; Column temp 40° C. |

Additional compounds of the invention were prepared by modifications of the methods exemplified herein and are shown in Table 3.

TABLE 3

| Example No | Structure | LCMS [M + H]+ | IUPAC Name |
|---|---|---|---|
| 163 | 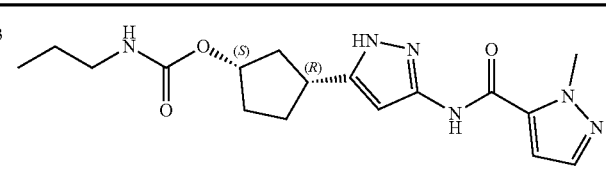 | 361.3 | (1S,3R)-3-(3-{[(1-methyl-1H-pyrazol-5-yl)carbonyl]amino}-1H-pyrazol-5-yl)cyclopentyl propylcarbamate |

TABLE 3-continued

| Example No | Structure | LCMS [M + H]+ | IUPAC Name |
|---|---|---|---|
| 164 | 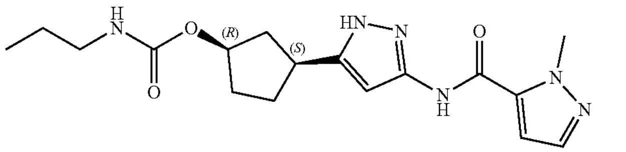 | 361.4 | (1R,3S)-3-(3-{[(1-methyl-1H-pyrazol-5-yl)carbonyl]amino}-1H-pyrazol-5-yl)cyclopentyl propylcarbamate |
| 165 | 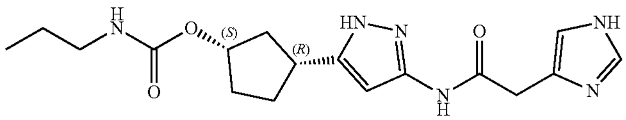 | 361.2 | (1S,3R)-3-{3-[(1H-imidazol-4-ylacetyl)amino]-1H-pyrazol-5-yl}cyclopentyl propylcarbamate |
| 166 | 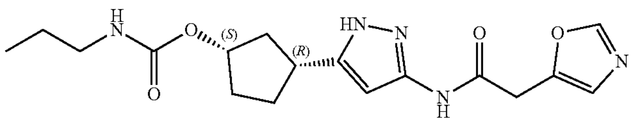 | 362.3 | (1S,3R)-3-{3-[(1,3-oxazol-5-ylacetyl)amino]-1H-pyrazol-5-yl}cyclopentyl propylcarbamate |
| 167 | 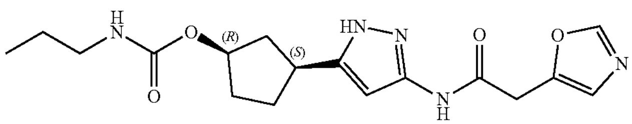 | 362.1 | (1R,3S)-3-{3-[(1,3-oxazol-5-ylacetyl)amino]-1H-pyrazol-5-yl}cyclopentyl propylcarbamate |
| 168 | 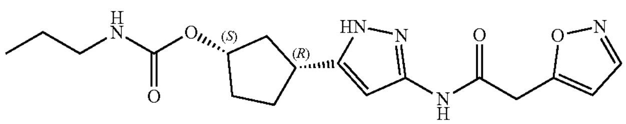 | 362.3 | (1S,3R)-3-{3-[(1,2-oxazol-5-ylacetyl)amino]-1H-pyrazol-5-yl}cyclopentyl propylcarbamate |
| 169 | 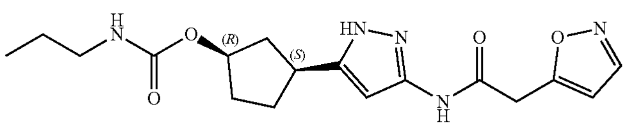 | 362.3 | (1R,3S)-3-{3-[(1,2-oxazol-5-ylacetyl)amino]-1H-pyrazol-5-yl}cyclopentyl propylcarbamate |
| 170 | 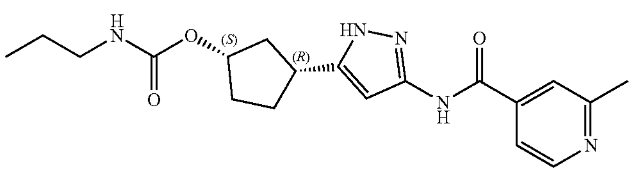 | 372.3 | (1S,3R)-3-(3-{[(2-methylpyridin-4-yl)carbonyl]amino}-1H-pyrazol-5-yl)cyclopentyl propylcarbamate |
| 171 | 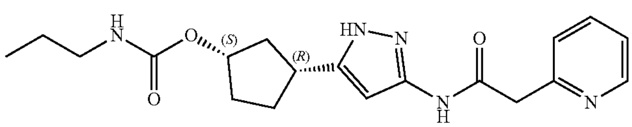 | 372.3 | (1S,3R)-3-{3-[(pyridin-2-ylacetyl)amino]-1H-pyrazol-5-yl}cyclopentyl propylcarbamate |
| 172 | 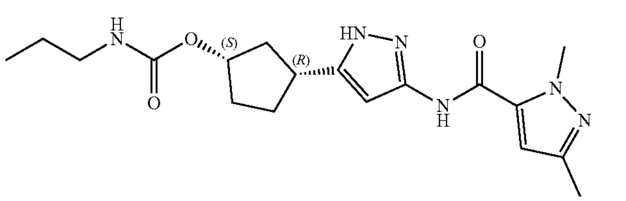 | 375.3 | (1S,3R)-3-(3-{[(1,3-dimethyl-1H-pyrazol-5-yl)carbonyl]amino}-1H-pyrazol-5-yl)cyclopentyl propylcarbamate |
| 173 | 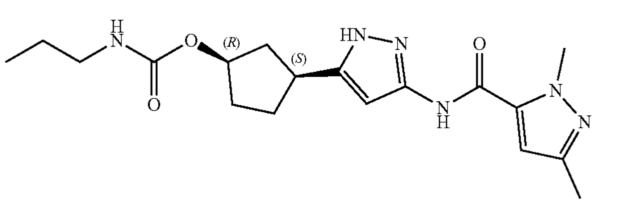 | 375.3 | (1R,3S)-3-(3-{[(1,3-dimethyl-1H-pyrazol-5-yl)carbonyl]amino}-1H-pyrazol-5-yl)cyclopentyl propylcarbamate |

TABLE 3-continued

| Example No | Structure | LCMS [M + H]+ | IUPAC Name |
|---|---|---|---|
| 174 | 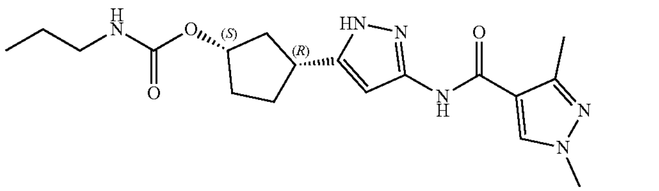 | 375.3 | (1S,3R)-3-(3-{[(1,3-dimethyl-1H-pyrazol-4-yl)carbonyl]amino}-1H-pyrazol-5-yl)cyclopentyl propylcarbamate |
| 175 | 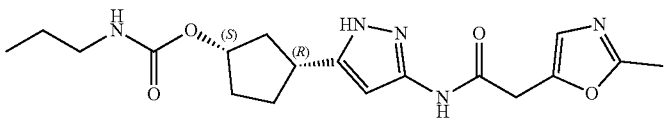 | 376.4 | (1S,3R)-3-(3-{[(2-methyl-1,3-oxazol-5-yl)acetyl]amino}-1H-pyrazol-5-yl)cyclopentyl propylcarbamate |
| 176 | 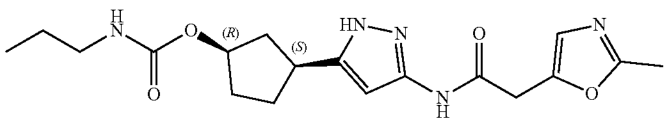 | 376.0 | (1R,3S)-3-(3-{[(2-methyl-1,3-oxazol-5-yl)acetyl]amino}-1H-pyrazol-5-yl)cyclopentyl propylcarbamate |
| 177 | 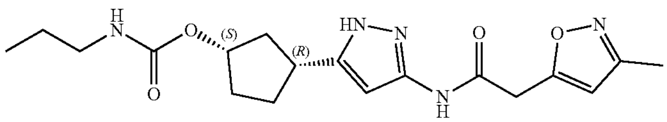 | 376.4 | (1S,3R)-3-(3-{[(3-methyl-1,2-oxazol-5-yl)acetyl]amino}-1H-pyrazol-5-yl)cyclopentyl propylcarbamate |
| 178 | 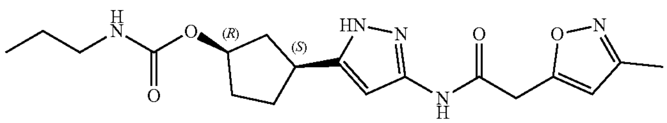 | 376.0 | (1R,3S)-3-(3-{[(3-methyl-1,2-oxazol-5-yl)acetyl]amino}-1H-pyrazol-5-yl)cyclopentyl propylcarbamate |
| 179 | 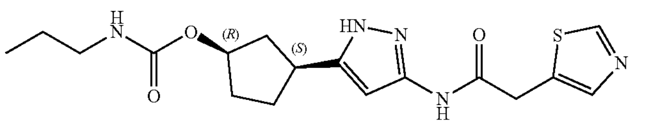 | 378.09 | (1R,3S)-3-{3-[(1,3-thiazol-5-ylacetyl)amino]-1H-pyrazol-5-yl}cyclopentyl propylcarbamate |
| 180 | 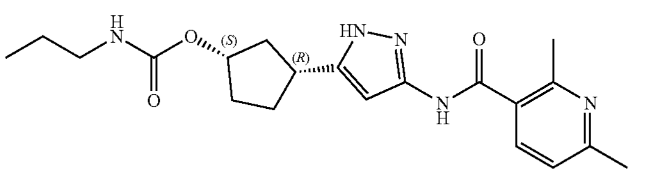 | 386.3 | (1S,3R)-3-(3-{[(2,6-dimethylpyridin-3-yl)carbonyl]amino}-1H-pyrazol-5-yl)cyclopentyl propylcarbamate |
| 181 | 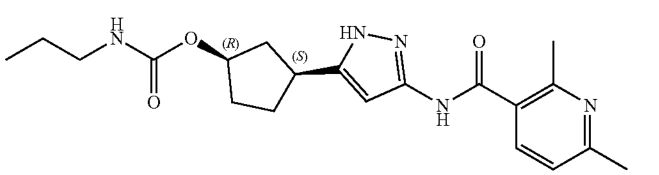 | 386.4 | (1R,3S)-3-(3-{[(2,6-dimethylpyridin-3-yl)carbonyl]amino}-1H-pyrazol-5-yl)cyclopentyl propylcarbamate |
| 182 | 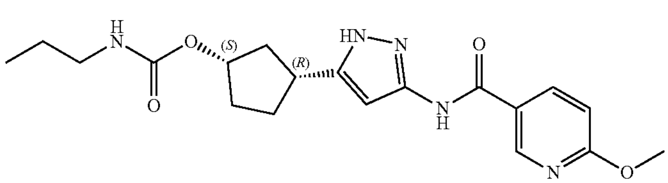 | 388.4 | (1S,3R)-3-(3-{[(6-methoxypyridin-3-yl)carbonyl]amino}-1H-pyrazol-5-yl)cyclopentyl propylcarbamate |

TABLE 3-continued

| Example No | Structure | LCMS [M + H]+ | IUPAC Name |
|---|---|---|---|
| 183 | 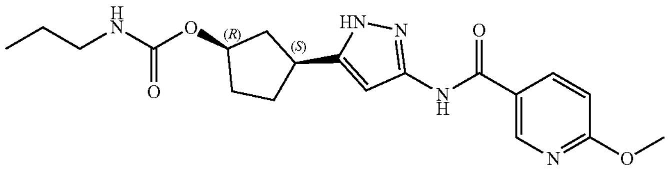 | 388.4 | (1R,3S)-3-(3-{[(6-methoxypyridin-3-yl)carbonyl]amino}-1H-pyrazol-5-yl)cyclopentyl propylcarbamate |
| 184 | 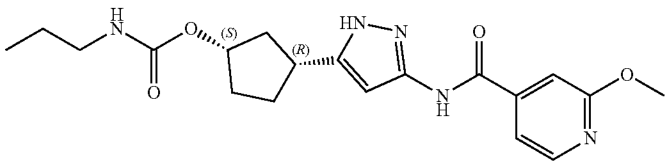 | 388.2 | (1S,3R)-3-(3-{[(2-methoxypyridin-4-yl)carbonyl]amino}-1H-pyrazol-5-yl)cyclopentyl propylcarbamate |
| 185 | 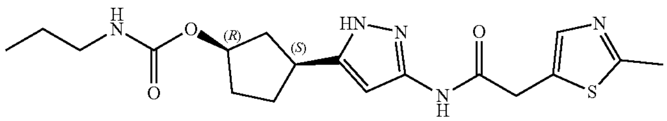 | 392.1 | (1R,3S)-3-(3-{[(2-methyl-1,3-thiazol-5-yl)acetyl]amino}-1H-pyrazol-5-yl)cyclopentyl propylcarbamate |
| 186 | 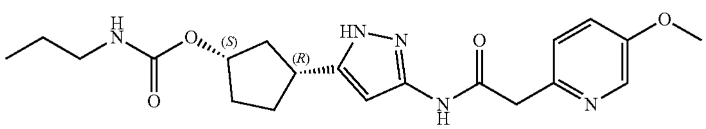 | 402.3 | (1S,3R)-3-(3-{[(5-methoxypyridin-2-yl)acetyl]amino}-1H-pyrazol-5-yl)cyclopentyl propylcarbamate |
| 187 | 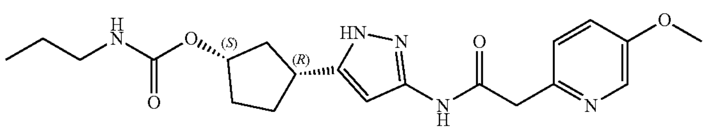 | 402.3 | (1R,3S)-3-(3-{[(5-methoxypyridin-2-yl)acetyl]amino}-1H-pyrazol-5-yl)cyclopentyl propylcarbamate |
| 188 | 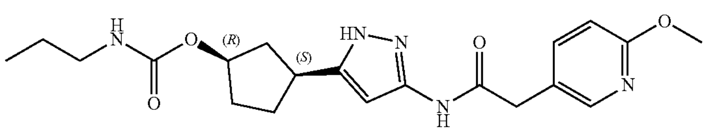 | 402.3 | (1R,3S)-3-(3-{[(6-methoxypyridin-3-yl)acetyl]amino}-1H-pyrazol-5-yl)cyclopentyl propylcarbamate |
| 189 | 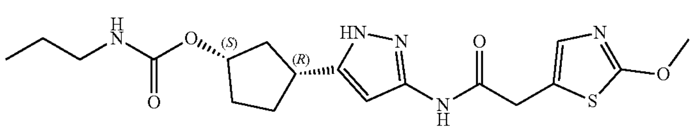 | 408.1 | (1S,3R)-3-(3-{[(2-methoxy-1,3-thiazol-5-yl)acetyl]amino}-1H-pyrazol-5-yl)cyclopentyl propylcarbamate |
| 190 | 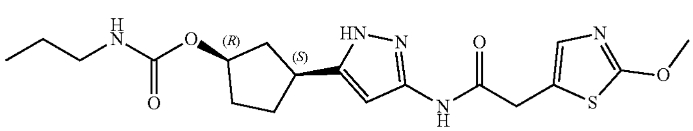 | 408.1 | (1R,3S)-3-(3-{[(2-methoxy-1,3-thiazol-5-yl)acetyl]amino}-1H-pyrazol-5-yl)cyclopentyl propylcarbamate |
| 191 | 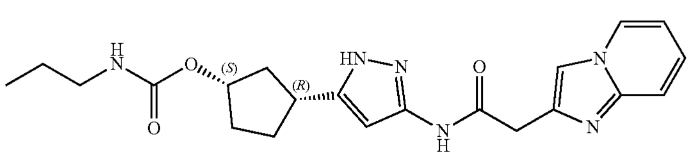 | 411.3 | (1S,3R)-3-{3-[(imidazo[1,2-a]pyridin-2-ylacetyl)amino]-1H-pyrazol-5-yl}cyclopentyl propylcarbamate |
| 192 | 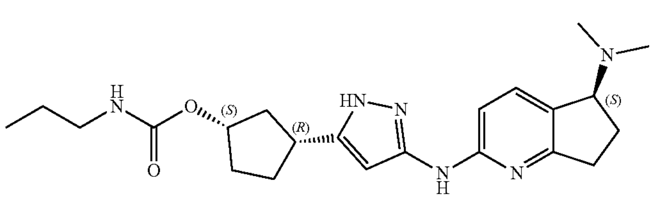 | 413.3 | (1S,3R)-3-(3-{[(5S)-5-(dimethylamino)-6,7-dihydro-5H-cyclopenta[b]pyridin-2-yl]amino}-1H-pyrazol-5-yl)cyclopentyl propylcarbamate |

TABLE 3-continued

| Example No | Structure | LCMS [M + H]+ | IUPAC Name |
|---|---|---|---|
| 193 | 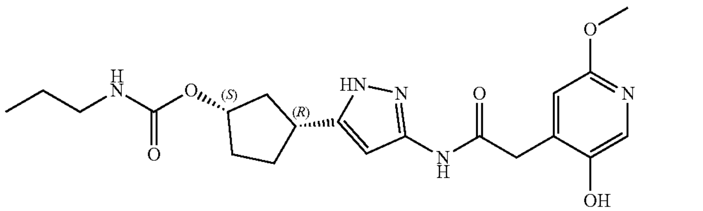 | 418.2 | (1S,3R)-3-(3-{[(5-hydroxy-2-methoxypyridin-4-yl)acetyl]amino}-1H-pyrazol-5-yl)cyclopentyl propylcarbamate |
| 194 | 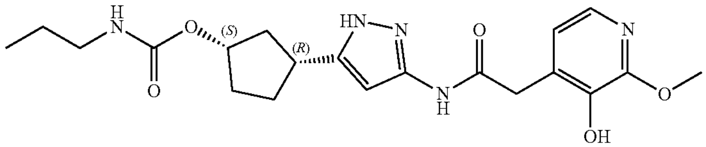 | 418.2 | (1S,3R)-3-(3-{[(3-hydroxy-2-methoxypyridin-4-yl)acetyl]amino}-1H-pyrazol-5-yl)cyclopentyl propylcarbamate |
| 195 | 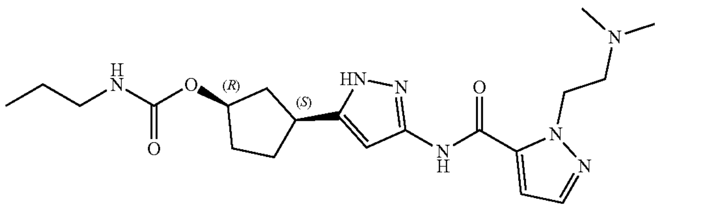 | 418.4 | (1R,3S)-3-{3-[({1-[2-(dimethylamino)ethyl]-1H-pyrazol-5-yl}carbonyl)amino]-1H-pyrazol-5-yl}cyclopentyl propylcarbamate |
| 196 | 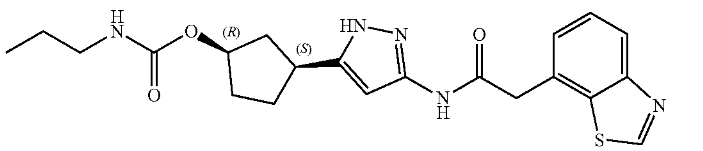 | 428.1 | (1R,3S)-3-{3-[(1,3-benzothiazol-7-ylacetyl)amino]-1H-pyrazol-5-yl}cyclopentyl propylcarbamate |
| 197 | 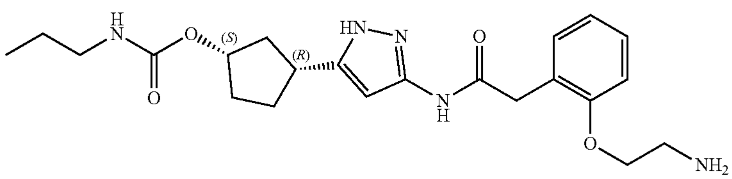 | 430.4 | (1S,3R)-3-[3-({[2-(2-aminoethoxy)phenyl]acetyl}amino)-1H-pyrazol-5-yl]cyclopentyl propylcarbamate |
| 198 | 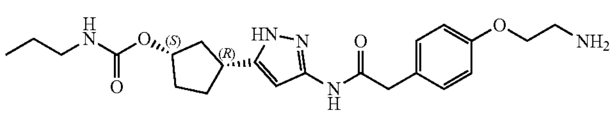 | [M + Na]+ 452.2 | (1S,3R)-3-[3-({[4-(2-aminoethoxy)phenyl]acetyl}amino)-1H-pyrazol-5-yl]cyclopentyl propylcarbamate |
| 199 | 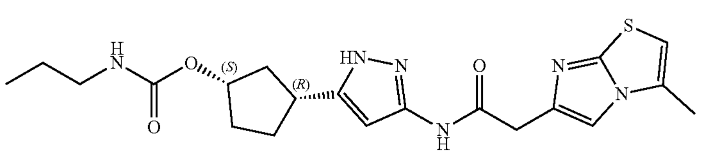 | 431.3 | (1S,3R)-3-(3-{[(3-methylimidazo[2,1-b][1,3]thiazol-6-yl)acetyl]amino}-1H-pyrazol-5-yl)cyclopentyl propylcarbamate |
| 200 | 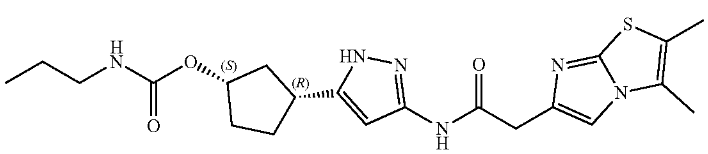 | 445.2 | (1S,3R)-3-(3-{[(2,3-dimethylimidazo[2,1-b][1,3]thiazol-6-yl)acetyl]amino}-1H-pyrazol-5-yl)cyclopentyl propylcarbamate |
| 201 | 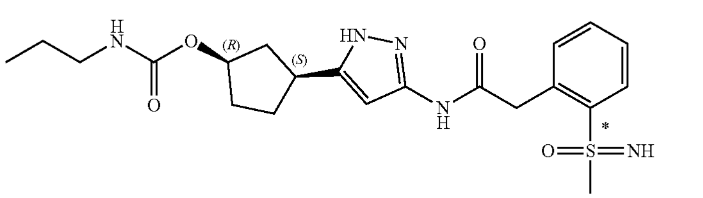 | 448.2 | (1R,3S)-3-[3-({[2-(ξ-methylsulfonimidoyl)phenyl]acetyl}amino)-1H-pyrazol-5-yl]cyclopentyl propylcarbamate - Isomer A |

TABLE 3-continued

| Example No | Structure | LCMS [M + H]+ | IUPAC Name |
|---|---|---|---|
| 202 | 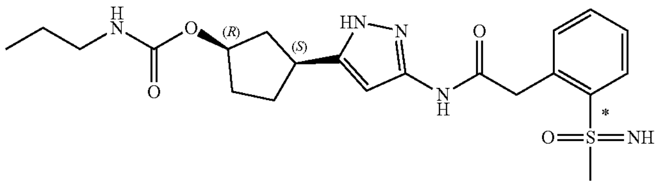 | 448.2 | (1R,3S)-3-[3-({[2-(ξ-methylsulfonimidoyl)-phenyl]acetyl}amino)-1H-pyrazol-5-yl]cyclopentyl propylcarbamate - Isomer B |
| 203 | 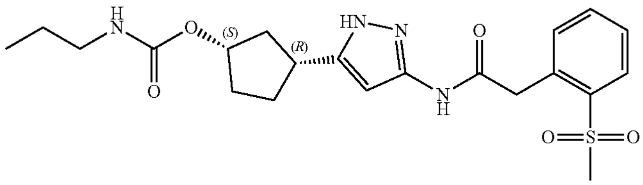 | 449.3 | (1S,3R)-3-[3-({[2-(methylsulfonyl)phenyl]-acetyl}amino-1H-pyrazol-5-yl]cyclopentyl propylcarbamate |
| 204 | 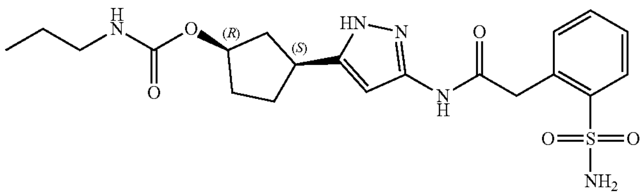 | 449.9 | (1R,3S)-3-(3-{[(2-sulfamoylphenyl)acetyl]-amino}-1H-pyrazol-5-yl)cyclopentyl propylcarbamate |
| 205 | 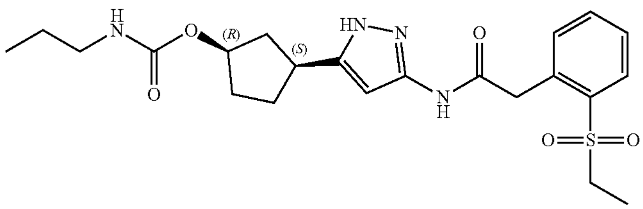 | 463.4 | (1R,3S)-3-[3-({[2-(ethylsulfonyl)phenyl]-acetyl}amino)-1H-pyrazol-5-yl]cyclopentyl propylcarbamate |
| 206 | 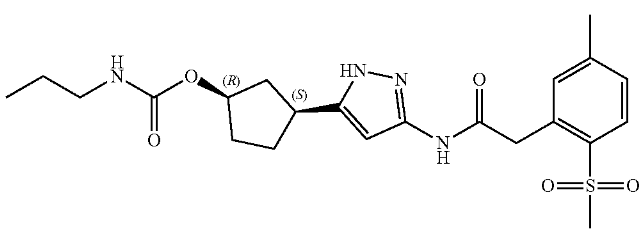 | 463.4 | (1R,3S)-3-[3-({[5-methyl-2-(methylsulfonyl)phenyl]acetyl}amino)-1H-pyrazol-5-yl]cyclopentyl propylcarbamate |
| 207 | 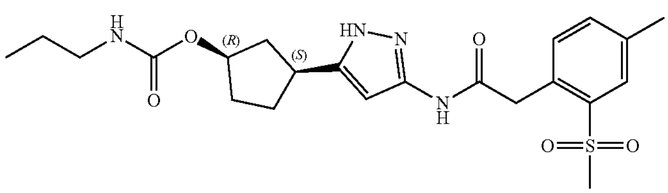 | 463.4 | (1R,3S)-3-[3-({[4-methyl-2-(methylsulfonyl)phenyl]acetyl}amino)-1H-pyrazol-5-yl]cyclopentyl propylcarbamate |
| 208 | 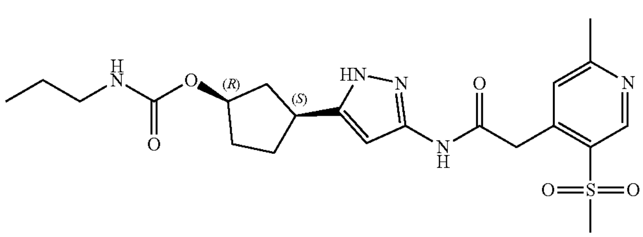 | 464.3 | (1R,3S)-3-[3-({[2-methyl-5-(methylsulfonyl)pyridin-4-yl]acetyl}amino)-1H-pyrazol-5-yl]cyclopentyl propylcarbamate |

TABLE 3-continued

| Example No | Structure | LCMS [M + H]+ | IUPAC Name |
|---|---|---|---|
| 209 | 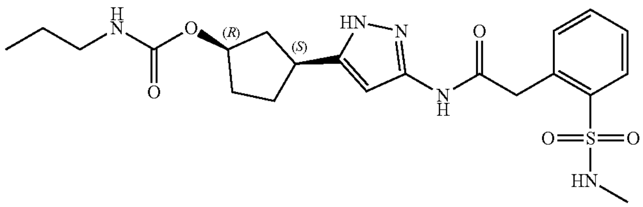 | 463.8 | (1R,3S)-3-[3-({[2-(methylsulfamoyl)phenyl]acetyl}amino)-1H-pyrazol-5-yl]cyclopentyl propylcarbamate |
| 210 | 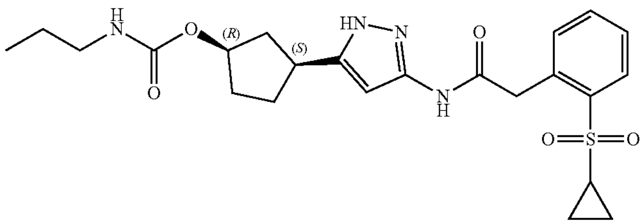 | 475.4 | (1R,3S)-3-[3-({[2-(cyclopropylsulfonyl)phenyl]acetyl}amino)-1H-pyrazol-5-yl]cyclopentyl propylcarbamate |
| 211 | 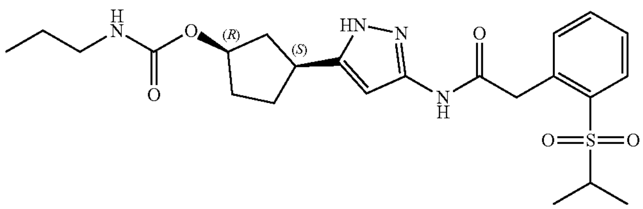 | 477.3 | (1R,3S)-3-[3-({[2-(propan-2-ylsulfonyl)phenyl]acetyl}amino)-1H-pyrazol-5-yl]cyclopentyl propylcarbamate |
| 212 | 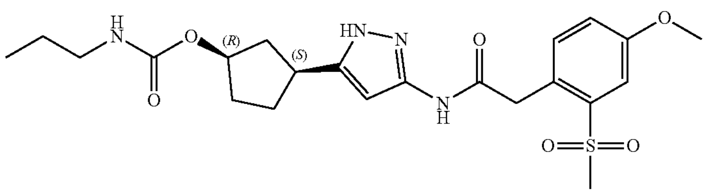 | 479.3 | (1R,3S)-3-[3-({[4-methoxy-2-(methylsulfonyl)phenyl]acetyl}amino)-1H-pyrazol-5-yl]cyclopentyl propylcarbamate |
| 213 | 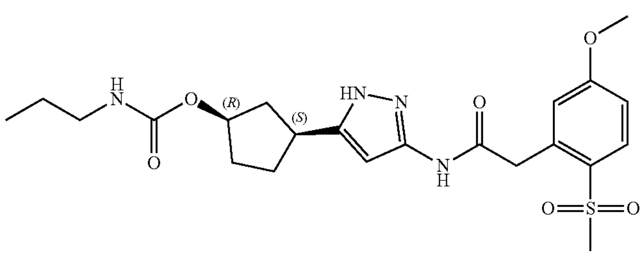 | 479.1 | (1R,3S)-3-[3-({[5-methoxy-2-(methylsulfonyl)phenyl]acetyl}amino)-1H-pyrazol-5-yl]cyclopentyl propylcarbamate |
| 214 | 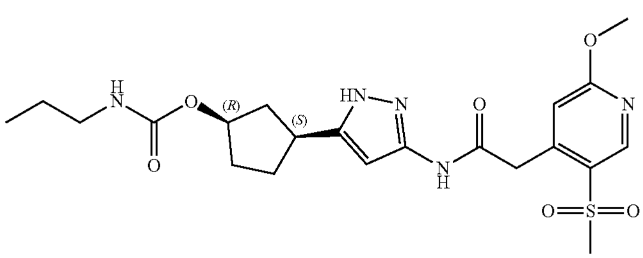 | 480.3 | (1R,3S)-3-[3-({[2-methoxy-5-(methylsulfonyl)pyridin-4-yl]acetyl}amino)-1H-pyrazol-5-yl]cyclopentyl propylcarbamate |
| 215 | 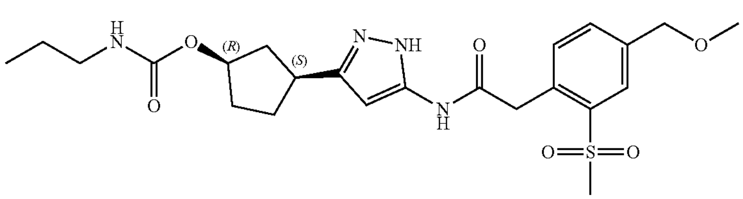 | 493.3 | (1R,3S)-3-[5-({[4-(methoxymethyl)-2-(methylsulfonyl)phenyl]acetyl}amino)-1H-pyrazol-3-yl]cyclopentyl propylcarbamate |

TABLE 3-continued

| Example No | Structure | LCMS [M + H]+ | IUPAC Name |
|---|---|---|---|
| 216 | 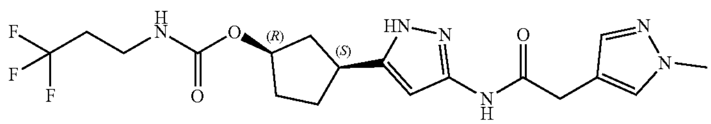 | 429.3 | (1R,3S)-3-(3-{[(1-methyl-1H-pyrazol-4-yl)acetyl]amino}-1H-pyrazol-5-yl)cyclopentyl (3,3,3-trifluoropropyl)carbamate |
| 217 | 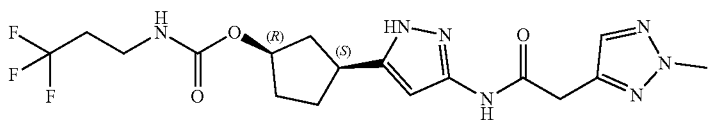 | 430.4 | (1R,3S)-3-(3-{[(2-methyl-2H-1,2,3-triazol-4-yl)acetyl]amino}-1H-pyrazol-5-yl)cyclopentyl (3,3,3-trifluoropropyl)carbamate |
| 218 | 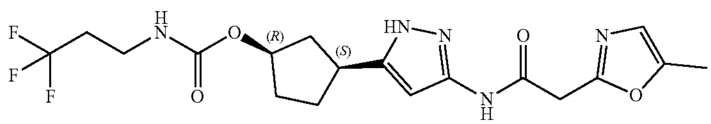 | 430.4 | (1R,3S)-3-(3-{[(5-methyl-1,3-oxazol-2-yl)acetyl]amino}-1H-pyrazol-5-yl)cyclopentyl (3,3,3-trifluoropropyl)carbamate |
| 219 | 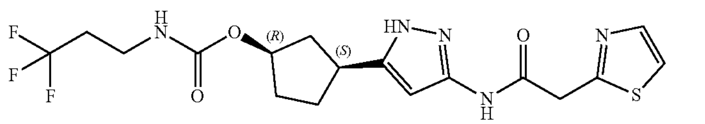 | 432.3 | (1R,3S)-3-{3-[(1,3-thiazol-2-ylacetyl)amino]-1H-pyrazol-5-yl}cyclopentyl (3,3,3-trifluoropropyl)carbamate |
| 220 | 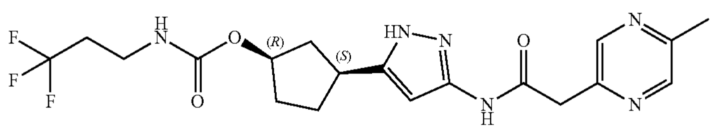 | 441.3 | (1R,3S)-3-(3-{[(5-methylpyrazin-2-yl)acetyl]amino}-1H-pyrazol-5-yl)cyclopentyl (3,3,3-trifluoropropyl)carbamate |
| 221 | 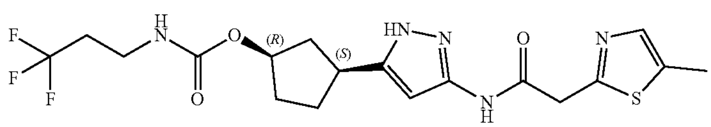 | 446.3 | (1R,3S)-3-(3-{[(5-methyl-1,3-thiazol-2-yl)acetyl]amino}-1H-pyrazol-5-yl)cyclopentyl (3,3,3-trifluoropropyl)carbamate |
| 222 | 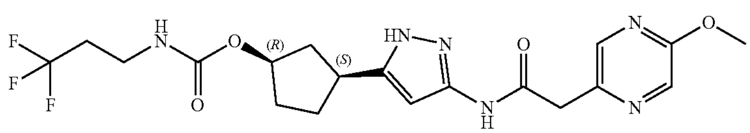 | 457.4 | (1R,3S)-3-(3-{[(5-methoxypyrazin-2-yl)acetyl]amino}-1H-pyrazol-5-yl)cyclopentyl (3,3,3-trifluoropropyl)carbamate |
| 223 | 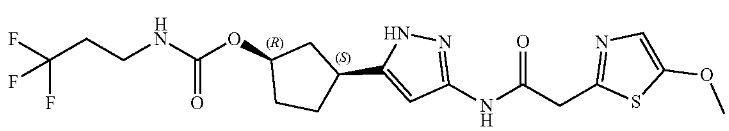 | 462.1 | (1R,3S)-3-(3-{[(5-methoxy-1,3-thiazol-2-yl)acetyl]amino}-1H-pyrazol-5-yl)cyclopentyl (3,3,3-trifluoropropyl)carbamate |
| 224 | 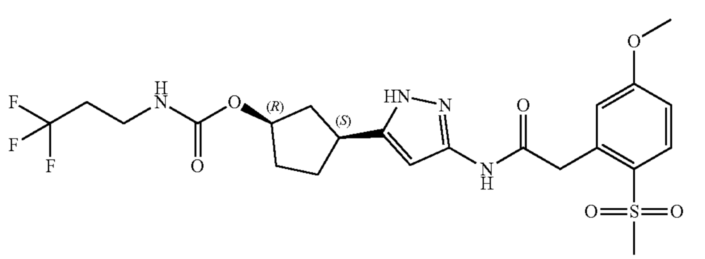 | 533.3 | (1R,3S)-3-[3-({[5-methoxy-2-(methylsulfonyl)phenyl]acetyl}amino)-1H-pyrazol-5-yl]cyclopentyl (3,3,3-trifluoropropyl)carbamate |
| 225 | 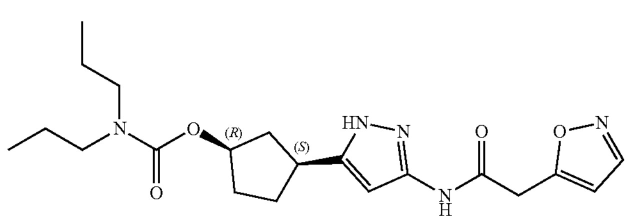 | 403.9 | (1R,3S)-3-{3-[(1,2-oxazol-5-ylacetyl)amino]-1H-pyrazol-5-yl}cyclopentyl dipropylcarbamate |

TABLE 3-continued

| Example No | Structure | LCMS [M + H]+ | IUPAC Name |
|---|---|---|---|
| 226 | 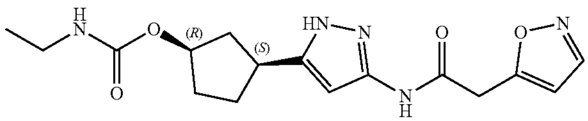 | 347.9 | (1R,3S)-3-{3-[(1,2-oxazol-5-ylacetyl)amino]-1H-pyrazol-5-yl}cyclopentyl ethylcarbamate |
| 227 | 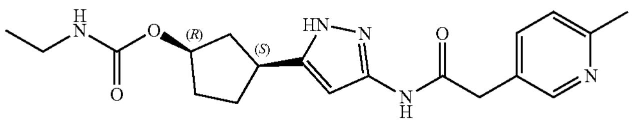 | 372.3 | (1R,3S)-3-(3-{[(6-methylpyridin-3-yl)acetyl]amino}-1H-pyrazol-5-yl)cyclopentyl ethylcarbamate |
| 228 | 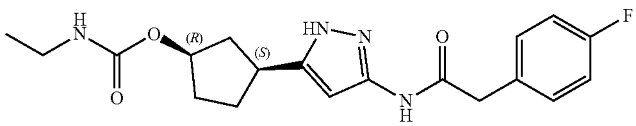 | 375.1 | (1R,3S)-3-(3-{[(4-fluorophenyl)acetyl]amino}-1H-pyrazol-5-yl)cyclopentyl ethylcarbamate |
| 229 | 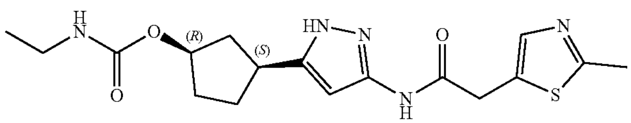 | 378.3 | (1R,3S)-3-(3-{[(2-methyl-1,3-thiazol-5-yl)acetyl]amino}-1H-pyrazol-5-yl)cyclopentyl ethylcarbamate |
| 230 | 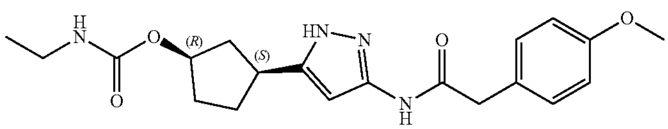 | 387.3 | (1R,3S)-3-(3-{[(4-methoxyphenyl)acetyl]amino}-1H-pyrazol-5-yl)cyclopentyl ethylcarbamate |
| 231 | 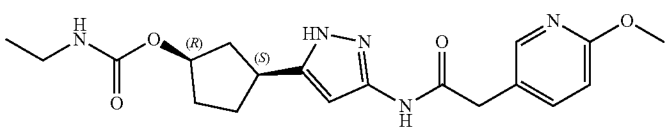 | 388.2 | (1R,3S)-3-(3-{[(6-methoxypyridin-3-yl)acetyl]amino}-1H-pyrazol-5-yl)cyclopentyl ethylcarbamate |
| 232 | 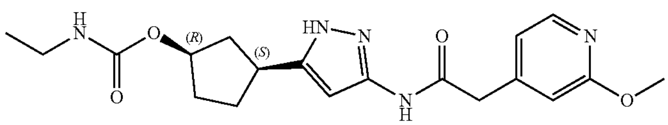 | 388.2 | (1R,3S)-3-(3-{[(2-methoxypyridin-4-yl)acetyl]amino}-1H-pyrazol-5-yl)cyclopentyl ethylcarbamate |
| 233 | 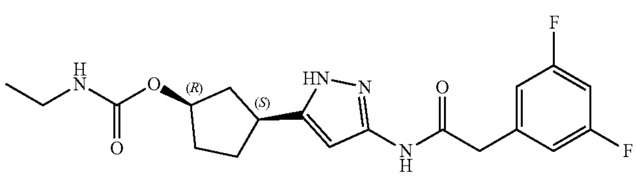 | 393.1 | (1R,3S)-3-(3-{[(3,5-difluorophenyl)acetyl]amino}-1H-pyrazol-5-yl)cyclopentyl ethylcarbamate |
| 234 | 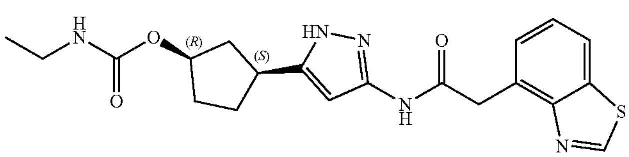 | 414.3 | (1R,3S)-3-{3-[(1,3-benzothiazol-4-ylacetyl)amino]-1H-pyrazol-5-yl}cyclopentyl ethylcarbamate |
| 235 | 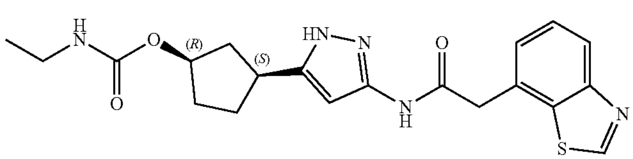 | 413.8 | (1R,3S)-3-{3-[(1,3-benzothiazol-7-ylacetyl)amino]-1H-pyrazol-5-yl}cyclopentyl ethylcarbamate |

TABLE 3-continued

| Example No | Structure | LCMS [M + H]+ | IUPAC Name |
|---|---|---|---|
| 236 | 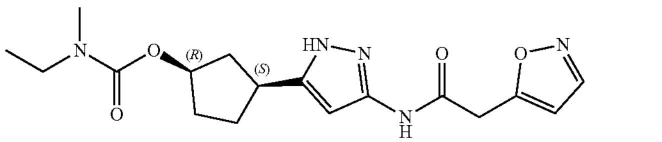 | 361.9 | (1R,3S)-3-{3-[(1,2-oxazol-5-ylacetyl)amino]-1H-pyrazol-5-yl}cyclopentyl ethyl(methyl)carbamate |
| 237 | 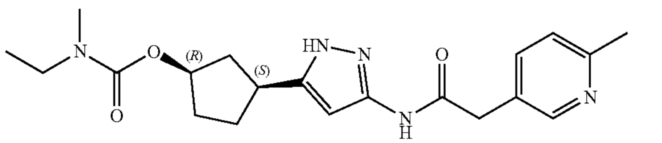 | 386.3 | (1R,3S)-3-(3-{[(6-methylpyridin-3-yl)acetyl]amino}-1H-pyrazol-5-yl)cyclopentyl ethyl(methyl)carbamate |
| 238 | 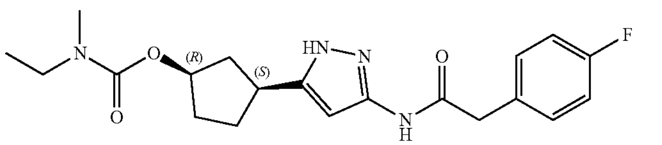 | 389.3 | (1R,3S)-3-(3-{[(4-fluorophenyl)acetyl]amino}-1H-pyrazol-5-yl)cyclopentyl ethyl(methyl)carbamate |
| 239 | 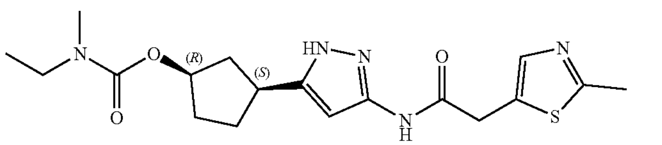 | 392.3 | (1R,3S)-3-(3-{[(2-methyl-1,3-thiazol-5-yl)acetyl]amino}-1H-pyrazol-5-yl)cyclopentyl ethyl(methyl)carbamate |
| 240 | 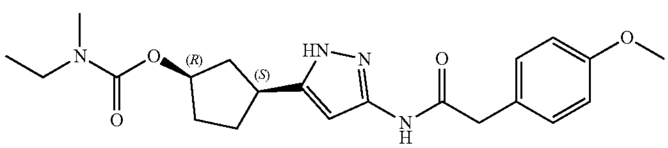 | 401.3 | (1R,3S)-3-(3-{[(4-methoxyphenyl)acetyl]amino}-1H-pyrazol-5-yl)cyclopentyl ethyl(methyl)carbamate |
| 241 | 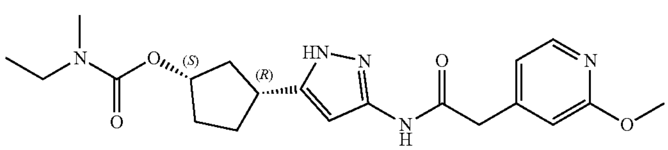 | 402.3 | (1S,3R)-3-(3-{[(2-methoxypyridin-4-yl)acetyl]amino}-1H-pyrazol-5-yl)cyclopentyl ethyl(methyl)carbamate |
| 242 | 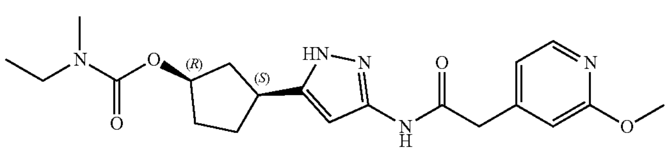 | 402.3 | (1R,3S)-3-(3-{[(2-methoxypyridin-4-yl)acetyl]amino}-1H-pyrazol-5-yl)cyclopentyl ethyl(methyl)carbamate |
| 243 | 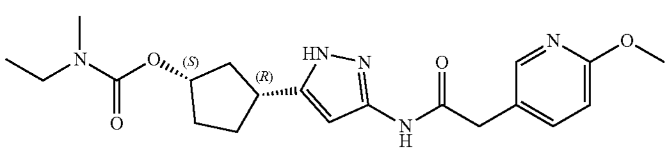 | 402.3 | (1S,3R)-3-(3-{[(6-methoxypyridin-3-yl)acetyl]amino}-1H-pyrazol-5-yl)cyclopentyl ethyl(methyl)carbamate |
| 244 | 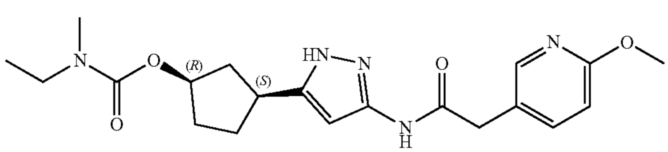 | 402.3 | (1R,3S)-3-(3-{[(6-methoxypyridin-3-yl)acetyl]amino}-1H-pyrazol-5-yl)cyclopentyl ethyl(methyl)carbamate |
| 245 | 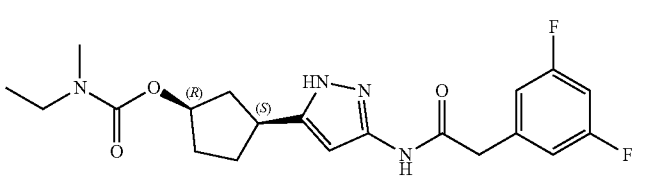 | 407.3 | (1R,3S)-3-(3-{[(3,5-difluorophenyl)acetyl]amino}-1H-pyrazol-5-yl)cyclopentyl ethyl(methyl)carbamate |

TABLE 3-continued

| Example No | Structure | LCMS [M + H]+ | IUPAC Name |
|---|---|---|---|
| 246 | 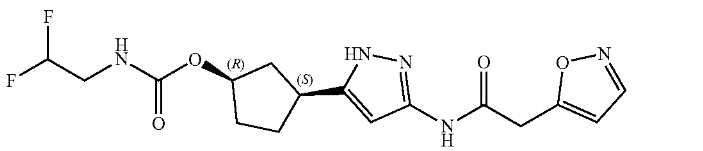 | 384.0 | (1R,3S)-3-{3-[(1,2-oxazol-5-ylacetyl)amino]-1H-pyrazol-5-yl}cyclopentyl (2,2-difluoroethyl)carbamate |
| 247 | 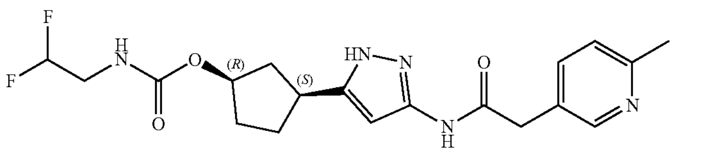 | 408.3 | (1R,3S)-3-(3-{[(6-methylpyridin-3-yl)acetyl]amino}-1H-pyrazol-5-yl)cyclopentyl (2,2-difluoroethyl)carbamate |
| 248 | 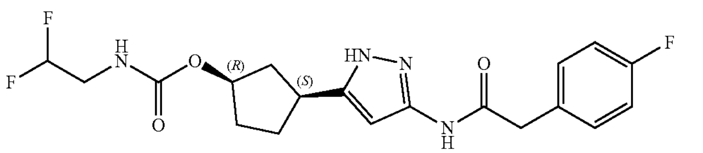 | 411.1 | (1R,3S)-3-(3-{[(4-fluorophenyl)acetyl]amino}-1H-pyrazol-5-yl)cyclopentyl (2,2-difluoroethyl)carbamate |
| 249 | 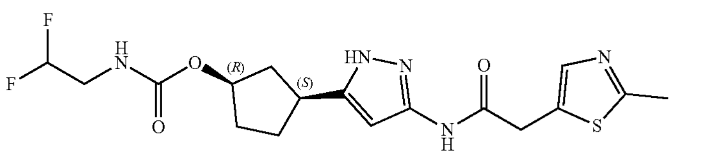 | 414.1 | (1R,3S)-3-(3-{[(2-methyl-1,3-thiazol-5-yl)acetyl]amino}-1H-pyrazol-5-yl)cyclopentyl (2,2-difluoroethyl)carbamate |
| 250 | 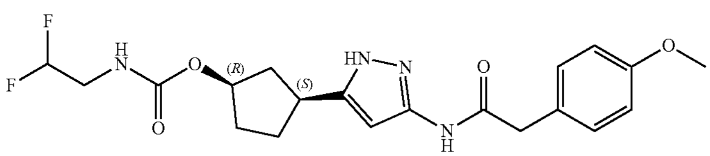 | 423.2 | (1R,3S)-3-(3-{[(4-methoxyphenyl)acetyl]amino}-1H-pyrazol-5-yl)cyclopentyl (2,2-difluoroethyl)carbamate |
| 251 | 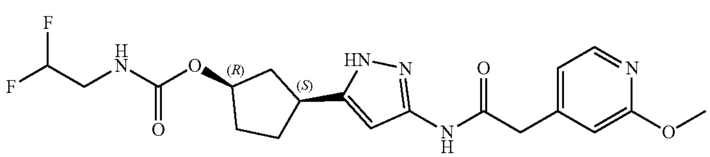 | 424.2 | (1R,3S)-3-(3-{[(2-methoxypyridin-4-yl)acetyl]amino}-1H-pyrazol-5-yl)cyclopentyl (2,2-difluoroethyl)carbamate |
| 252 | 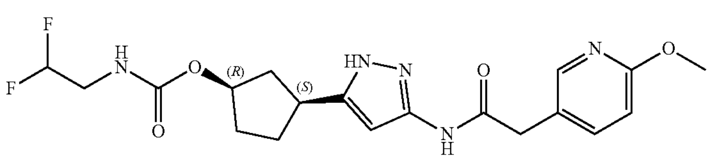 | 424.2 | (1R,3S)-3-(3-{[(6-methoxypyridin-3-yl)acetyl]amino}-1H-pyrazol-5-yl)cyclopentyl (2,2-difluoroethyl)carbamate |
| 253 | 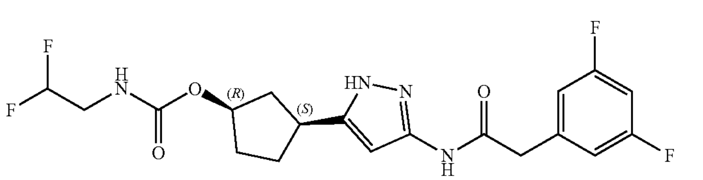 | 429.1 | (1R,3S)-3-(3-{[(3,5-difluorophenyl)acetyl]amino}-1H-pyrazol-5-yl)cyclopentyl (2,2-difluoroethyl)carbamate |
| 254 | 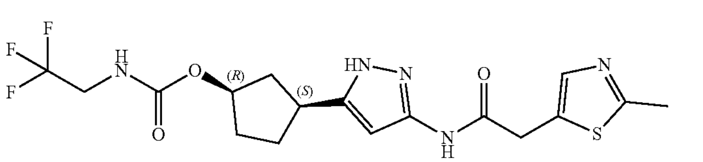 | 432.3 | (1R,3S)-3-(3-{[(2-methyl-1,3-thiazol-5-yl)acetyl]amino}-1H-pyrazol-5-yl)cyclopentyl (2,2,2-trifluoroethyl)carbamate |

TABLE 3-continued

| Example No | Structure | LCMS [M + H]+ | IUPAC Name |
|---|---|---|---|
| 255 | 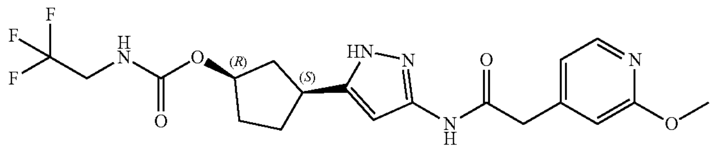 | 442.2 | (1R,3S)-3-(3-{[(2-methoxypyridin-4-yl)acetyl]amino}-1H-pyrazol-5-yl)cyclopentyl (2,2,2-trifluoroethyl)carbamate |
| 256 | 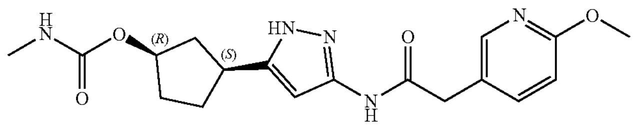 | 374.3 | (1R,3S)-3-(3-{[(6-methoxypyridin-3-yl)acetyl]amino}-1H-pyrazol-5-yl)cyclopentyl methylcarbamate |
| 257 | 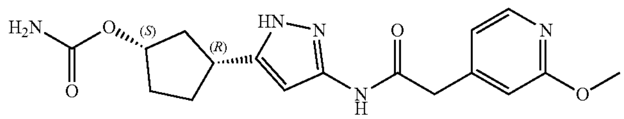 | 360.2 | (1S,3R)-3-(3-{[(2-methoxypyridin-4-yl)acetyl]amino}-1H-pyrazol-5-yl)cyclopentyl carbamate |
| 258 | 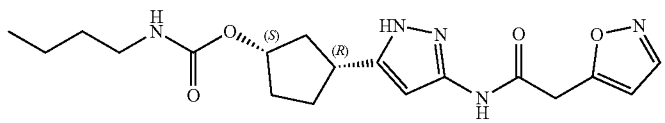 | 376.2 | (1S,3R)-3-{3-[(1,2-oxazol-5-ylacetyl)amino]-1H-pyrazol-5-yl}cyclopentyl butylcarbamate |
| 259 | 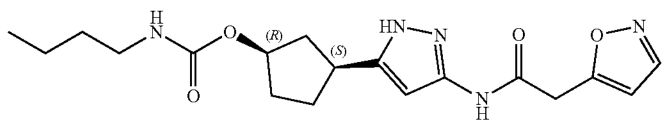 | 376.1 | (1R,3S)-3-{3-[(1,2-oxazol-5-ylacetyl)amino]-1H-pyrazol-5-yl}cyclopentyl butylcarbamate |
| 260 | 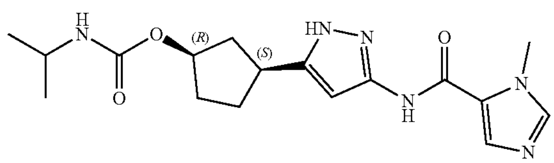 | 361.4 | (1R,3S)-3-(3-{[(1-methyl-1H-imidazol-5-yl)carbonyl]amino}-1H-pyrazol-5-yl)cyclopentyl propan-2-ylcarbamate |
| 261 | 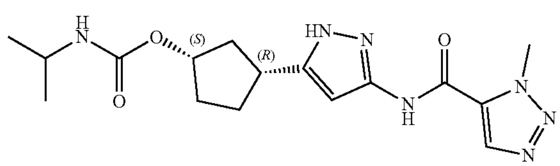 | 362.4 | (1S,3R)-3-(3-{[(1-methyl-1H-1,2,3-triazol-5-yl)carbonyl]amino}-1H-pyrazol-5-yl)cyclopentyl propan-2-ylcarbamate |
| 262 | 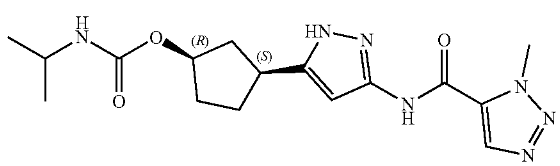 | 362.3 | (1R,3S)-3-(3-{[(1-methyl-1H-1,2,3-triazol-5-yl)carbonyl]amino}-1H-pyrazol-5-yl)cyclopentyl propan-2-ylcarbamate |
| 263 | 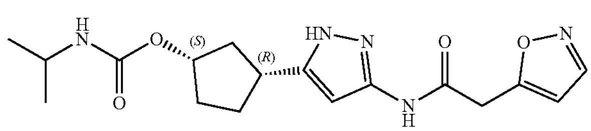 | 362.3 | (1S,3R)-3-{3-[(1,2-oxazol-5-ylacetyl)amino]-1H-pyrazol-5-yl}cyclopentyl propan-2-ylcarbamate |
| 264 | 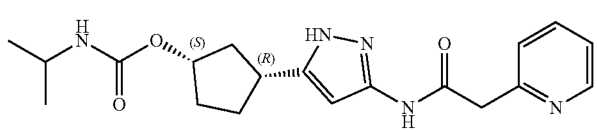 | 372.3 | (1S,3R)-3-{3-[(pyridin-2-ylacetyl)amino]-1H-pyrazol-5-yl}cyclopentyl propan-2-ylcarbamate |

TABLE 3-continued

| Example No | Structure | LCMS [M + H]+ | IUPAC Name |
|---|---|---|---|
| 265 | 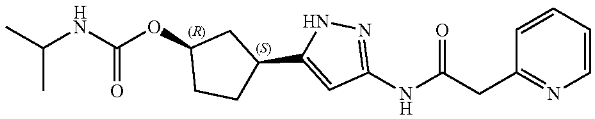 | 372.2 | (1R,3S)-3-{3-[(pyridin-2-ylacetyl)amino]-1H-pyrazol-5-yl}cyclopentyl propan-2-ylcarbamate |
| 266 | 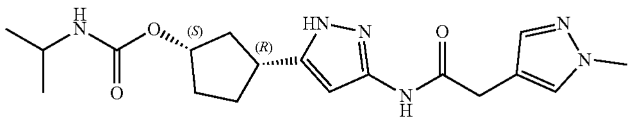 | 375.3 | (1S,3R)-3-(3-{[(1-methyl-1H-pyrazol-4-yl)acetyl]amino}-1H-pyrazol-5-yl)cyclopentyl propan-2-ylcarbamate |
| 267 | 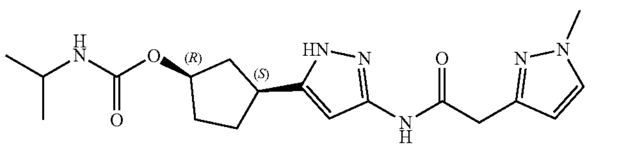 | 375.3 | (1R,3S)-3-(3-{[(1-methyl-1H-pyrazol-3-yl)acetyl]amino}-1H-pyrazol-5-yl)cyclopentyl propan-2-ylcarbamate |
| 268 | 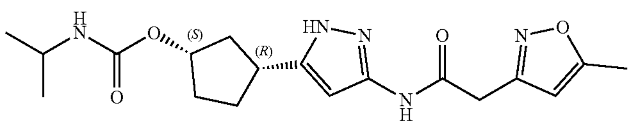 | 376.4 | (1S,3R)-3-(3-{[(5-methyl-1,2-oxazol-3-yl)acetyl]amino}-1H-pyrazol-5-yl)cyclopentyl propan-2-ylcarbamate |
| 269 | 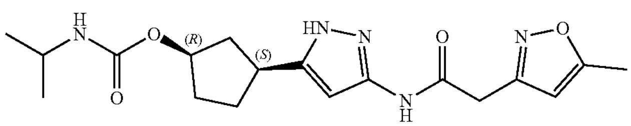 | 376.3 | (1R,3S)-3-(3-{[(5-methyl-1,2-oxazol-3-yl)acetyl]amino}-1H-pyrazol-5-yl)cyclopentyl propan-2-ylcarbamate |
| 270 | 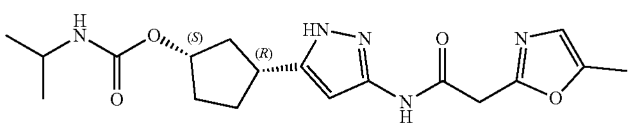 | 376.4 | (1S,3R)-3-(3-{[(5-methyl-1,3-oxazol-2-yl)acetyl]amino}-1H-pyrazol-5-yl)cyclopentyl propan-2-ylcarbamate |
| 271 | 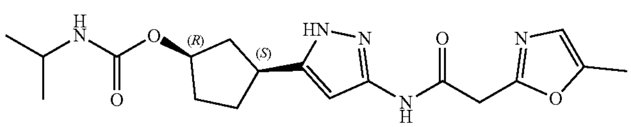 | 376.4 | (1R,3S)-3-(3-{[(5-methyl-1,3-oxazol-2-yl)acetyl]amino}-1H-pyrazol-5-yl)cyclopentyl propan-2-ylcarbamate |
| 272 | 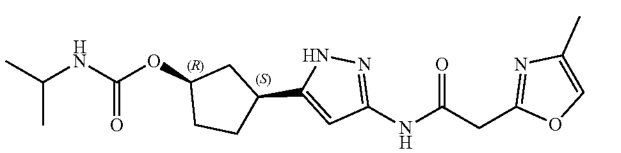 | 376.4 | (1R,3S)-3-(3-{[(4-methyl-1,3-oxazol-2-yl)acetyl]amino}-1H-pyrazol-5-yl)cyclopentyl propan-2-ylcarbamate |
| 273 | 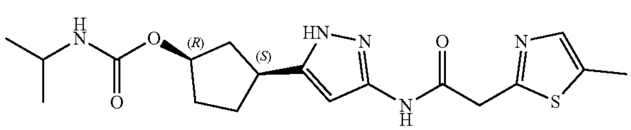 | 392.3 | (1R,3S)-3-(3-{[(5-methyl-1,3-thiazol-2-yl)acetyl]amino}-1H-pyrazol-5-yl)cyclopentyl propan-2-ylcarbamate |
| 274 | 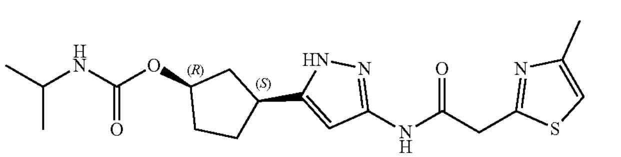 | 392.3 | (1R,3S)-3-(3-{[(4-methyl-1,3-thiazol-2-yl)acetyl]amino}-1H-pyrazol-5-yl)cyclopentyl propan-2-ylcarbamate |
| 275 | 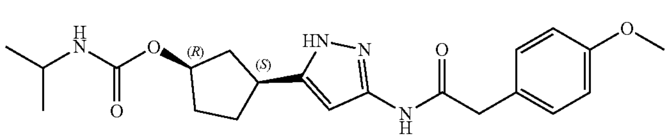 | 401.3 | (1R,3S)-3-(3-{[(4-methoxyphenyl)acetyl]amino}-1H-pyrazol-5-yl)cyclopentyl propan-2-ylcarbamate |

TABLE 3-continued

| Example No | Structure | LCMS [M + H]+ | IUPAC Name |
|---|---|---|---|
| 276 | 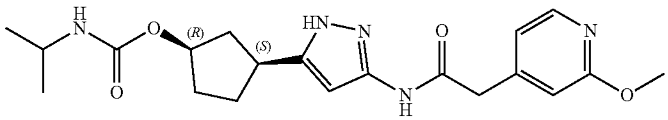 | 402.3 | (1R,3S)-3-(3-{[(2-methoxypyridin-4-yl)acetyl]amino}-1H-pyrazol-5-yl)cyclopentyl propan-2-ylcarbamate |
| 277 | 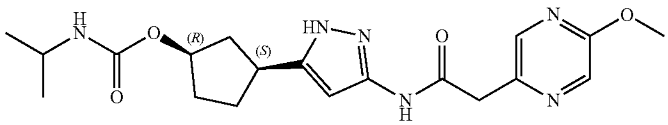 | 403.4 | (1R,3S)-3-(3-{[(5-methoxypyrazin-2-yl)acetyl]amino}-1H-pyrazol-5-yl)cyclopentyl propan-2-ylcarbamate |
| 278 | 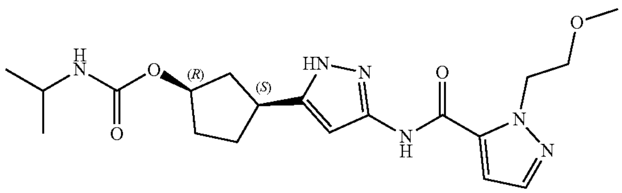 | 405.3 | (1R,3S)-3-[3-({[1-(2-methoxyethyl)-1H-pyrazol-5-yl]carbonyl}amino)-1H-pyrazol-5-yl]cyclopentyl propan-2-ylcarbamate |
| 279 | 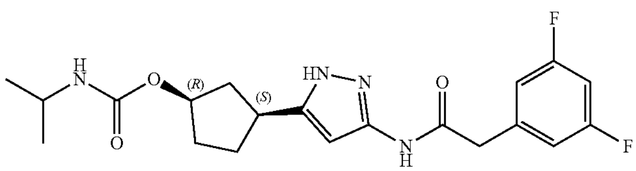 | 407.4 | (1R,3S)-3-(3-{[(3,5-difluorophenyl)acetyl]amino}-1H-pyrazol-5-yl)cyclopentyl propan-2-ylcarbamate |
| 280 | 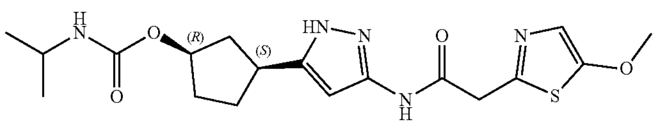 | 408.3 | (1R,3S)-3-(3-{[(5-methoxy-1,3-thiazol-2-yl)acetyl]amino}-1H-pyrazol-5-yl)cyclopentyl propan-2-ylcarbamate |
| 281 | 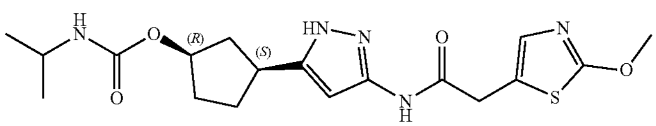 | 408.3 | (1R,3S)-3-(3-{[(2-methoxy-1,3-thiazol-5-yl)acetyl]amino}-1H-pyrazol-5-yl)cyclopentyl propan-2-ylcarbamate |
| 282 | 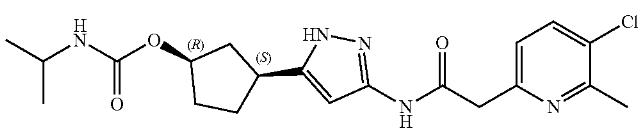 | 419.9 | (1R,3S)-3-(3-{[(5-chloro-6-methylpyridin-2-yl)acetyl]amino}-1H-pyrazol-5-yl)cyclopentyl propan-2-ylcarbamate |
| 283 | 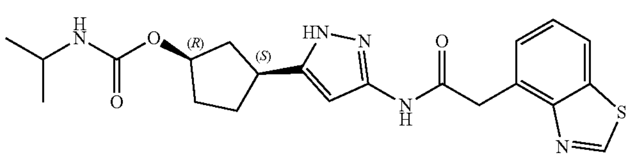 | 428.4 | (1R,3S)-3-{3-[(1,3-benzothiazol-4-ylacetyl)amino]-1H-pyrazol-5-yl}cyclopentyl propan-2-ylcarbamate |
| 284 | 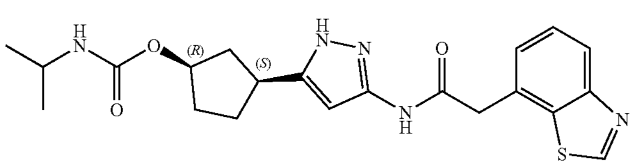 | 427.8 | (1R,3S)-3-{3-[(1,3-benzothiazol-7-ylacetyl)amino]-1H-pyrazol-5-yl}cyclopentyl propan-2-ylcarbamate |

TABLE 3-continued

| Example No | Structure | LCMS [M + H]+ | IUPAC Name |
|---|---|---|---|
| 285 | 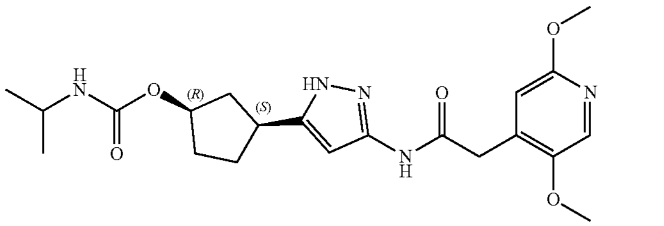 | 432.5 | (1R,3S)-3-(3-{[(2,5-dimethoxypyridin-4-yl)acetyl]amino}-1H-pyrazol-5-yl)cyclopentyl propan-2-ylcarbamate |
| 286 | 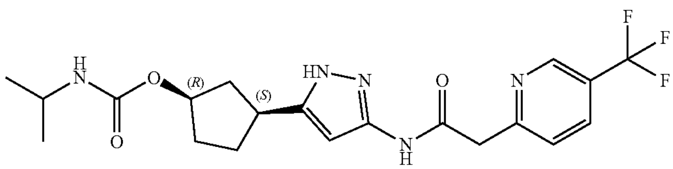 | 440.3 | (1R,3S)-3-[3-({[5-(trifluoromethyl)pyridin-2-yl]acetyl}amino)-1H-pyrazol-5-yl]cyclopentyl propan-2-ylcarbamate |
| 287 | 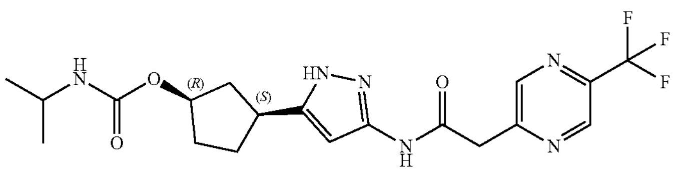 | 441.1 | (1R,3S)-3-[3-({[5-(trifluoromethyl)pyrazin-2-yl]acetyl}amino)-1H-pyrazol-5-yl]cyclopentyl propan-2-ylcarbamate |
| 288 | 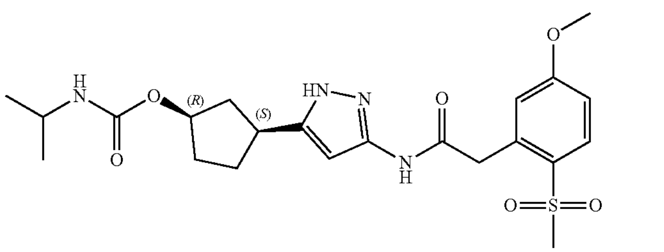 | 479.3 | (1R,3S)-3-[3-({[5-methoxy-2-(methylsulfonyl)phenyl]acetyl}amino)-1H-pyrazol-5-yl]cyclopentyl propan-2-ylcarbamate |
| 289 | 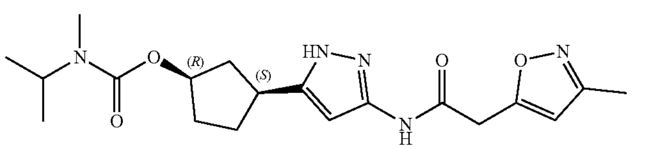 | 390.3 | (1R,3S)-3-(3-{[(3-methyl-1,2-oxazol-5-yl)acetyl]amino}-1H-pyrazol-5-yl)cyclopentyl methyl(propan-2-yl)carbamate |
| 290 | 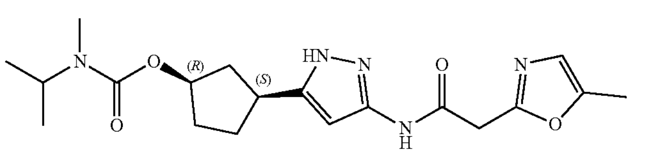 | 390.3 | (1R,3S)-3-(3-{[(5-methyl-1,3-oxazol-2-yl)acetyl]amino}-1H-pyrazol-5-yl)cyclopentyl methyl(propan-2-yl)carbamate |
| 291 | 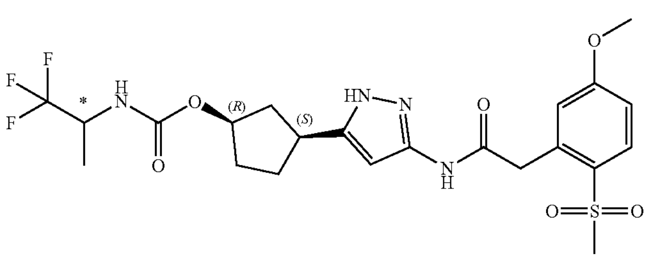 | 533.3 | (1R,3S)-3-[3-({[5-methoxy-2-(methylsulfonyl)phenyl]acetyl}amino)-1H-pyrazol-5-yl]cyclopentyl [(2ξ)-1,1,1-trifluoropropan-2-yl]carbamate - Isomer A |

TABLE 3-continued

| Example No | Structure | LCMS [M + H]+ | IUPAC Name |
|---|---|---|---|
| 292 | 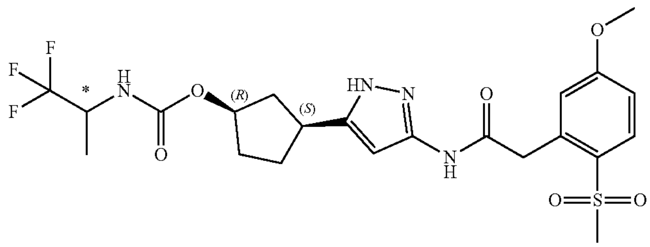 | 533.3 | (1R,3S)-3-[3-({[5-methoxy-2-(methylsulfonyl)phenyl]acetyl}amino)-1H-pyrazol-5-yl]cyclopentyl [(2ξ)-1,1,1-trifluoropropan-2-yl]carbamate - Isomer B |
| 293 | 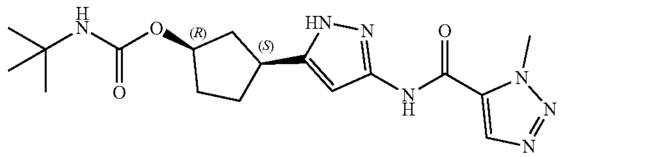 | 376.2 | (1R,3S)-3-(3-{[(1-methyl-1H-1,2,3-triazol-5-yl)carbonyl]amino}-1H-pyrazol-5-yl)cyclopentyl tert-butylcarbamate |
| 294 | 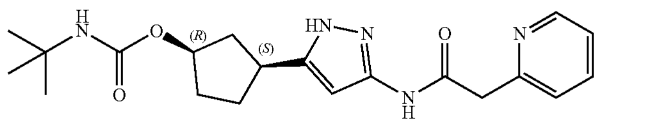 | 386.4 | (1R,3S)-3-{3-[(pyridin-2-ylacetyl)amino]-1H-pyrazol-5-yl}cyclopentyl tert-butylcarbamate |
| 295 | 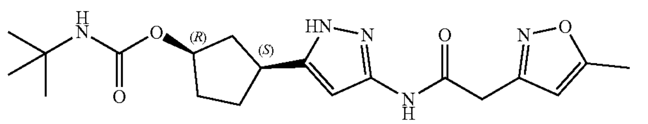 | 390.4 | (1R,3S)-3-(3-{[(5-methyl-1,2-oxazol-3-yl)acetyl]amino}-1H-pyrazol-5-yl)cyclopentyl tert-butylcarbamate |
| 296 | 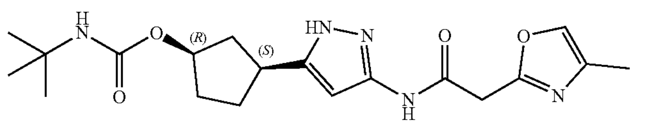 | 390.4 | (1R,3S)-3-(3-{[(4-methyl-1,3-oxazol-2-yl)acetyl]amino}-1H-pyrazol-5-yl)cyclopentyl tert-butylcarbamate |
| 297 | 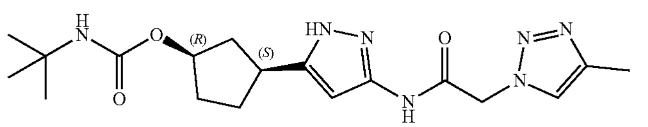 | 390.1 | (1R,3S)-3-(3-{[(4-methyl-1H-1,2,3-triazol-1-yl)acetyl]amino}-1H-pyrazol-5-yl)cyclopentyl tert-butylcarbamate |
| 298 | 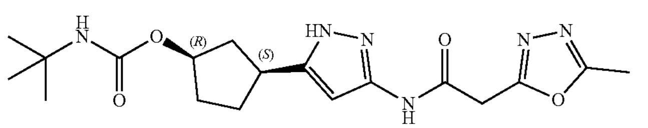 | 391.4 | (1R,3S)-3-(3-{[(5-methyl-1,3,4-oxadiazol-2-yl)acetyl]amino}-1H-pyrazol-5-yl)cyclopentyl tert-butylcarbamate |
| 299 | 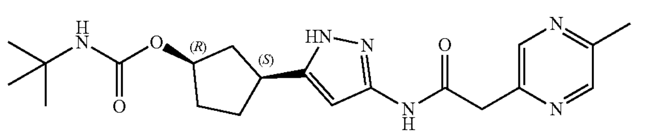 | 401.4 | (1R,3S)-3-(3-{[(5-methylpyrazin-2-yl)acetyl]amino}-1H-pyrazol-5-yl)cyclopentyl tert-butylcarbamate |
| 300 | 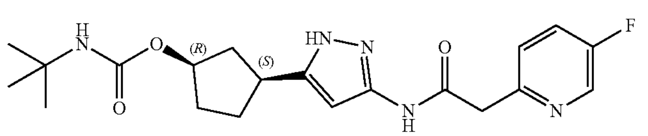 | 404.3 | (1R,3S)-3-(3-{[(5-fluoropyridin-2-yl)acetyl]amino}-1H-pyrazol-5-yl)cyclopentyl tert-butylcarbamate |
| 301 | 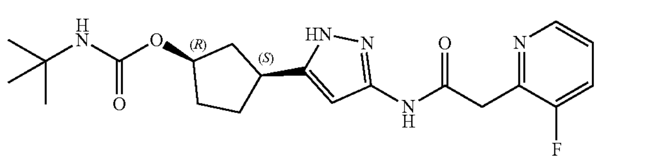 | 404.4 | (1R,3S)-3-(3-{[(3-fluoropyridin-2-yl)acetyl]amino}-1H-pyrazol-5-yl)cyclopentyl tert-butylcarbamate |

TABLE 3-continued

| Example No | Structure | LCMS [M + H]+ | IUPAC Name |
|---|---|---|---|
| 302 | 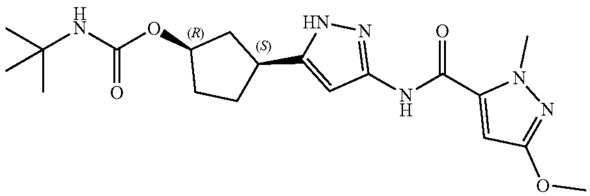 | 405.3 | (1R,3S)-3-(3-{[(3-methoxy-1-methyl-1H-pyrazol-5-yl)carbonyl]amino}-1H-pyrazol-5-yl)cyclopentyl tert-butylcarbamate |
| 303 | 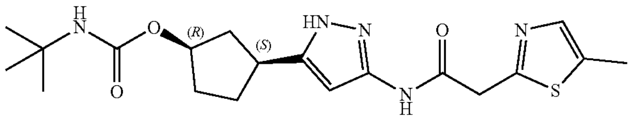 | 406.2 | (1R,3S)-3-(3-{[(5-methyl-1,3-thiazol-2-yl)acetyl]amino}-1H-pyrazol-5-yl)cyclopentyl tert-butylcarbamate |
| 304 | 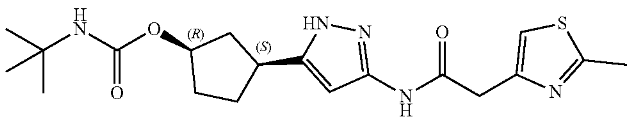 | 406.0 | (1R,3S)-3-(3-{[(2-methyl-1,3-thiazol-4-yl)acetyl]amino}-1H-pyrazol-5-yl)cyclopentyl tert-butylcarbamate |
| 305 | 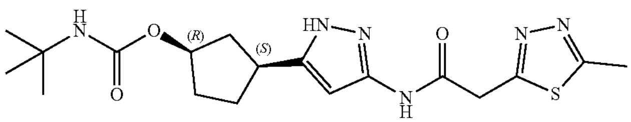 | 407.4 | (1R,3S)-3-(3-{[(5-methyl-1,3,4-thiadiazol-2-yl)acetyl]amino}-1H-pyrazol-5-yl)cyclopentyl tert-butylcarbamate |
| 306 | 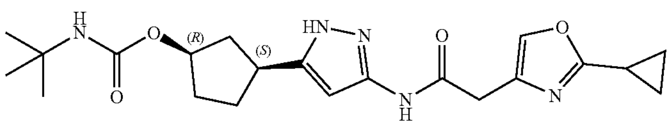 | 416.4 | (1R,3S)-3-(3-{[(2-cyclopropyl-1,3-oxazol-4-yl)acetyl]amino}-1H-pyrazol-5-yl)cyclopentyl tert-butylcarbamate |
| 307 | 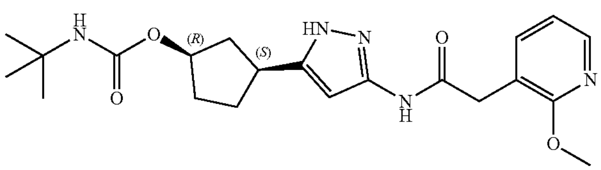 | 416.3 | (1R,3S)-3-(3-{[(2-methoxypyridin-3-yl)acetyl]amino}-1H-pyrazol-5-yl)cyclopentyl tert-butylcarbamate |
| 308 | 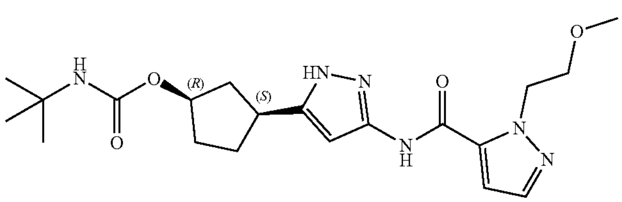 | 419.4 | (1R,3S)-3-[3-({[1-(2-methoxyethyl)-1H-pyrazol-5-yl]carbonyl}amino)-1H-pyrazol-5-yl]cyclopentyl tert-butylcarbamate |
| 309 | 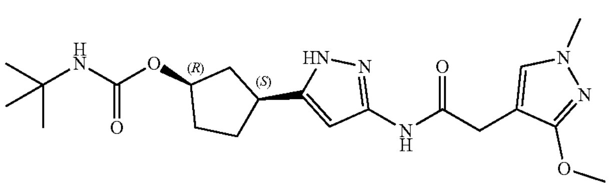 | 419.4 | (1R,3S)-3-(3-{[(3-methoxy-1-methyl-1H-pyrazol-4-yl)acetyl]amino}-1H-pyrazol-5-yl)cyclopentyl tert-butylcarbamate |
| 310 | 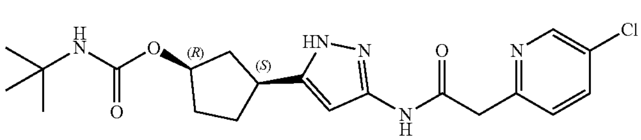 | 420.3 | (1R,3S)-3-(3-{[(5-chloropyridin-2-yl)acetyl]amino}-1H-pyrazol-5-yl)cyclopentyl tert-butylcarbamate |

TABLE 3-continued

| Example No | Structure | LCMS [M + H]+ | IUPAC Name |
|---|---|---|---|
| 311 | 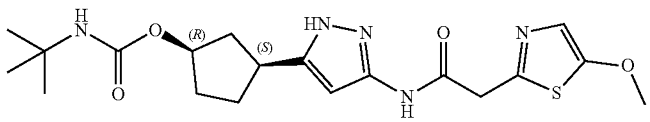 | 422.3 | (1R,3S)-3-(3-{[(5-methoxy-1,3-thiazol-2-yl)acetyl]amino}-1H-pyrazol-5-yl)cyclopentyl tert-butylcarbamate |
| 312 | 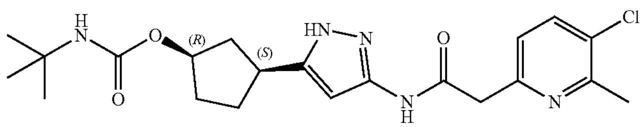 | 433.9 | (1R,3S)-3-(3-{[(5-chloro-6-methylpyridin-2-yl)acetyl]amino}-1H-pyrazol-5-yl)cyclopentyl tert-butylcarbamate |
| 313 | 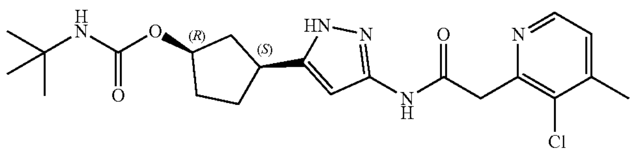 | 433.9 | (1R,3S)-3-(3-{[(3-chloro-4-methylpyridin-2-yl)acetyl]amino}-1H-pyrazol-5-yl)cyclopentyl tert-butylcarbamate |
| 314 | 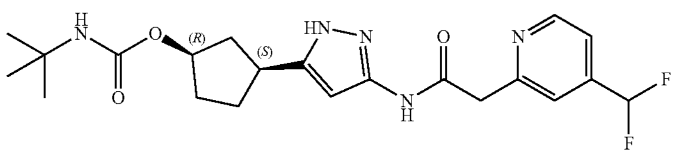 | 436.4 | (1R,3S)-3-[3-({[4-(difluoromethyl)pyridin-2-yl]acetyl}amino)-1H-pyrazol-5-yl]cyclopentyl tert-butylcarbamate |
| 315 | 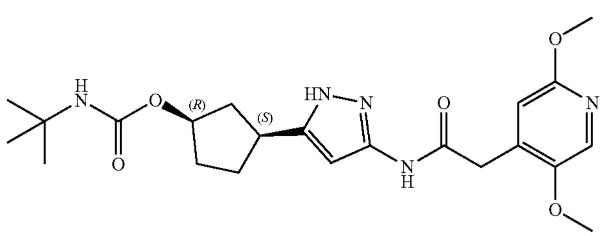 | 446.4 | (1R,3S)-3-(3-{[(2,5-dimethoxypyridin-4-yl)acetyl]amino}-1H-pyrazol-5-yl)cyclopentyl tert-butylcarbamate |
| 316 | 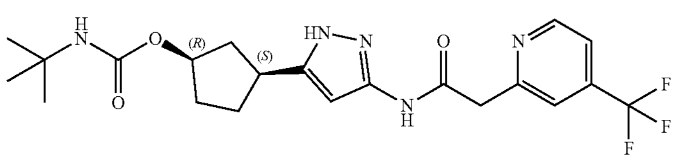 | 454.4 | (1R,3S)-3-[3-({[4-(trifluoromethyl)pyridin-2-yl]acetyl}amino)-1H-pyrazol-5-yl]cyclopentyl tert-butylcarbamate |
| 317 | 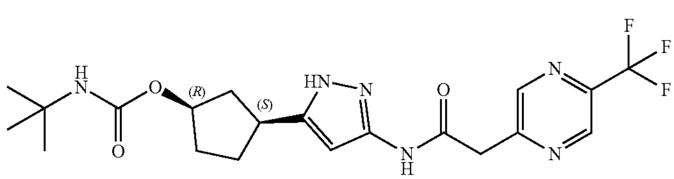 | 455.4 | (1R,3S)-3-[3-({[5-(trifluoromethyl)pyrazin-2-yl]acetyl}amino)-1H-pyrazol-5-yl]cyclopentyl tert-butylcarbamate |
| 318 | 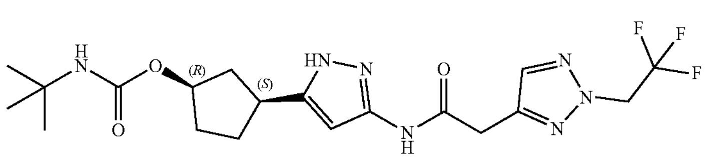 | 458.1 | (1R,3S)-3-[3-({[2-(2,2,2-trifluoroethyl)-2H-1,2,3-triazol-4-yl]acetyl}amino)-1H-pyrazol-5-yl]cyclopentyl tert-butylcarbamate |

TABLE 3-continued

| Example No | Structure | LCMS [M + H]+ | IUPAC Name |
|---|---|---|---|
| 319 | 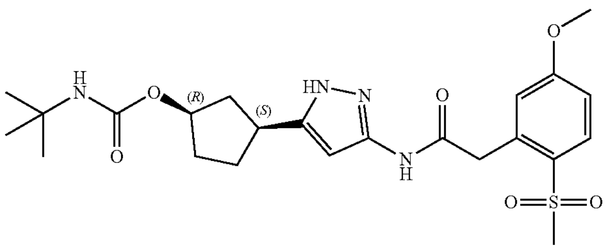 | 493.4 | (1R,3S)-3-[3-({[5-methoxy-2-(methylsulfonyl)phenyl]acetyl}amino)-1H-pyrazol-5-yl]cyclopentyl tert-butylcarbamate |
| 320 | 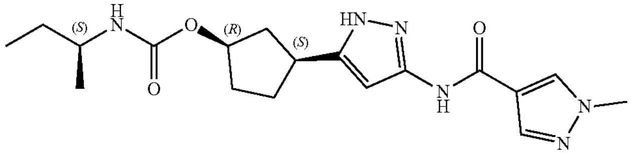 | 375.3 | (1R,3S)-3-(3-{[(1-methyl-1H-pyrazol-4-yl)carbonyl]amino}-1H-pyrazol-5-yl)cyclopentyl (2S)-butan-2-ylcarbamate |
| 321 | 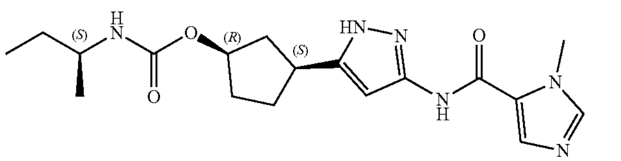 | 375.3 | (1R,3S)-3-(3-{[(1-methyl-1H-imidazol-5-yl)carbonyl]amino}-1H-pyrazol-5-yl)cyclopentyl (2S)-butan-2-ylcarbamate |
| 322 | 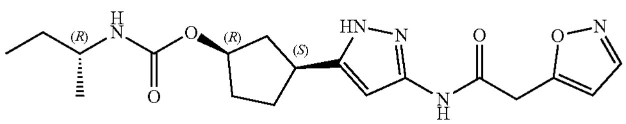 | 376.2 | (1R,3S)-3-{3-[(1,2-oxazol-5-ylacetyl)amino]-1H-pyrazol-5-yl}cyclopentyl (2R)-butan-2-ylcarbamate |
| 323 | 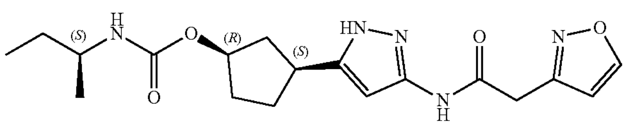 | 376.2 | (1R,3S)-3-{3-[(1,2-oxazol-3-ylacetyl)amino]-1H-pyrazol-5-yl}cyclopentyl (2S)-butan-2-ylcarbamate |
| 324 | 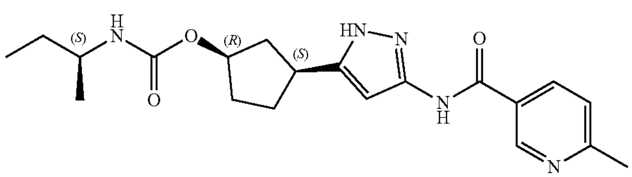 | 386.3 | (1R,3S)-3-(3-{[(6-methylpyridin-3-yl)carbonyl]amino}-1H-pyrazol-5-yl)cyclopentyl (2S)-butan-2-ylcarbamate |
| 325 | 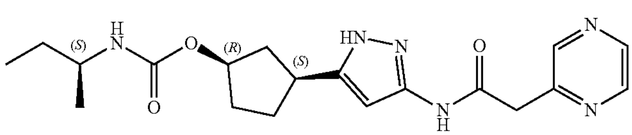 | 387.3 | (1R,3S)-3-{3-[(pyrazin-2-ylacetyl)amino]-1H-pyrazol-5-yl}cyclopentyl (2S)-butan-2-ylcarbamate |
| 326 | 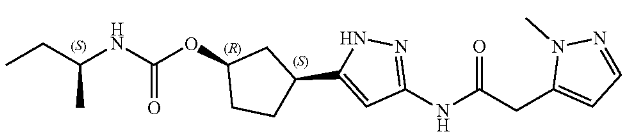 | 389.3 | (1R,3S)-3-(3-{[(1-methyl-1H-pyrazol-5-yl)acetyl]amino}-1H-pyrazol-5-yl)cyclopentyl (2S)-butan-2-ylcarbamate |
| 327 | 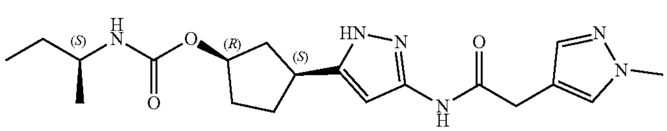 | 389.3 | (1R,3S)-3-(3-{[(1-methyl-1H-pyrazol-4-yl)acetyl]amino}-1H-pyrazol-5-yl)cyclopentyl (2S)-butan-2-ylcarbamate |

TABLE 3-continued

| Example No | Structure | LCMS [M + H]+ | IUPAC Name |
|---|---|---|---|
| 328 | 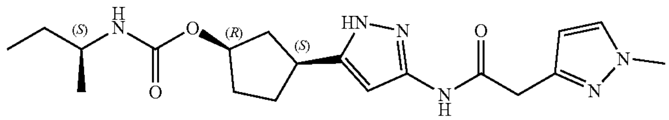 | 389.4 | (1R,3S)-3-(3-{[(1-methyl-1H-pyrazol-3-yl)acetyl]amino}-1H-pyrazol-5-yl)cyclopentyl (2S)-butan-2-ylcarbamate |
| 329 | 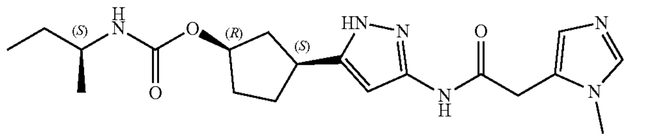 | 389.4 | (1R,3S)-3-(3-{[(1-methyl-1H-imidazol-5-yl)acetyl]amino}-1H-pyrazol-5-yl)cyclopentyl (2S)-butan-2-ylcarbamate |
| 330 | 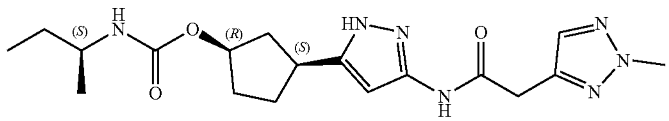 | 390.3 | (1R,3S)-3-(3-{[(2-methyl-2H-1,2,3-triazol-4-yl)acetyl]amino}-1H-pyrazol-5-yl)cyclopentyl (2S)-butan-2-ylcarbamate |
| 331 | 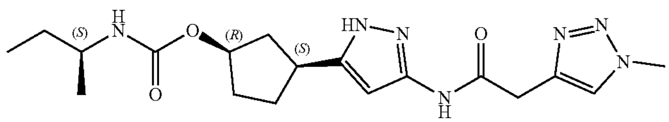 | 390.3 | (1R,3S)-3-(3-{[(1-methyl-1H-1,2,3-triazol-4-yl)acetyl]amino}-1H-pyrazol-5-yl)cyclopentyl (2S)-butan-2-ylcarbamate |
| 332 | 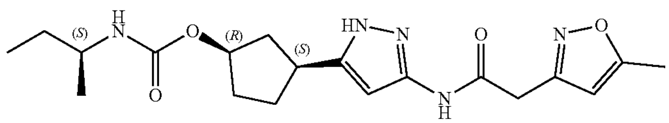 | 390.3 | (1R,3S)-3-(3-{[(5-methyl-1,2-oxazol-3-yl)acetyl]amino}-1H-pyrazol-5-yl)cyclopentyl (2S)-butan-2-ylcarbamate |
| 333 | 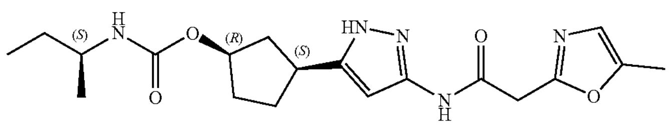 | 390.3 | (1R,3S)-3-(3-{[(5-methyl-1,3-oxazol-2-yl)acetyl]amino}-1H-pyrazol-5-yl)cyclopentyl (2S)-butan-2-ylcarbamate |
| 334 | 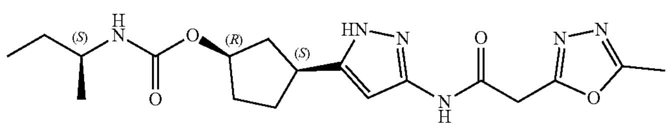 | 391.4 | (1R,3S)-3-(3-{[(5-methyl-1,3,4-oxadiazol-2-yl)acetyl]amino}-1H-pyrazol-5-yl)cyclopentyl (2S)-butan-2-ylcarbamate |
| 335 | 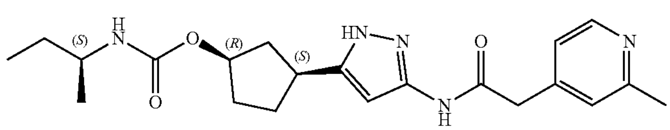 | 400.4 | (1R,3S)-3-(3-{[(2-methylpyridin-4-yl)acetyl]amino}-1H-pyrazol-5-yl)cyclopentyl (2S)-butan-2-ylcarbamate |
| 336 | 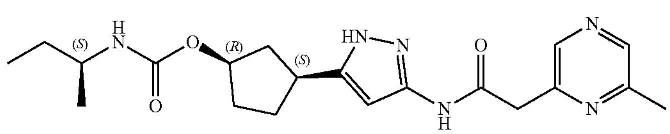 | 401.2 | (1R,3S)-3-(3-{[(6-methylpyrazin-2-yl)acetyl]amino}-1H-pyrazol-5-yl)cyclopentyl (2S)-butan-2-ylcarbamate |
| 337 | 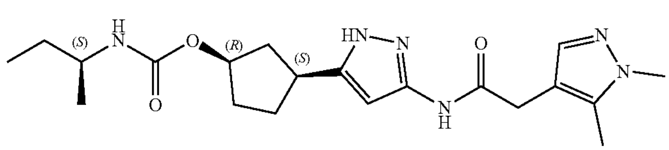 | 403.4 | (1R,3S)-3-(3-{[(1,5-dimethyl-1H-pyrazol-4-yl)acetyl]amino}-1H-pyrazol-5-yl)cyclopentyl (2S)-butan-2-ylcarbamate |
| 338 | 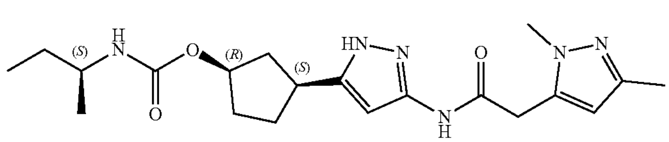 | 403.4 | (1R,3S)-3-(3-{[(1,3-dimethyl-1H-pyrazol-5-yl)acetyl]amino}-1H-pyrazol-5-yl)cyclopentyl (2S)-butan-2-ylcarbamate |

TABLE 3-continued

| Example No | Structure | LCMS [M + H]+ | IUPAC Name |
|---|---|---|---|
| 339 | 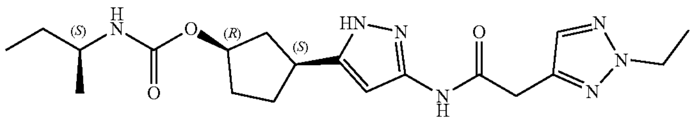 | 404.1 | (1R,3S)-3-(3-{[(2-ethyl-2H-1,2,3-triazol-4-yl)acetyl]amino}-1H-pyrazol-5-yl)cyclopentyl (2S)-butan-2-ylcarbamate |
| 340 | 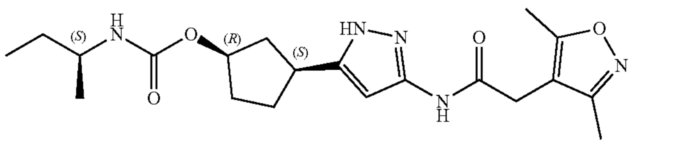 | 404.4 | (1R,3S)-3-(3-{[(3,5-dimethyl-1,2-oxazol-4-yl)acetyl]amino}-1H-pyrazol-5-yl)cyclopentyl (2S)-butan-2-ylcarbamate |
| 341 | 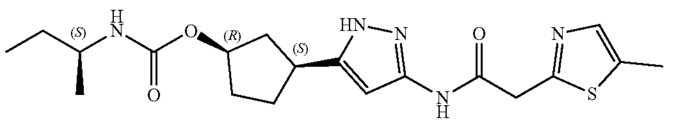 | 406.3 | (1R,3S)-3-(3-{[(5-methyl-1,3-thiazol-2-yl)acetyl]amino}-1H-pyrazol-5-yl)cyclopentyl (2S)-butan-2-ylcarbamate |
| 342 | 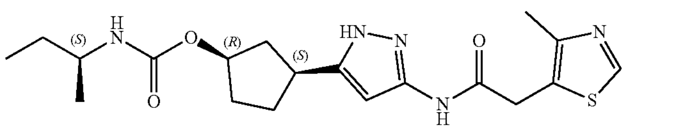 | 406.2 | (1R,3S)-3-(3-{[(4-methyl-1,3-thiazol-5-yl)acetyl]amino}-1H-pyrazol-5-yl)cyclopentyl (2S)-butan-2-ylcarbamate |
| 343 | 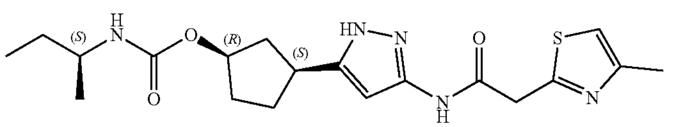 | 406.2 | (1R,3S)-3-(3-{[(4-methyl-1,3-thiazol-2-yl)acetyl]amino}-1H-pyrazol-5-yl)cyclopentyl (2S)-butan-2-ylcarbamate |
| 344 | 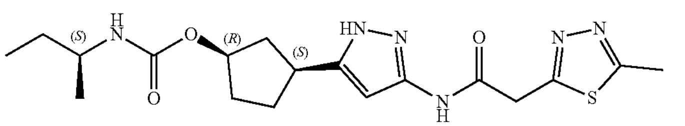 | 407.3 | (1R,3S)-3-(3-{[(5-methyl-1,3,4-thiadiazol-2-yl)acetyl]amino}-1H-pyrazol-5-yl)cyclopentyl (2S)-butan-2-ylcarbamate |
| 345 | 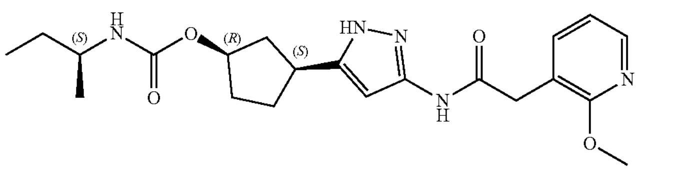 | 416.4 | (1R,3S)-3-(3-{[(2-methoxypyridin-3-yl)acetyl]amino}-1H-pyrazol-5-yl)cyclopentyl (2S)-butan-2-ylcarbamate |
| 346 | 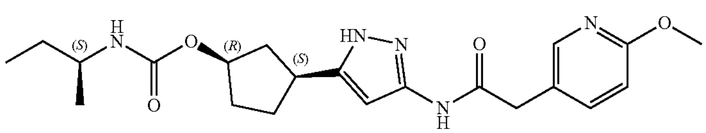 | 416.3 | (1R,3S)-3-(3-{[(6-methoxypyridin-3-yl)acetyl]amino}-1H-pyrazol-5-yl)cyclopentyl (2S)-butan-2-ylcarbamate |
| 347 | 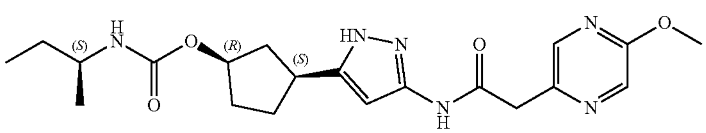 | 417.1 | (1R,3S)-3-(3-{[(5-methoxypyrazin-2-yl)acetyl]amino}-1H-pyrazol-5-yl)cyclopentyl (2S)-butan-2-ylcarbamate |
| 348 | 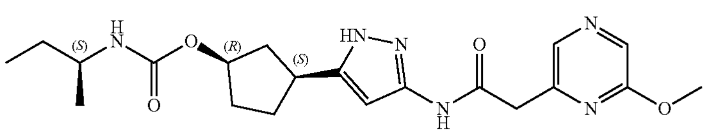 | 417.3 | (1R,3S)-3-(3-{[(6-methoxypyrazin-2-yl)acetyl]amino}-1H-pyrazol-5-yl)cyclopentyl (2S)-butan-2-ylcarbamate |
| 349 | 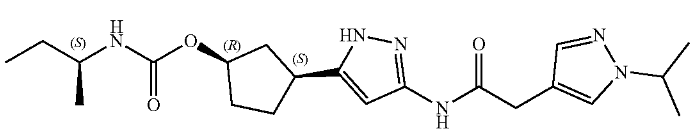 | 417.3 | (1R,3S)-3-[3-({[1-(propan-2-yl)-1H-pyrazol-4-yl]acetyl}amino)-1H-pyrazol-5-yl]cyclopentyl (2S)-butan-2-ylcarbamate |

TABLE 3-continued

| Example No | Structure | LCMS [M + H]+ | IUPAC Name |
|---|---|---|---|
| 350 | 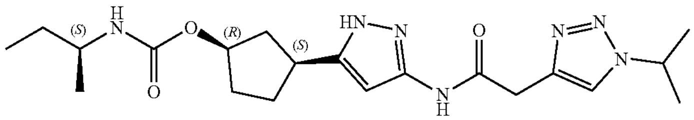 | 418.2 | (1R,3S)-3-[3-({[1-(propan-2-yl)-1H-1,2,3-triazol-4-yl]acetyl}amino)-1H-pyrazol-5-yl]cyclopentyl (2S)-butan-2-ylcarbamate |
| 351 | 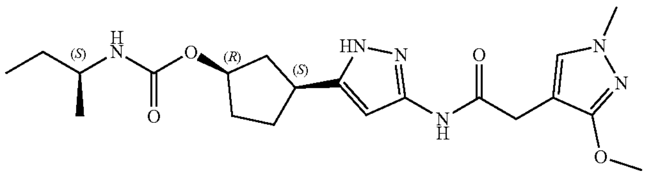 | 419.4 | (1R,3S)-3-(3-{[(3-methoxy-1-methyl-1H-pyrazol-4-yl)acetyl]amino}-1H-pyrazol-5-yl)cyclopentyl (2S)-butan-2-ylcarbamate |
| 352 | 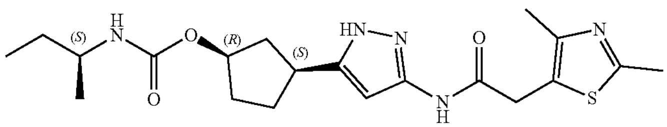 | 420.3 | (1R,3S)-3-(3-{[(2,4-dimethyl-1,3-thiazol-5-yl)acetyl]amino}-1H-pyrazol-5-yl)cyclopentyl (2S)-butan-2-ylcarbamate |
| 353 | 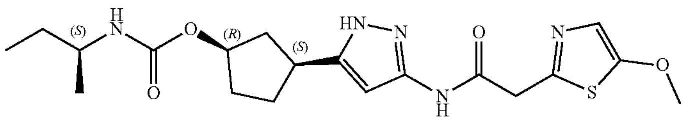 | 422.4 | (1R,3S)-3-(3-{[(5-methoxy-1,3-thiazol-2-yl)acetyl]amino}-1H-pyrazol-5-yl)cyclopentyl (2S)-butan-2-ylcarbamate |
| 354 | 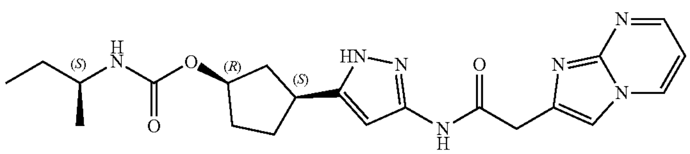 | 426.3 | (1R,3S)-3-{3-[(imidazo[1,2-a]pyrimidin-2-ylacetyl)amino]-1H-pyrazol-5-yl}cyclopentyl (2S)-butan-2-ylcarbamate |
| 355 | 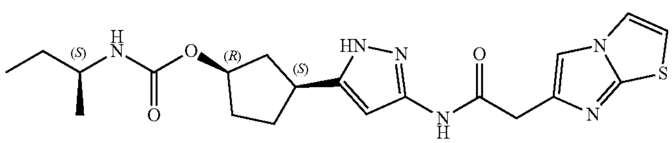 | 431.3 | (1R,3S)-3-{3-[(imidazo[2,1-b][1,3]thiazol-6-ylacetyl)amino]-1H-pyrazol-5-yl}cyclopentyl (2S)-butan-2-ylcarbamate |
| 356 | 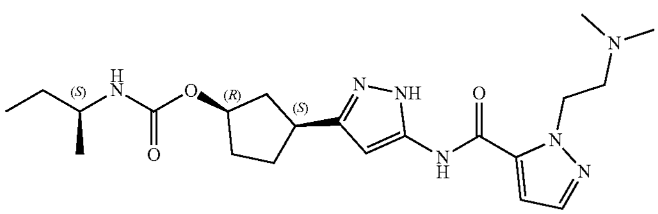 | 432.2 | (1R,3S)-3-{5-[({1-[2-(dimethylamino)ethyl]-1H-pyrazol-5-yl}carbonyl)amino]-1H-pyrazol-3-yl}cyclopentyl (2S)-butan-2-ylcarbamate |
| 357 | 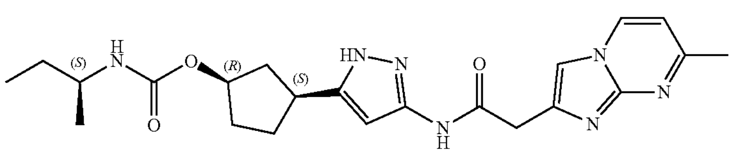 | 440.4 | (1R,3S)-3-(3-{[(7-methylimidazo[1,2-a]pyrimidin-2-yl)acetyl]amino}-1H-pyrazol-5-yl)cyclopentyl (2S)-butan-2-ylcarbamate |
| 358 | 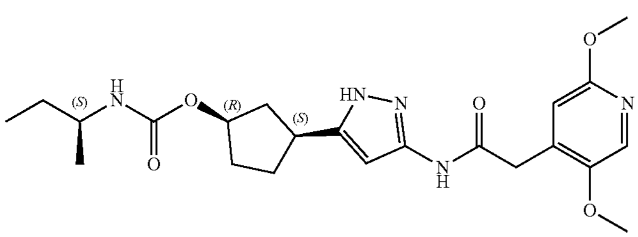 | 446.4 | (1R,3S)-3-(3-{[(2,5-dimethoxypyridin-4-yl)acetyl]amino}-1H-pyrazol-5-yl)cyclopentyl (2S)-butan-2-ylcarbamate |

TABLE 3-continued

| Example No | Structure | LCMS [M + H]+ | IUPAC Name |
|---|---|---|---|
| 359 | 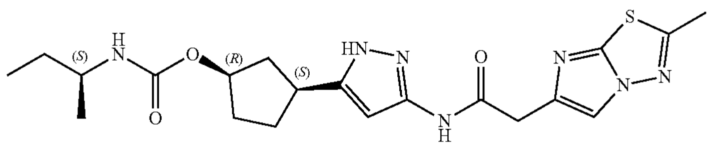 | 446.3 | (1R,3S)-3-(3-{[(2-methylimidazo[2,1-b][1,3,4]thiadiazol-6-yl)acetyl]amino}-1H-pyrazol-5-yl)cyclopentyl (2S)-butan-2-ylcarbamate |
| 360 | 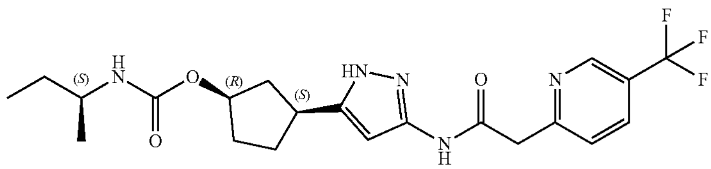 | 454.4 | (1R,3S)-3-[3-({[5-(trifluoromethyl)pyridin-2-yl]acetyl}amino)-1H-pyrazol-5-yl]cyclopentyl (2S)-butan-2-ylcarbamate |
| 361 | 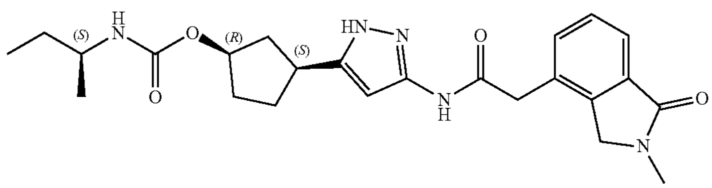 | 454.4 | (1R,3S)-3-(3-{[(2-methyl-1-oxo-2,3-dihydro-1H-isoindol-4-yl)acetyl]amino}-1H-pyrazol-5-yl)cyclopentyl (2S)-butan-2-ylcarbamate |
| 362 | 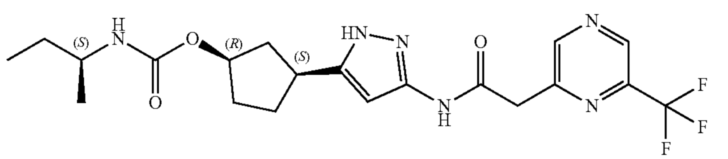 | 455.1 | (1R,3S)-3-[3-({[6-(trifluoromethyl)pyrazin-2-yl]acetyl}amino)-1H-pyrazol-5-yl]cyclopentyl (2S)-butan-2-ylcarbamate |
| 363 | 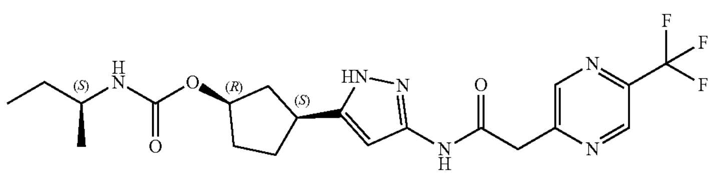 | 455.3 | (1R,3S)-3-[3-({[5-(trifluoromethyl)pyrazin-2-yl]acetyl}amino)-1H-pyrazol-5-yl]cyclopentyl (2S)-butan-2-ylcarbamate |
| 364 | 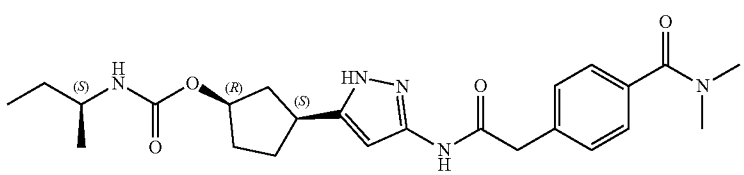 | 456.3 | (1R,3S)-3-[3-({[4-(dimethylcarbamoyl)phenyl]acetyl}amino)-1H-pyrazol-5-yl]cyclopentyl (2S)-butan-2-ylcarbamate |
| 365 | 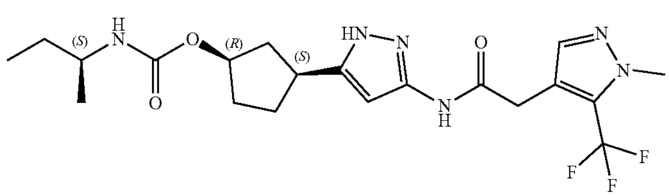 | 457.4 | (1R,3S)-3-[3-({[1-methyl-5-(trifluoromethyl)-1H-pyrazol-4-yl]acetyl}amino)-1H-pyrazol-5-yl]cyclopentyl (2S)-butan-2-ylcarbamate |
| 366 | 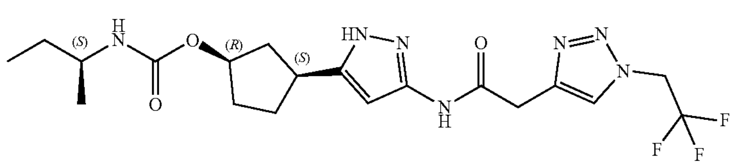 | 458.1 | (1R,3S)-3-[3-({[1-(2,2,2-trifluoroethyl)-1H-1,2,3-triazol-4-yl]acetyl}amino)-1H-pyrazol-5-yl]cyclopentyl (2S)-butan-2-ylcarbamate |
| 367 | 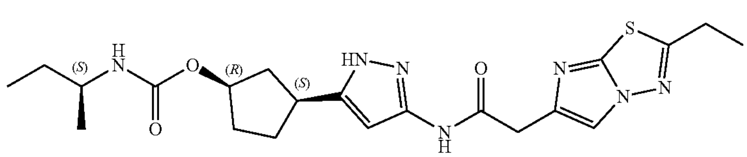 | 460.4 | (1R,3S)-3-(3-{[(2-ethylimidazo[2,1-b][1,3,4]thiadiazol-6-yl)acetyl]amino}-1H-pyrazol-5-yl)cyclopentyl (2S)-butan-2-ylcarbamate |

TABLE 3-continued

| Example No | Structure | LCMS [M + H]+ | IUPAC Name |
|---|---|---|---|
| 368 | 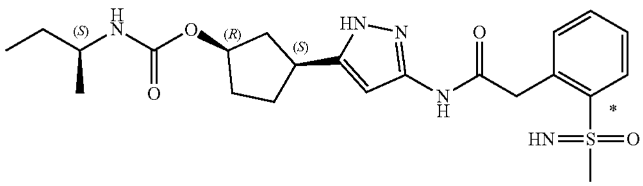 | 462.3 | (1R,3S)-3-[3-({[2-(ξ-methylsulfonimidoyl)-phenyl]acetyl}amino)-1H-pyrazol-5-yl]cyclopentyl (2S)-butan-2-ylcarbamate - Isomer A |
| 369 | 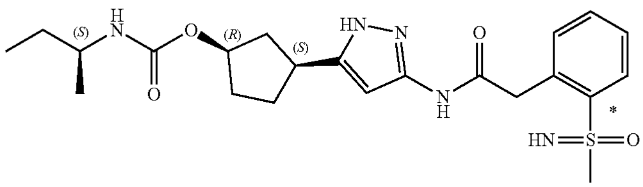 | 462.3 | (1R,3S)-3-[3-({[2-(ξ-methylsulfonimidoyl)-phenyl]acetyl}amino)-1H-pyrazol-5-yl]cyclopentyl (2S)-butan-2-ylcarbamate - Isomer B |
| 370 | 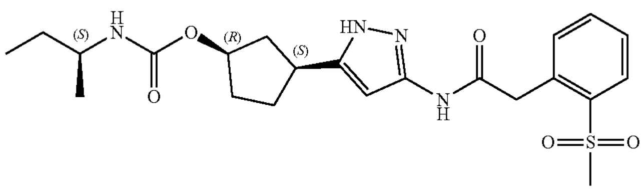 | 463.4 | (1R,3S)-3-[3-({[2-(methylsulfonyl)phenyl]acetyl}amino)-1H-pyrazol-5-yl]cyclopentyl (2S)-butan-2-ylcarbamate |
| 371 | 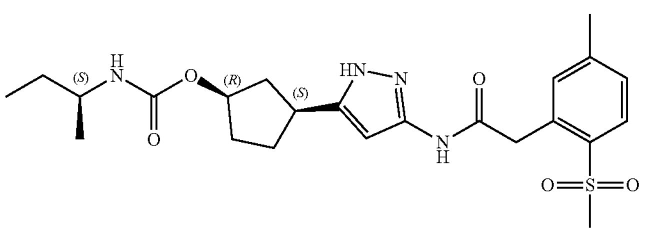 | 477.3 | (1R,3S)-3-[3-({[5-methyl-2-(methylsulfonyl)phenyl]acetyl}amino)-1H-pyrazol-5-yl]cyclopentyl (2S)-butan-2-ylcarbamate |
| 372 | 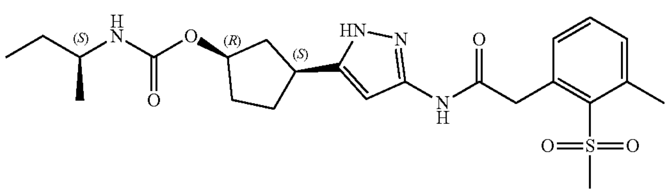 | 477.3 | (1R,3S)-3-[3-({[3-methyl-2-(methylsulfonyl)phenyl]acetyl}amino)-1H-pyrazol-5-yl]cyclopentyl (2S)-butan-2-ylcarbamate |
| 373 | 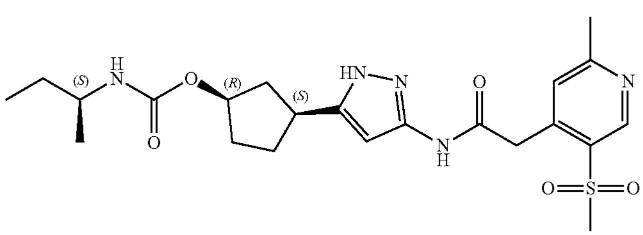 | 478.4 | (1R,3S)-3-[3-({[2-methyl-5-(methylsulfonyl)pyridin-4-yl]acetyl}amino)-1H-pyrazol-5-yl]cyclopentyl (2S)-butan-2-ylcarbamate |
| 374 | 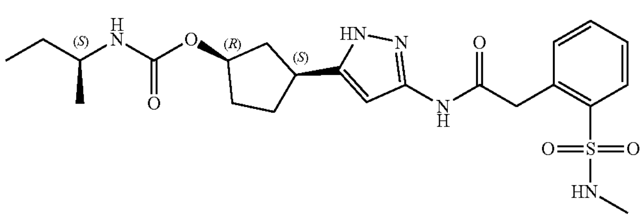 | 477.9 | (1R,3S)-3-[3-({[2-(methylsulfamoyl)phenyl]acetyl}amino)-1H-pyrazol-5-yl]cyclopentyl (2S)-butan-2-ylcarbamate |

TABLE 3-continued

| Example No | Structure | LCMS [M + H]+ | IUPAC Name |
|---|---|---|---|
| 375 | 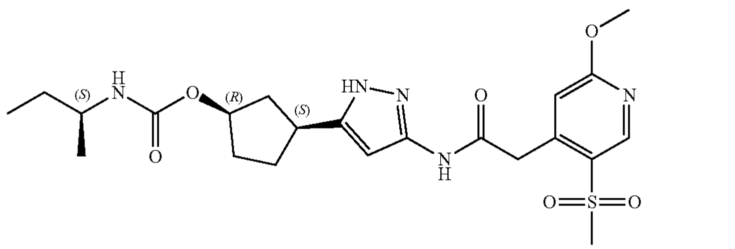 | 494.4 | (1R,3S)-3-[3-({[2-methoxy-5-(methylsulfonyl)pyridin-4-yl]acetyl}amino)-1H-pyrazol-5-yl]cyclopentyl (2S)-butan-2-ylcarbamate |
| 376 | 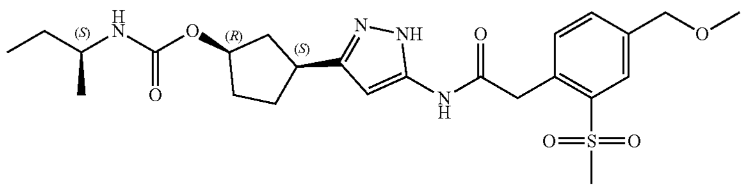 | 507.3 | (1R,3S)-3-[5-({[4-(methoxymethyl)-2-(methylsulfonyl)phenyl]acetyl}amino)-1H-pyrazol-3-yl]cyclopentyl (2S)-butan-2-ylcarbamate |
| 377 | 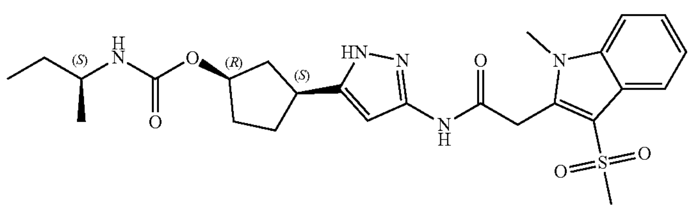 | 516.3 | (1R,3S)-3-[3-({[1-methyl-3-(methylsulfonyl)-1H-indol-2-yl]acetyl}amino)-1H-pyrazol-5-yl]cyclopentyl (2S)-butan-2-ylcarbamate |
| 378 | 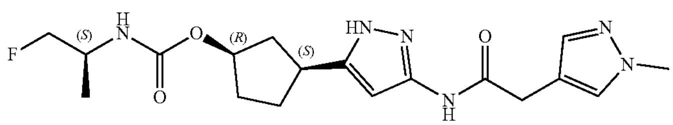 | 393.3 | (1R,3S)-3-(3-{[(1-methyl-1H-pyrazol-4-yl)acetyl]amino}-1H-pyrazol-5-yl)cyclopentyl [(2S)-1-fluoropropan-2-yl]carbamate |
| 379 | 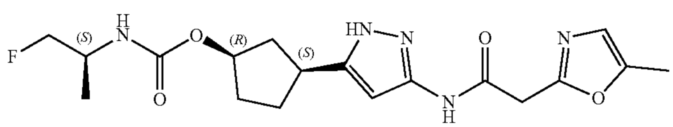 | 394.4 | (1R,3S)-3-(3-{[(5-methyl-1,3-oxazol-2-yl)acetyl]amino}-1H-pyrazol-5-yl)cyclopentyl [(2S)-1-fluoropropan-2-yl]carbamate |
| 380 | 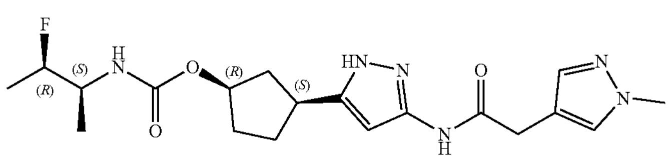 | 407.3 | (1R,3S)-3-(3-{[(1-methyl-1H-pyrazol-4-yl)acetyl]amino}-1H-pyrazol-5-yl)cyclopentyl [(2S,3R)-3-fluorobutan-2-yl]carbamate |
| 381 | 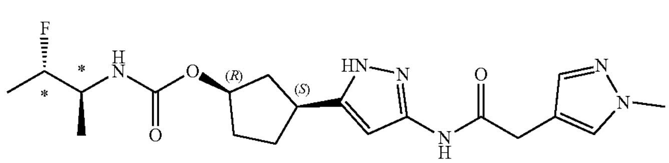 | 407.3 | (1R,3S)-3-(3-{[(1-methyl-1H-pyrazol-4-yl)acetyl]amino}-1H-pyrazol-5-yl)cyclopentyl [(2S*,3S*)-3-fluorobutan-2-yl]carbamate - Isomer A |
| 382 | 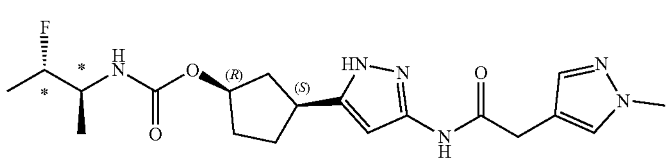 | 407.4 | (1R,3S)-3-(3-{[(1-methyl-1H-pyrazol-4-yl)acetyl]amino}-1H-pyrazol-5-yl)cyclopentyl [(2S*,3S*)-3-fluorobutan-2-yl]carbamate - Isomer B |
| 383 | 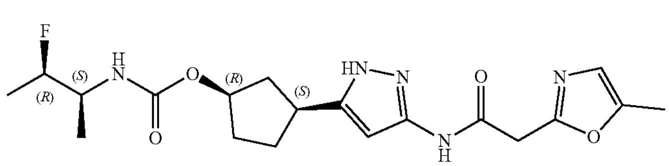 | 408.3 | (1R,3S)-3-(3-{[(5-methyl-1,3-oxazol-2-yl)acetyl]amino}-1H-pyrazol-5-yl)cyclopentyl [(2S,3R)-3-fluorobutan-2-yl]carbamate |

TABLE 3-continued

| Example No | Structure | LCMS [M + H]+ | IUPAC Name |
|---|---|---|---|
| 384 | 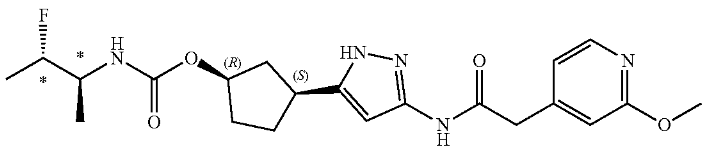 | 434.4 | (1R,3S)-3-(3-{[(2-methoxypyridin-4-yl)acetyl]amino}-1H-pyrazol-5-yl)cyclopentyl [(2S*,3S*)-3-fluorobutan-2-yl]carbamate - Isomer A |
| 385 | 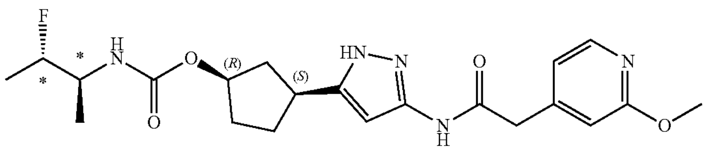 | 434.4 | (1R,3S)-3-(3-{[(2-methoxypyridin-4-yl) acetyl]amino}-1H-pyrazol-5-yl)cyclopentyl [(2S*,3S*)-3-fluorobutan-2-yl]carbamate - Isomer B |
| 386 | 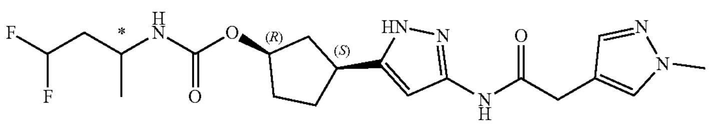 | 425.4 | (1R,3S)-3-(3-{[(1-methyl-1H-pyrazol-4-yl)acetyl]amino}-1H-pyrazol-5-yl)cyclopentyl[(2ξ)-4,4-difluorobutan-2-yl]carbamate - Isomer A |
| 387 | 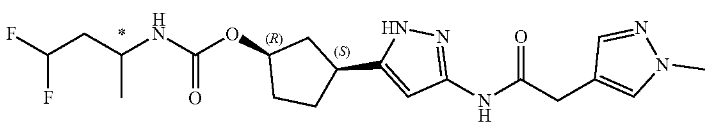 | 425.4 | (1R,3S)-3-(3-{[(1-methyl-1H-pyrazol-4-yl)acetyl]amino}-1H-pyrazol-5-yl)cyclopentyl[(2ξ)-4,4-difluorobutan-2-yl]carbamate - Isomer B |
| 388 | 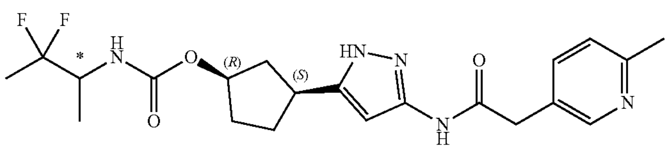 | 436.4 | (1R,3S)-3-(3-{[(6-methylpyridin-3-yl)acetyl]amino}-1H-pyrazol-5-yl)cyclopentyl[(2ξ)-3,3-difluorobutan-2-yl]carbamate - Isomer A |
| 389 | 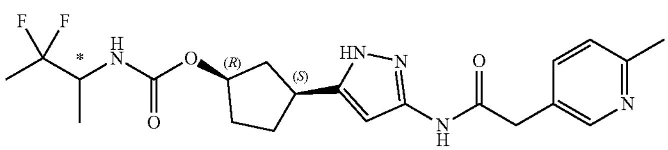 | 436.4 | (1R,3S)-3-(3-{[(6-methylpyridin-3-yl)acetyl]amino}-1H-pyrazol-5-yl)cyclopentyl [(2ξ)-3,3-difluorobutan-2-yl]carbamate - Isomer B |
| 390 | 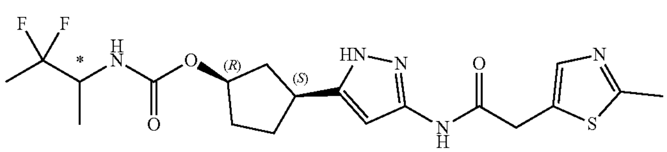 | 442.4 | (1R,3S)-3-(3-{[(2-methyl-1,3-thiazol-5-yl)acetyl]amino}-1H-pyrazol-5-yl)cyclopentyl[(2ξ)-3,3-difluorobutan-2-yl]carbamate - Isomer A |
| 391 | 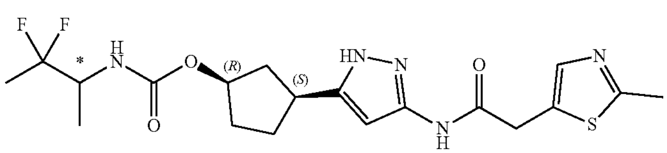 | 442.2 | (1R,3S)-3-(3-{[(2-methyl-1,3-thiazol-5-yl)acetyl]amino}-1H-pyrazol-5-yl)cyclopentyl [(2ξ)-3,3-difluorobutan-2-yl]carbamate - Isomer B |
| 392 | 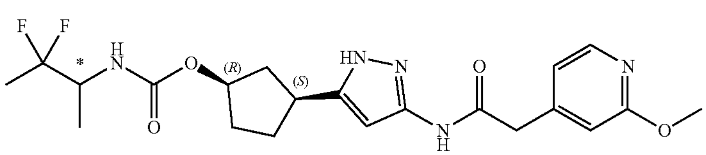 | 452.3 | (1R,3S)-3-(3-{[(2-methoxypyridin-4-yl)acetyl]amino}-1H-pyrazol-5-yl)cyclopentyl [(2ξ)-3,3-difluorobutan-2-yl]carbamate - Isomer A |
| 393 | 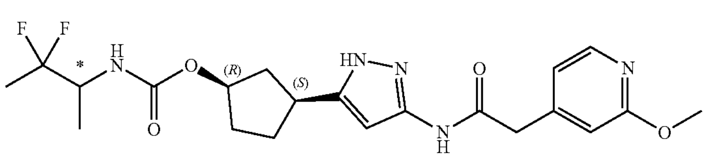 | 452.3 | (1R,3S)-3-(3-{[(2-methoxypyridin-4-yl)acetyl]amino}-1H-pyrazol-5-yl)cyclopentyl [(2ξ)-3,3-difluorobutan-2-yl]carbamate - Isomer B |

TABLE 3-continued

| Example No | Structure | LCMS [M + H]+ | IUPAC Name |
|---|---|---|---|
| 394 | 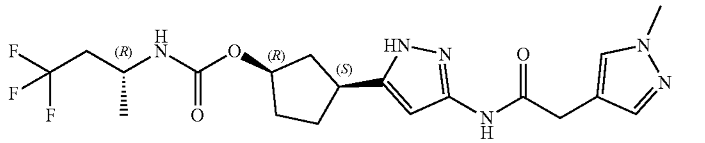 | 443.4 | (1R,3S)-3-(3-{[(1-methyl-1H-pyrazol-4-yl)acetyl]amino}-1H-pyrazol-5-yl)cyclopentyl [(2R)-4,4,4-trifluorobutan-2-yl]carbamate |
| 395 | 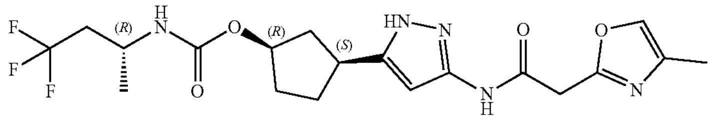 | 444.3 | (1R,3S)-3-(3-{[(4-methyl-1,3-oxazol-2-yl)acetyl]amino}-1H-pyrazol-5-yl)cyclopentyl [(2R)-4,4,4-trifluorobutan-2-yl]carbamate |
| 396 | 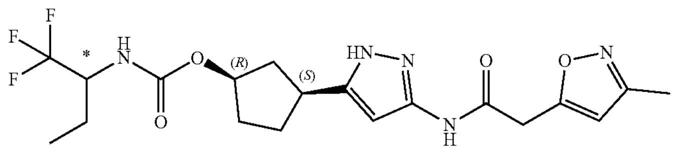 | 444.3 | (1R,3S)-3-(3-{[(3-methyl-1,2-oxazol-5-yl)acetyl]amino}-1H-pyrazol-5-yl)cyclopentyl [(2ξ)-1,1,1-trifluorobutan-2-yl]carbamate - Isomer A |
| 397 | 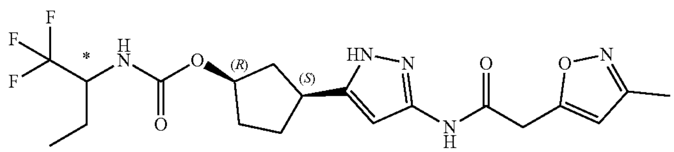 | 444.3 | (1R,3S)-3-(3-{[(3-methyl-1,2-oxazol-5-yl)acetyl]amino}-1H-pyrazol-5-yl)cyclopentyl [(2ξ)-1,1,1-trifluorobutan-2-yl]carbamate - Isomer B |
| 398 | 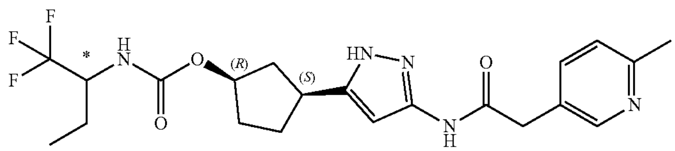 | 454.4 | (1R,3S)-3-(3-{[(6-methylpyridin-3-yl)acetyl]amino}-1H-pyrazol-5-yl)cyclopentyl [(2ξ)-1,1,1-trifluorobutan-2-yl]carbamate - Isomer A |
| 399 | 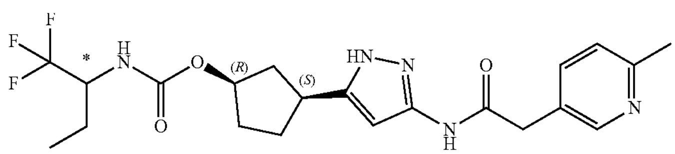 | 454.4 | (1R,3S)-3-(3-{[(6-methylpyridin-3-yl)acetyl]amino}-1H-pyrazol-5-yl)cyclopentyl [(2ξ)-1,1,1-trifluorobutan-2-yl]carbamate - Isomer B |
| 400 | 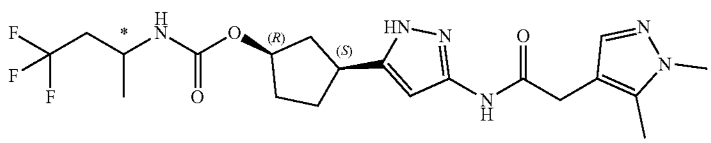 | 457.4 | (1R,3S)-3-(3-{[(1,5-dimethyl-1H-pyrazol-4-yl)acetyl]amino}-1H-pyrazol-5-yl)cyclopentyl [(2ξ)-4,4,4-trifluorobutan-2-yl]carbamate - Isomer A |
| 401 | 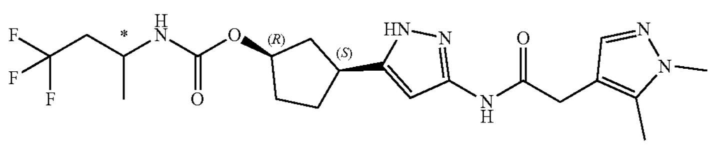 | 457.4 | (1R,3S)-3-(3-{[(1,5-dimethyl-1H-pyrazol-4-yl)acetyl]amino}-1H-pyrazol-5-yl)cyclopentyl [(2ξ)-4,4,4-trifluorobutan-2-yl]carbamate - Isomer B |
| 402 | 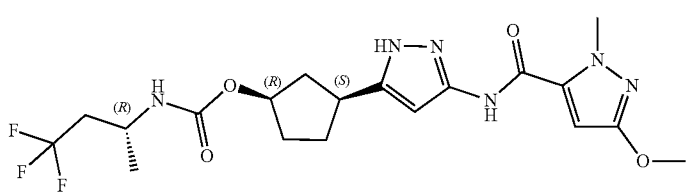 | 459.3 | (1R,3S)-3-(3-{[(3-methoxy-1-methyl-1H-pyrazol-5-yl)carbonyl]amino}-1H-pyrazol-5-yl)cyclopentyl [(2R)-4,4,4-trifluorobutan-2-yl]carbamate |

TABLE 3-continued

| Example No | Structure | LCMS [M + H]+ | IUPAC Name |
|---|---|---|---|
| 403 | 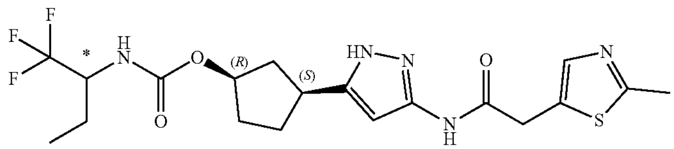 | 460.4 | (1R,3S)-3-(3-{[(2-methyl-1,3-thiazol-5-yl)acetyl]amino}-1H-pyrazol-5-yl)cyclopentyl [(2ξ)-1,1,1-trifluorobutan-2-yl]carbamate - Isomer A |
| 404 | 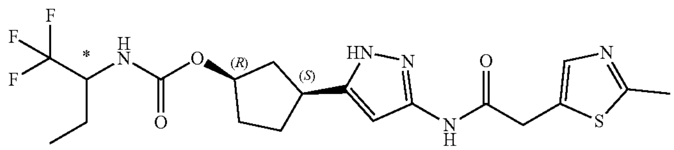 | 460.4 | (1R,3S)-3-(3-{[(2-methyl-1,3-thiazol-5-yl)acetyl]amino}-1H-pyrazol-5-yl)cyclopentyl [(2ξ)-1,1,1-trifluorobutan-2-yl]carbamate - Isomer B |
| 405 | 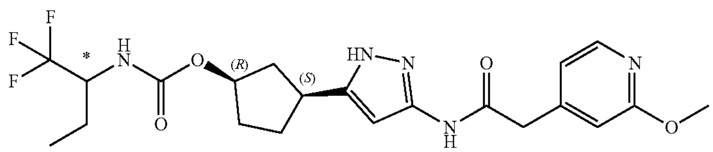 | 470.3 | (1R,3S)-3-(3-{[(2-methoxypyridin-4-yl)acetyl]amino}-1H-pyrazol-5-yl)cyclopentyl [(2ξ)-1,1,1-trifluorobutan-2-yl]carbamate - Isomer A |
| 406 | 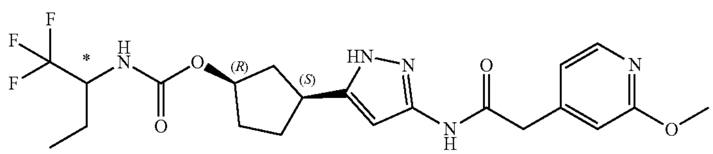 | 470.3 | (1R,3S)-3-(3-{[(2-methoxypyridin-4-yl)acetyl]amino}-1H-pyrazol-5-yl)cyclopentyl [(2ξ)-1,1,1-trifluorobutan-2-yl]carbamate - Isomer B |
| 407 | 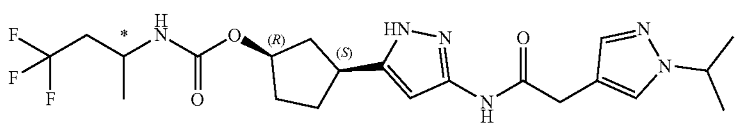 | 471.3 | (1R,3S)-3-[3-({[1-(propan-2-yl)-1H-pyrazol-4-yl]acetyl}amino)-1H-pyrazol-5-yl]cyclopentyl [(2ξ)-4,4,4-trifluorobutan-2-yl]carbamate - Isomer A |
| 408 | 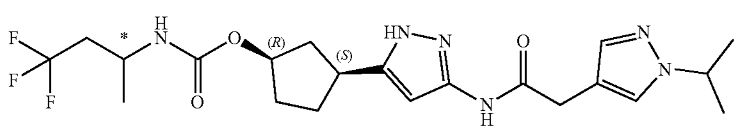 | 471.3 | (1R,3S)-3-[3-({[1-(propan-2-yl)-1H-pyrazol-4-yl]acetyl}amino)-1H-pyrazol-5-yl]cyclopentyl [(2ξ)-4,4,4-trifluorobutan-2-yl]carbamate - Isomer B |
| 409 | 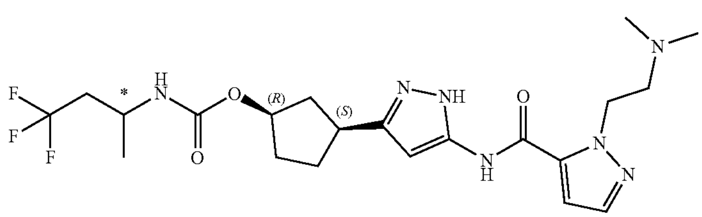 | 486.5 | (1R,3S)-3-{5-[({1-[2-(dimethylamino)ethyl]-1H-pyrazol-5-yl}carbonyl)amino]-1H-pyrazol-3-yl}cyclopentyl [(2ξ)-4,4,4-trifluorobutan-2-yl]carbamate - Isomer A |
| 410 | 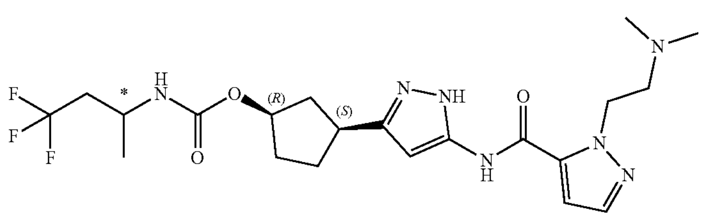 | 486.5 | (1R,3S)-3-{5-[({1-[2-(dimethylamino)ethyl]-1H-pyrazol-5-yl}carbonyl)amino]-1H-pyrazol-3-yl}cyclopentyl [(2ξ)-4,4,4-trifluorobutan-2-yl]carbamate - Isomer B |
| 411 | 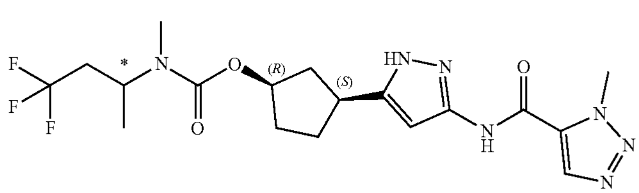 | 444.2 | (1R,3S)-3-(3-{[(1-methyl-1H-1,2,3-triazol-5-yl)carbonyl]amino}-1H-pyrazol-5-yl)cyclopentyl methyl[(2ξ)-4,4,4-trifluorobutan-2-yl]carbamate - Isomer A |

TABLE 3-continued

| Example No | Structure | LCMS [M + H]+ | IUPAC Name |
|---|---|---|---|
| 412 | 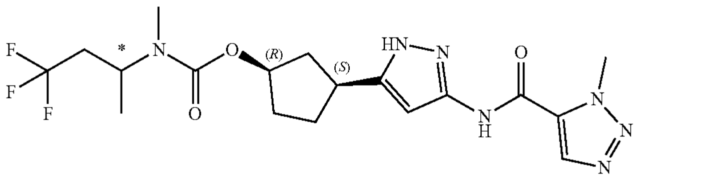 | 444.2 | (1R,3S)-3-(3-{[(1-methyl-1H-1,2,3-triazol-5-yl)carbonyl]amino}-1H-pyrazol-5-yl)cyclopentyl methyl[(2ξ)-4,4,4-trifluorobutan-2-yl]carbamate - Isomer B |
| 413 | 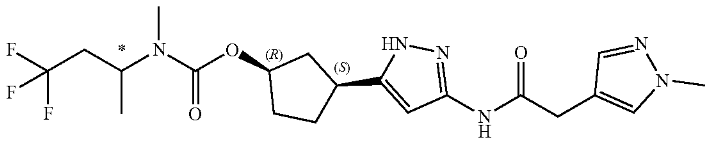 | 457.4 | (1R,3S)-3-(3-{[(1-methyl-1H-pyrazol-4-yl)acetyl]amino}-1H-pyrazol-5-yl)cyclopentyl methyl[(2ξ)-4,4,4-trifluorobutan-2-yl]carbamate - Isomer A |
| 414 | 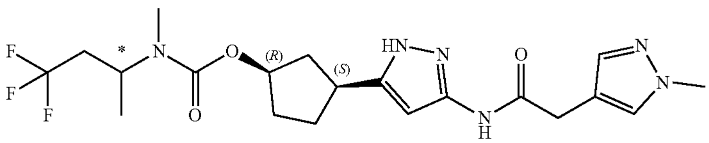 | 457.4 | (1R,3S)-3-(3-{[(1-methyl-1H-pyrazol-4-yl)acetyl]amino}-1H-pyrazol-5-yl)cyclopentyl methyl[(2ξ)-4,4,4-trifluorobutan-2-yl]carbamate - Isomer B |
| 415 | 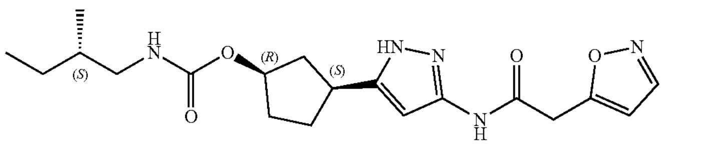 | 390.3 | (1R,3S)-3-{3-[(1,2-oxazol-5-ylacetyl)amino]-1H-pyrazol-5-yl}cyclopentyl [(2S)-2-methylbutyl]carbamate |
| 416 | 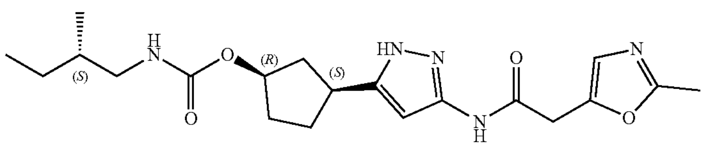 | 404.3 | (1R,3S)-3-(3-{[(2-methyl-1,3-oxazol-5-yl)acetyl]amino}-1H-pyrazol-5-yl)cyclopentyl [(2S)-2-methylbutyl]carbamate |
| 417 | 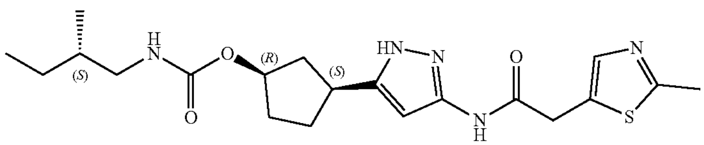 | 420.3 | (1R,3S)-3-(3-{[(2-methyl-1,3-thiazol-5-yl)acetyl]amino}-1H-pyrazol-5-yl)cyclopentyl [(2S)-2-methylbutyl]carbamate |
| 418 | 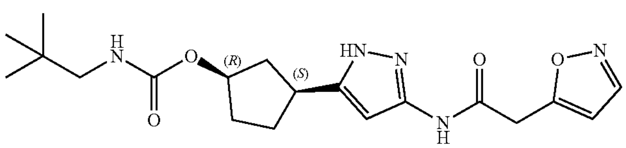 | 390.0 | (1R,3S)-3-{3-[(1,2-oxazol-5-ylacetyl)amino]-1H-pyrazol-5-yl}cyclopentyl (2,2-dimethylpropyl)carbamate |
| 419 | 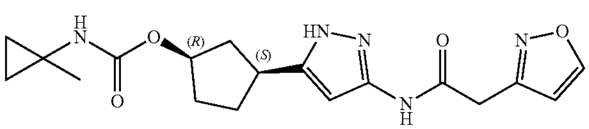 | 374.3 | (1R,3S)-3-{3-[(1,2-oxazol-3-ylacetyl)amino]-1H-pyrazol-5-yl}cyclopentyl (1-methylcyclopropyl)carbamate |
| 420 | 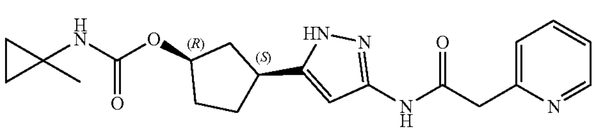 | 384.3 | (1R,3S)-3-{3-[(pyridin-2-ylacetyl)amino]-1H-pyrazol-5-yl}cyclopentyl (1-methylcyclopropyl)carbamate |
| 421 | 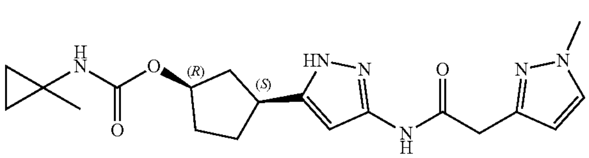 | 387.3 | (1R,3S)-3-(3-{[(1-methyl-1H-pyrazol-3-yl)acetyl]amino}-1H-pyrazol-5-yl)cyclopentyl (1-methylcyclopropyl)carbamate |

TABLE 3-continued

| Example No | Structure | LCMS [M + H]+ | IUPAC Name |
|---|---|---|---|
| 422 | 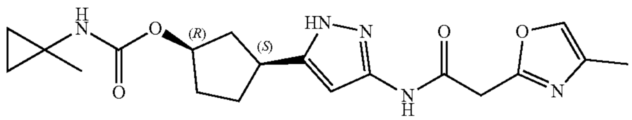 | 388.4 | (1R,3S)-3-(3-{[(4-methyl-1,3-oxazol-2-yl)acetyl]amino}-1H-pyrazol-5-yl)cyclopentyl (1-methylcyclopropyl)carbamate |
| 423 | 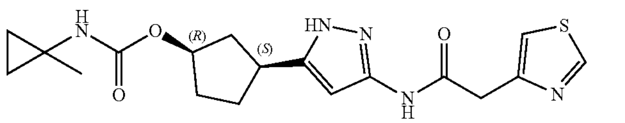 | 390.3 | (1R,3S)-3-{3-[(1,3-thiazol-4-ylacetyl]amino]-1H-pyrazol-5-yl}cyclopentyl (1-methylcyclopropyl)carbamate |
| 424 | 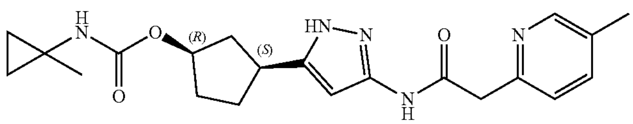 | 398.3 | (1R,3S)-3-(3-{[(5-methylpyridin-2-yl)acetyl]amino}-1H-pyrazol-5-yl)cyclopentyl (1-methylcyclopropyl)carbamate |
| 425 | 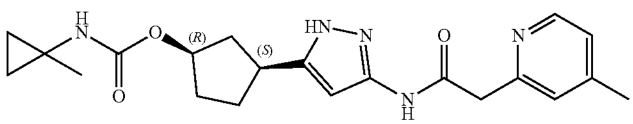 | 398.4 | (1R,3S)-3-(3-{[(4-methylpyridin-2-yl)acetyl]amino}-1H-pyrazol-5-yl)cyclopentyl (1-methylcyclopropyl)carbamate |
| 426 | 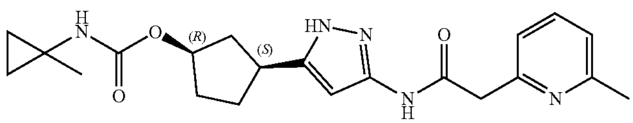 | 398.4 | (1R,3S)-3-(3-{[(6-methylpyridin-2-yl)acetyl]amino}-1H-pyrazol-5-yl)cyclopentyl (1-methylcyclopropyl)carbamate |
| 427 | 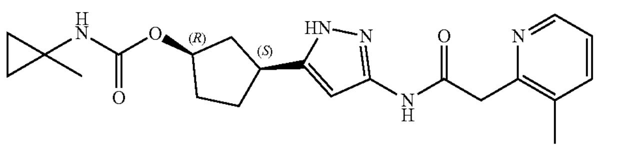 | 398.4 | (1R,3S)-3-(3-{[(3-methylpyridin-2-yl)acetyl]amino}-1H-pyrazol-5-yl)cyclopentyl (1-methylcyclopropyl)carbamate |
| 428 | 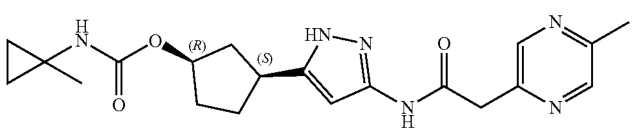 | 399.4 | (1R,3S)-3-(3-{[(5-methylpyrazin-2-yl)acetyl]amino}-1H-pyrazol-5-yl)cyclopentyl (1-methylcyclopropyl)carbamate |
| 429 | 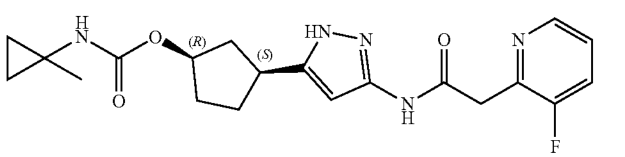 | 402.3 | (1R,3S)-3-(3-{[(3-fluoropyridin-2-yl)acetyl]amino}-1H-pyrazol-5-yl)cyclopentyl (1-methylcyclopropyl)carbamate |
| 430 | 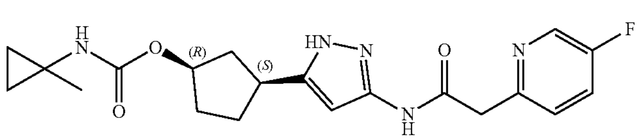 | 402.3 | (1R,3S)-3-(3-{[(5-fluoropyridin-2-yl)acetyl]amino}-1H-pyrazol-5-yl)cyclopentyl (1-methylcyclopropyl)carbamate |
| 431 | 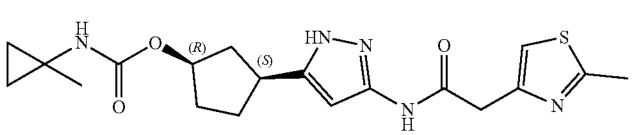 | 404.3 | (1R,3S)-3-(3-{[(2-methyl-1,3-thiazol-4-yl)acetyl]amino}-1H-pyrazol-5-yl)cyclopentyl (1-methylcyclopropyl)carbamate |
| 432 | 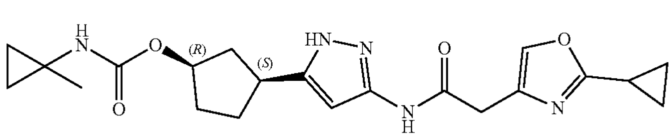 | 414.3 | (1R,3S)-3-(3-{[(2-cyclopropyl-1,3-oxazol-4-yl)acetyl]amino}-1H-pyrazol-5-yl)cyclopentyl (1-methylcyclopropyl)carbamate |

TABLE 3-continued

| Example No | Structure | LCMS [M + H]+ | IUPAC Name |
|---|---|---|---|
| 433 | 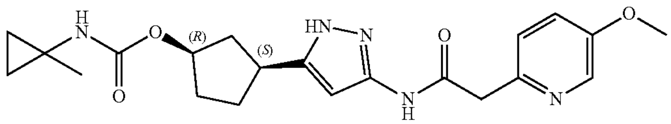 | 414.3 | (1R,3S)-3-(3-{[(5-methoxypyridin-2-yl)acetyl]amino}-1H-pyrazol-5-yl)cyclopentyl (1-methylcyclopropyl)carbamate |
| 434 | 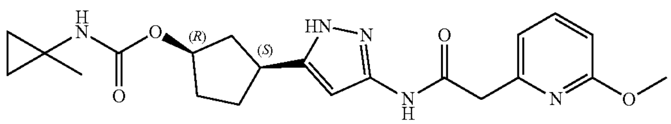 | 414.3 | (1R,3S)-3-(3-{[(6-methoxypyridin-2-yl)acetyl]amino}-1H-pyrazol-5-yl)cyclopentyl (1-methylcyclopropyl)carbamate |
| 435 | 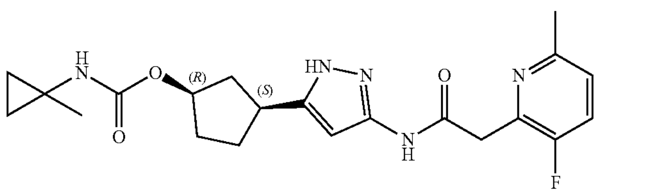 | 416.4 | (1R,3S)-3-(3-{[(3-fluoro-6-methylpyridin-2-yl)acetyl]amino}-1H-pyrazol-5-yl)cyclopentyl (1-methylcyclopropyl)carbamate |
| 436 | 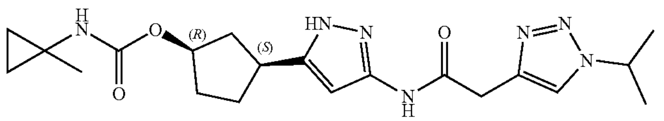 | 416.1 | (1R,3S)-3-[3-({[1-(propan-2-yl)-1H-1,2,3-triazol-4-yl]acetyl}amino)-1H-pyrazol-5-yl]cyclopentyl (1-methylcyclopropyl)carbamate |
| 437 | 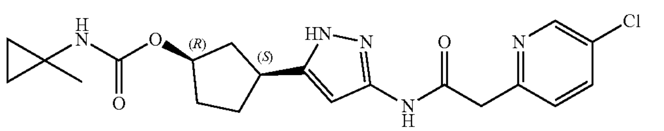 | 418.4 | (1R,3S)-3-(3-{[(5-chloropyridin-2-yl)acetyl]amino}-1H-pyrazol-5-yl)cyclopentyl (1-methylcyclopropyl)carbamate |
| 438 | 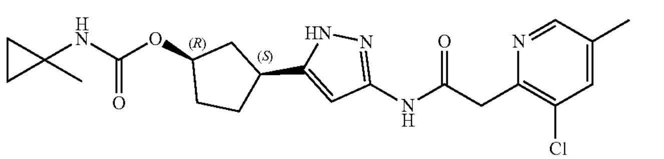 | 432.3 | (1R,3S)-3-(3-{[(3-chloro-5-methylpyridin-2-yl)acetyl]amino}-1H-pyrazol-5-yl)cyclopentyl (1-methylcyclopropyl)carbamate |
| 439 | 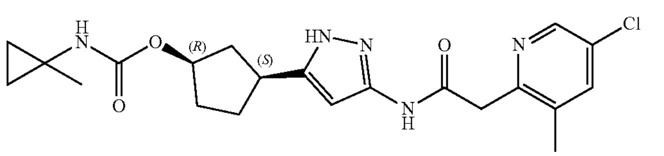 | 432.3 | (1R,3S)-3-(3-{[(5-chloro-3-methylpyridin-2-yl)acetyl]amino}-1H-pyrazol-5-yl)cyclopentyl (1-methylcyclopropyl)carbamate |
| 440 | 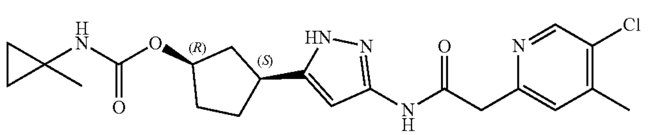 | 432.3 | (1R,3S)-3-(3-{[(5-chloro-4-methylpyridin-2-yl)acetyl]amino}-1H-pyrazol-5-yl)cyclopentyl (1-methylcyclopropyl)carbamate |
| 441 | 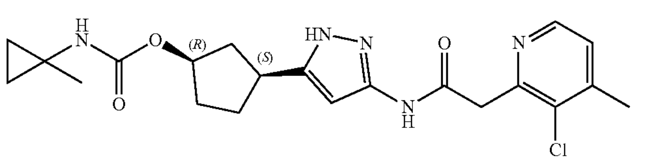 | 432.3 | (1R,3S)-3-(3-{[(3-chloro-4-methylpyridin-2-yl)acetyl]amino}-1H-pyrazol-5-yl)cyclopentyl (1-methylcyclopropyl)carbamate |
| 442 | 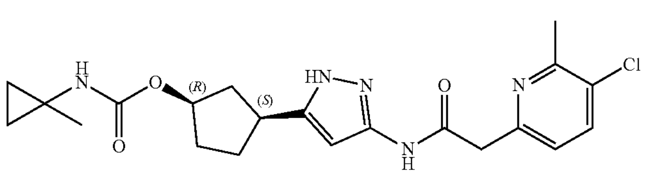 | 432.3 | (1R,3S)-3-(3-{[(5-chloro-6-methylpyridin-2-yl)acetyl]amino}-1H-pyrazol-5-yl)cyclopentyl (1-methylcyclopropyl)carbamate |

TABLE 3-continued

| Example No | Structure | LCMS [M + H]+ | IUPAC Name |
|---|---|---|---|
| 443 | 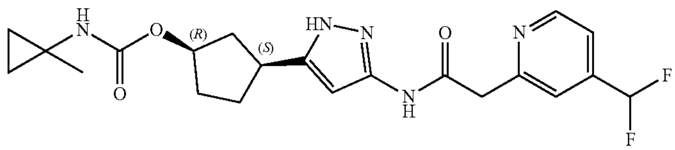 | 434.4 | (1R,3S)-3-[3-({[4-(difluoromethyl)pyridin-2-yl]acetyl}amino)-1H-pyrazol-5-yl]cyclopentyl (1-methylcyclopropyl)carbamate |
| 444 | 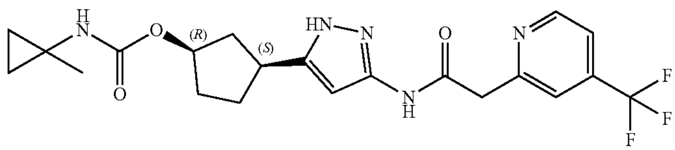 | 452.4 | (1R,3S)-3-[3-({[4-(trifluoromethyl)pyridin-2-yl]acetyl}amino)-1H-pyrazol-5-yl]cyclopentyl (1-methylcyclopropyl)carbamate |
| 445 | 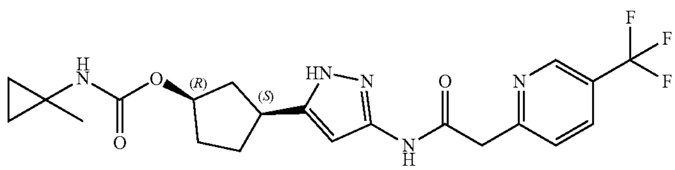 | 452.4 | (1R,3S)-3-[3-({[5-(trifluoromethyl)pyridin-2-yl]acetyl}amino)-1H-pyrazol-5-yl]cyclopentyl (1-methylcyclopropyl)carbamate |
| 446 | 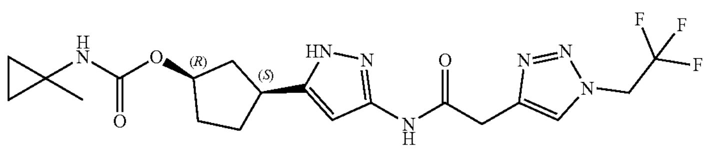 | 456.0 | (1R,3S)-3-[3-({[1-(2,2,2-trifluoroethyl)-1H-1,2,3-triazol-4-yl]acetyl}amino)-1H-pyrazol-5-yl]cyclopentyl (1-methylcyclopropyl)carbamate |
| 447 | 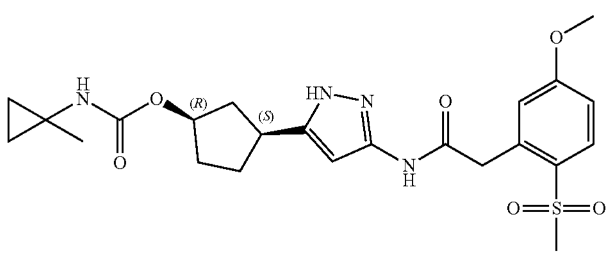 | 491.4 | (1R,3S)-3-[3-({[5-methoxy-2-(methylsulfonyl)phenyl]acetyl}amino)-1H-pyrazol-5-yl]cyclopentyl (1-methylcyclopropyl)carbamate |
| 448 | 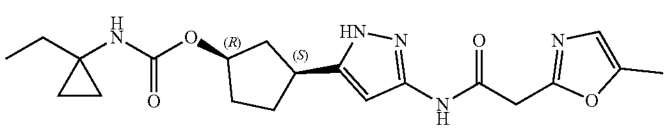 | 402.3 | (1R,3S)-3-(3-{[(5-methyl-1,3-oxazol-2-yl)acetyl]amino}-1H-pyrazol-5-yl)cyclopentyl (1-ethylcyclopropyl)carbamate |
| 449 | 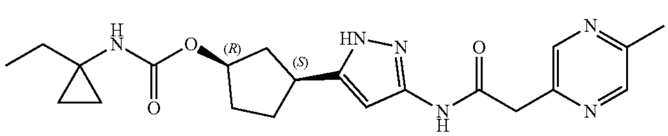 | 413.4 | (1R,3S)-3-(3-{[(5-methylpyrazin-2-yl)acetyl]amino}-1H-pyrazol-5-yl)cyclopentyl (1-ethylcyclopropyl)carbamate |
| 450 | 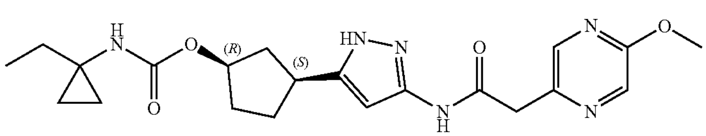 | 429.3 | (1R,3S)-3-(3-{[(5-methoxypyrazin-2-yl)acetyl]amino}-1H-pyrazol-5-yl)cyclopentyl (1-ethylcyclopropyl)carbamate |
| 451 | 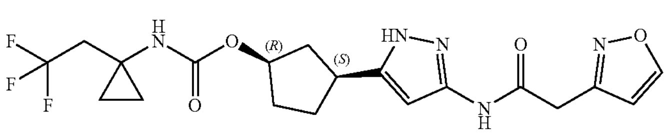 | 442.4 | (1R,3S)-3-{3-[(1,2-oxazol-3-ylacetyl)amino]-1H-pyrazol-5-yl}cyclopentyl [1-(2,2,2-trifluoroethyl)cyclopropyl]carbamate |

TABLE 3-continued

| Example No | Structure | LCMS [M + H]+ | IUPAC Name |
|---|---|---|---|
| 452 | 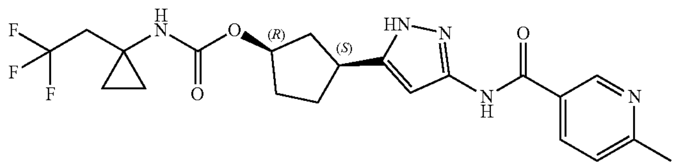 | 452.1 | (1R,3S)-3-(3-{[(6-methylpyridin-3-yl)carbonyl]amino}-1H-pyrazol-5-yl)cyclopentyl [1-2,2,2-trifluoroethyl)cyclopropyl]carbamate |
| 453 | 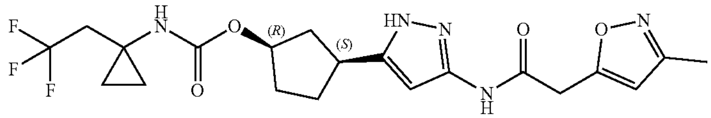 | 456.3 | (1R,3S)-3-(3-{[(3-methyl-1,2-oxazol-5-yl)acetyl]amino}-1H-pyrazol-5-yl)cyclopentyl [1-(2,2,2-trifluoroethyl)cyclopropyl]carbamate |
| 454 | 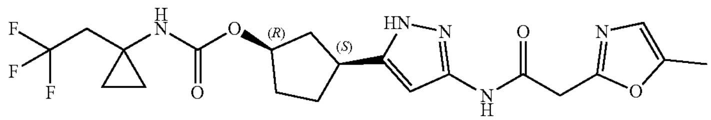 | 456.1 | (1R,3S)-3-(3-{[(5-methyl-1,3-oxazol-2-yl)acetyl]amino}-1H-pyrazol-5-yl)cyclopentyl[1-(2,2,2-trifluoroethyl)cyclopropyl]carbamate |
| 455 | 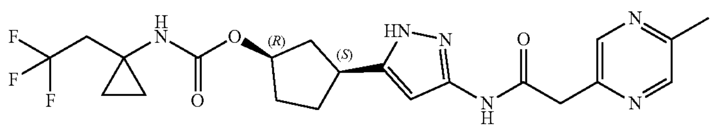 | 467.3 | (1R,3S)-3-(3-{[(5-methylpyrazin-2-yl)acetyl]amino}-1H-pyrazol-5-yl)cyclopentyl [1-2,2,2-trifluoroethyl)cyclopropyl]carbamate |
| 456 | 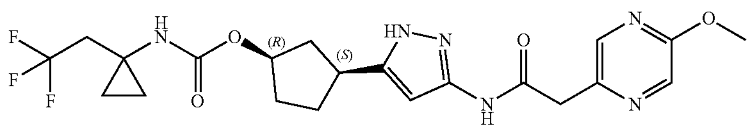 | 483.3 | (1R,3S)-3-(3-{[(5-methoxypyrazin-2-yl)acetyl]amino}-1H-pyrazol-5-yl)cyclopentyl [1-2,2,2-trifluoroethyl)cyclopropyl]carbamate |
| 457 | 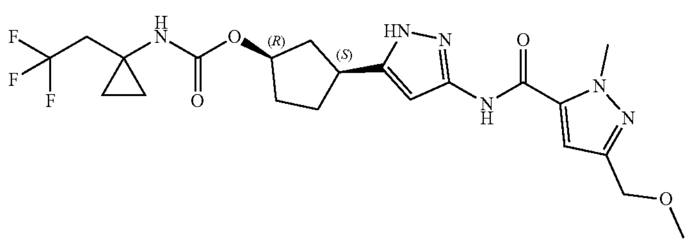 | 485.4 | (1R,3S)-3-[3-({[3-(methoxymethyl)-1-methyl-1H-pyrazol-5-yl]carbonyl}amino)-1H-pyrazol-5-yl]cyclopentyl [1-(2,2,2-trifluoroethyl)cyclopropyl]carbamate |
| 458 | 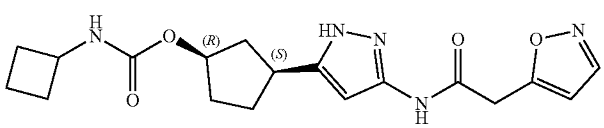 | 374.3 | (1R,3S)-3-{3-[(1,2-oxazol-5-ylacetyl)amino]-1H-pyrazol-5-yl}cyclopentyl cyclobutylcarbamate |
| 459 | 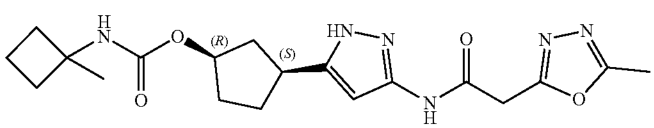 | 403.4 | (1R,3S)-3-(3-{[(5-methyl-1,3,4-oxadiazol-2-yl)acetyl]amino}-1H-pyrazol-5-yl)cyclopentyl (1-methylcyclobutyl)carbamate |
| 460 | 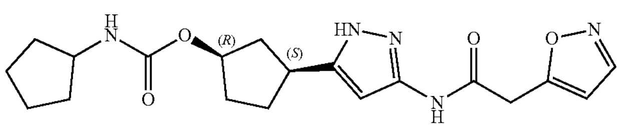 | 387.9 | (1R,3S)-3-{3-[(1,2-oxazol-5-ylacetyl)amino]-1H-pyrazol-5-yl}cyclopentyl cyclopentylcarbamate |
| 461 | 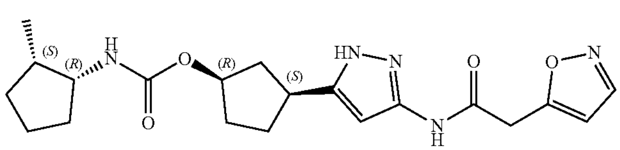 | 402.3 | (1R,3S)-3-{3-[(1,2-oxazol-5-ylacetyl)amino]-1H-pyrazol-5-yl}cyclopentyl [(1R,2S)-2-methylcyclopentyl]carbamate |

TABLE 3-continued

| Example No | Structure | LCMS [M + H]+ | IUPAC Name |
|---|---|---|---|
| 462 | 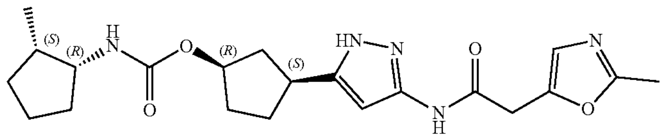 | 416.3 | (1R,3S)-3-(3-{[(2-methyl-1,3-oxazol-5-yl)acetyl]amino}-1H-pyrazol-5-yl)cyclopentyl [(1R,2S)-2-methylcyclopentyl]carbamate |
| 463 | 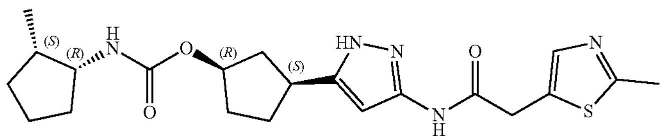 | 432.3 | (1R,3S)-3-(3-{[(2-methyl-1,3-thiazol-5-yl)acetyl]amino}-1H-pyrazol-5-yl)cyclopentyl [(1R,2S)-2-methylcyclopentyl]carbamate |
| 464 | 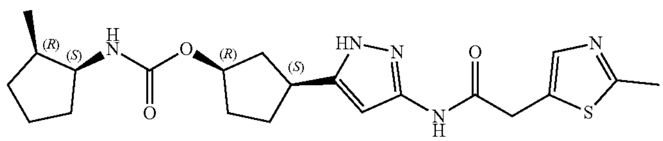 | 432.3 | (1R,3S)-3-(3-{[(2-methyl-1,3-thiazol-5-yl)acetyl]amino}-1H-pyrazol-5-yl)cyclopentyl [(1S,2R)-2-methylcyclopentyl]carbamate |
| 465 | 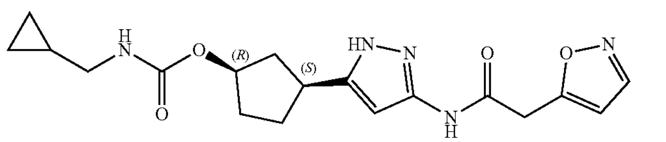 | 374.3 | (1R,3S)-3-{3-[(1,2-oxazol-5-ylacetyl)amino]-1H-pyrazol-5-yl}cyclopentyl (cyclopropylmethyl)carbamate |
| 466 | 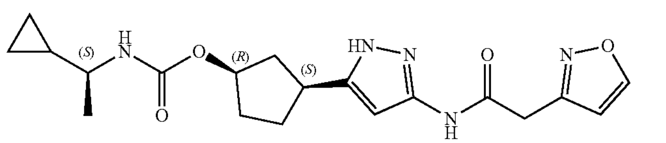 | 388.4 | (1R,3S)-3-{3-[(1,2-oxazol-3-ylacetyl)amino]-1H-pyrazol-5-yl}cyclopentyl [(1S)-1-cyclopropylethyl]carbamate |
| 467 | 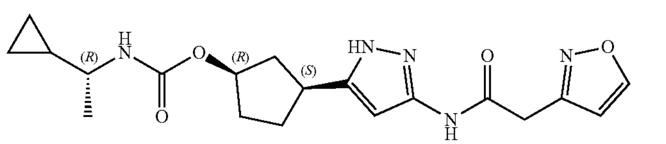 | 388.2 | (1R,3S)-3-{3-[(1,2-oxazol-3-ylacetyl)amino]-1H-pyrazol-5-yl}cyclopentyl [(1R)-1-cyclopropylethyl]carbamate |
| 468 | 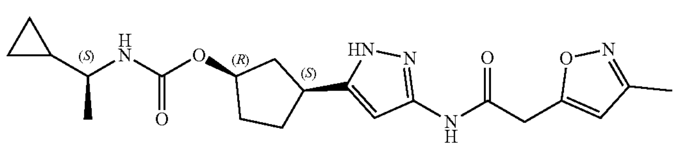 | 402.3 | (1R,3S)-3-(3-{[(3-methyl-1,2-oxazol-5-yl)acetyl]amino}-1H-pyrazol-5-yl)cyclopentyl [(1S)-1-cyclopropylethyl]carbamate |
| 469 | 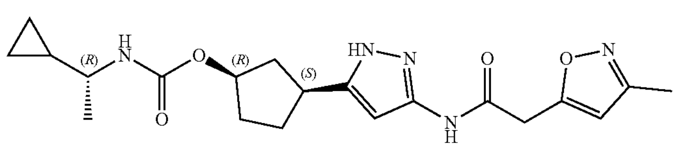 | 402.3 | (1R,3S)-3-(3-{[(3-methyl-1,2-oxazol-5-yl)acetyl]amino}-1H-pyrazol-5-yl)cyclopentyl [(1R)-1-cyclopropylethyl]carbamate |
| 470 | 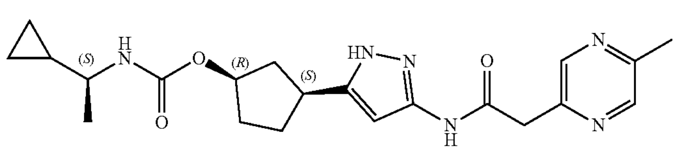 | 413.4 | (1R,3S)-3-(3-{[(5-methylpyrazin-2-yl)acetyl]amino}-1H-pyrazol-5-yl)cyclopentyl [(1S)-1-cyclopropylethyl]carbamate |
| 471 | 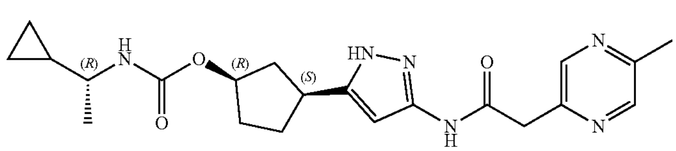 | 413.4 | (1R,3S)-3-(3-{[(5-methylpyrazin-2-yl)acetyl]amino}-1H-pyrazol-5-yl)cyclopentyl [(1R)-1-cyclopropylethyl]carbamate |

TABLE 3-continued

| Example No | Structure | LCMS [M + H]+ | IUPAC Name |
|---|---|---|---|
| 472 | 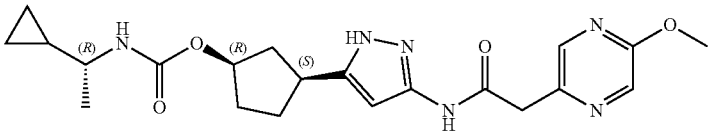 | 429.3 | (1R,3S)-3-(3-{[(5-methoxypyrazin-2-yl)acetyl]amino}-1H-pyrazol-5-yl)cyclopentyl [(1R)-1-cyclopropylethyl]carbamate |
| 473 | 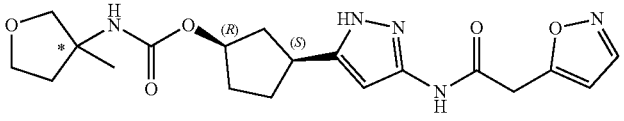 | 404.3 | (1R,3S)-3-{3-[(1,2-oxazol-5-ylacetyl)amino]-1H-pyrazol-5-yl}cyclopentyl [(3ξ)-3-methyltetrahydrofuran-3-yl]carbamate - Isomer A |
| 474 | 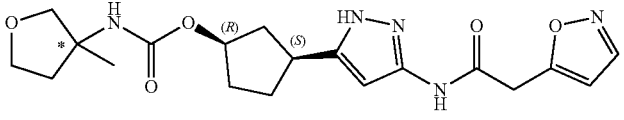 | 404.3 | (1R,3S)-3-{3-[(1,2-oxazol-5-ylacetyl)amino]-1H-pyrazol-5-yl}cyclopentyl [(3ξ)-3-methyltetrahydrofuran-3-yl]carbamate - Isomer B |
| 475 | 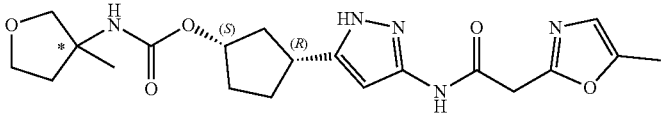 | 418.4 | (1S,3R)-3-(3-{[(5-methyl-1,3-oxazol-2-yl)acetyl]amino}-1H-pyrazol-5-yl)cyclopentyl [(3ξ)-3-methyltetrahydrofuran-3-yl]carbamate - Isomer A |
| 476 | 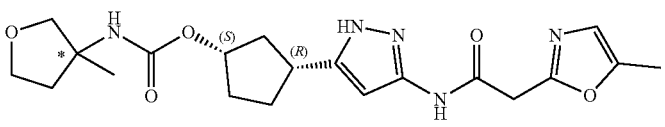 | 418.4 | (1S,3R)-3-(3-{[(5-methyl-1,3-oxazol-2-yl)acetyl]amino}-1H-pyrazol-5-yl)cyclopentyl [(3ξ)-3-methyltetrahydrofuran-3-yl]carbamate - Isomer B |
| 477 | 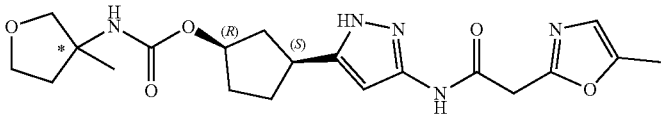 | 418.4 | (1R,3S)-3-(3-{[(5-methyl-1,3-oxazol-2-yl)acetyl]amino}-1H-pyrazol-5-yl)cyclopentyl [(3ξ)-3-methyltetrahydrofuran-3-yl]carbamate - Isomer A |
| 478 | 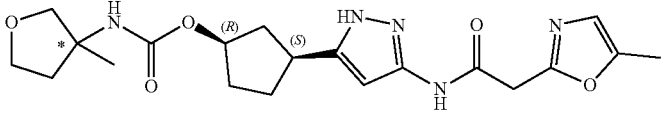 | 418.4 | (1R,3S)-3-(3-{[(5-methyl-1,3-oxazol-2-yl)acetyl]amino}-1H-pyrazol-5-yl)cyclopentyl [(3ξ)-3-methyltetrahydrofuran-3-yl]carbamate - Isomer B |
| 479 | 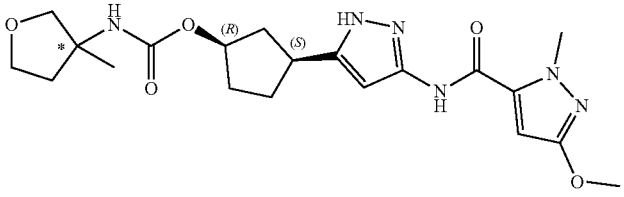 | 433.4 | (1R,3S)-3-(3-{[(3-methoxy-1-methyl-1H-pyrazol-5-yl)carbonyl]amino}-1H-pyrazol-5-yl)cyclopentyl [(3ξ)-3-methyltetrahydrofuran-3-yl]carbamate - Isomer A |
| 480 | 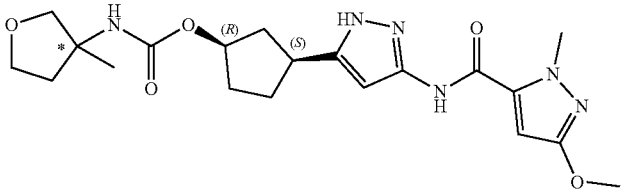 | 433.4 | (1R,3S)-3-(3-{[(3-methoxy-1-methyl-1H-pyrazol-5-yl)carbonyl]amino}-1H-pyrazol-5-yl)cyclopentyl [(3ξ)-3-methyltetrahydrofuran-3-yl]carbamate - Isomer B |
| 481 | 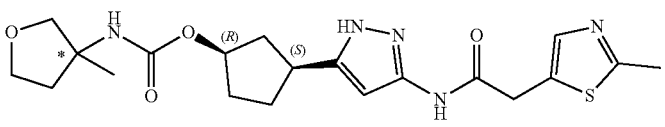 | 434.3 | (1R,3S)-3-(3-{[(2-methyl-1,3-thiazol-5-yl)acetyl]amino}-1H-pyrazol-5-yl)cyclopentyl [3ξ)-3-methyltetrahydrofuran-3-yl]carbamate - Isomer A |

TABLE 3-continued

| Example No | Structure | LCMS [M + H]+ | IUPAC Name |
|---|---|---|---|
| 482 | 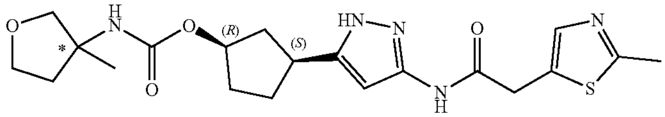 | 434.3 | (1R,3S)-3-(3-{[(2-methyl-1,3-thiazol-5-yl)acetyl]amino}-1H-pyrazol-5-yl)cyclopentyl [3ξ)-3-methyltetrahydrofuran-3-yl]carbamate - Isomer B |
| 483 | 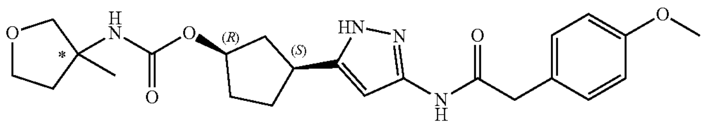 | 442.9 | (1R,3S)-3-(3-{[(4-methoxyphenyl)acetyl]amino}-1H-pyrazol-5-yl)cyclopentyl [(3ξ)-3-methyltetrahydrofuran-3-yl]carbamate - Isomer A |
| 484 | 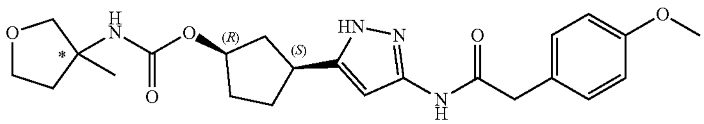 | 442.9 | (1R,3S)-3-(3-{[(4-methoxyphenyl)acetyl]amino}-1H-pyrazol-5-yl)cyclopentyl [(3ξ)-3-methyltetrahydrofuran-3-yl]carbamate - Isomer B |
| 485 | 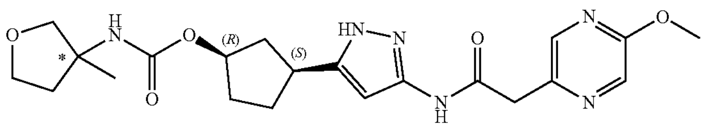 | 445.4 | (1R,3S)-3-(3-{[(5-methoxypyrazin-2-yl)acetyl]amino}-1H-pyrazol-5-yl)cyclopentyl [(3ξ)-3-methyltetrahydrofuran-3-yl]carbamate - Isomer A |
| 486 | 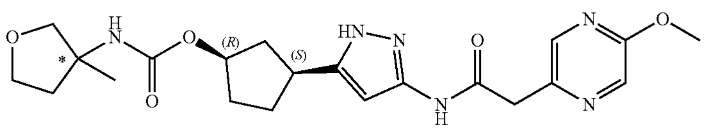 | 445.4 | (1R,3S)-3-(3-{[(5-methoxypyrazin-2-yl)acetyl]amino}-1H-pyrazol-5-yl)cyclopentyl [(3ξ)-3-methyltetrahydrofuran-3-yl]carbamate - Isomer B |
| 487 | 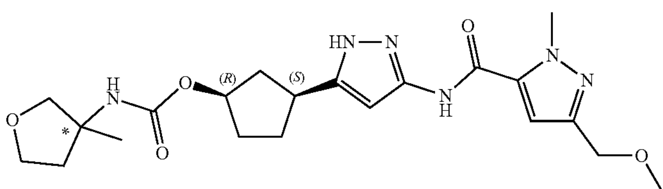 | 447.5 | (1R,3S)-3-[3-({[3-(methoxymethyl)-1-methyl-1H-pyrazol-5-yl]carbonyl}amino)-1H-pyrazol-5-yl]cyclopentyl [(3ξ)-3-methyltetrahydrofuran-3-yl]carbamate - Isomer A |
| 488 | 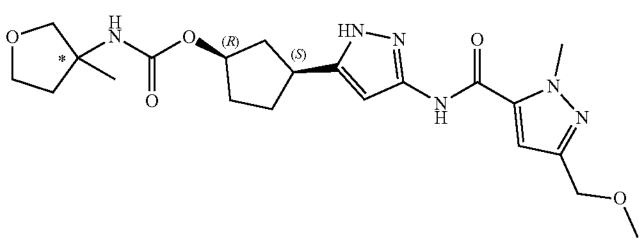 | 447.5 | (1R,3S)-3-[3-({[3-(methoxymethyl)-1-methyl-1H-pyrazol-5-yl]carbonyl}amino)-1H-pyrazol-5-yl]cyclopentyl [(3ξ)-3-methyltetrahydrofuran-3-yl]carbamate - Isomer B |
| 489 | 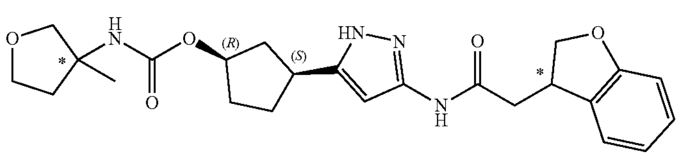 | 455.4 | (1R,3S)-3-(3-{[(3ξ)-2,3-dihydro-1-benzofuran-3-ylacetyl]amino}-1H-pyrazol-5-yl)cyclopentyl [(3ξ)-3-methyltetrahydrofuran-3-yl]carbamate - Isomer A |
| 490 | 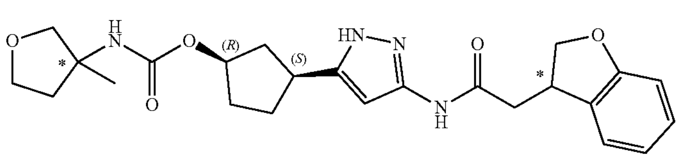 | 455.4 | (1R,3S)-3-(3-{[(3ξ)-2,3-dihydro-1-benzofuran-3-ylacetyl]amino}-1H-pyrazol-5-yl)cyclopentyl [(3ξ)-3-methyltetrahydrofuran-3-yl]carbamate - Isomer B |

TABLE 3-continued

| Example No | Structure | LCMS [M + H]+ | IUPAC Name |
|---|---|---|---|
| 491 | 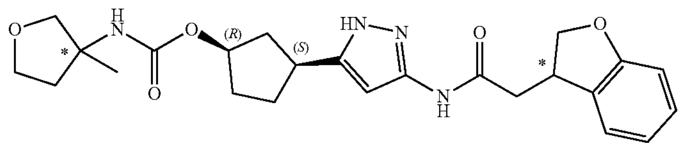 | 455.4 | (1R,3S)-3-(3-{[(3ξ)-2,3-dihydro-1-benzofuran-3-ylacetyl]amino}-1H-pyrazol-5-yl)cyclopentyl [(3ξ)-3-methyltetrahydrofuran-3-yl]carbamate - Isomer C |
| 492 | 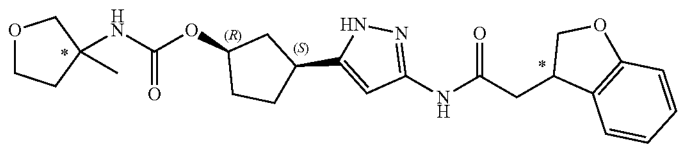 | 455.4 | (1R,3S)-3-(3-{[(3ξ)-2,3-dihydro-1-benzofuran-3-ylacetyl]amino}-1H-pyrazol-5-yl)cyclopentyl [(3ξ)-3-methyltetrahydrofuran-3-yl]carbamate - Isomer D |
| 493 | 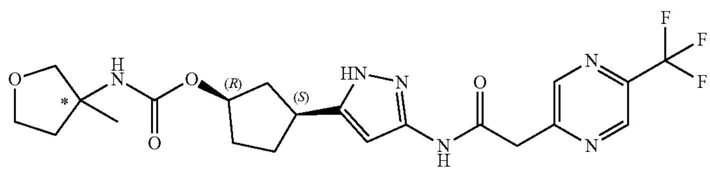 | 483.3 | (1R,3S)-3-[3-({[5-(trifluoromethyl)pyrazin-2-yl]acetyl}amino)-1H-pyrazol-5-yl]cyclopentyl [(3ξ)-3-methyltetrahydrofuran-3-yl]carbamate - Isomer A |
| 494 | 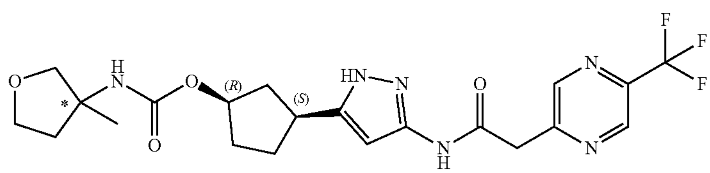 | 483.3 | (1R,3S)-3-[3-({[5-(trifluoromethyl)pyrazin-2-yl]acetyl}amino)-1H-pyrazol-5-yl]cyclopentyl [(3ξ)-3-methyltetrahydrofuran-3-yl]carbamate - Isomer B |
| 495 | 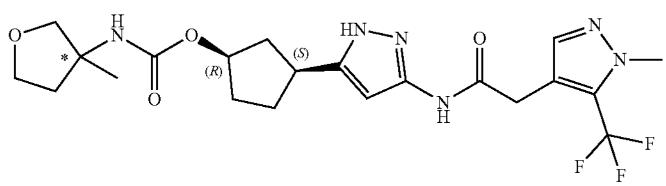 | 485.4 | (1R,3S)-3-[3-({[1-methyl-5-(trifluoromethyl)-1H-pyrazol-4-yl]acetyl}amino)-1H-pyrazol-5-yl]cyclopentyl [(3ξ)-3-methyltetrahydrofuran-3-yl]carbamate - Isomer A |
| 496 | 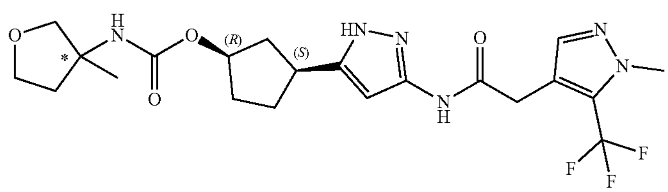 | 485.4 | (1R,3S)-3-[3-({[1-methyl-5-(trifluoromethyl)-1H-pyrazol-4-yl]acetyl}amino)-1H-pyrazol-5-yl]cyclopentyl [(3ξ)-3-methyltetrahydrofuran-3-yl]carbamate - Isomer B |
| 497 | 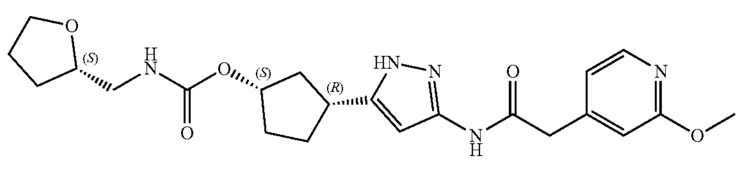 | 444.2 | (1S,3R)-3-(3-{[(2-methoxypyridin-4-yl)acetyl]amino}-1H-pyrazol-5-yl)cyclopentyl [(2S)-tetrahydrofuran-2-ylmethyl]carbamate |
| 498 | 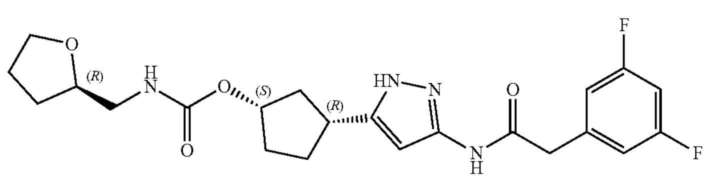 | 449.3 | (1S,3R)-3-(3-{[(3,5-difluorophenyl)acetyl]amino}-1H-pyrazol-5-yl)cyclopentyl [(2R)-tetrahydrofuran-2-ylmethyl]carbamate |

TABLE 3-continued

| Example No | Structure | LCMS [M + H]+ | IUPAC Name |
|---|---|---|---|
| 499 | 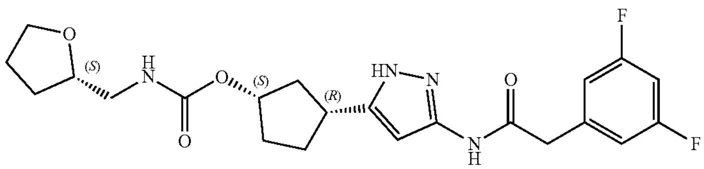 | 449.3 | (1S,3R)-3-(3-{[(3,5-difluorophenyl)acetyl]amino}-1H-pyrazol-5-yl)cyclopentyl [(2S)-tetrahydrofuran-2-ylmethyl]carbamate |
| 500 | 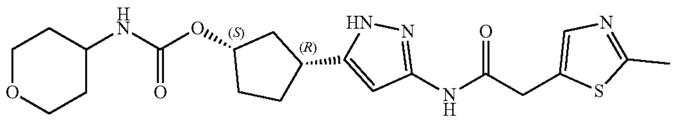 | 434.3 | (1S,3R)-3-(3-{[(2-methyl-1,3-thiazol-5-yl)acetyl]amino}-1H-pyrazol-5-yl)cyclopentyl tetrahydro-2H-pyran-4-ylcarbamate |
| 501 | 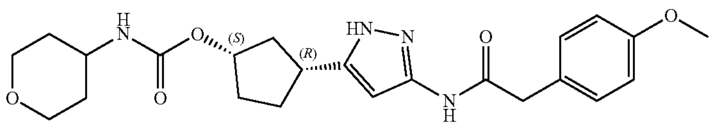 | 443.3 | (1S,3R)-3-(3-{[(4-methoxyphenyl)acetyl]amino}-1H-pyrazol-5-yl)cyclopentyl tetrahydro-2H-pyran-4-ylcarbamate |
| 502 | 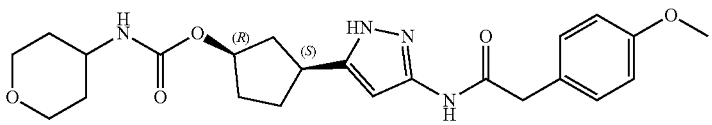 | 443.3 | (1R,3S)-3-(3-{[(4-methoxyphenyl)acetyl]amino}-1H-pyrazol-5-yl)cyclopentyl tetrahydro-2H-pyran-4-ylcarbamate |
| 503 | 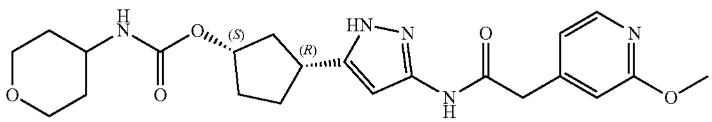 | 444.3 | (1S,3R)-3-(3-{[(2-methoxypyridin-4-yl)acetyl]amino}-1H-pyrazol-5-yl)cyclopentyl tetrahydro-2H-pyran-4-ylcarbamate |
| 504 | 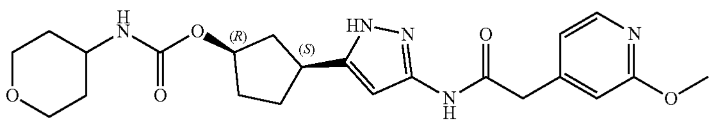 | 444.3 | (1R,3S)-3-(3-{[(2-methoxypyridin-4-yl)acetyl]amino}-1H-pyrazol-5-yl)cyclopentyl tetrahydro-2H-pyran-4-ylcarbamate |
| 505 | 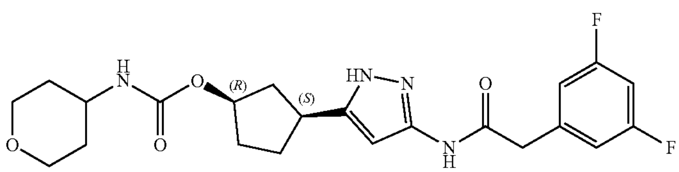 | 449.4 | (1R,3S)-3-(3-{[(3,5-difluorophenyl)acetyl]amino}-1H-pyrazol-5-yl)cyclopentyl tetrahydro-2H-pyran-4-ylcarbamate |
| 506 | 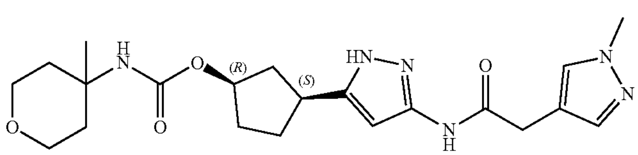 | 431.3 | (1R,3S)-3-(3-{[(1-methyl-1H-pyrazol-4-yl)acetyl]amino}-1H-pyrazol-5-yl)cyclopentyl (4-methyltetrahydro-2H-pyran-4-yl)carbamate |
| 507 | 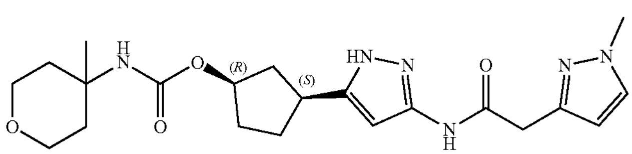 | 431.4 | (1R,3S)-3-(3-{[(1-methyl-1H-pyrazol-3-yl)acetyl]amino}-1H-pyrazol-5-yl)cyclopentyl (4-methyltetrahydro-2H-pyran-4-yl)carbamate |
| 508 | 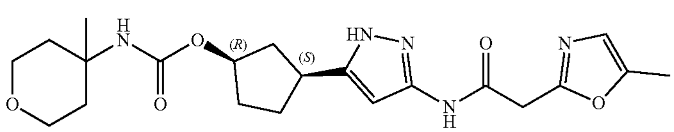 | 432.3 | (1R,3S)-3-(3-{[(5-methyl-1,3-oxazol-2-yl)acetyl]amino}-1H-pyrazol-5-yl)cyclopentyl (4-methyltetrahydro-2H-pyran-4-yl)carbamate |

TABLE 3-continued

| Example No | Structure | LCMS [M + H]+ | IUPAC Name |
|---|---|---|---|
| 509 | 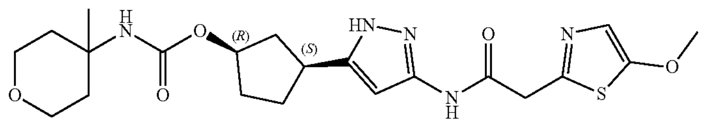 | [M + Na]+ 486.0 | (1R,3S)-3-(3-{[(2-methoxy-1,3-thiazol-5-yl)acetyl]amino}-1H-pyrazol-5-yl)cyclopentyl (4-methyltetrahydro-2H-pyran-4-yl)carbamate |
| 510 | 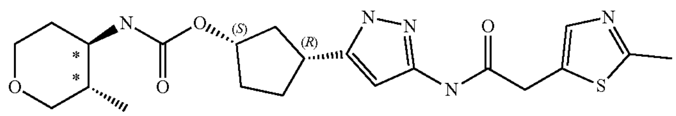 | 448.2 | (1S,3R)-3-(3-{[(2-methyl-1,3-thiazol-5-yl)acetyl]amino}-1H-pyrazol-5-yl)cyclopentyl [(3S*,4R*)-3-methyltetrahydro-2H-pyran-4-yl]carbamate - Isomer A |
| 511 | 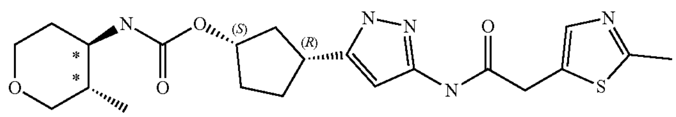 | 448.2 | (1S,3R)-3-(3-{[(2-methyl-1,3-thiazol-5-yl)acetyl]amino}-1H-pyrazol-5-yl)cyclopentyl [(3S*,4R*)-3-methyltetrahydro-2H-pyran-4-yl]carbamate - Isomer B |
| 512 | 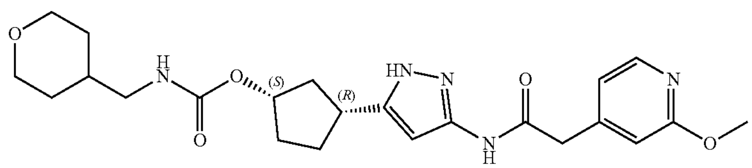 | 458.3 | (1S,3R)-3-(3-{[(2-methoxypyridin-4-yl)acetyl]amino}-1H-pyrazol-5-yl)cyclopentyl (tetrahydro-2H-pyran-4-ylmethyl)carbamate |
| 513 | 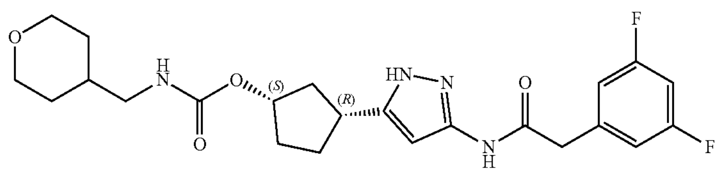 | 463.4 | (1S,3R)-3-(3-{[(3,5-difluorophenyl)acetyl]amino}-1H-pyrazol-5-yl)cyclopentyl (tetrahydro-2H-pyran-4-ylmethyl)carbamate |
| 514 | 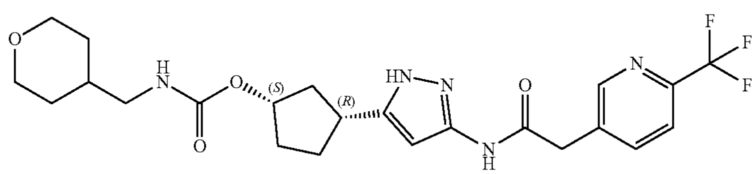 | 496.4 | (1S,3R)-3-[3-({[6-(trifluoromethyl)pyridin-3-yl]acetyl}amino)-1H-pyrazol-5-yl]cyclopentyl (tetrahydro-2H-pyran-4-ylmethyl)carbamate |
| 515 | 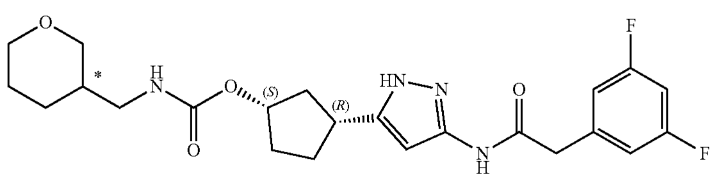 | 463.4 | (1S,3R)-3-(3-{[(3,5-difluorophenyl)acetyl]amino}-1H-pyrazol-5-yl)cyclopentyl [(3ξ)-tetrahydro-2H-pyran-3-ylmethyl]carbamate - Isomer A |
| 516 | 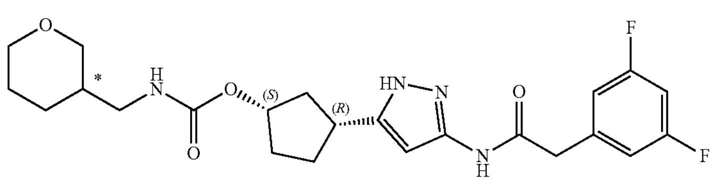 | 463.3 | (1S,3R)-3-(3-{[(3,5-difluorophenyl)acetyl]amino}-1H-pyrazol-5-yl)cyclopentyl [(3ξ)-tetrahydro-2H-pyran-3-ylmethyl]carbamate - Isomer B |
| 517 | 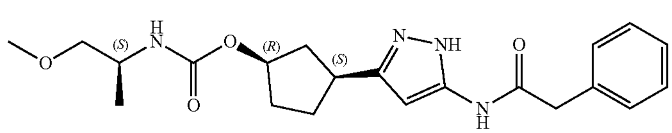 | 401.4 | (1R,3S)-3-{5-[(phenylacetyl)amino]-1H-pyrazol-3-yl}cyclopentyl [(2S)-1-methoxypropan-2-yl]carbamate |

TABLE 3-continued

| Example No | Structure | LCMS [M + H]+ | IUPAC Name |
|---|---|---|---|
| 518 | 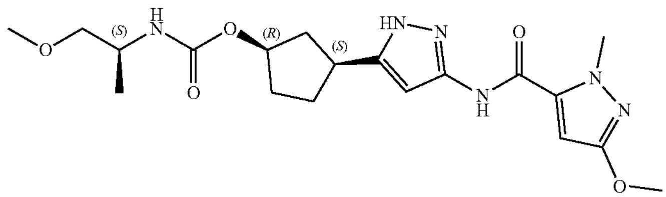 | 421.4 | (1R,3S)-3-(3-{[(3-methoxy-1-methyl-1H-pyrazol-5-yl)carbonyl]amino}-1H-pyrazol-5-yl)cyclopentyl [(2S)-1-methoxypropan-2-yl]carbamate |
| 519 | 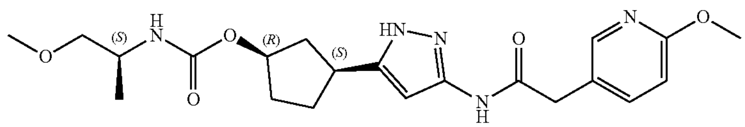 | 432.3 | (1R,3S)-3-(3-{[(6-methoxypyridin-3-yl)acetyl]amino}-1H-pyrazol-5-yl)cyclopentyl [(2S)-1-methoxypropan-2-yl]carbamate |
| 520 | 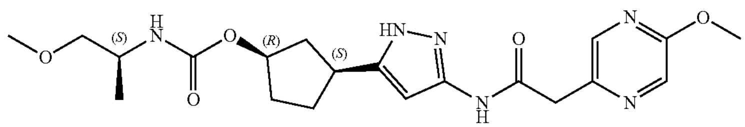 | 433.4 | (1R,3S)-3-(3-{[(5-methoxypyrazin-2-yl)acetyl]amino}-1H-pyrazol-5-yl)cyclopentyl [(2S)-1-methoxypropan-2-yl]carbamate |
| 521 | 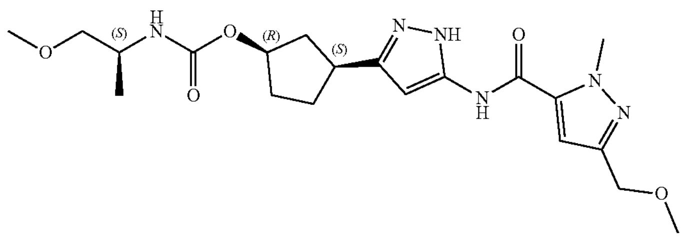 | 435.4 | (1R,3S)-3-[5-({[3-(methoxymethyl)-1-methyl-1H-pyrazol-5-yl]carbonyl}amino)-1H-pyrazol-3-yl]cyclopentyl [(2S)-1-methoxypropan-2-yl]carbamate |
| 522 | 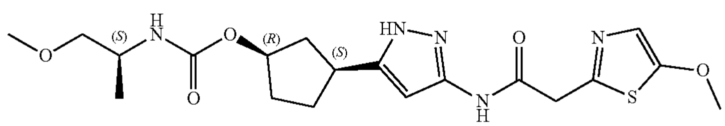 | 438.3 | (1R,3S)-3-(3-{[(5-methoxy-1,3-thiazol-2-yl)acetyl]amino}-1H-pyrazol-5-yl)cyclopentyl [(2S)-1-methoxypropan-2-yl]carbamate |
| 523 | 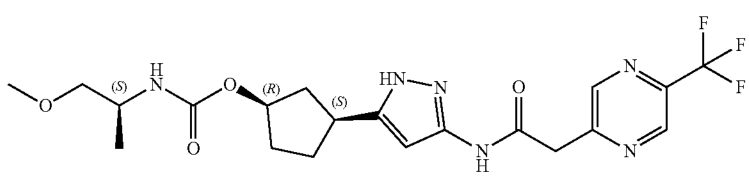 | 471.3 | (1R,3S)-3-[3-({[5-(trifluoromethyl)pyrazin-2-yl]acetyl}amino)-1H-pyrazol-5-yl]cyclopentyl [(2S)-1-methoxypropan-2-yl]carbamate |
| 524 | 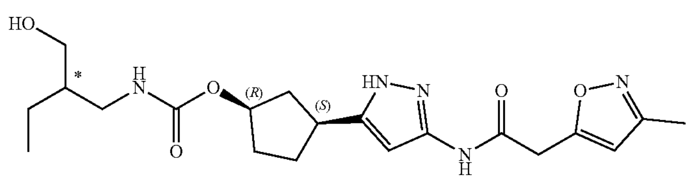 | 420.0 | (1R,3S)-3-(3-{[(3-methyl-1,2-oxazol-5-yl)acetyl]amino}-1H-pyrazol-5-yl)cyclopentyl [(2ξ)-2-(hydroxymethyl)butyl]carbamate - Isomer A |
| 525 | 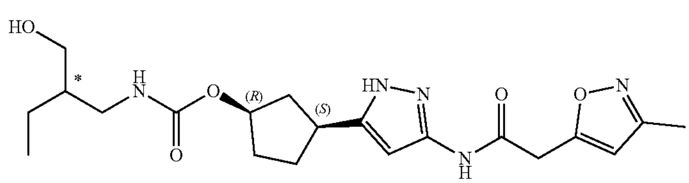 | 420.1 | (1R,3S)-3-(3-{[(3-methyl-1,2-oxazol-5-yl)acetyl]amino}-1H-pyrazol-5-yl)cyclopentyl [(2ξ)-2-(hydroxymethyl)butyl]carbamate - Isomer B |

TABLE 3-continued

| Example No | Structure | LCMS [M + H]+ | IUPAC Name |
|---|---|---|---|
| 526 | 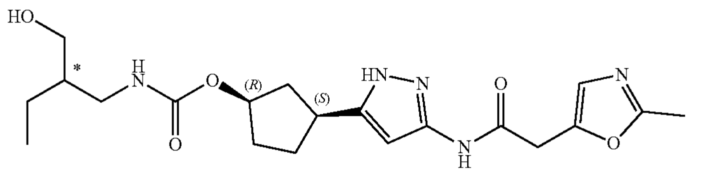 | 420.1 | (1R,3S)-3-(3-{[(2-methyl-1,3-oxazol-5-yl)acetyl]amino}-1H-pyrazol-5-yl)cyclopentyl [(2ξ)-2-(hydroxymethyl)butyl] carbamate - Isomer A |
| 527 | 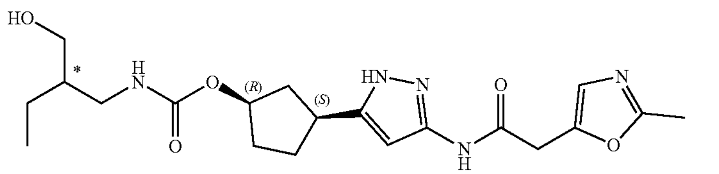 | 420.0 | (1R,3S)-3-(3-{[(2-methyl-1,3-oxazol-5-yl)acetyl]amino}-1H-pyrazol-5-yl)cyclopentyl [(2ξ)-2-(hydroxymethyl)butyl] carbamate - Isomer B |
| 528 | 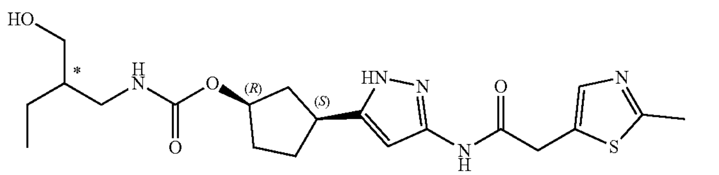 | 436.1 | (1R,3S)-3-(3-{[(2-methyl-1,3-thiazol-5-yl)acetyl]amino}-1H-pyrazol-5-yl)cyclopentyl [(2ξ)-2-(hydroxymethyl)butyl] carbamate - Isomer A |
| 529 | 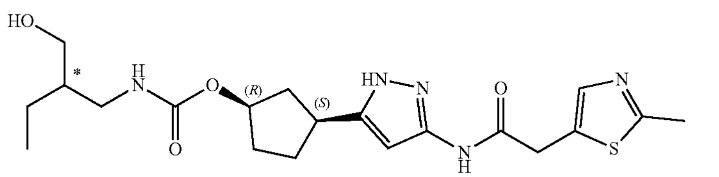 | 436.1 | (1R,3S)-3-(3-{[(2-methyl-1,3-thiazol-5-yl)acetyl]amino}-1H-pyrazol-5-yl)cyclopentyl [(2ξ)-2-(hydroxymethyl)butyl] carbamate - Isomer B |
| 530 | 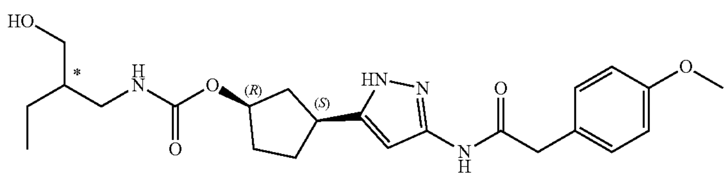 | 445.4 | (1R,3S)-3-(3-{[(4-methoxyphenyl)acetyl]amino}-1H-pyrazol-5-yl)cyclopentyl [(2ξ)-2-(hydroxymethyl)butyl] carbamate - Isomer A |
| 531 | 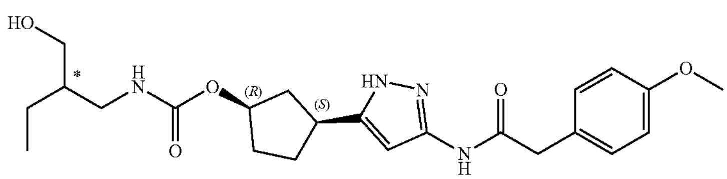 | 445.4 | (1R,3S)-3-(3-{[(4-methoxyphenyl)acetyl]amino}-1H-pyrazol-5-yl)cyclopentyl [(2ξ)-2-(hydroxymethyl)butyl] carbamate - Isomer B |
| 532 | 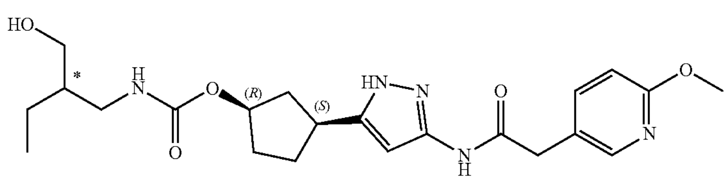 | 446.2 | (1R,3S)-3-(3-{[(6-methoxypyridin-3-yl)acetyl]amino}-1H-pyrazol-5-yl)cyclopentyl [(2ξ)-2-(hydroxymethyl)butyl] carbamate - Isomer A |
| 533 | 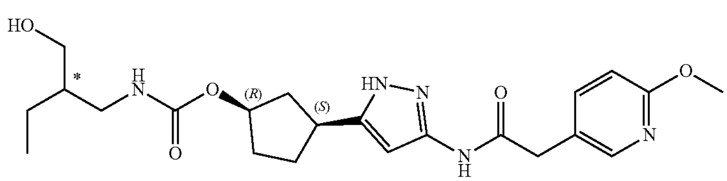 | 446.2 | (1R,3S)-3-(3-{[(6-methoxypyridin-3-yl)acetyl]amino}-1H-pyrazol-5-yl)cyclopentyl [(2ξ)-2-(hydroxymethyl)butyl] carbamate - Isomer B |

TABLE 3-continued

| Example No | Structure | LCMS [M + H]+ | IUPAC Name |
|---|---|---|---|
| 534 | 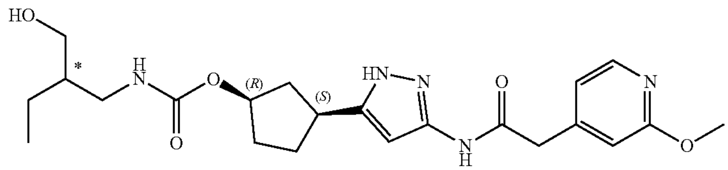 | 446.2 | (1R,3S)-3-(3-{[(2-methoxypyridin-4-yl)acetyl]amino}-1H-pyrazol-5-yl)cyclopentyl [(2ξ)-2-(hydroxymethyl)butyl] carbamate - Isomer A |
| 535 | 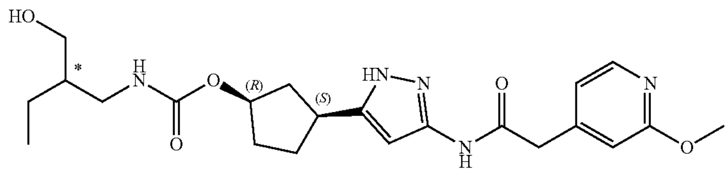 | 446.2 | (1R,3S)-3-(3-{[(2-methoxypyridin-4-yl)acetyl]amino}-1H-pyrazol-5-yl)cyclopentyl [(2ξ)-2-(hydroxymethyl)butyl] carbamate - Isomer B |
| 536 | 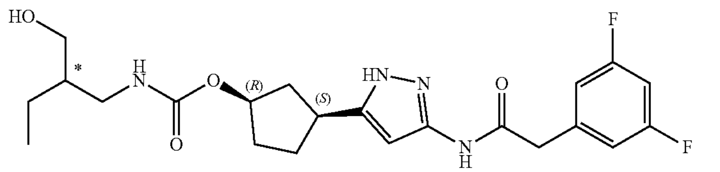 | 451.2 | (1R,3S)-3-(3-{[(3,5-difluorophenyl)acetyl]amino}-1H-pyrazol-5-yl)cyclopentyl [(2ξ)-2-(hydroxymethyl)butyl] carbamate - Isomer A |
| 537 | 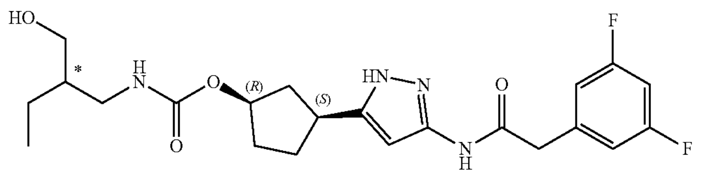 | 451.2 | (1R,3S)-3-(3-{[(3,5-difluorophenyl)acetyl]amino}-1H-pyrazol-5-yl)cyclopentyl [(2ξ)-2-(hydroxymethyl)butyl] carbamate - Isomer B |
| 538 | 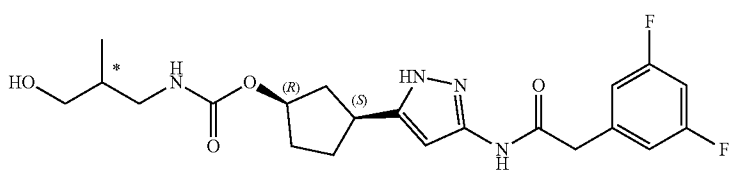 | 437.3 | (1R,3S)-3-(3-{[(3,5-difluorophenyl)acetyl]amino}-1H-pyrazol-5-yl)cyclopentyl [(2ξ)-3-hydroxy-2-methylpropyl]carbamate - Isomer A |
| 539 | 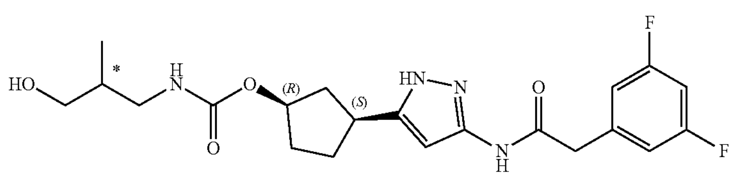 | 437.3 | (1R,3S)-3-(3-{[(3,5-difluorophenyl)acetyl]amino}-1H-pyrazol-5-yl)cyclopentyl [(2ξ)-3-hydroxy-2-methylpropyl]carbamate - Isomer B |
| 540 | 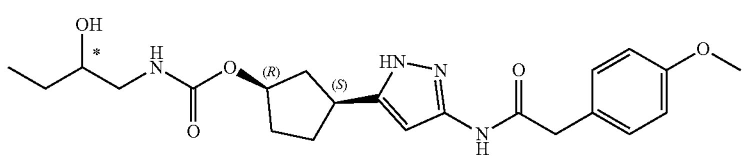 | 431.3 | (1R,3S)-3-(3-{[(4-methoxyphenyl)acetyl]amino}-1H-pyrazol-5-yl)cyclopentyl [(2ξ)-2-hydroxybutyl] carbamate - Isomer A |
| 541 | 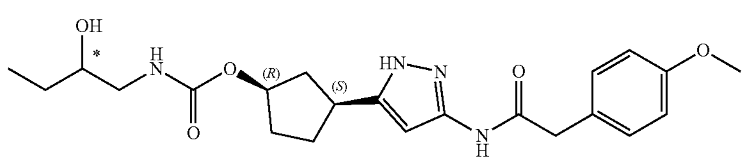 | 431.3 | (1R,3S)-3-(3-{[(4-methoxyphenyl)acetyl]amino}-1H-pyrazol-5-yl)cyclopentyl [(2ξ)-2-hydroxybutyl] carbamate - Isomer B |

TABLE 3-continued

| Example No | Structure | LCMS [M + H]+ | IUPAC Name |
|---|---|---|---|
| 542 | 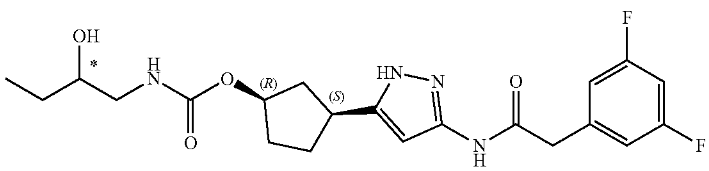 | 437.3 | (1R,3S)-3-(3-{[(3,5-difluorophenyl)acetyl]amino}-1H-pyrazol-5-yl)cyclopentyl [(2ξ)-2-hydroxybutyl] carbamate - Isomer A |
| 543 | 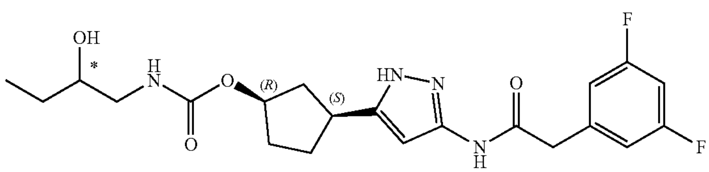 | 437.3 | (1R,3S)-3-(3-{[(3,5-difluorophenyl)acetyl]amino}-1H-pyrazol-5-yl)cyclopentyl [(2ξ)-2-hydroxybutyl] carbamate - Isomer B |
| 544 | 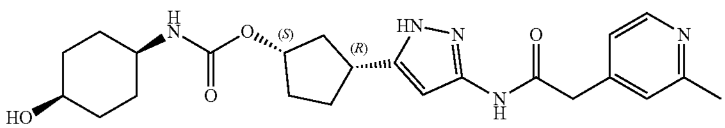 | 442.4 | (1S,3R)-3-(3-{[(2-methylpyridin-4-yl)acetyl]amino}-1H-pyrazol-5-yl)cyclopentyl (cis-4-hydroxycyclohexyl)carbamate |
| 545 | 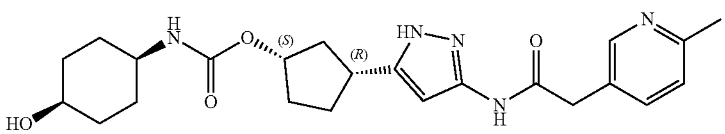 | 442.4 | (1S,3R)-3-(3-{[(6-methylpyridin-3-yl)acetyl]amino}-1H-pyrazol-5-yl)cyclopentyl (cis-4-hydroxycyclohexyl)carbamate |
| 546 | 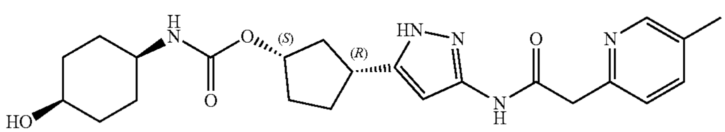 | 442.4 | (1S,3R)-3-(3-{[(5-methylpyridin-2-yl)acetyl]amino}-1H-pyrazol-5-yl)cyclopentyl (cis-4-hydroxycyclohexyl)carbamate |
| 547 | 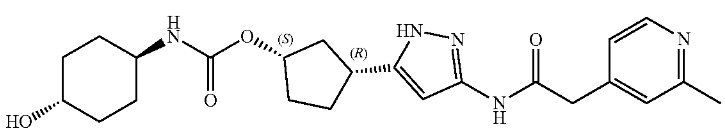 | 442.4 | (1S,3R)-3-(3-{[(2-methylpyridin-4-yl)acetyl]amino}-1H-pyrazol-5-yl)cyclopentyl (trans-4-hydroxycyclohexyl)carbamate |
| 548 | 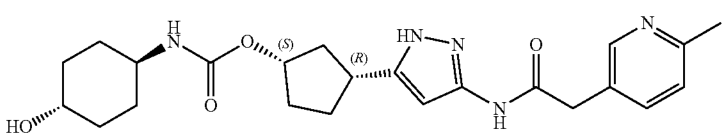 | 442.4 | (1S,3R)-3-(3-{[(6-methylpyridin-3-yl)acetyl]amino}-1H-pyrazol-5-yl)cyclopentyl (trans-4-hydroxycyclohexyl)carbamate |
| 549 | 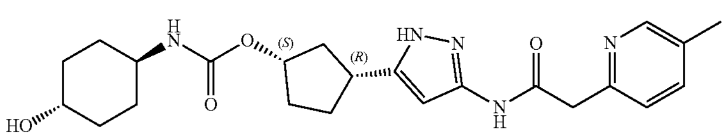 | 442.4 | (1S,3R)-3-(3-{[(5-methylpyridin-2-yl)acetyl]amino}-1H-pyrazol-5-yl)cyclopentyl (trans-4-hydroxycyclohexyl)carbamate |
| 550 | 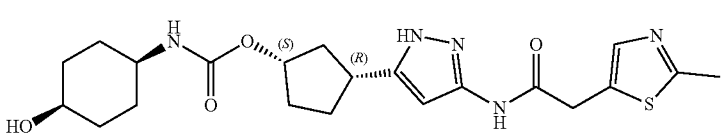 | 448.4 | (1S,3R)-3-(3-{[(2-methyl-1,3-thiazol-5-yl)acetyl]amino}-1H-pyrazol-5-yl)cyclopentyl (cis-4-hydroxycyclohexyl)carbamate |
| 551 | 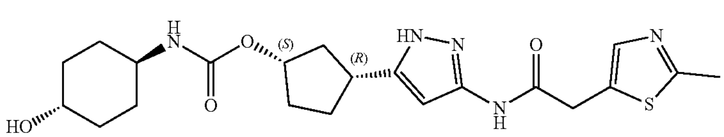 | 448.4 | (1S,3R)-3-(3-{[(2-methyl-1,3-thiazol-5-yl)acetyl]amino}-1H-pyrazol-5-yl)cyclopentyl (trans-4-hydroxycyclohexyl)carbamate |

TABLE 3-continued

| Example No | Structure | LCMS [M + H]+ | IUPAC Name |
|---|---|---|---|
| 552 | 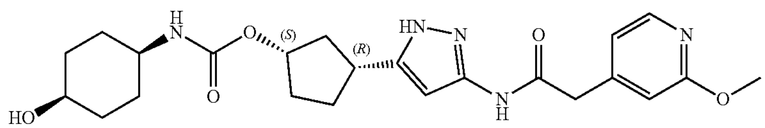 | 458.3 | (1S,3R)-3-(3-{[(2-methoxypyridin-4-yl)acetyl]amino}-1H-pyrazol-5-yl)cyclopentyl (cis-4-hydroxycyclohexyl)carbamate |
| 553 | 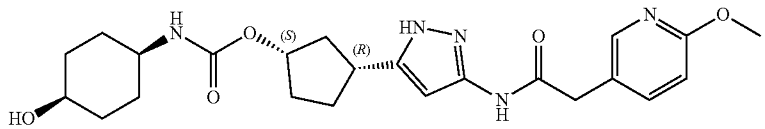 | 458.4 | (1S,3R)-3-(3-{[(6-methoxypyridin-3-yl)acetyl]amino}-1H-pyrazol-5-yl)cyclopentyl (cis-4-hydroxycyclohexyl)carbamate |
| 554 | 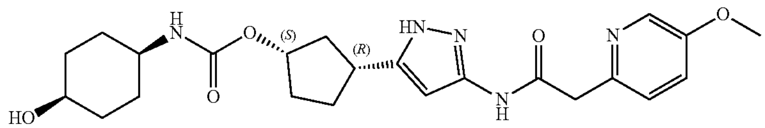 | 458.4 | (1S,3R)-3-(3-{[(5-methoxypyridin-2-yl)acetyl]amino}-1H-pyrazol-5-yl)cyclopentyl (cis-4-hydroxycyclohexyl)carbamate |
| 555 | 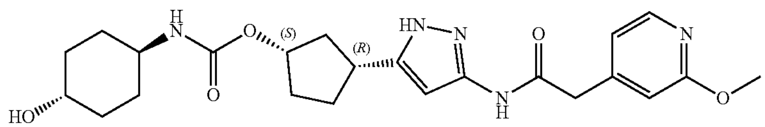 | 458.3 | (1S,3R)-3-(3-{[(2-methoxypyridin-4-yl)acetyl]amino}-1H-pyrazol-5-yl)cyclopentyl (trans-4-hydroxycyclohexyl)carbamate |
| 556 | 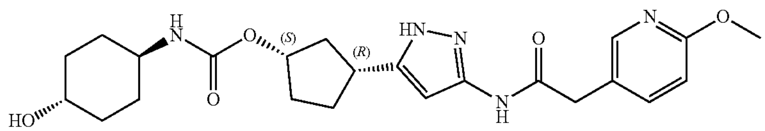 | 458.3 | (1S,3R)-3-(3-{[(6-methoxypyridin-3-yl)acetyl]amino}-1H-pyrazol-5-yl)cyclopentyl (trans-4-hydroxycyclohexyl)carbamate |
| 557 | 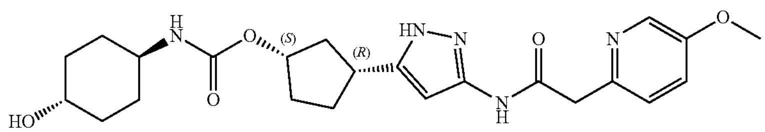 | 458.3 | (1S,3R)-3-(3-{[(5-methoxypyridin-2-yl)acetyl]amino}-1H-pyrazol-5-yl)cyclopentyl (trans-4-hydroxycyclohexyl)carbamate |
| 558 | 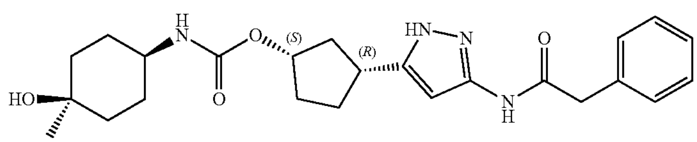 | 441.3 | (1S,3R)-3-{3-[(phenylacetyl)amino]-1H-pyrazol-5-yl}cyclopentyl (cis-4-hydroxy-4-methylcyclohexyl)carbamate |
| 559 | 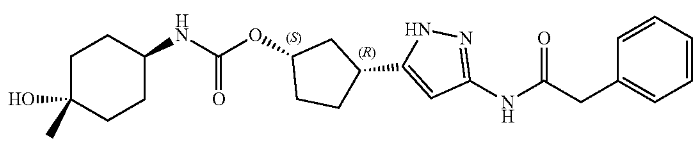 | 441.3 | (1S,3R)-3-{3-[(phenylacetyl)amino]-1H-pyrazol-5-yl}cyclopentyl (trans-4-hydroxy-4-methylcyclohexyl)carbamate |
| 560 | 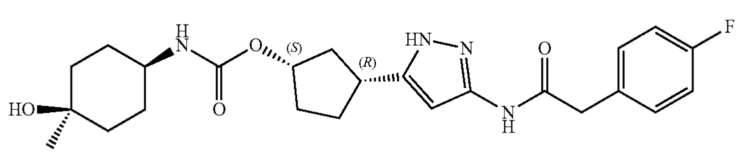 | 459.3 | (1S,3R)-3-(3-{[(4-fluorophenyl)acetyl]amino}-1H-pyrazol-5-yl)cyclopentyl (cis-4-hydroxy-4-methylcyclohexyl)carbamate |
| 561 | 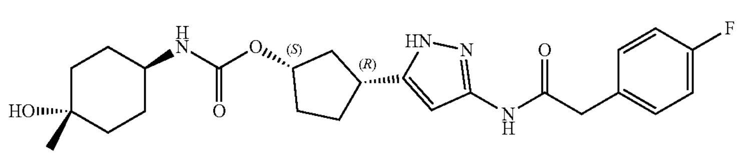 | 459.3 | (1S,3R)-3-(3-{[(4-fluorophenyl)acetyl]amino}-1H-pyrazol-5-yl)cyclopentyl (trans-4-hydroxy-4-methylcyclohexyl)carbamate |

TABLE 3-continued

| Example No | Structure | LCMS [M + H]+ | IUPAC Name |
|---|---|---|---|
| 562 | 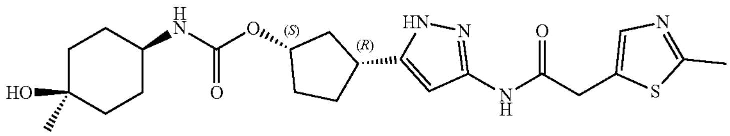 | 462.3 | (1S,3R)-3-(3-{[(2-methyl-1,3-thiazol-5-yl)acetyl]amino}-1H-pyrazol-5-yl)cyclopentyl (cis-4-hydroxy-4-methylcyclohexyl)carbamate |
| 563 | 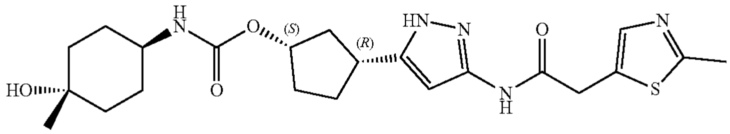 | 462.3 | (1S,3R)-3-(3-{[(2-methyl-1,3-thiazol-5-yl)acetyl]amino}-1H-pyrazol-5-yl)cyclopentyl (trans-4-hydroxy-4-methylcyclohexyl)carbamate |
| 564 | 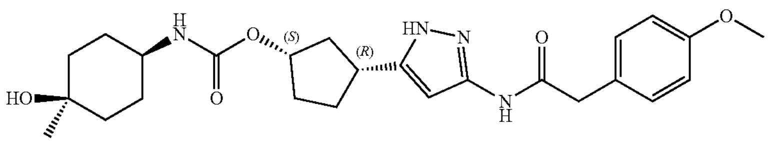 | 471.3 | (1S,3R)-3-(3-{[(4-methoxyphenyl)acetyl]amino}-1H-pyrazol-5-yl)cyclopentyl (cis-4-hydroxy-4-methylcyclohexyl)carbamate |
| 565 | 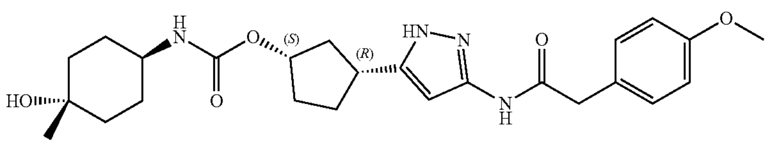 | 471.3 | (1S,3R)-3-(3-{[(4-methoxyphenyl)acetyl]amino}-1H-pyrazol-5-yl)cyclopentyl (trans-4-hydroxy-4-methylcyclohexyl)carbamate |
| 566 | 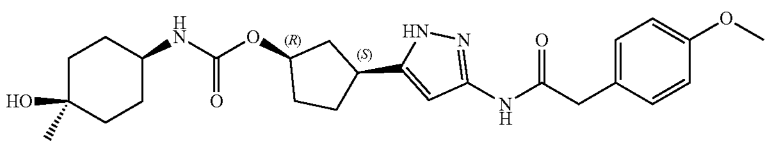 | 471.3 | (1R,3S)-3-(3-{[(4-methoxyphenyl)acetyl]amino}-1H-pyrazol-5-yl)cyclopentyl (cis-4-hydroxy-4-methylcyclohexyl)carbamate |
| 567 | 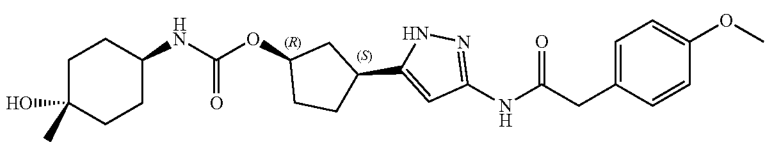 | 471.3 | (1R,3S)-3-(3-{[(4-methoxyphenyl)acetyl]amino}-1H-pyrazol-5-yl)cyclopentyl (trans-4-hydroxy-4-methylcyclohexyl)carbamate |
| 568 | 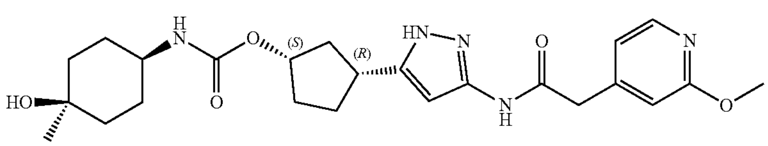 | 472.4 | (1S,3R)-3-(3-{[(2-methoxypyridin-4-yl)acetyl]amino}-1H-pyrazol-5-yl)cyclopentyl (cis-4-hydroxy-4-methylcyclohexyl)carbamate |
| 569 | 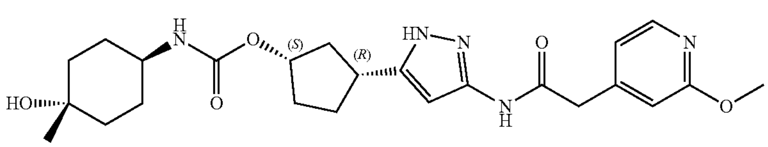 | 472.4 | (1S,3R)-3-(3-{[(2-methoxypyridin-4-yl)acetyl]amino}-1H-pyrazol-5-yl)cyclopentyl (trans-4-hydroxy-4-methylcyclohexyl)carbamate |
| 570 | 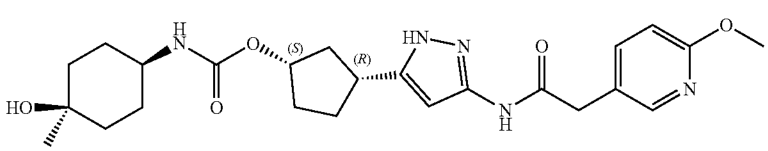 | 472.4 | (1S,3R)-3-(3-{[(6-methoxypyridin-3-yl)acetyl]amino}-1H-pyrazol-5-yl)cyclopentyl (cis-4-hydroxy-4-methylcyclohexyl)carbamate |
| 571 | 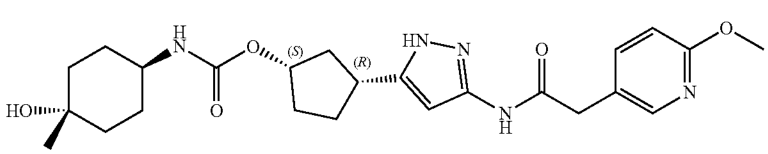 | 472.4 | (1S,3R)-3-(3-{[(6-methoxypyridin-3-yl)acetyl]amino}-1H-pyrazol-5-yl)cyclopentyl (trans-4-hydroxy-4-methylcyclohexyl)carbamate |

TABLE 3-continued

| Example No | Structure | LCMS [M + H]+ | IUPAC Name |
|---|---|---|---|
| 572 | 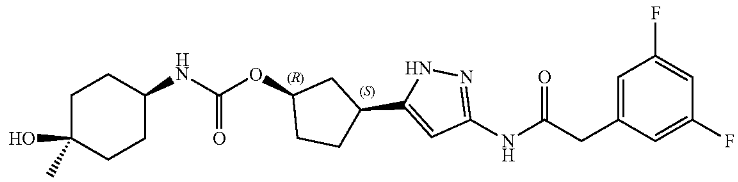 | 477.3 | (1R,3S)-3-(3-{[(3,5-difluorophenyl)acetyl]amino}-1H-pyrazol-5-yl)cyclopentyl (cis-4-hydroxy-4-methylcyclohexyl)carbamate |
| 573 | 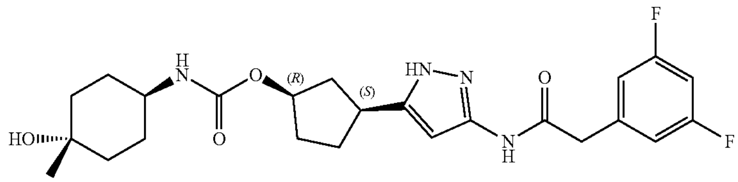 | 477.3 | (1R,3S)-3-(3-{[(3,5-difluorophenyl)acetyl]amino}-1H-pyrazol-5-yl)cyclopentyl (trans-4-hydroxy-4-methylcyclohexyl)carbamate |
| 574 | 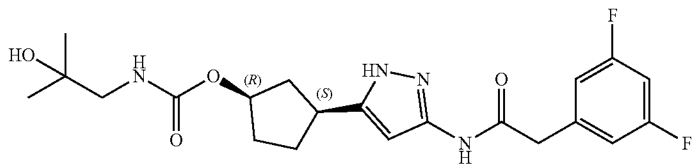 | 437.3 | (1R,3S)-3-(3-{[(3,5-difluorophenyl)acetyl]amino}-1H-pyrazol-5-yl)cyclopentyl (2-hydroxy-2-methylpropyl)carbamate |
| 575 | 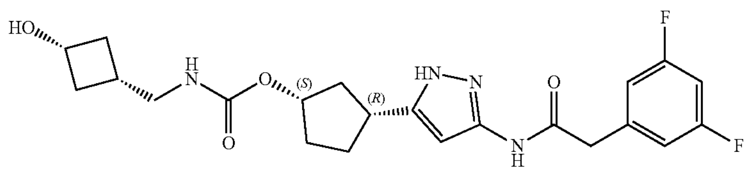 | 449.3 | (1S,3R)-3-(3-{[(3,5-difluorophenyl)acetyl]amino}-1H-pyrazol-5-yl)cyclopentyl [(cis-3-hydroxycyclobutyl)methyl]carbamate |
| 576 | 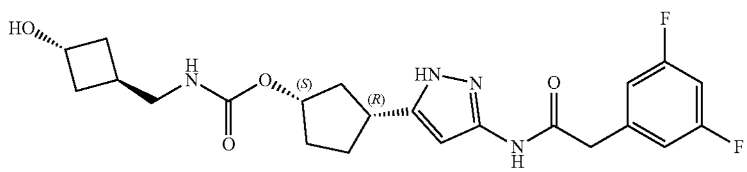 | 449.4 | (1S,3R)-3-(3-{[(3,5-difluorophenyl)acetyl]amino}-1H-pyrazol-5-yl)cyclopentyl [(trans-3-hydroxycyclobutyl)methyl]carbamate |
| 577 | 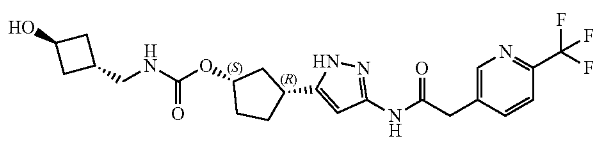 | 482.3 | (1S,3R)-3-[3-({[6-(trifluoromethyl)pyridin-3-yl]acetyl}amino)-1H-pyrazol-5-yl]cyclopentyl[(trans-3-hydroxycyclobutyl)methyl]-carbamate |
| 578 | 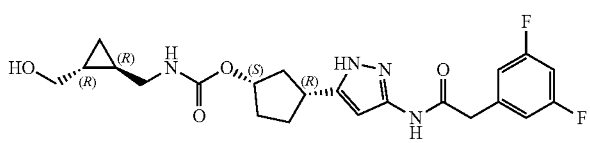 | 449.3 | (1S,3R)-3-(3-{[(3,5-difluorophenyl)acetyl]amino}-1H-pyrazol-5-yl)cyclopentyl {[(1R,2R)-2-(hydroxymethyl)cyclopropyl]-methyl}carbamate |
| 579 | 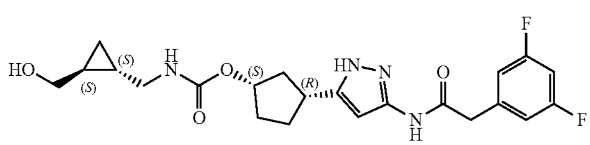 | 449.3 | (1S,3R)-3-(3-{[(3,5-difluorophenyl)acetyl]amino}-1H-pyrazol-5-yl)cyclopentyl {[(1S,2S)-2-(hydroxymethyl)cyclopropyl]-methyl}carbamate |
| 580 | 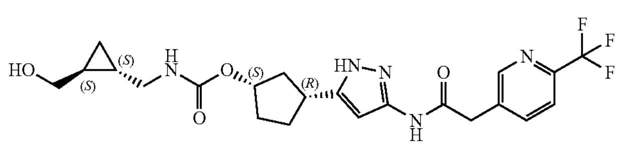 | 482.3 | (1S,3R)-3-[3-({[6-(trifluoromethyl)pyridin-3-yl]acetyl}amino)-1H-pyrazol-5-yl]cyclopentyl {[(1S,2S)-2-(hydroxymethyl)cyclopropyl]-methyl}carbamate |

TABLE 3-continued

| Example No | Structure | LCMS [M + H]+ | IUPAC Name |
|---|---|---|---|
| 581 | 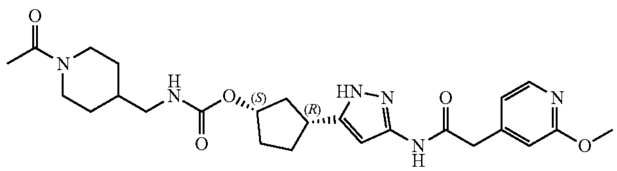 | 499.2 | (1S,3R)-3-(3-{[(2-methoxypyridin-4-yl)acetyl]amino}-1H-pyrazol-5-yl)cyclopentyl[(1-acetylpiperidin-4-yl)methyl]carbamate |
| 582 | 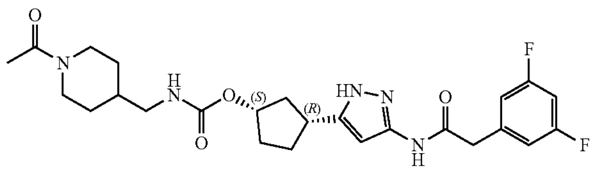 | 504.3 | (1S,3R)-3-(3-{[(3,5-difluorophenyl)acetyl]amino}-1H-pyrazol-5-yl)cyclopentyl [(1-acetylpiperidin-4-yl)methyl]carbamate |
| 583 | 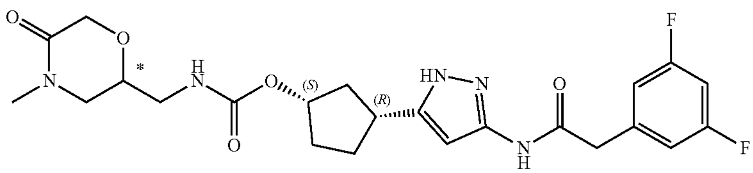 | 492.1 | (1S,3R)-3-(3-{[(3,5-difluorophenyl)acetyl]amino}-1H-pyrazol-5-yl)cyclopentyl {[(2ξ)-4-methyl-5-oxomorpholin-2-yl]methyl}carbamate - Isomer A |
| 584 | 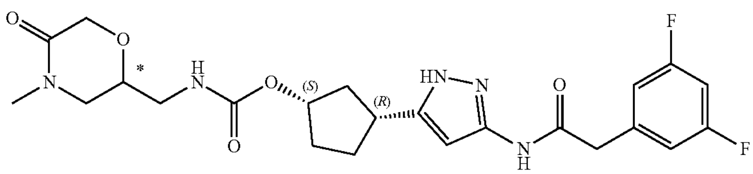 | 492.0 | (1S,3R)-3-(3-{[(3,5-difluorophenyl)acetyl]amino}-1H-pyrazol-5-yl)cyclopentyl {[(2ξ)-4-methyl-5-oxomorpholin-2-yl]methyl}carbamate - Isomer B |
| 585 | 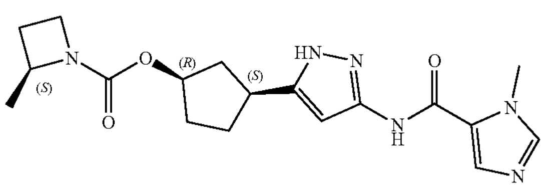 | 372.9 | (1R,3S)-3-(3-{[(1-methyl-1H-imidazol-5-yl)carbonyl]amino}-1H-pyrazol-5-yl)cyclopentyl (2S)-2-methylazetidine-1-carboxylate |
| 586 | 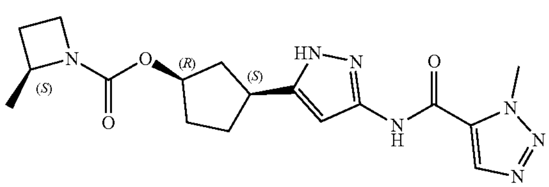 | 374.3 | (1R,3S)-3-(3-{[(1-methyl-1H-1,2,3-triazol-5-yl)carbonyl]amino}-1H-pyrazol-5-yl)cyclopentyl (2S)-2-methylazetidine-1-carboxylate |
| 587 | 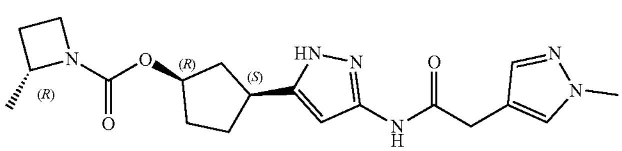 | 386.9 | (1R,3S)-3-(3-{[(1-methyl-1H-pyrazol-4-yl)acetyl]amino}-1H-pyrazol-5-yl)cyclopentyl (2R)-2-methylazetidine-1-carboxylate |
| 588 | 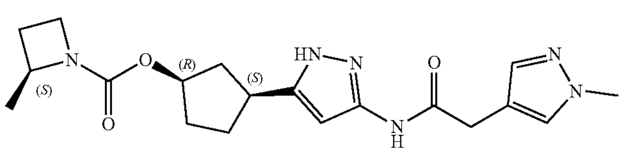 | 408.9 | (1R,3S)-3-(3-{[(1-methyl-1H-pyrazol-4-yl)acetyl]amino}-1H-pyrazol-5-yl)cyclopentyl (2S)-2-methylazetidine-1-carboxylate |
| 589 | 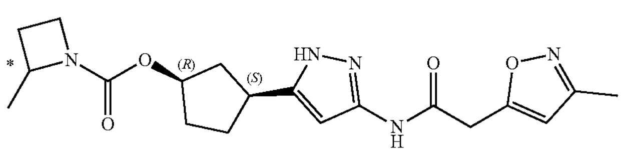 | 388.4 | (1R,3S)-3-(3-{[(3-methyl-1,2-oxazol-5-yl)acetyl]amino}-1H-pyrazol-5-yl)cyclopentyl (2ξ)-2-methylazetidine-1-carboxylate - Isomer A |

TABLE 3-continued

| Example No | Structure | LCMS [M + H]+ | IUPAC Name |
|---|---|---|---|
| 590 | 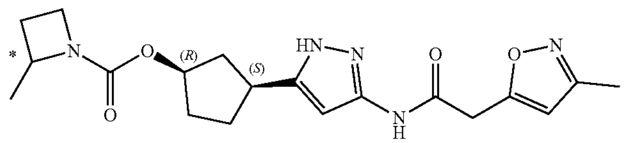 | 388.4 | (1R,3S)-3-(3-{[(3-methyl-1,2-oxazol-5-yl)acetyl]amino}-1H-pyrazol-5-yl)cyclopentyl (2ξ)-2-methylazetidine-1-carboxylate - Isomer B |
| 591 | 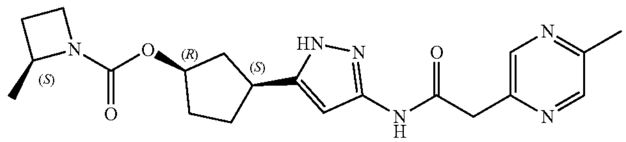 | 399.3 | (1R,3S)-3-(3-{[(5-methylpyrazin-2-yl)acetyl]amino}-1H-pyrazol-5-yl)cyclopentyl (2S)-2-methylazetidine-1-carboxylate |
| 592 | 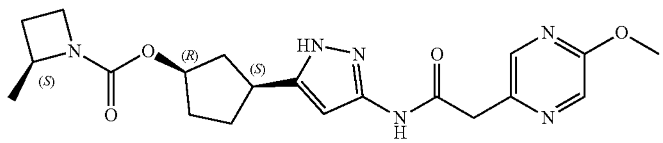 | 415.4 | (1R,3S)-3-(3-{[(5-methoxypyrazin-2-yl)acetyl]amino}-1H-pyrazol-5-yl)cyclopentyl (2S)-2-methylazetidine-1-carboxylate |
| 593 | 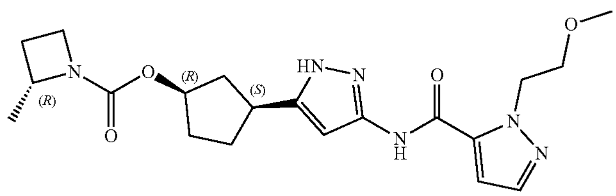 | 417.3 | (1R,3S)-3-[3-({[1-(2-methoxyethyl)-1H-pyrazol-5-yl]carbonyl}amino)-1H-pyrazol-5-yl]cyclopentyl (2R)-2-methylazetidine-1-carboxylate |
| 594 | 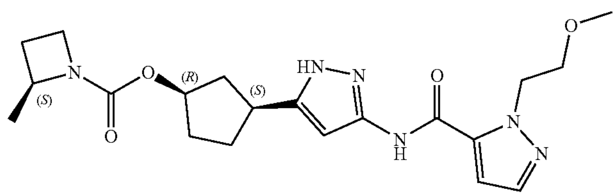 | 417.3 | (1R,3S)-3-[3-({[1-(2-methoxyethyl)-1H-pyrazol-5-yl]carbonyl}amino)-1H-pyrazol-5-yl]cyclopentyl (2S)-2-methylazetidine-1-carboxylate |
| 595 | 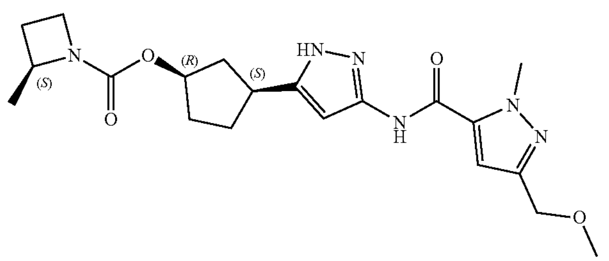 | 417.3 | (1R,3S)-3-[3-({[3-(methoxymethyl)-1-methyl-1H-pyrazol-5-yl]carbonyl}amino)-1H-pyrazol-5-yl]cyclopentyl (2S)-2-methylazetidine-1-carboxylate |
| 596 | 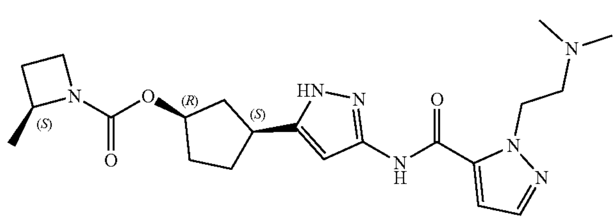 | 430.4 | (1R,3S)-3-{3-[({1-[2-(dimethylamino)ethyl]-1H-pyrazol-5-yl}carbonyl)amino]-1H-pyrazol-5-yl}cyclopentyl (2S)-2-methylazetidine-1-carboxylate |
| 597 | 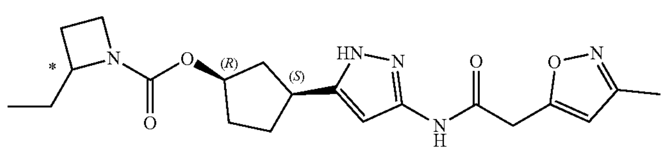 | 402.3 | (1R,3S)-3-(3-{[(3-methyl-1,2-oxazol-5-yl)acetyl]amino}-1H-pyrazol-5-yl)cyclopentyl (2ξ)-2-ethylazetidine-1-carboxylate - Isomer A |

TABLE 3-continued

| Example No | Structure | LCMS [M + H]+ | IUPAC Name |
|---|---|---|---|
| 598 | 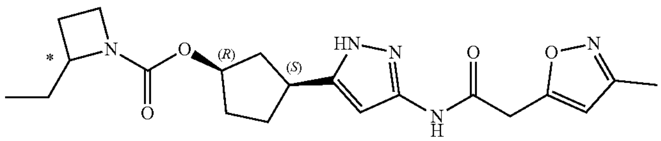 | 402.3 | (1R,3S)-3-(3-{[(3-methyl-1,2-oxazol-5-yl)acetyl]amino}-1H-pyrazol-5-yl)cyclopentyl (2ξ)-2-ethylazetidine-1-carboxylate - Isomer B |
| 599 | 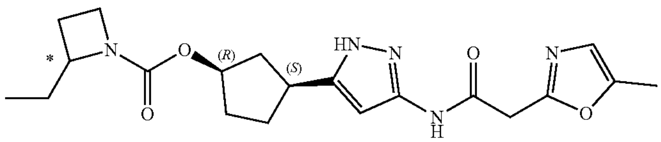 | 402.1 | (1R,3S)-3-(3-{[(5-methyl-1,3-oxazol-2-yl)acetyl]amino}-1H-pyrazol-5-yl)cyclopentyl (2ξ)-2-ethylazetidine-1-carboxylate - Isomer A |
| 600 | 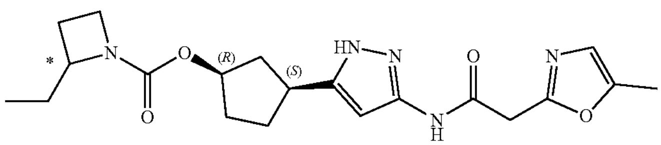 | 402.1 | (1R,3S)-3-(3-{[(5-methyl-1,3-oxazol-2-yl)acetyl]amino}-1H-pyrazol-5-yl)cyclopentyl (2ξ)-2-ethylazetidine-1-carboxylate - Isomer B |
| 601 | 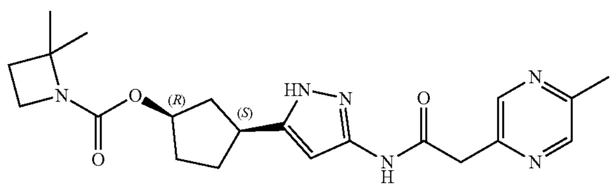 | 413.3 | (1R,3S)-3-(3-{[(5-methylpyrazin-2-yl)acetyl]amino}-1H-pyrazol-5-yl)cyclopentyl 2,2-dimethylazetidine-1-carboxylate |
| 602 | 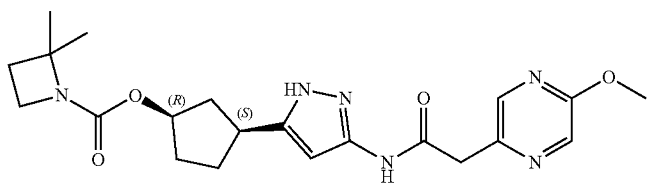 | 429.3 | (1R,3S)-3-(3-{[(5-methoxypyrazin-2-yl)acetyl]amino}-1H-pyrazol-5-yl)cyclopentyl 2,2-dimethylazetidine-1-carboxylate |
| 603 | 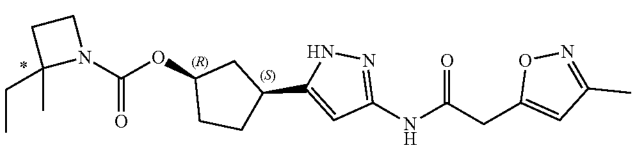 | 416.3 | (1R,3S)-3-(3-{[(3-methyl-1,2-oxazol-5-yl)acetyl]amino}-1H-pyrazol-5-yl)cyclopentyl (2ξ)-2-ethyl-2-methylazetidine-1-carboxylate - Isomer A |
| 604 | 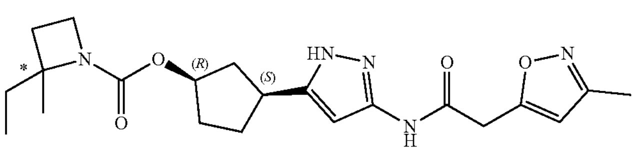 | 416.4 | (1R,3S)-3-(3-{[(3-methyl-1,2-oxazol-5-yl)acetyl]amino}-1H-pyrazol-5-yl)cyclopentyl (2ξ)-2-ethyl-2-methylazetidine-1-carboxylate - Isomer B |
| 605 | 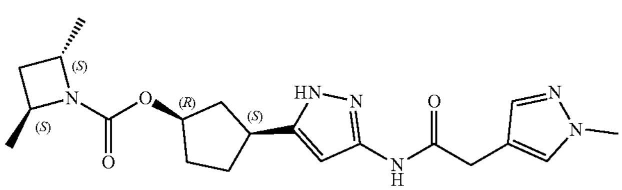 | 401.4 | (1R,3S)-3-(3-{[(1-methyl-1H-pyrazol-4-yl)acetyl]amino}-1H-pyrazol-5-yl)cyclopentyl (2S,4S)-2,4-dimethylazetidine-1-carboxylate |
| 606 | 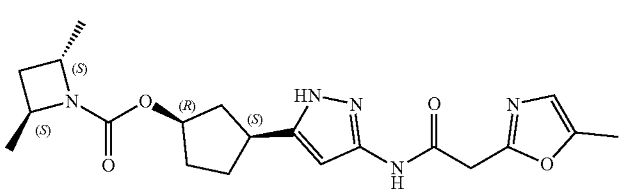 | 402.1 | (1R,3S)-3-(3-{[(5-methyl-1,3-oxazol-2-yl)acetyl]amino}-1H-pyrazol-5-yl)cyclopentyl (2S,4S)-2,4-dimethylazetidine-1-carboxylate |

TABLE 3-continued

| Example No | Structure | LCMS [M + H]+ | IUPAC Name |
|---|---|---|---|
| 607 | 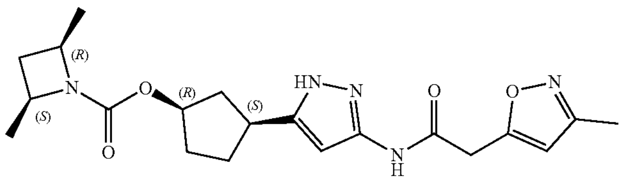 | 402.3 | (1R,3S)-3-(3-{[(3-methyl-1,2-oxazol-5-yl)acetyl]amino}-1H-pyrazol-5-yl)cyclopentyl (2R,4S)-2,4-dimethylazetidine-1-carboxylate |
| 608 | 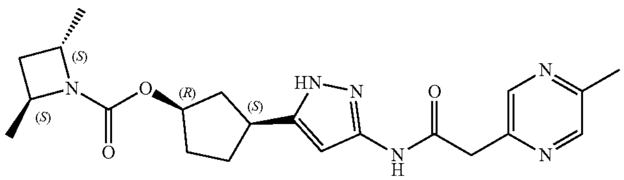 | 413.3 | (1R,3S)-3-(3-{[(5-methylpyrazin-2-yl)acetyl]amino}-1H-pyrazol-5-yl)cyclopentyl (2S,4S)-2,4-dimethylazetidine-1-carboxylate |
| 609 | 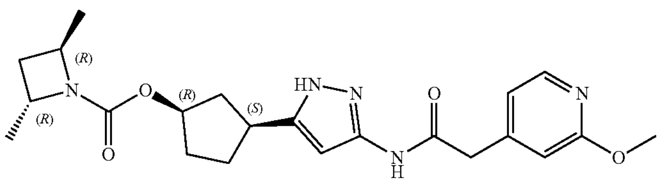 | 428.3 | (1R,3S)-3-(3-{[(2-methoxypyridin-4-yl)acetyl]amino}-1H-pyrazol-5-yl)cyclopentyl (2R,4R)-2,4-dimethylazetidine-1-carboxylate |
| 610 | 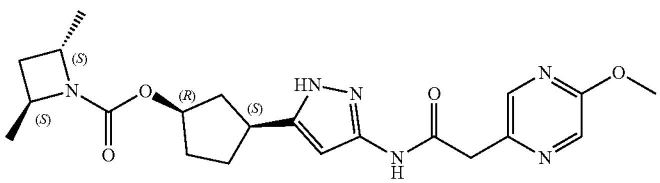 | 429.3 | (1R,3S)-3-(3-{[(5-methoxypyrazin-2-yl)acetyl]amino}-1H-pyrazol-5-yl)cyclopentyl (2S,4S)-2,4-dimethylazetidine-1-carboxylate |
| 611 | 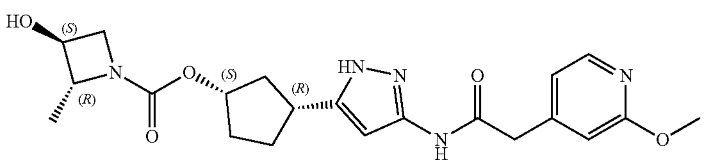 | 430.3 | (1S,3R)-3-(3-{[(2-methoxypyridin-4-yl)acetyl]amino}-1H-pyrazol-5-yl)cyclopentyl (2R,3S)-3-hydroxy-2-methylazetidine-1-carboxylate |
| 612 | 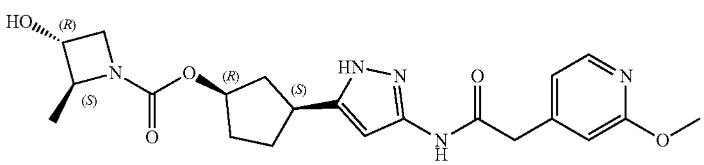 | 430.4 | (1R,3S)-3-(3-{[(2-methoxypyridin-4-yl)acetyl]amino}-1H-pyrazol-5-yl)cyclopentyl (2S,3R)-3-hydroxy-2-methylazetidine-1-carboxylate |
| 613 | 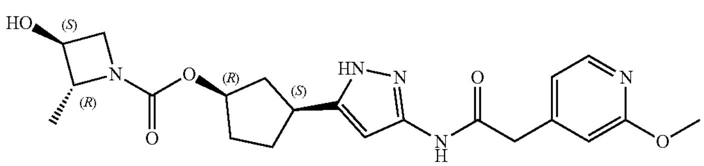 | 430.4 | (1R,3S)-3-(3-{[(2-methoxypyridin-4-yl)acetyl]amino}-1H-pyrazol-5-yl)cyclopentyl (2R,3S)-3-hydroxy-2-methylazetidine-1-carboxylate |
| 614 | 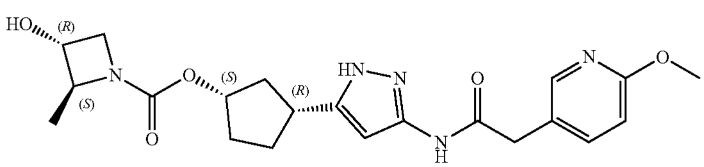 | 430.4 | (1S,3R)-3-(3-{[(6-methoxypyridin-3-yl)acetyl]amino}-1H-pyrazol-5-yl)cyclopentyl (2S,3R)-3-hydroxy-2-methylazetidine-1-carboxylate |

TABLE 3-continued

| Example No | Structure | LCMS [M + H]+ | IUPAC Name |
|---|---|---|---|
| 615 | 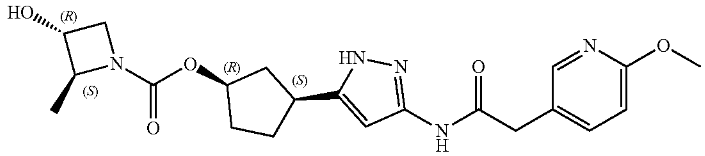 | 430.4 | (1R,3S)-3-(3-{[(6-methoxypyridin-3-yl)acetyl]amino}-1H-pyrazol-5-yl)cyclopentyl (2S,3R)-3-hydroxy-2-methylazetidine-1-carboxylate |
| 616 | 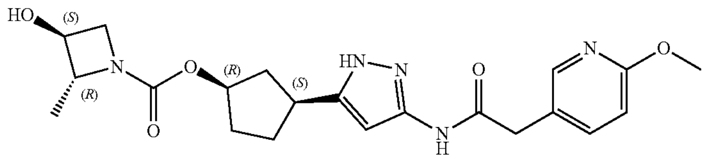 | 430.4 | (1R,3S)-3-(3-{[(6-methoxypyridin-3-yl)acetyl]amino}-1H-pyrazol-5-yl)cyclopentyl (2R,3S)-3-hydroxy-2-methylazetidine-1-carboxylate |
| 617 | 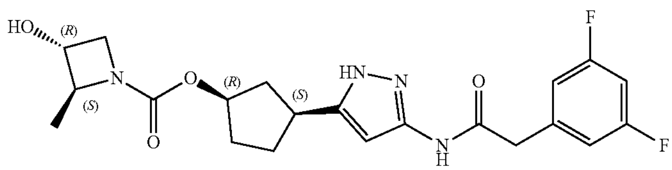 | 435.0 | (1R,3S)-3-(3-{[(3,5-difluorophenyl)acetyl]amino}-1H-pyrazol-5-yl)cyclopentyl (2S,3R)-3-hydroxy-2-methylazetidine-1-carboxylate |
| 618 | 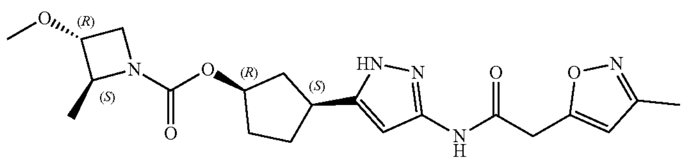 | 418.4 | (1R,3S)-3-(3-{[(3-methyl-1,2-oxazol-5-yl)acetyl]amino}-1H-pyrazol-5-yl)cyclopentyl (2S,3R)-3-methoxy-2-methylazetidine-1-carboxylate |
| 619 | 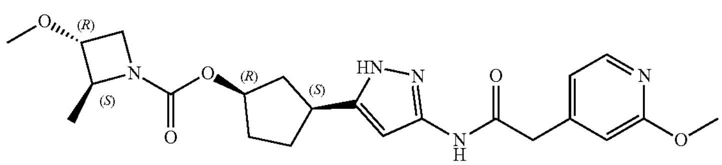 | 443.9 | (1R,3S)-3-(3-{[(2-methoxypyridin-4-yl)acetyl]amino}-1H-pyrazol-5-yl)cyclopentyl (2S,3R)-3-methoxy-2-methylazetidine-1-carboxylate |
| 620 | 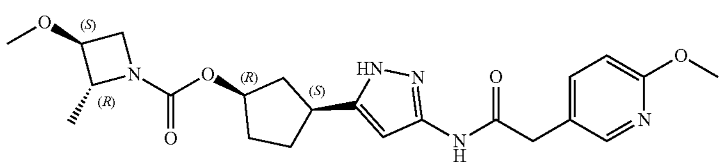 | 444.3 | (1R,3S)-3-(3-{[(6-methoxypyridin-3-yl)acetyl]amino}-1H-pyrazol-5-yl)cyclopentyl (2R,3S)-3-methoxy-2-methylazetidine-1-carboxylate |
| 621 | 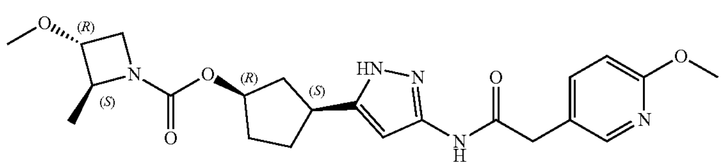 | 443.9 | (1R,3S)-3-(3-{[(6-methoxypyridin-3-yl)acetyl]amino}-1H-pyrazol-5-yl)cyclopentyl (2S,3R)-3-methoxy-2-methylazetidine-1-carboxylate |
| 622 | 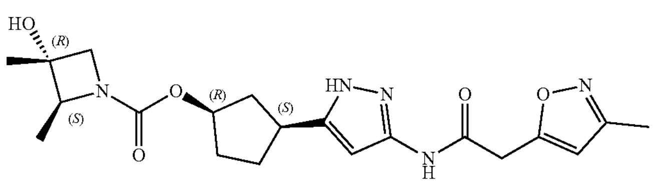 | 418.3 | (1R,3S)-3-(3-{[(3-methyl-1,2-oxazol-5-yl)acetyl]amino}-1H-pyrazol-5-yl)cyclopentyl (2S,3R)-3-hydroxy-2,3-dimethylazetidine-1-carboxylate |
| 623 | 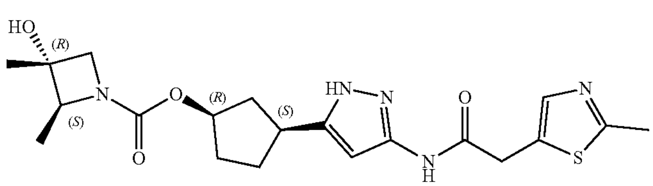 | 434.3 | (1R,3S)-3-(3-{[(2-methyl-1,3-thiazol-5-yl)acetyl]amino}-1H-pyrazol-5-yl)cyclopentyl (2S,3R)-3-hydroxy-2,3-dimethylazetidine-1-carboxylate |

TABLE 3-continued

| Example No | Structure | LCMS [M + H]+ | IUPAC Name |
|---|---|---|---|
| 624 | 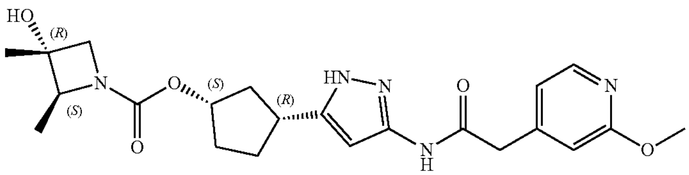 | 444.3 | (1S,3R)-3-(3-{[(2-methoxypyridin-4-yl)acetyl]amino}-1H-pyrazol-5-yl)cyclopentyl (2S,3R)-3-hydroxy-2,3-dimethylazetidine-1-carboxylate |
| 625 | 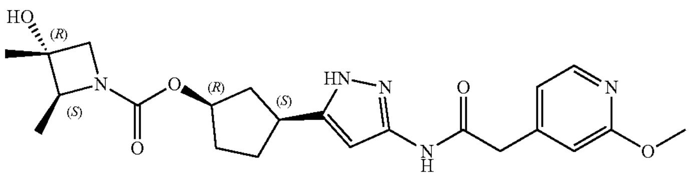 | 444.3 | (1R,3S)-3-(3-{[(2-methoxypyridin-4-yl)acetyl]amino}-1H-pyrazol-5-yl)cyclopentyl (2S,3R)-3-hydroxy-2,3-dimethylazetidine-1-carboxylate |
| 626 | 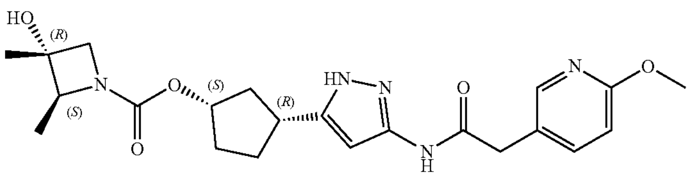 | 444.3 | (1S,3R)-3-(3-{[(6-methoxypyridin-3-yl)acetyl]amino}-1H-pyrazol-5-yl)cyclopentyl (2S,3R)-3-hydroxy-2,3-dimethylazetidine-1-carboxylate |
| 627 | 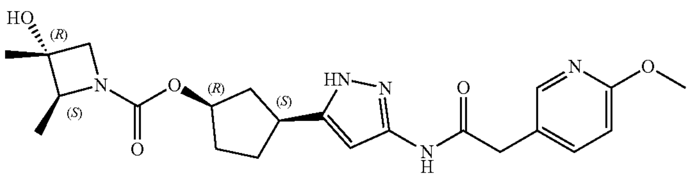 | 444.3 | (1R,3S)-3-(3-{[(6-methoxypyridin-3-yl)acetyl]amino}-1H-pyrazol-5-yl)cyclopentyl (2S,3R)-3-hydroxy-2,3-dimethylazetidine-1-carboxylate |
| 628 | 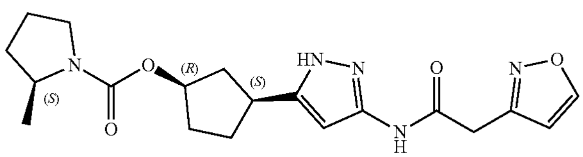 | 388.1 | (1R,3S)-3-{3-[(1,2-oxazol-3-ylacetyl)amino]-1H-pyrazol-5-yl}cyclopentyl (2S)-2-methylpyrrolidine-1-carboxylate |
| 629 | 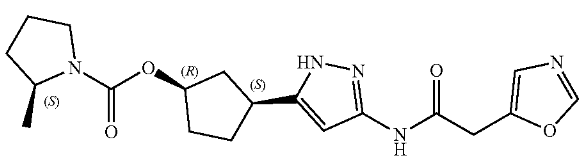 | 388.1 | (1R,3S)-3-{3-[(1,3-oxazol-5-ylacetyl)amino]-1H-pyrazol-5-yl}cyclopentyl (2S)-2-methylpyrrolidine-1-carboxylate |
| 630 | 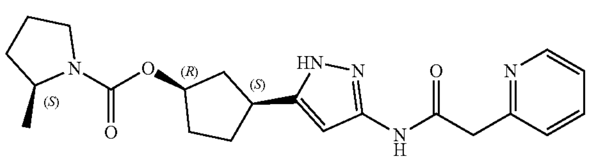 | 398.3 | (1R,3S)-3-{3-[(pyridin-2-ylacetyl)amino]-1H-pyrazol-5-yl}cyclopentyl (2S)-2-methylpyrrolidine-1-carboxylate |
| 631 | 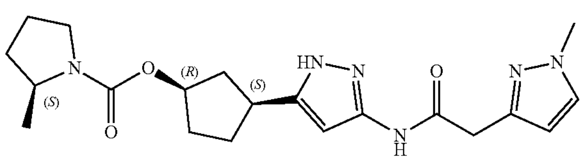 | 401.4 | (1R,3S)-3-(3-{[(1-methyl-1H-pyrazol-3-yl)acetyl]amino}-1H-pyrazol-5-yl)cyclopentyl (2S)-2-methylpyrrolidine-1-carboxylate |
| 632 | 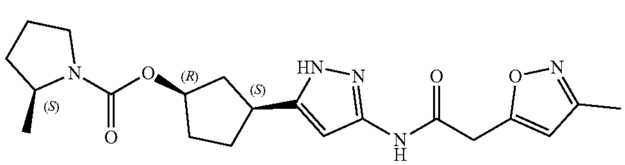 | 402.3 | (1R,3S)-3-(3-{[(3-methyl-1,2-oxazol-5-yl)acetyl]amino}-1H-pyrazol-5-yl)cyclopentyl (2S)-2-methylpyrrolidine-1-carboxylate |

TABLE 3-continued

| Example No | LCMS [M + H]+ | IUPAC Name |
|---|---|---|
| 633 | 401.9 | (1R,3S)-3-(3-{[(3-methyl-1,2-oxazol-5-yl)acetyl]amino}-1H-pyrazol-5-yl)cyclopentyl (2R)-2-methylpyrrolidine-1-carboxylate |
| 634 | 402.1 | (1R,3S)-3-(3-{[(5-methyl-1,2-oxazol-3-yl)acetyl]amino}-1H-pyrazol-5-yl)cyclopentyl (2S)-2-methylpyrrolidine-1-carboxylate |
| 635 | 402.1 | (1R,3S)-3-(3-{[(5-methyl-1,3-oxazol-2-yl)acetyl]amino}-1H-pyrazol-5-yl)cyclopentyl (2S)-2-methylpyrrolidine-1-carboxylate |
| 636 | 402.3 | (1R,3S)-3-(3-{[(4-methyl-1,3-oxazol-2-yl)acetyl]amino}-1H-pyrazol-5-yl)cyclopentyl (2S)-2-methylpyrrolidine-1-carboxylate |
| 637 | 418.4 | (1R,3S)-3-(3-{[(4-methyl-1,3-thiazol-2-yl)acetyl]amino}-1H-pyrazol-5-yl)cyclopentyl (2S)-2-methylpyrrolidine-1-carboxylate |
| 638 | 416.3 | (1R,3S)-3-(3-{[(3-methyl-1,2-oxazol-5-yl)acetyl]amino}-1H-pyrazol-5-yl)cyclopentyl (2S,5S)-2,5-dimethylpyrrolidine-1-carboxylate |
| 639 | 415.4 | (1R,3S)-3-(3-{[(1-methyl-1H-pyrazol-3-yl)acetyl]amino}-1H-pyrazol-5-yl)cyclopentyl 2,2-dimethylpyrrolidine-1-carboxylate |
| 640 | 415.4 | (1R,3S)-3-(3-{[(3-methyl-1,2-oxazol-5-yl)acetyl]amino}-1H-pyrazol-5-yl)cyclopentyl (2S)-2-methylpiperidine-1-carboxylate |
| 641 | 416.4 | (1R,3S)-3-(3-{[(3-methyl-1,2-oxazol-5-yl)acetyl]amino}-1H-pyrazol-5-yl)cyclopentyl (2R)-2-methylpiperidine-1-carboxylate |

TABLE 3-continued

| Example No | Structure | LCMS [M + H]+ | IUPAC Name |
|---|---|---|---|
| 642 | 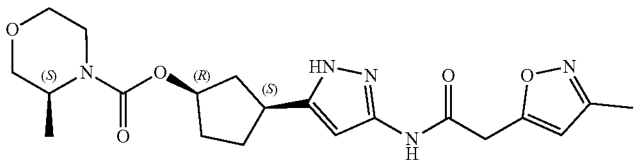 | 418.4 | (1R,3S)-3-(3-{[(3-methyl-1,2-oxazol-5-yl)acetyl]amino}-1H-pyrazol-5-yl)cyclopentyl (3S)-3-methylmorpholine-4-carboxylate |
| 643 | 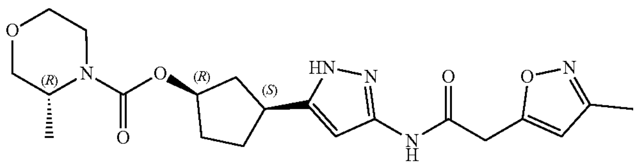 | 418.4 | (1R,3S)-3-(3-{[(3-methyl-1,2-oxazol-5-yl)acetyl]amino}-1H-pyrazol-5-yl)cyclopentyl (3R)-3-methylmorpholine-4-carboxylate |
| 644 | 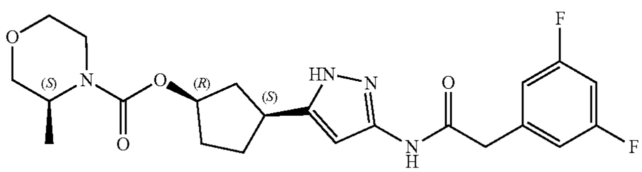 | 449.2 | (1R,3S)-3-(3-{[(3,5-difluorophenyl)acetyl]amino}-1H-pyrazol-5-yl)cyclopentyl (3S)-3-methylmorpholine-4-carboxylate |
| 645 | 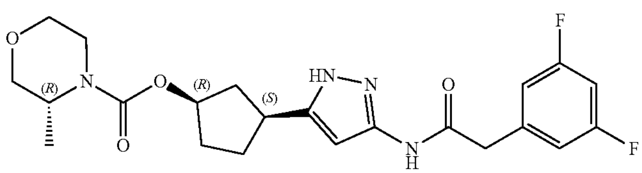 | 449.2 | (1R,3S)-3-(3-{[(3,5-difluorophenyl)acetyl]amino}-1H-pyrazol-5-yl)cyclopentyl (3R)-3-methylmorpholine-4-carboxylate |
| 646 | 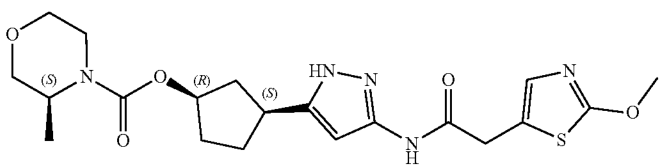 | 450.1 | (1R,3S)-3-(3-{[(2-methoxy-1,3-thiazol-5-yl)acetyl]amino}-1H-pyrazol-5-yl)cyclopentyl (3S)-3-methylmorpholine-4-carboxylate |
| 647 | 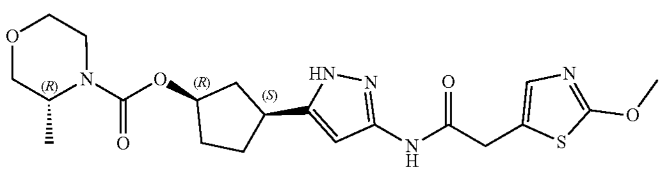 | 450.3 | (1R,3S)-3-(3-{[(2-methoxy-1,3-thiazol-5-yl)acetyl]amino}-1H-pyrazol-5-yl)cyclopentyl (3R)-3-methylmorpholine-4-carboxylate |
| 648 | 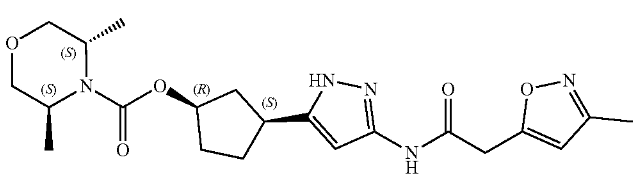 | 432.3 | (1R,3S)-3-(3-{[(3-methyl-1,2-oxazol-5-yl)acetyl]amino}-1H-pyrazol-5-yl)cyclopentyl (3S,5S)-3,5-dimethylmorpholine-4-carboxylate |
| 649 | 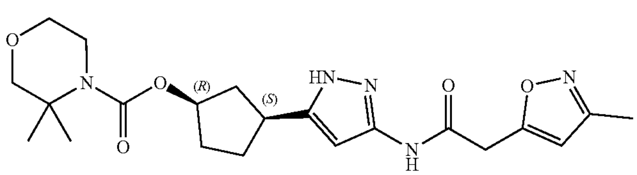 | 432.3 | (1R,3S)-3-(3-{[(3-methyl-1,2-oxazol-5-yl)acetyl]amino}-1H-pyrazol-5-yl)cyclopentyl 3,3-dimethylmorpholine-4-carboxylate |

Biochemical Assays

Cdk2/Cyclin E1 Full Length Mobility Shift Assay

The purpose of CDK2/Cyclin E1 assay is to evaluate the inhibition (% inhibition, $K_{iapp}$ and $K_i$ values) of small molecule inhibitors by using a fluorescence-based microfluidic mobility shift assay. CDK2/Cyclin E1 full length catalyzes the production of ADP from ATP that accompanies the phosphoryl transfer to the substrate peptide FL-Peptide-18 (5-FAM-QSPKKG-CONH$_2$, CPC Scientific, Sunnyvale, Calif.) (SEQ ID NO:1). The mobility shift assay electrophoretically separates the fluorescently labeled peptides (substrate and phosphorylated product) following the kinase reaction. Both substrate and product are measured and the ratio of these values is used to generate % conversion of substrate to product by the LabChip EZ Reader. Wild-type CDK2/wild-type full length Cyclin E1 enzyme complex was produced in-house (baculoviral expression, LJIC-2080/LJIC-2103) and phosphorylated by CDK7/Cyclin H1/Mat1 enzyme complex with CDK2:CDK7 ratio of 50:1 (concentration mg/mL) in the presence of 10 mM MgCl$_2$ and 5 mM ATP at room temperature for one hour. Typical reaction solutions (50 µL final reaction volume) contained 2% DMSO (±inhibitor), 4 mM MgCl$_2$, 1 mM DTT, 150 µM ATP (ATP $K_m$=67.4 µM), 0.005% Tween-20, 3 µM FL-Peptide-18, and 0.36 nM (catalytically competent active site) phosphorylated wild-type full length CDK2/Cyclin E1 enzyme complex in 25 mM HEPES buffer at pH 7.15. The assay was initiated with the addition of ATP, following a fifteen minutes pre-incubation of enzyme and inhibitor at room temperature in the reaction mixture. The reaction was stopped after 45 minutes at room temperature by the addition of 50 µL of 80 mM EDTA. The $K_i$ value was determined from the fit of the data to the Morrison tight-binding competitive inhibition equation with the enzyme concentration as a variable[1, 2].

GSK3beta (GSK3β) Mobility Shift Assay

The purpose of GSK3β assay is to evaluate the inhibition (% inhibition, $K_{iapp}$ and $K_i$ values) of small molecule inhibitors by using a fluorescence-based microfluidic mobility shift assay. GSK3β catalyzes the production of ADP from ATP that accompanies the phosphoryl transfer to the substrate peptide FL-Peptide-15 (5-FAM-KRREILSRRPpSYR-COOH, CPC Scientific, Sunnyvale, Calif.) (SEQ ID NO:2). The mobility shift assay electrophoretically separates the fluorescently labeled peptides (substrate and phosphorylated product) following the kinase reaction. Both substrate and product are measured and the ratio of these values is used to generate % conversion of substrate to product by the LabChip EZ Reader. Active GSK3β (H350L) was purchased from Upstate/Millipore. Typical reaction solutions (50 µL final reaction volume) contained 2% DMSO (±inhibitor), 4 mM MgCl$_2$, 1 mM DTT, 40 µM ATP (ATP $K_m$=9.43 µM), 0.005% Tween-20, 2 µM FL-Peptide-15, and 0.6 nM GSK3β in 25 mM HEPES buffer at pH 7.5. The assay was initiated with the addition of ATP, following 15 minutes pre-incubation of enzyme and inhibitor at room temperature in the reaction mixture. The reaction was stopped after 30 minutes at room temperature by the addition of 50 µL of 80 mM EDTA. The $K_i$ value was determined from the fit of the data to the Morrison tight-binding competitive inhibition equation with the enzyme concentration as a variable. See Morrison, J. F. (1969) Kinetics of the reversible inhibition of enzyme-catalysed reactions by tight-binding inhibitors, *Biochimica et biophysica acta* 185, 269-286; Murphy, D. J. (2004) Determination of accurate KI values for tight-binding enzyme inhibitors: an in silico study of experimental error and assay design, *Analytical biochemistry* 327, 61-67.

CDK4/Cyclin D$_1$ Mobility Shift Assay

The purpose CDK4/Cyclin D$_1$ assay is to evaluate the inhibition (% inhibition, $K_{iapp}$ and $K_i$ values) in the presence of small molecule inhibitors by using a fluorescence based microfluidic mobility shift assay. CDK4/Cyclin D$_3$ catalyses the production of ADP from ATP that accompanies the phosphoryl transfer to the substrate peptide 5-FAM-Dyrktide (5-FAM-RRRFRPASPLRGPPK) (SEQ ID NO:3). The mobility shift assay electrophoretically separates the fluorescently labelled peptides (substrate and phosphorylated product) following the kinase reaction. Both substrate and product are measured and the ratio of these values is used to generate % conversion of substrate to product by the LabChip EZ Reader. Typical reaction solutions contained 2% DMSO (±inhibitor), 10 mM MgCl$_2$, 1 mM DTT, 3.5 mM ATP, 0.005% TW-20, 3 µM 5-FAM-Dyrktide, 3 nM (active sites) activated CDK4/Cyclin D$_1$ in 40 mM HEPES buffer at pH 7.5.

Inhibitor $K_i$ determinations for activated CDK4/Cyclin D$_1$ (2007 E1/2008+PO4) were initiated with the addition of ATP (50 µL final reaction volume), following an eighteen minute pre-incubation of enzyme and inhibitor at 22° C. in the reaction mix. The reaction was stopped after 195 minutes by the addition of 50 µL of 30 mM EDTA. $K_i$ determinations were made from a plot of the fractional velocity as a function of inhibitor concentration fit to the Morrison equation with the enzyme concentration as a variable.

CDK6/Cyclin D$_3$ Mobility Shift Assay

The purpose of the CDK6/Cyclin D$_3$ assay is to evaluate the inhibition (% inhibition, $K_{iapp}$ and $K_i$ values) in the presence of small molecule inhibitors by using a fluorescence based microfluidic mobility shift assay. CDK6/Cyclin D$_3$ catalyses the production of ADP from ATP that accompanies the phosphoryl transfer to the substrate peptide 5-FAM-Dyrktide (5-FAM-RRRFRPASPLRGPPK) (SEQ ID NO:3). The mobility shift assay electrophoretically separates the fluorescently labelled peptides (substrate and phosphorylated product) following the kinase reaction. Both substrate and product are measured and the ratio of these values is used to generate % conversion of substrate to product by the LabChip EZ Reader. Typical reaction solutions contained 2% DMSO (±inhibitor), 2% glycerol, 10 mM MgCl$_2$, 1 mM DTT, 3.5 mM ATP, 0.005% Tween 20 (TW-20), 3 µM 5-FAM-Dyrktide, 4 nM (active sites) activated CDK6/Cyclin D$_3$ in 40 mM HEPES buffer at pH 7.5.

Inhibitor $K_i$ determinations for activated CDK6/Cyclin D$_3$ (LJIC-2009G1/2010+PO$_4$) were initiated with the addition of ATP (50 µL final reaction volume), following an eighteen minute pre-incubation of enzyme and inhibitor at 22° C. in the reaction mix. The reaction was stopped after 95 minutes by the addition of 50 µL of 30 mM EDTA. $K_i$ determinations were made from a plot of the fractional velocity as a function of inhibitor concentration fit to the Morrison equation with the enzyme concentration as a variable.

For fitting tight-binding inhibitor data generated by CDK4 and CDK6 mobility shift assays, equations and principles are derived from Morrison, J. F. (1969) Kinetics of the reversible inhibition of enzyme-catalysed reactions by tight-binding inhibitors, *Biochimica et biophysica acta* 185, 269-286; and Murphy, D. J. (2004) and Determination of accurate K$_i$ values for tight-binding enzyme inhibitors: an in silico study of experimental error and assay design, *Analytical biochemistry* 327, 61-67.

Biological Activity Data

Biological activity data for representative compounds of the invention are provided in Table 4 below.

TABLE 4

| Example No. | CDK2/cyclin $E_1$ Ki (nM) | GSK3β Ki (nM) |
| --- | --- | --- |
| 1 | 0.55 | 26.18 |
| 2 | 0.31 | 40.43 |
| 3 | 0.34 | 10.04 |
| 4 | 0.10 | 109.99 |
| 5 | 0.40 | 39.40 |
| 6 | 0.38 | 32.29 |
| 7 | 0.61 | |
| 8 | 0.50 | 666.56 |
| 9 | 1.14 | >95.31 |
| 10 | 0.25 | 100.53 |
| 11 | 0.32 | 36.21 |
| 12 | 0.13 | 4.86 |
| 13 | 1.16 | 537.81 |
| 14 | 0.27 | 293.53 |
| 15 | 0.17 | 29.30 |
| 16 | 0.37 | 51.67 |
| 17 | 0.33 | 65.76 |
| 18 | 0.17 | |
| 19 | 0.17 | 20.83 |
| 20 | 0.21 | 27.85 |
| 21 | 0.25 | 4.20 |
| 22 | 0.23 | >190.72 |
| 23 | 0.11 | 2.45 |
| 24 | 0.26 | 20.55 |
| 25 | 2.70 | 135.07 |
| 26 | 0.21 | 13.69 |
| 27 | 0.24 | 3.57 |
| 28 | 0.18 | 4.50 |
| 29 | 0.16 | 19.73 |
| 30 | 0.16 | 20.55 |
| 31 | 0.16 | 45.12 |
| 32 | 0.36 | 35.67 |
| 33 | 0.17 | 26.35 |
| 34 | 0.33 | 31.21 |
| 35 | 0.22 | 12.49 |
| 36 | 0.17 | 21.26 |
| 37 | 0.19 | 23.39 |
| 38 | 0.18 | 69.70 |
| 39 | 0.14 | 23.95 |
| 40 | 0.24 | 64.47 |
| 41 | 0.20 | 342.89 |
| 42 | 0.05 | 34.42 |
| 43 | 0.04 | 45.43 |
| 44 | 0.21 | 47.75 |
| 45 | 0.11 | 61.35 |
| 46 | 0.18 | 20.56 |
| 47 | 0.11 | 10.16 |
| 48 | 0.17 | 9.58 |
| 49 | 0.19 | |
| 50 | 0.17 | 116.87 |
| 51 | 0.20 | 54.01 |
| 52 | 0.20 | 10.91 |
| 53 | 0.10 | 45.70 |
| 54 | 0.24 | 9.25 |
| 55 | 0.10 | 10.37 |
| 56 | 0.25 | 42.81 |
| 57 | 3.54 | |
| 58 | 0.21 | 9.86 |
| 59 | 0.15 | 2.89 |
| 60 | 0.33 | 92.52 |
| 61 | 0.11 | 42.27 |
| 62 | 0.21 | 24.01 |
| 63 | 1.25 | |
| 64 | 0.14 | 18.73 |
| 65 | 2.21 | |
| 66 | 0.17 | 17.88 |
| 67 | 1.50 | |
| 68 | 0.36 | 16.30 |
| 69 | 4.26 | |
| 70 | 0.35 | 31.34 |
| 71 | 1.01 | 33.82 |
| 72 | 0.15 | 12.81 |
| 73 | 2.31 | |
| 74 | 0.30 | 13.21 |
| 75 | 0.26 | 9.59 |
| 76 | 0.10 | 4.96 |
| 77 | 0.39 | 19.72 |
| 78 | 0.15 | 8.90 |
| 79 | 0.54 | 16.46 |
| 80 | 0.15 | 8.85 |
| 81 | 1.48 | 32.94 |
| 82 | 0.19 | 12.61 |
| 83 | 0.69 | 33.29 |
| 84 | 0.10 | 12.03 |
| 85 | 1.06 | |
| 86 | 0.25 | 12.89 |
| 87 | 1.32 | |
| 88 | 0.15 | |
| 89 | 0.85 | |
| 90 | 0.23 | 2.36 |
| 91 | 0.09 | 28.14 |
| 92 | 0.10 | 16.59 |
| 93 | 0.22 | 7.64 |
| 94 | 0.15 | |
| 95 | 0.25 | 32.23 |
| 96 | 2.05 | |
| 97 | 0.39 | 18.00 |
| 98 | 0.33 | 21.59 |
| 99 | 0.09 | |
| 100 | 0.43 | 41.69 |
| 101 | 0.28 | 20.91 |
| 102 | 0.39 | 9.90 |
| 103 | 1.37 | >47.63 |
| 104 | 0.17 | >47.63 |
| 105 | 0.47 | >47.63 |
| 106 | 0.76 | |
| 107 | 0.19 | 27.09 |
| 108 | 0.15 | 38.75 |
| 109 | 0.68 | 39.20 |
| 110 | 0.29 | |
| 111 | 0.38 | 771.75 |
| 112 | 0.15 | 40.19 |
| 113 | 0.16 | 11.10 |
| 114 | 0.19 | 5.65 |
| 115 | 0.23 | |
| 116 | 0.13 | 8.86 |
| 117 | 0.14 | 15.91 |
| 118 | 0.22 | 17.78 |
| 119 | 0.13 | 19.28 |
| 120 | 0.09 | 34.89 |
| 121 | 0.08 | 19.36 |
| 122 | 0.22 | 12.73 |
| 123 | 0.13 | 8.87 |
| 124 | 0.19 | 80.65 |
| 125 | 0.34 | |
| 126 | 0.27 | 26.56 |
| 127 | 0.23 | 20.12 |
| 128 | 0.15 | 55.36 |
| 129 | 0.20 | 31.57 |
| 130 | 0.25 | |
| 131 | 0.20 | |
| 132 | 0.19 | |
| 133 | 0.11 | 7.00 |
| 134 | 0.12 | 7.12 |
| 135 | 0.19 | 11.72 |
| 136 | 0.22 | 8.22 |
| 137 | 0.09 | 6.07 |
| 138 | 0.23 | 7.06 |
| 139 | 0.21 | 8.48 |
| 140 | 0.19 | 15.27 |
| 141 | 0.08 | 5.75 |
| 142 | 0.22 | 17.74 |
| 143 | 0.25 | 15.82 |
| 144 | 0.10 | 1.26 |
| 145 | 0.12 | 0.95 |
| 146 | 0.07 | 3.47 |
| 147 | 0.25 | 6.87 |
| 148 | 0.24 | 5.57 |
| 149 | 0.06 | 5.58 |

TABLE 4-continued

| Example No. | CDK2/cyclin $E_1$ Ki (nM) | GSK3β Ki (nM) |
| --- | --- | --- |
| 150 | 0.25 | 8.35 |
| 151 | 0.15 | 3.89 |
| 152 | 1.06 | |
| 153 | 0.22 | 9.15 |
| 154 | 1.77 | |
| 155 | 0.13 | 1.63 |
| 156 | 2.21 | |
| 157 | 1.86 | |
| 158 | 0.17 | 0.78 |
| 159 | 3.63 | |
| 160 | 0.15 | 1.72 |
| 161 | 0.15 | 5.93 |
| 162 | 3.01 | |
| 163 | 0.32 | 16.64 |
| 164 | 0.72 | 44.74 |
| 165 | 2.28 | |
| 166 | 0.40 | 24.29 |
| 167 | 1.40 | 33.85 |
| 168 | 0.36 | 25.84 |
| 169 | 1.63 | 29.63 |
| 170 | 1.37 | >190.72 |
| 171 | 1.73 | 18.22 |
| 172 | 1.20 | 101.69 |
| 173 | 2.29 | >190.72 |
| 174 | 3.00 | >95.33 |
| 175 | 0.82 | 39.66 |
| 176 | 2.50 | 46.08 |
| 177 | 0.43 | 19.04 |
| 178 | 1.10 | 21.38 |
| 179 | 0.54 | 13.50 |
| 180 | 0.81 | >95.33 |
| 181 | 3.91 | >190.72 |
| 182 | 0.82 | 90.62 |
| 183 | 3.68 | >95.33 |
| 184 | 1.35 | >95.33 |
| 185 | 0.71 | 13.02 |
| 186 | 1.03 | 9.64 |
| 187 | 4.59 | 23.93 |
| 188 | 0.44 | 9.32 |
| 189 | 0.38 | 11.41 |
| 190 | 0.81 | 26.12 |
| 191 | 3.33 | |
| 192 | 0.70 | >190.72 |
| 193 | 0.41 | |
| 194 | 0.80 | |
| 195 | 4.39 | |
| 196 | 1.44 | |
| 197 | 0.49 | >190.72 |
| 198 | 0.28 | 52.14 |
| 199 | 3.45 | |
| 200 | 2.87 | |
| 201 | 1.91 | |
| 202 | 1.85 | |
| 203 | 0.29 | 34.19 |
| 204 | 1.13 | |
| 205 | 0.76 | 97.69 |
| 206 | 1.22 | >95.33 |
| 207 | 0.66 | |
| 208 | 3.18 | |
| 209 | 1.21 | |
| 210 | 3.80 | |
| 211 | 4.87 | |
| 212 | 0.67 | 77.19 |
| 213 | 0.32 | 183.00 |
| 214 | 0.37 | 131.31 |
| 215 | 1.26 | |
| 216 | 0.86 | 28.16 |
| 217 | 2.22 | |
| 218 | 2.09 | 30.64 |
| 219 | 3.81 | |
| 220 | 3.26 | |
| 221 | 1.73 | |
| 222 | 2.93 | |
| 223 | 2.33 | |
| 224 | 0.31 | |
| 225 | 2.67 | |
| 226 | 3.72 | 131.65 |
| 227 | 1.21 | 18.92 |
| 228 | 1.84 | |
| 229 | 2.06 | |
| 230 | 1.55 | 48.59 |
| 231 | 1.18 | 15.57 |
| 232 | 1.54 | 34.13 |
| 233 | 0.85 | 43.44 |
| 234 | 4.11 | |
| 235 | 2.33 | |
| 236 | 3.16 | |
| 237 | 0.64 | 5.23 |
| 238 | 1.13 | 14.73 |
| 239 | 1.15 | 9.44 |
| 240 | 0.73 | 16.08 |
| 241 | 1.04 | 13.36 |
| 242 | 0.81 | 9.70 |
| 243 | 0.75 | 5.35 |
| 244 | 0.57 | 3.70 |
| 245 | 0.53 | 19.18 |
| 246 | 3.29 | |
| 247 | 1.36 | 12.15 |
| 248 | 2.41 | |
| 249 | 2.32 | |
| 250 | 1.62 | 27.37 |
| 251 | 1.83 | |
| 252 | 1.39 | 10.56 |
| 253 | 1.26 | 28.80 |
| 254 | 2.17 | |
| 255 | 1.69 | |
| 256 | 2.58 | |
| 257 | 4.20 | |
| 258 | 0.74 | 10.69 |
| 259 | 0.68 | 17.38 |
| 260 | 2.89 | |
| 261 | 1.00 | 121.36 |
| 262 | 0.64 | >47.63 |
| 263 | 0.52 | 31.91 |
| 264 | 1.83 | |
| 265 | 1.91 | |
| 266 | 0.39 | 32.63 |
| 267 | 3.02 | |
| 268 | 0.97 | |
| 269 | 1.68 | |
| 270 | 0.86 | 39.88 |
| 271 | 1.57 | |
| 272 | 2.63 | 40.85 |
| 273 | 3.08 | |
| 274 | 2.62 | |
| 275 | 0.49 | 53.15 |
| 276 | 0.64 | 33.09 |
| 277 | 0.98 | |
| 278 | 0.52 | 56.69 |
| 279 | 0.32 | 53.18 |
| 280 | 2.12 | |
| 281 | 0.33 | 24.42 |
| 282 | 2.34 | |
| 283 | 4.60 | |
| 284 | 0.60 | |
| 285 | 3.97 | |
| 286 | 4.14 | |
| 287 | 2.26 | |
| 288 | 0.39 | |
| 289 | 0.49 | 10.63 |
| 290 | 1.45 | |
| 291 | 0.43 | >47.63 |
| 292 | 0.86 | |
| 293 | 0.85 | >95.31 |
| 294 | 0.62 | 31.97 |
| 295 | 0.38 | 56.13 |
| 296 | 0.30 | |
| 297 | 1.17 | |
| 298 | 0.68 | 72.02 |
| 299 | 0.26 | 29.89 |
| 300 | 0.65 | |
| 301 | 0.55 | |
| 302 | 0.50 | |
| 303 | 0.33 | |

TABLE 4-continued

| Example No. | CDK2/cyclin $E_1$ Ki (nM) | GSK3β Ki (nM) |
|---|---|---|
| 304 | 1.41 | |
| 305 | 0.52 | |
| 306 | 1.09 | |
| 307 | 0.73 | |
| 308 | 0.30 | 89.06 |
| 309 | 1.55 | |
| 310 | 0.69 | |
| 311 | 0.36 | |
| 312 | 0.43 | |
| 313 | 0.63 | |
| 314 | 0.41 | 40.58 |
| 315 | 0.65 | 132.72 |
| 316 | 1.30 | |
| 317 | 0.26 | 45.99 |
| 318 | 0.53 | |
| 319 | 0.39 | 123.24 |
| 320 | 2.95 | |
| 321 | 0.63 | >190.68 |
| 322 | 0.93 | 81.21 |
| 323 | 1.07 | 74.13 |
| 324 | 0.54 | 94.28 |
| 325 | 0.81 | 54.02 |
| 326 | 1.17 | 72.42 |
| 327 | 0.44 | 57.75 |
| 328 | 1.77 | |
| 329 | 1.02 | 107.07 |
| 330 | 0.55 | 85.98 |
| 331 | 1.49 | |
| 332 | 1.05 | 61.28 |
| 333 | 0.41 | 63.16 |
| 334 | 1.60 | |
| 335 | 0.41 | 23.86 |
| 336 | 0.39 | 53.47 |
| 337 | 0.58 | 94.93 |
| 338 | 1.58 | 94.40 |
| 339 | 0.66 | |
| 340 | 2.24 | |
| 341 | 0.64 | |
| 342 | 0.74 | 40.03 |
| 343 | 0.77 | 26.14 |
| 344 | 0.58 | |
| 345 | 2.66 | |
| 346 | 0.26 | 10.74 |
| 347 | 0.37 | 45.60 |
| 348 | 0.59 | 54.15 |
| 349 | 0.40 | 57.31 |
| 350 | 3.45 | |
| 351 | 2.77 | |
| 352 | 0.82 | 58.42 |
| 353 | 0.50 | 29.47 |
| 354 | 3.74 | |
| 355 | 1.13 | 18.13 |
| 356 | 0.67 | 148.05 |
| 357 | 4.08 | |
| 358 | 1.65 | |
| 359 | 0.39 | 28.46 |
| 360 | 1.46 | |
| 361 | 0.94 | 25.61 |
| 362 | 0.84 | |
| 363 | 0.35 | 52.03 |
| 364 | 0.82 | 59.92 |
| 365 | 2.08 | |
| 366 | 1.79 | |
| 367 | 0.27 | 23.52 |
| 368 | 0.41 | |
| 369 | 0.84 | |
| 370 | 0.28 | 50.81 |
| 371 | 0.32 | 160.53 |
| 372 | 0.85 | 114.62 |
| 373 | 0.47 | 74.30 |
| 374 | 0.32 | 10.83 |
| 375 | 0.31 | 115.98 |
| 376 | 0.40 | 99.35 |
| 377 | 1.14 | |
| 378 | 0.83 | |
| 379 | 3.05 | |
| 380 | 0.63 | |
| 381 | 3.11 | |
| 382 | 0.77 | 74.18 |
| 383 | 1.34 | 43.17 |
| 384 | 1.24 | |
| 385 | 0.52 | 25.86 |
| 386 | 0.66 | 45.93 |
| 387 | 0.30 | |
| 388 | 2.34 | 36.88 |
| 389 | 0.83 | 18.31 |
| 390 | 3.74 | |
| 391 | 1.38 | 37.96 |
| 392 | 3.14 | |
| 393 | 0.97 | 34.05 |
| 394 | 0.42 | 42.71 |
| 395 | 1.43 | |
| 396 | 2.10 | 139.07 |
| 397 | 1.87 | 155.22 |
| 398 | 0.65 | 44.11 |
| 399 | 0.47 | 68.80 |
| 400 | 1.29 | |
| 401 | 0.34 | 32.95 |
| 402 | 1.54 | |
| 403 | 1.76 | 76.11 |
| 404 | 1.38 | 84.27 |
| 405 | 1.37 | 97.90 |
| 406 | 1.81 | 73.33 |
| 407 | 1.16 | |
| 408 | 0.29 | 17.91 |
| 409 | 4.15 | |
| 410 | 0.42 | 55.54 |
| 411 | 2.58 | |
| 412 | 0.19 | |
| 413 | 0.44 | 14.69 |
| 414 | 0.42 | 3.44 |
| 415 | 1.48 | 26.45 |
| 416 | 2.27 | |
| 417 | 0.81 | 12.56 |
| 418 | 2.69 | |
| 419 | 0.36 | |
| 420 | 0.54 | |
| 421 | 0.94 | |
| 422 | 0.55 | |
| 423 | 0.60 | |
| 424 | 0.51 | 14.40 |
| 425 | 1.05 | |
| 426 | 0.53 | 17.04 |
| 427 | 1.78 | |
| 428 | 0.40 | 30.11 |
| 429 | 1.15 | |
| 430 | 1.14 | |
| 431 | 1.19 | |
| 432 | 1.25 | |
| 433 | 0.50 | 17.12 |
| 434 | 0.48 | 39.83 |
| 435 | 1.49 | |
| 436 | 3.30 | |
| 437 | 0.51 | 15.87 |
| 438 | 2.50 | |
| 439 | 2.37 | |
| 440 | 1.47 | |
| 441 | 1.42 | |
| 442 | 0.37 | |
| 443 | 0.36 | |
| 444 | 1.41 | |
| 445 | 0.60 | |
| 446 | 1.70 | |
| 447 | 0.36 | >47.63 |
| 448 | 0.29 | |
| 449 | 0.39 | |
| 450 | 0.38 | |
| 451 | 0.46 | |
| 452 | 0.51 | |
| 453 | 0.29 | |
| 454 | 0.48 | |
| 455 | 0.47 | 21.28 |
| 456 | 0.38 | |
| 457 | 0.38 | |

TABLE 4-continued

| Example No. | CDK2/cyclin $E_1$ Ki (nM) | GSK3β Ki (nM) |
|---|---|---|
| 458 | 3.07 | |
| 459 | 0.32 | |
| 460 | 1.62 | 39.91 |
| 461 | 1.75 | |
| 462 | 1.74 | |
| 463 | 0.55 | 28.32 |
| 464 | 2.63 | |
| 465 | 1.95 | |
| 466 | 1.02 | |
| 467 | 1.20 | |
| 468 | 0.35 | |
| 469 | 0.31 | |
| 470 | 0.83 | |
| 471 | 1.43 | |
| 472 | 1.17 | |
| 473 | 0.36 | 66.25 |
| 474 | 0.44 | |
| 475 | 0.83 | 23.95 |
| 476 | 0.45 | 30.89 |
| 477 | 1.04 | 59.19 |
| 478 | 1.13 | |
| 479 | 0.89 | |
| 480 | 2.01 | |
| 481 | 0.53 | 44.64 |
| 482 | 0.55 | 36.16 |
| 483 | 0.32 | |
| 484 | 0.32 | 30.32 |
| 485 | 1.41 | |
| 486 | 1.46 | |
| 487 | 0.67 | >47.63 |
| 488 | 1.40 | |
| 489 | 3.71 | |
| 490 | 3.68 | |
| 491 | 3.87 | |
| 492 | 2.39 | |
| 493 | 0.98 | 156.95 |
| 494 | 1.02 | 53.29 |
| 495 | 1.79 | |
| 496 | 2.25 | |
| 497 | 4.38 | |
| 498 | 4.28 | |
| 499 | 2.55 | |
| 500 | 2.36 | |
| 501 | 1.43 | 12.54 |
| 502 | 3.71 | |
| 503 | 2.13 | |
| 504 | 3.64 | |
| 505 | 1.60 | |
| 506 | 0.76 | 77.63 |
| 507 | 3.69 | |
| 508 | 1.46 | |
| 509 | 0.50 | 30.23 |
| 510 | 0.19 | 13.98 |
| 511 | 1.52 | 4.74 |
| 512 | 3.20 | |
| 513 | 3.19 | |
| 514 | 2.78 | |
| 515 | 1.25 | 11.30 |
| 516 | 3.24 | |
| 517 | 1.29 | |
| 518 | 1.43 | |
| 519 | 0.56 | |
| 520 | 2.88 | |
| 521 | 1.95 | |
| 522 | 3.05 | |
| 523 | 2.49 | |
| 524 | 1.69 | 10.88 |
| 525 | 1.24 | 7.01 |
| 526 | 3.95 | |
| 527 | 2.63 | |
| 528 | 1.11 | 3.60 |
| 529 | 0.73 | 3.92 |
| 530 | 2.03 | |
| 531 | 1.51 | |
| 532 | 0.89 | 2.97 |
| 533 | 0.77 | 1.41 |
| 534 | 0.85 | 4.63 |
| 535 | 1.21 | 3.80 |
| 536 | 2.07 | |
| 537 | 1.34 | 10.73 |
| 538 | 2.72 | |
| 539 | 2.35 | |
| 540 | 2.65 | |
| 541 | 1.85 | |
| 542 | 2.41 | |
| 543 | 1.96 | |
| 544 | 0.54 | 1.96 |
| 545 | 0.39 | 2.20 |
| 546 | 1.85 | 3.51 |
| 547 | 0.61 | 3.62 |
| 548 | 0.39 | 2.10 |
| 549 | 0.90 | 3.24 |
| 550 | 0.36 | 3.12 |
| 551 | 0.34 | 2.94 |
| 552 | 0.29 | 2.41 |
| 553 | 0.41 | 1.90 |
| 554 | 1.76 | 5.11 |
| 555 | 0.37 | 3.58 |
| 556 | 0.46 | 1.85 |
| 557 | 1.01 | 2.60 |
| 558 | 0.41 | 18.59 |
| 559 | 1.44 | 8.58 |
| 560 | 0.60 | 9.84 |
| 561 | 1.80 | |
| 562 | 0.43 | 4.85 |
| 563 | 1.80 | 4.35 |
| 564 | 0.37 | 10.07 |
| 565 | 1.24 | 4.07 |
| 566 | 0.79 | 37.61 |
| 567 | 1.61 | |
| 568 | 0.41 | 5.12 |
| 569 | 1.25 | 4.31 |
| 570 | 0.35 | 3.29 |
| 571 | 1.08 | 2.28 |
| 572 | 0.37 | 24.23 |
| 573 | 0.83 | 14.08 |
| 574 | 4.07 | |
| 575 | 2.28 | |
| 576 | 1.99 | |
| 577 | 3.36 | |
| 578 | 3.64 | |
| 579 | 2.41 | |
| 580 | 3.38 | |
| 581 | 2.62 | |
| 582 | 2.23 | |
| 583 | 2.71 | |
| 584 | 3.84 | |
| 585 | 2.57 | |
| 586 | 0.88 | 51.55 |
| 587 | 2.77 | |
| 588 | 0.75 | |
| 589 | 0.59 | 18.16 |
| 590 | 2.86 | |
| 591 | 1.67 | |
| 592 | 2.27 | |
| 593 | 2.21 | |
| 594 | 0.62 | 14.35 |
| 595 | 1.52 | |
| 596 | 1.75 | |
| 597 | 0.54 | 20.86 |
| 598 | 0.78 | 16.39 |
| 599 | 1.38 | |
| 600 | 2.12 | |
| 601 | 0.39 | 7.32 |
| 602 | 0.30 | |
| 603 | 0.07 | 13.82 |
| 604 | 0.08 | 5.00 |
| 605 | 0.32 | 9.89 |
| 606 | 0.63 | 11.50 |
| 607 | 1.90 | |
| 608 | 1.11 | |
| 609 | 4.81 | |
| 610 | 1.04 | |
| 611 | 1.67 | 13.94 |

TABLE 4-continued

| Example No. | CDK2/cyclin $E_1$ Ki (nM) | GSK3β Ki (nM) |
|---|---|---|
| 612 | 0.45 | 8.01 |
| 613 | 2.98 | |
| 614 | 1.66 | 6.58 |
| 615 | 1.99 | |
| 616 | 0.28 | 4.05 |
| 617 | 0.27 | 7.18 |
| 618 | 0.78 | 8.57 |
| 619 | 0.42 | 5.75 |
| 620 | 3.91 | |
| 621 | 0.36 | 2.77 |
| 622 | 4.00 | |
| 623 | 1.17 | 6.31 |
| 624 | 4.18 | 16.26 |
| 625 | 0.45 | 4.97 |
| 626 | 4.73 | |
| 627 | 0.51 | 2.76 |
| 628 | 0.92 | 20.77 |
| 629 | 0.40 | 10.58 |
| 630 | 1.43 | |
| 631 | 1.12 | 11.78 |
| 632 | 0.36 | 12.67 |
| 633 | 2.11 | |
| 634 | 0.99 | 14.37 |
| 635 | 0.53 | 16.29 |
| 636 | 0.83 | |
| 637 | 1.47 | |
| 638 | 0.28 | 14.94 |
| 639 | 0.47 | 6.34 |
| 640 | 0.48 | 13.27 |
| 641 | 0.59 | 14.45 |
| 642 | 1.37 | 10.33 |
| 643 | 1.84 | |
| 644 | 0.33 | 8.71 |
| 645 | 0.37 | 7.23 |
| 646 | 1.03 | 5.18 |
| 647 | 1.08 | 3.39 |
| 648 | 0.47 | 12.25 |
| 649 | 0.31 | 9.20 |

Additional biological activity data for selected compounds is provided in Table 5 below.

TABLE 5

| Example No. | Biochemical Assay | Ki (nM) |
|---|---|---|
| 13 | CDK1/cyclin $A_2$ | 110 |
| 13 | CDK4/cyclin $D_1$ | 238 |
| 13 | CDK6/cyclin $D_3$ | 465 |
| 13 | CDK9 | 177 |
| 15 | CDK1/cyclin $A_2$ | 16.4 |
| 15 | CDK4/cyclin $D_1$ | 26.6 |
| 15 | CDK6/cyclin $D_3$ | 58.6 |
| 15 | CDK9 | 6.3 |

All publications and patent applications cited in the specification are herein incorporated by reference in their entirety. It will be apparent to those of ordinary skill in the art that certain changes and modifications may be made thereto without departing from the spirit or scope of the appended claims.

What is claimed is:

1. A compound (1R,3S)-3-[3-({[3-(methoxymethyl)-1-methyl-1H-pyrazol-5-yl]carbonyl}amino)-1H-pyrazol-5-yl] cyclopentyl propan-2-ylcarbamate, having the structure:

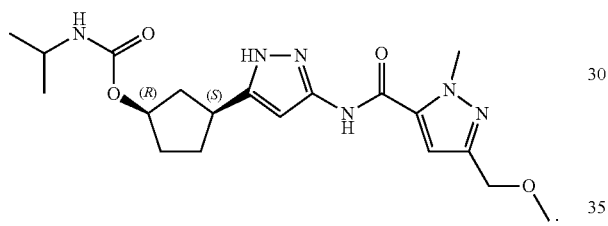

2. A pharmaceutical composition comprising the compound of claim 1, and a pharmaceutically acceptable carrier or excipient.

3. A compound (1R,3S)-3-[3-({[3-(methoxymethyl)-1-methyl-1H-pyrazol-5-yl]carbonyl}amino)-1H-pyrazol-5-yl] cyclopentyl propan-2-ylcarbamate, having the structure:

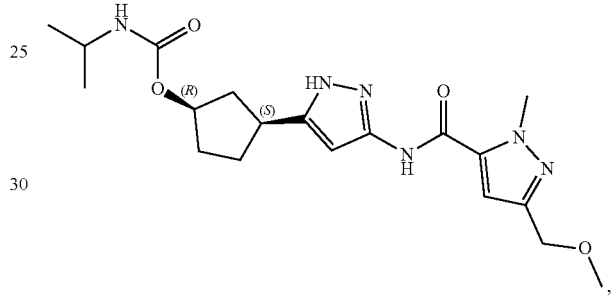

or a pharmaceutically acceptable salt thereof.

4. A pharmaceutical composition comprising the compound of claim 3, or a pharmaceutically acceptable salt thereof, and a pharmaceutically acceptable carrier or excipient.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 5-FAM labeled Glutamine
<220> FEATURE:
<221> NAME/KEY: MOD_RES_AMIDATION
<222> LOCATION: (6)..(6)
<223> OTHER INFORMATION: Amidation on Glycine

<400> SEQUENCE: 1

Gln Ser Pro Lys Lys Gly
1               5

<210> SEQ ID NO 2
<211> LENGTH: 13
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 5-FAM labeled Lysine
<220> FEATURE:
<221> NAME/KEY: MOD_RES_PHOSPHORYLATION
<222> LOCATION: (11)..(11)
<223> OTHER INFORMATION: Phosphorylation on Serine
```

```
<400> SEQUENCE: 2

Lys Arg Arg Glu Ile Leu Ser Arg Arg Pro Ser Tyr Arg
1               5                   10

<210> SEQ ID NO 3
<211> LENGTH: 15
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 5-FAM labeled Arginine

<400> SEQUENCE: 3

Arg Arg Arg Phe Arg Pro Ala Ser Pro Leu Arg Gly Pro Pro Lys
1               5                   10                  15
```